(12) United States Patent
Deretic et al.

(10) Patent No.: US 9,572,820 B2
(45) Date of Patent: Feb. 21, 2017

(54) METHODS OF TREATING AUTOPHAGY-ASSOCIATED DISORDERS AND RELATED PHARMACEUTICAL COMPOSITIONS, DIAGNOSTICS, SCREENING TECHNIQUES AND KITS

(75) Inventors: Vojo Deretic, Placitas, NM (US); Eliseo Castillo, Albuquerque, NM (US); Steven Bradfute, Albuquerque, NM (US); Larry A. Sklar, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 52 days.

(21) Appl. No.: 14/116,581

(22) PCT Filed: May 10, 2012

(86) PCT No.: PCT/US2012/037300
§ 371 (c)(1),
(2), (4) Date: Nov. 8, 2013

(87) PCT Pub. No.: WO2012/154944
PCT Pub. Date: Nov. 15, 2012

(65) Prior Publication Data
US 2014/0135296 A1 May 15, 2014

Related U.S. Application Data

(60) Provisional application No. 61/484,653, filed on May 10, 2011.

(51) Int. Cl.

| | |
|---|---|
| *A61K 31/519* | (2006.01) |
| *A61K 31/12* | (2006.01) |
| *A61K 31/65* | (2006.01) |
| *C07K 16/18* | (2006.01) |
| *G01N 33/68* | (2006.01) |
| *A61K 31/436* | (2006.01) |
| *A61K 31/4365* | (2006.01) |
| *A61K 31/4535* | (2006.01) |
| *A61K 31/472* | (2006.01) |
| *A61K 31/473* | (2006.01) |
| *A61K 31/517* | (2006.01) |
| *A61K 31/522* | (2006.01) |
| *A61K 31/54* | (2006.01) |
| *A61K 31/546* | (2006.01) |
| *A61K 31/5685* | (2006.01) |
| *A61K 31/585* | (2006.01) |
| *G01N 33/569* | (2006.01) |

(52) U.S. Cl.
CPC .............. *A61K 31/65* (2013.01); *A61K 31/436* (2013.01); *A61K 31/4365* (2013.01); *A61K 31/4535* (2013.01); *A61K 31/472* (2013.01); *A61K 31/473* (2013.01); *A61K 31/517* (2013.01); *A61K 31/519* (2013.01); *A61K 31/522* (2013.01); *A61K 31/54* (2013.01); *A61K 31/546* (2013.01); *A61K 31/5685* (2013.01); *A61K 31/585* (2013.01); *C07K 16/18* (2013.01); *G01N 33/56972* (2013.01); *G01N 33/6893* (2013.01); *G01N 2333/9015* (2013.01)

(58) Field of Classification Search
CPC .............. A61K 31/436; A61K 31/4365; A61K 31/4535; A61K 31/472; A61K 31/473; A61K 31/517; A61K 31/519; A61K 31/522; A61K 31/54; A61K 31/546; A61K 31/5685; A61K 31/585; A61K 31/65; C07K 16/18; G01N 2333/9015; G01N 33/56972; G01N 33/6893
USPC ........................ 514/152, 154, 169, 171, 203, 227.5, 514/262.1, 263.34, 266.24, 291, 298, 301, 309,514/324
See application file for complete search history.

(56) References Cited

U.S. PATENT DOCUMENTS

| | | | | |
|---|---|---|---|---|
| 2008/0161324 | A1* | 7/2008 | Johansen et al. | ........ 514/255.03 |
| 2011/0263520 | A1* | 10/2011 | Horikoshi et al. | .............. 514/30 |
| 2015/0250808 | A1* | 9/2015 | Deretic | .............. G01N 33/5695 424/158.1 |
| 2016/0136123 | A1* | 5/2016 | Deretic | .................... C12Q 1/61 424/450 |

FOREIGN PATENT DOCUMENTS

| | | | | |
|---|---|---|---|---|
| WO | 2007003941 | A1 | 1/2007 | |
| WO | 2008036254 | A2 | 3/2008 | |
| WO | WO 2008122038 | A1 * | 10/2008 | ........... A61K 31/405 |
| WO | 2010129681 | A1 | 11/2010 | |
| WO | 2011003883 | A1 | 1/2011 | |

OTHER PUBLICATIONS

Youle RJ, Narendra DP. Mechanisms of mitophagy. Nat Rev Mol Cell Biol, 2011;12:9-14.
Mayer-Barber KD, et al. Caspase-1 independent IL-1beta production is critical for host resistance to *Mycobacterium tuberculosis* and does not require TLR signaling in vivo. J Immunol, 2010;184:3326-3330.
McCarroll SA, et al. Deletion polymorphism upstream of IRGM associated with altered IRGM expression and Crohn's disease. Nat Genet, 2008;40:1107-1112.
Mishra BB, et al. *Mycobacterium tuberculosis* protein ESAT-6 is a potent activator of the NLRP3/ASC inflammasome. Cell Microbiol, 2010;12:1046-1063.
Mizushima N, et al. The role of atg proteins in autophagosome formation. Annu Rev Cell Dev Biol, 2011;27:107-132.

(Continued)

*Primary Examiner* — My-Chau T Tran
(74) *Attorney, Agent, or Firm* — Henry D. Coleman; R. Neil Sudol

(57) ABSTRACT

The invention provides methods of treating autophagy mediated diseases and disorders and related pharmaceutical compositions, diagnostics, screening techniques and kits. In one embodiment, the invention provides a method of determin- (Continued)

ing whether a subject suffers from, or is at risk of developing, and autophagy mediated disease state and/or condition by evaluating LC3 levels.

5 Claims, 53 Drawing Sheets

(56) References Cited

OTHER PUBLICATIONS

Moreira AL, et al. Mycobacterial antigens exacerbate disease manifestations in *Mycobacterium tuberculosis*-infected mice. Infect Immun, 2002;70:2100-2107.
Moscat J, Diaz-Meco MT. p62 at the crossroads of autophagy, apoptosis, and cancer. Cell, 2009;137:1001-1004.
Nakagawa I, et al. Autophagy defends cells against invading group A *Streptococcus*. Science, 2004;306:1037-1040.
Narita M, et al. Spatial coupling of mTOR and autophagy augments secretory phenotypes. Science, 2011;332:966-970.
Nedjic J, et al. Autophagy in the thymic epithelium shapes the T-cell repertoire and is essential for tolerance. Nature, 2008;455:396-400.
Nunn P, et al. Tuberculosis control in the era of HIV. Nat Rev Immunol, 2005;5:819-826.
Orvedahl A, et al. Autophagy Protects against Sindbis Virus Infection of the Central Nervous System. Cell Host Microbe, 2010;7:115-127.
Paludan C, et al. Endogenous MHC class II processing of a viral nuclear antigen after autophagy. Science, 2005;307:593-596.
Ponpuak M, et al. Delivery of cytosolic components by autophagic adaptor protein p62 endows autophagosomes with unique antimicrobial properties. Immunity, 2010;32:329-341.
Pua HH, et al. Autophagy is essential for mitochondrial clearance in mature T lymphocytes. J Immunol, 2009;182:4046-4055.
Saitoh T, Akira S. Regulation of innate immune responses by autophagy-related proteins. J Cell Biol, 2010;189:925-935.
Sancak Y, et al. Ragulator-Rag complex targets mTORC1 to the lysosomal surface and is necessary for its activation by amino acids. Cell, 2010;141:290-303.
Singh SB, et al. Human IRGM induces autophagy to eliminate intracellular mycobacteria. Science, 2006;313:1438-1441.
Singh SB, et al. Human IRGM regulates autophagy and cell-autonomous immunity functions through mitochondria. Nat Cell Biol, 2010;12:1154-1165.
Taylor JL, et al. Pulmonary necrosis resulting from DNA vaccination against tuberculosis. Infect Immun, 2003;71:2192-2198.
Thurston TL, et al. The TBK1 adaptor and autophagy receptor NDP52 restricts the proliferation of ubiquitin-coated bacteria. Nat Immunol, 2009;10:1215-1221.
Tooze SA, Yoshimori T. The origin of the autophagosomal membrane. Nat Cell Biol, 2010;12:831-835.
Travassos LH, et al. Nod1 and Nod2 direct autophagy by recruiting ATG16L1 to the plasma membrane at the site of bacterial entry. Nat Immunol, 2010;11:55-62.
Turner J, et al. Effective preexposure tuberculosis vaccines fail to protect when they are given in an immunotherapeutic mode. Infect lmmun, 2000;68:1706-1709.
Van De Veerdonk FL, et al. Inflammasome activation and IL-1beta and IL-18 processing during infection. Trends Immunol, 2011;32:110-116.
Vergne I, et al. Cell biology of mycobacterium tuberculosis phagosome. Annu Rev Cell Dev Biol, 2004;20:367-394.
Weidberg H, et al. LC3 and GATE-16/GABARAP subfamilies are both essential yet act differently in autophagosome biogenesis. Embo J, 2010;29:1792-1802.
Wild P, et al. Phosphorylation of the autophagy receptor optineurin restricts *Salmonella* growth. Science, 2011;333:228-233.
Willingham SB, et al. NLRP3 (NALP3, Cryopyrin) facilitates in vivo caspase-1 activation, necrosis, and HMGB1 release via inflammasome-dependent and -independent pathways. J Immunol, 2009;183:2008-2015.
Xia Y, et al. RelB modulation of IkappaBalpha stability as a mechanism of transcription suppression of interleukin-1alpha (IL-lalpha), IL-1beta, and tumor necrosis factor alpha in fibroblasts. Mol Cell Biol, 1999;19:7688-7696.
Xu Y, et al. Toll-like receptor 4 is a sensor for autophagy associated with innate immunity. Immunity, 2007;27:135-144.
Yang H, et al. Three protein cocktails mediate delayed-type hypersensitivity responses indistinguishable from that elicited by purified protein derivative in the guinea pig model of *Mycobacterium tuberculosis* infection. Infect Immun, 2011;79:716-723.
Yang Z, Klionsky DJ. Eaten alive: a history of macroautophagy. Nat Cell Biol, 2010;12:814-822.
Yazdi AS, et al. Nanoparticles activate the NLR pyrin domain containing 3 (Nlrp3) inflammasome and cause pulmonary inflammation through release of IL-1alpha and IL-1beta. Proc Natl Acad Sci USA, 2010;107:19449-19454.
Yoshikawa Y, et al. Listeria monocytogenes ActA-mediated escape from autophagic recognition. Nat Cell Biol, 2009;11:1233-1240.
Yuk JM, et al. Vitamin D3 induces autophagy in human monocytes/macrophages via cathelicidin. Cell Host Microbe, 2009a;6:231-243.
Zhao Z, et al. Autophagosomeindependent essential function for the autophagy protein Atg5 in cellular immunity to intracellular pathogens. Cell Host Microbe, 2008;4:458-469.
Bjorkoy G, et al. p62/SQSTM1 forms protein aggregates degraded by autophagy and has a protective effect on huntingtin-induced cell death. J Cell Biol, 2005;171:603-614.
Bjorkqvist M, et al. A novel pathogenic pathway of immune activation detectable before clinical onset in Huntington's disease. J Exp Med, 2008;205:1869-1877.
Cadwell K, et al. Virus-plus18 susceptibility gene interaction determined Crohn's disease gene Atg16L1phenotypes in intestine. Cell, 2010;141:1135-1145.
Chaturvedi A, et al. The B cell receptor governs the subcellar location of Toll-like receptor 9 leading to hyperresponses to DNA containing antigens. Immunity, 2008;28:799-809.
Che N, et al. Identification of a novel IRGM promoter single nucleotide polymorphism associated with tuberculosis. Clin Chim Acta, 2010;411:1645-1649.
Chen S, et al. Rab8b and its interacting partner TRIP8b are involved in regulated secretion in AtT20 cells. J Biol Chem, 2001;276:13209-13216.
Clark K, et al. Novel cross-talk within the IKK family controls innate immunity. The Biochemical journal, 2010;434:93-104.
Clark K, et al. Use of the pharmacological inhibitor BX795 to study the regulation and physiological roles of TBK1 and IkappaB kinase epsilon: a distinct upstream kinase mediates Ser-172 phosphorylation and activation. J Biol Chem, 2009;284:14136-14146.
Comb WC, et al. IKKdependent, NF-kappaB-independent control of autophagic gene expression. Oncogene, 2011;30:1727-1732.
Consortium. Genome-wide association study of 14,000 cases of seven common diseases and 3,000 shared controls. Nature, 2007;447:661-678.
Cooney R, et al. NOD2 stimulation induces autophagy in dendritic cells influencing bacterial handling and antigen presentation. Nat Med, 2010;16:90-97.
Criollo A, et al. The IKK complex contributes to the induction of autophagy. Embo J, 2010;29:619-631.
Del Toro D, et al. Mutant huntingtin impairs post-Golgi trafficking to lysosomes by delocalizing optineurin/Rab8 complex from the Golgi apparatus. Mol Biol Cell, 2009;20:1478-1492.
Shen RR, Hahn WC. Emerging roles for the non-canonical IKKs in cancer. Oncogene, 2011;30:631-641.
Shevchenko A, et al. Mass spectrometric sequencing of proteins silver-stained polyacrylamide gels. Anal Chem, 1996;68:850-858.
Shi CS, Kehri JH. TRAF6 and A20 regulate lysine 63-linked ubiquitination of Beclin-1 to control TLR4-induced autophagy. Sci Signal, 2010;3:ra42.

(56) References Cited

OTHER PUBLICATIONS

Stenmark H. Rab GTPases as coordinators of vesicle traffic. Nat Rev Mol Cell Biol, 2009;10:513-525.

Tang D, et al. Endogenous HMGB1 regulates autophagy. J Cell Biol, 2010;190:881-892.

Von Muhlinen N, et al. NDP52, a novel autophagy receptor for ubiquitin-decorated cytosolic bacteria. Autophagy, 2010;6:288-289.

Yano T, et al. Autophagic control of listeria through intracellular innate immune recognition in Drosophila. Nat Immunol, 2008;9:908-916.

Zhong Y, et al. Distinct regulation of autophagic activity by Atg14L and Rubicon associated with Beclin 1-phosphatidylinositol-3-kinase complex. Nat Cell Biol, 2009;11(4):468-476.

Zhou R, et al. A role for mitochondria in NLRP3 inflammasome activation. Nature, 2011;469:221-225.

Alavez S, et al. Amyloid-binding compounds maintain protein homeostasis during ageing and extend lifespan. Nature, 2011;472:226-229.

Andersson U, Tracey KJ. HMGB1 is a therapeutic target for sterile inflammation and infection. Annu Rev Immunol, 2011;29:139-162.

Barr FA, et al. GRASP65, a protein involved in the stacking of Golgi cisternae. Cell, 1997;91:253-262.

Bodemann BO, et al. RalB and the exocyst mediate the cellular starvation response by direct activation of autophagosome assembly. Cell, 2011;144:253-267.

Bravo-Cordero JJ, et al. MT1-MMP proinvasive activity is regulated by a novel Rab8-dependent exocytic pathway. EMBO J, 2007;26:1499-1510.

Davis BK, et al. The inflammasome NLRs in immunity, inflammation, and associated diseases. Annu Rev Immunol, 2011;29:707-735.

Deretic V. Autophagy in immunity and cell-autonomous defense against intracellular microbes. Immunol Rev, 2011;240:92-104.

Dou Z, et al. The class IA phosphatidylinositol 3-kinase p110-beta subunity is a positive regulator of autophagy. J Cell Biol, 2010;191:827-843.

Duran JM, et al. Unconventional secretion of Acb1 is mediated by autophagosomes. J Cell Biol, 2010;188:527-536.

Eisenbarth SC, et al. Crucial role for the Nalp3 inflammasome in the immunostimulatory properties of aluminium adjuvants. Nature, 2008;453:1122-1126.

Gee HY, et al. Rescue of DeltaF508-CFTR trafficking via a GRASP-dependent unconventional secretion pathway. Cell, 2011;146:746-760.

Giuliani F, et al. Unconventional secretion: a stress on GRASP. Curr Opin Cell Biol, 2011;23:498-504.

Gonzalez CD, et al. The emerging role of autophagy in the pathophysiology of diabetes mellitus. Autophagy, 2011;7:2-11.

Guo JY, et al. Activated Ras requires autophagy to maintain oxidative metabolism and tumorigenesis. Genes Dev, 2011;25:460-470.

Halle A, et al. The NALP3 inflammasome is involved in the innate immune response to amyloid-beta. Nat Immunol, 2008;9:857-865.

Hornung V, et al. Silica crystals and aluminum salts activate the NALP3 inflammasome through phagosomal destabilization. Nat Immunol, 2008;9:847-856.

Kihara A, et al. Beclin-phosphatidylinositol 3-kinase complex functions at the trans-Golgi network. EMBO Rep, 2001;2:330-335.

Kim J, et al. AMPK and mTOR regulate autophagy through direct phosphorylation of Ulk1. Nat Cell Biol, 2011;13:132-141.

Kinseth MA, et al. The Golgi-associated protein GRASP is required for unconventional protein secretion during development. Cell, 2007;130:524-534.

Kroemer G, et al. Autophagy and the integrated stress response. Mol Cell, 2010;40:280-293.

Martinon F, et al. Gout associated uric acid crystals activate the NALP3 inflammasome. Nature, 2006;440:237-241.

Mazelova J, et al. Syntaxin 3 and SNAP-25 pairing, regulated by omega-3 docosahexaenoic acid, controls the delivery of rhodopsin for the biogenesis of cilia-derived sensory organelles, the rod outer segments. J Cell Sci, 2009;122:2003-2013.

Mizushima N, Levine B. Autophagy in mammalian development and differentiation. Nat Cell Biol, 2010;12:823-830.

Mizushima N, et al. In vivo analysis of autophagy in response to nutrient starvation using transgenic mice expressing a fluorescent autophagosome marker. Mol Biol Cell, 2004;15:1101-1111.

Mizushima N, et al. Methods in mammalian autophagy research. Cell, 2010;140:313-326.

Moore KJ, et al. A CD36-initiated signaling cascade mediates inflammatory effects of meta-amyloid. J Biol Chem, 2002;277:47373-47379.

Moritz OL, et al. Mutant rab8 Impairs docking and fusion of rhodopsinbearing post-Golgi membranes and causes cell death of transgenix Xenopus rods. Mol Biol Cell, 2001;12:2341-2351.

Nachury MV, et al. A core complex of BBS proteins cooperates with GTPase Rab8 to promote ciliary membrane biogenesis. Cell, 2007;129:1201-1213.

Nickel W, Rabouille C. Mechanisms of regulated unconventional protein secretion. Nat Rev Mol Cell Biol, 2009;10:148-155.

Renna M, et al. Chemical inducers of autophagy that enhance the clearance of mutant proteins in neurodegenerative diseases. J Biol Chem, 2010;285:11061-11067.

Romanello V, et al. Mitochondrial fission and remodeling contributes to muscle atrophy. EMBO J, 2010;29:1774-1785.

Rubartelli A, et al. A novel secretory pathway for interleukin-1 beta, a protein lacking a signal sequence. EMBO J, et al. 1990;9:1503-1510.

Shorter J, et al. GRASP55, a second mammalian GRASP protein involved in the stacking of Golgi cisternae in a cell-free system. EMBO J, 1999;18:4949-4960.

Strappazzon F, et al. Mitochondrial BCL-2 inhibits AMBRA1-induced autophagy. 2011;30:1195-1208.

Sun Y, et al. Rab8A and Rab13 are activated by insulin and regulate GLUT4 translocation in muscle cells. Proc Natl Acad Sci USA, 2010;107:19909-19914.

Vandanmagsar B, et al. The NLRP3 inflammasome instigates obesity-induced inflammation and insulin resistance. Nat Med, 2011;17:179-188.

Wen H, et al. Fatty acid-induced NLRP3-ASC inflammasome activation interferes with insulin signaling. Nat Immunol, 2011;12:408-415.

Wong E, Cuervo AM. Autophagy gone awry in neurodegenerative diseases. Nat Neurosci, 2010;13:805-811.

Yang Z, et al. Positive or negative roles of different cyclin-dependent kinase Pho85-cyclin complexes orchestrate induction of autophagy in Saccharomyces cerevisiae. Mol Cell, 2010;38:250-264.

Deretic V, et al. Autophagy as an innate immunity paradigm: expanding the scope and repertoire of pattern recognition receptors. Curr Opin lmmunol, 2012;24(1):21-31.

Edinger AL, et al. Rab7 prevents growth factor-independent survival by inhibiting cell-autonomous nutrient transporter expression. Dev Cell, 2003;5:571-582.

English L, et al. Autophagy enhances the presentation of endogenous viral antigens on MHC class I molecules during HSV-1 infection. Nat Immunol, 2009;10(5):1-18.

Ezaki J, et al. Liver autophagy contributes to the maintenance of blood glucose and amino acid levels. Autophagy, 2011;7:727-736.

Fransen M, et al. Comparison of the PTS1-and RAB8b-binding properties of PEX5p and PEX5Rp/TRIP8b. Biochimica et biophysica acta, 2008;1783:864-873.

Fratti RA, et al. Role of phosphatidylinositol 3-kinase and Rab5 effectors in phagosomal biogenesis and mycobacterial phagosome maturation arrest. J Cell Biol, 2001;154:631-644.

Gannage M, et al. Matrix protein 2 of influenza A virus blocks autophagosome fusion with lysosomes. Cell Host Microbe, 2009;6:367-380.

Grinde B, Seglen PO. Leucine inhibition of autophagic vacuole formation in isolated rat hepatocytes. Experimental cell research, 1981;134:33-39.

Harris J, et al. Autophagy control IL-1 {beta} secretion by targeting pro-IL-1 {beta} for degradation. J Biol Chem, 2011;286:9587-9597.

(56) References Cited

OTHER PUBLICATIONS

Hattula K, Peranen J. FIP-2, a coiled-coil protein, links Huntingtin to Rab8 and modulates cellular morphogenesis. Curr Biol, 2000;10:1603-1606.

Heidrych P, et al. Rab8b GTPase, a protein transport regulator, is an interacting partner of otoferlin, defective in a human autosomal recessive deafness form. Human molecular genetics, 2008;17:3814-3821.

Hirota Y, Tanaka Y. A small GTPase, human Rab32, is required for the formation of autophagic vacuoles under basal conditions. Cell Mol Life Sci, 2009.

Hjerpe R, et al. Efficient protection and isolation of ubiquitylated proteins using tandem ubiquitin-binding entities. EMBO Rep, 2009;10:1250-1258.

Huang J, et al. Activation of antibacterial autophagy by NADPH oxidases. Proc Natl Acad Sci USA, 2009;106(15):6226-6231.

Itoh T, et al. OATL1, a novel autophagosome-resident Rab33B-GAP, regulates autophagosomal maturation. The Journal of cell biology, 2011;192:839-853.

Jager S, et al. Role for Rab7 in maturation of late autophagic vacuoles. J Cell Sci, 2004;117:4837-4848.

Jia W, He YW. Temporal regulation of intracellular organelle homeostasis in T lymphocytes by autophagy. J Immunol, 2011;186:5313-5322.

Johansen T, Lamark T. Selective autophagy mediated by autophagic adapter proteins. Autophagy, 2011;7:279-296.

Jounai N, et al. The Atg5 Atg12 conjugate associates with innate antiviral immune responses. Proc Natl Acad Sci USA, 2007;104:14050-14055.

Kimura S, et al. Dissection of the autophagosome maturation process by a novel reporter protein, tandem fluorescent-tagged LC3. Autophagy, 2007;3:452-460.

Kirkin V, et al. A role for NBR1 in autophagosomal degradation of ubiquitinated substrates. Mol Cell, 2009;33:505-516.

Korolchuck VI, et al. Lysosomal positioning coordinates cellular nutrient responses. Nat Cell Biol, 2011;13(4):453-460.

Kroemer G, Levine B. Autophagic cell death: the story of a misnomer. Nat Rev Mol Cell Biol, 2008;9:1004-1010.

Lamark T, et al. Interaction codes within the family of mammalian Phox and Bem1p domain-containing proteins. J Biol Chem, 2003;278:34568-34581.

Laplantine E, et al. NEMO specifically recognizes K63-linked poly-ubiquitin chains through a new bipartite ubiquitin-binding domain. Embo J, 2009;28:2885-2895.

Larsen KB, et al. A reporter cell system to monitor autophagy based on p62/SQSTM1. Autophagy, 2010;6:784-793.

Lee JS, et al. FLIP-mediated autophagy regulation in cell death control. Nat Cell Biol, 2009;11:1355-1362.

Liang C, et al. Beclin1-binding UVRAG targets the class C Vps complex to coordinate autophagosome maturation and endocytic trafficking. Nat Cell Biol, 2008;10:776-787.

Maruyama H, et al. Mutations of optineurin in amyotrophic lateral sclerosis. Nature, 2010;465:223-226.

Matsumoto, et al. Serine 403 Phosphorylation of p62/SQSTM1 Regulates Selective Autophagic Clearance of Ubiquitinated Proteins. Molecular Cell, 2011;44:279-289.

Matsunaga K, et al. Two Beclin 1-binding proteins, Atg14L and Rubicon, reciprocally regulate autophagy at different stages. Nat Cell Biol, 2009;11:385-396.

McWhirter SM, et al. IFN-regulatory factor 3-dependent gene expression is defective in Tbk1-deficient mouse embryonic fibroblasts. Proceedings of the National Academy of Sciences of the Unites States of America, 2004;101:233-238.

Mizushima N, et al. Autophagy fights disease through cellular self-digestion. Nature, 2008;451:1069-1075.

Morton S, et al. Enhanced binding of TBK1 by an optineurin mutant that causes a familial form of primary open angle glaucoma. FEBS Lett, 2008;582:997-1002.

Munz C. Enhancing immunity through autophagy. Annu Ref Immunol, 2009;27:423-449.

N Kahira K, et al. Autophagy proteins regulate innate immune responses by inhibiting the release of mitochondrial DNA mediated by the NALP3 inflammasome. Nat Immunol, 2010;8(3):222-231.

Olkkonen VM, et al. Molecular cloning and subcellular localization of three GTP-binding proteins of the rab subfamily. J Cell Sci, 1993;106:1249-1261.

Orvedahl A, et al. HSV-1 ICP34.5 Confers Neurovirulence by Targeting the Beclin 1 Autophagy Protein. Cell Host and Microbe, 2007;1:23-35.

Osawa T, et al. Optineurin in neurodegenerative diseases. Neuropathology : official journal of the Japanese Society of Neuropathology, 2011;31:569-574.

Ou YH, et al. TBK1 Directly Engages Akt/PKB Survival Signaling to Support Oncogenic Transformation. Mol Cell, 2011;41:458-470.

Pankiv S, et al. p62/SQSTM1 binds directly to Atg8/LC3 to facilitate degradation of ubiquitinated protein aggregates by autophagy. J Biol Chem, 2007;282:24131-24145.

Perkins ND. Integrating cell-signalling pathways with NF-kappaB and IKK function. Nature reviews Molecular cell biology, 2007;8:49-62.

Ponpuak M, et al. Monitoring autophagy during Mycobacterium tuberculosis infection. Methods Enzymol, 2009;452:345-361.

Radtke AL, et al. TBK1 protects vasuolar integrity during intracellular bacterial infection. PLoS Pathog, 2007;3:e29.

Ravikumar B, et al. Rab5 modulates aggregation and toxicity of mutant huntingtin through macroautophagy in cell and fly models of Huntington disease. J Cell Sci, 2008;121:1649-1660.

Richmond A. Nf-kappa B, chemokine gene transcription and tumour growth. Nature reviews Immunology, 2002;2:664-674.

Roberts EA, Deretic V. Autophagic proteolysis of long-lived proteins in nonliver cells. Methods Mol Biol, 2008;445:111-117.

Saitoh T, et al. Atg9a controls dsDNA driven dynamic translocation of STING and the innate immune response. Proc Natl Acad Sci USA, 2009;106:20842-20846.

Sanjuan MA, et al. Toll-like receptor signaling in macrophages links the autophagy pathway to phagocytosis. Nature, 2007;450:1253-1257.

Sarkar S, et al. Small molecules enhance autophagy and reduce toxicity in Huntington's disease models. Nat Chem Biol, 2007;3:331-338.

Abadie V, et al. Neutrophils rapidly migrate via lymphatics after Mycobacterium bovis BCG intradermal vaccination and shuttle live bacilli to the draining lymph nodes. Blood, 2005;106:1843-1850.

Afonina IS, et al. Granzyme B-dependent proteolysis acts as a switch to enhance the proinflammatory activity of IL-1alpha. Molecular Cell, 2011;44:265-278.

Alonso S, et al. Lysosomal killing of Mycobacterium mediated by ubiquitin-derives peptides is enhanced by autophagy. Proc Natl Acad Sci USA, 2007;104:6031-6036.

Axe EL, et al. Autophagosome formation from membrane compartment enriched in phosphatidylinositol 3-phosphate and dynamically connected to the endoplasmic reticulum. J Cell Biol, 2008;182:685-701.

Berry MP, et al. An interferoninducible neutrophil-driven blood transcriptional signature in human tuberculosis. Nature, 2010;466:973-977.

Blanchet FP, et al. Human immunodeficiency virus-1 inhibition of immunoamphisomes in dendritic cells impairs early innate and adaptive immune responses. Immunity, 2010;32:654-669.

Chen CJ, et al. Identification of a key pathway required for the sterile inflammatory response triggered by dying cells. Nat Med, 2007;13:851-856.

Chung Y, et al. Critical regulation of early Th17 cell differentiation by interleukin-1 signaling. Immunity, 2009;30:576-587.

Craddock N, et al. Genomewide association study of CNVs in 16,000 cases of eight common diseases and 3,000 shared controls. Nature, 2010;464:713-720.

Criollo A, et al. Inhibition of autophagy by TAB2 and TAB3. Embo J, 2011;30:4908-4920.

Cruz A, et al. Pathological role of interleukin 17 in mice subjected to repeated BCG vaccination after infection with Mycobacterium tuberculosis. J Exp Med, 2010;207:1609-1616.

(56) References Cited

OTHER PUBLICATIONS

Delgado MA, et al. Toll-like receptors control autophagy. Embo J, 2008;27:1110-1121.
Deretic V. Autophagy in innate and adaptive immunity. Trends Immunol, 2005;26:523-528.
Deretic V, Levine B. Autophagy, immunity, and microbial adaptations. Cell Host Microbe, 2009;5:527-549.
Dinarello CA. Immunological and inflammatory functions of the interleukin-1 family. Annu Rev Immunol, 2009;27:519-550.
Dupont N, et al. Autophagy-based unconventional secretory pathway for extracellular delivery of IL-1beta. Embo J, 2011;30:4701-4711.
Dupont N, et al. Shigella phagocytic vacuolar membrane remnants participate in the cellular response to pathogen invasion and are regulated by autophagy. Cell Host Microbe, 2009;6:137-149.
Egan DF, et al. Phosphorylation of ULK1 (hATG1) by AMP-activated protein kinase connects energy sensing to mitophagy. Science, 2011;331:456-461.
Eruslanov EB, et al. Neutrophil responses to *Mycobacterium tuberculosis* infection in genetically susceptible and resistant mice. Infect Immun, 2005;73:1744-1753.
Eum SY, et al. Neutrophils are the predominant infected phagocytic cells in the airways of patients with active pulmonary TB. Chest, 2010;137:122-128.
Fettelschoss A, et al. Inflammasome activation and IL-1beta target IL-1alpha for secretion as opposed to surface expression. Proc Natl Acad Sci USA, 2011;108:18055-18060.
Flynn JL, Chan J. Immunology of tuberculosis. Annu Rev Immunol, 2001;19:93-129.
Fremond CM, et al. IL-1 receptor-mediated signal is an essential component of MyD88-dependent innate response to *Mycobacterium tuberculosis* infection. J Immunol, 2007;179:1178-1189.
Fujita N, et al. An Atg4B mutant hampers the lipidation of LC3 paralogues and causes defects in autophagosome closure. Mol Biol Cell, 2008;19:4651-4659.
Guler R, et al. Blocking IL-1alpha but not IL-1beta increases susceptibility to chronic *Mycobacterium tuberculosis* infection in mice. Vaccine, 2011;29:1339-1346.
Gutierrez MG, et al. Autophagy is a defense mechanism inhibiting BCG and *Mycobacterium tuberculosis* survival in Infected macrophages. Cell, 2004;119:753-766.
Harris J, et al. T helper 2 cytokines inhibit autophagic control of intracellular *Mycobacterium tuberculosis*. Immunity, 2007;27:505-517.
Hartman ML, Kornfeld H. Interactions between Naïve and Infected Macrophages Reduce *Mycobacterium tuberculosis* Viability. PLoS One, 2011;6:e27972.
He C, Levine B. The Beclin 1 interactome. Curr Opin Cell Biol, 2010;22:140-149.
Intemann CD, et al. Autophagy gene variant IRGM-261T contributes to protection from tuberculosis caused by *Mycobacterium tuberculosis* but not by *M. africanum* strains. PLoS Pathog, 2009;5:e1000577.

Itakura E, Mizushima N. p62 Targeting to the autophagosome formation site requires self-oligomerization but not LC3 binding. The Journal of Cell Biology, 2011;192:17-27.
Jain A, et al. p62/SQSTM1 is a garget gene for transcription factor NRF2 and creates a positive feedback loop by inducing antioxidant response element-driven gene transcription. J Biol Chem, 2010;285:22576-22591.
Jia W, et al. Autophagy regulates endoplasmic reticulum homeostasis and calcium mobilization in T lymphocytes. J Immunol, 2011;186:1564-1574.
Johansen P, et al. Relief from Zmp1-mediated arrest of phagosome maturation is associated with facilitate presentation and enhanced immunogenicity of mycobacterial antigens. Clin Vaccine Immunol, 2011;18:907-913.
Jounai N, et al. NLRP4 negatively regulates autophagic processes through an association with beclin1. J Immunol, 2011;186:1646-1655.
Keller M, et al. Active caspace-1 is a regulator of unconventional protein secretion. Cell, 2008;132:818-831.
Kim BH, et al. A family of IFN-gamma-inducible 65-kD GTPases protects against bacterial infection. Science, 2011;332:717-721.
Koch R. A Further Communication on a Remedy for Tuberculosis. Br Med J, 1891;1:125-127.
Kono H, et al. Identification of the cellular sensor that stimulates the inflammatory response to sterile cell death. J Immunol, 2010;184:4470-4478.
Korn T, et al. IL-17 and Th17 Cells. Annu Rev Immunol, 2009;27:485-517.
Kyei GB, et al. Autophagy pathway intersects with HIV-1 biosynthesis and regulates viral yields in macrophages. J Cell Biol, 2009;186:255-268.
Lamkanfi M. Emerging inflammasome effector mechanisms. Nature reviews Immunology, 2011;11:213:220.
Lamkanfi M, et al. Inflammasomedependent release of the alarmin HMGB1 in endotoxemia. J Immunol, 2010;185:4385-4392.
Lee HK, et al. Autophagy-dependent viral recognition by plasmacytoid dendritic cells. Science, 2007;315:1398-1401.
Lee HK, et al. In vivo requirement for Atg5 in antigen presentation by dendritic cells. Immunity, 2010;32:227-239.
Levine B, et al. Autophagy in immunity and inflammation. Nature, 2011;469:323-335.
Manjithaya R, et al. Unconventional secretion of Pichia pastoris Acb1 is dependent on GRASP protein, peroxisomal functions. And autophagosome formation. J Cell Biol, 2010;188:537-546.
Master SS, et al. *Mycobacterium tuberculosis* prevents inflammasome activation. Cell Host Microbe 3, 2008;224:232.
Mathew R, et al. Autophagy suppresses tumorigenesis through elimination of p62. Cell, 2009;137:1062-1075.
Mayer-Barber KD, et al. Innate and Adaptive Interferons Suppress IL-1alpha and IL-1beta Production by Distinct Pulmonary Myeloid Subsets during *Mycobacterium tuberculosis* Infection. Immunity, 2011;35:1023-1034.

* cited by examiner

Table 1

| Experiment | n | Deposition | Deaths |
|---|---|---|---|
| $e^4$ | 36 (Cre$^+$, Cre$^-$ n=18 ea.) | 66,875±5430 | Cre+ n=18<br>Cre- n=10 |
| $e^3$ | 40 (Cre$^+$, Cre$^-$ n=20 ea.) | 2140±771 | Cre+ n=0<br>Cre- n=0 |
| $e^2$ | 94 (Cre$^+$, Cre$^-$ n=47 ea.) | 65±15 | Cre+ n=2<br>Cre- n=0 |

FIGURE 1T

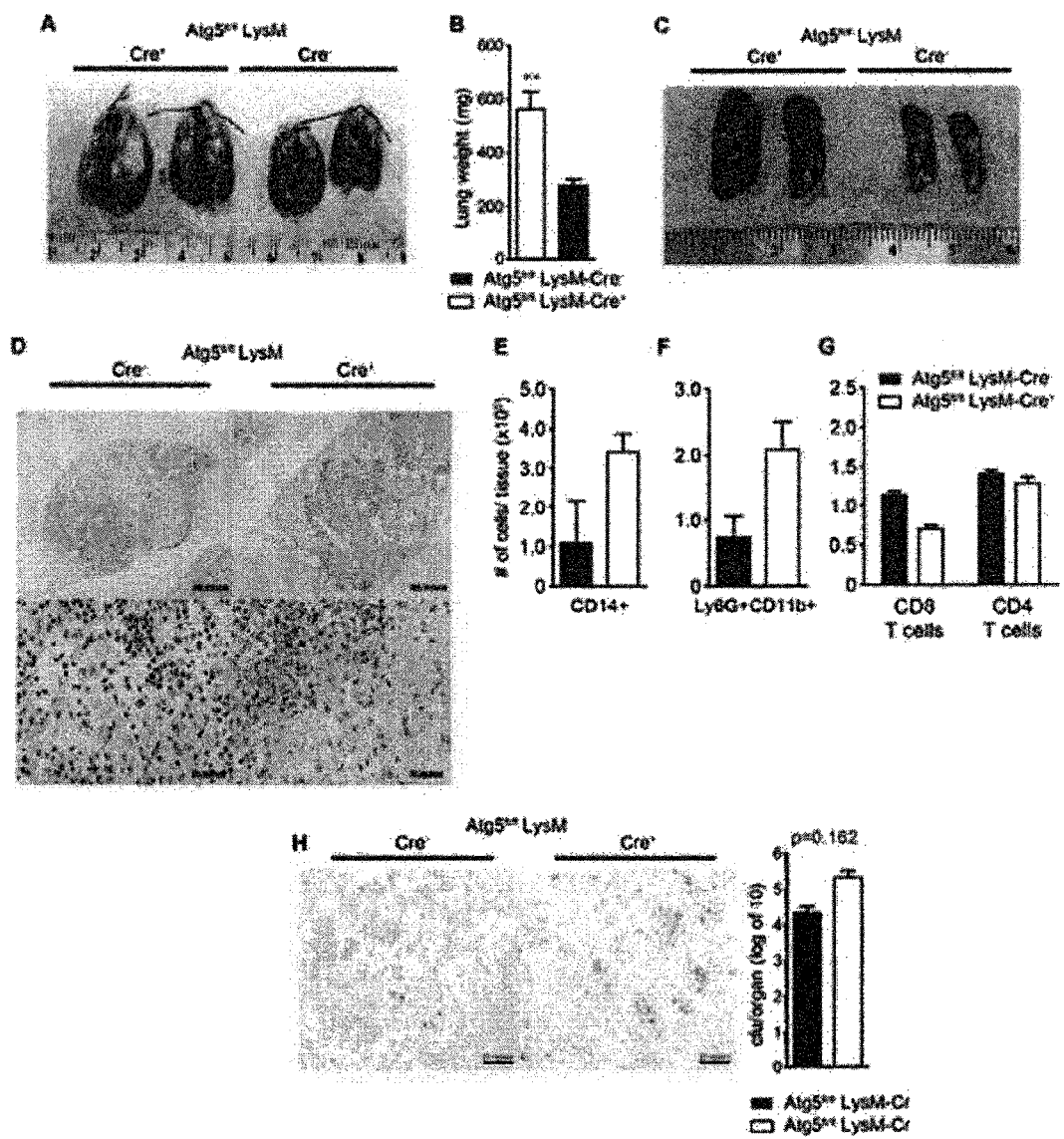
Supplementary Figure 1

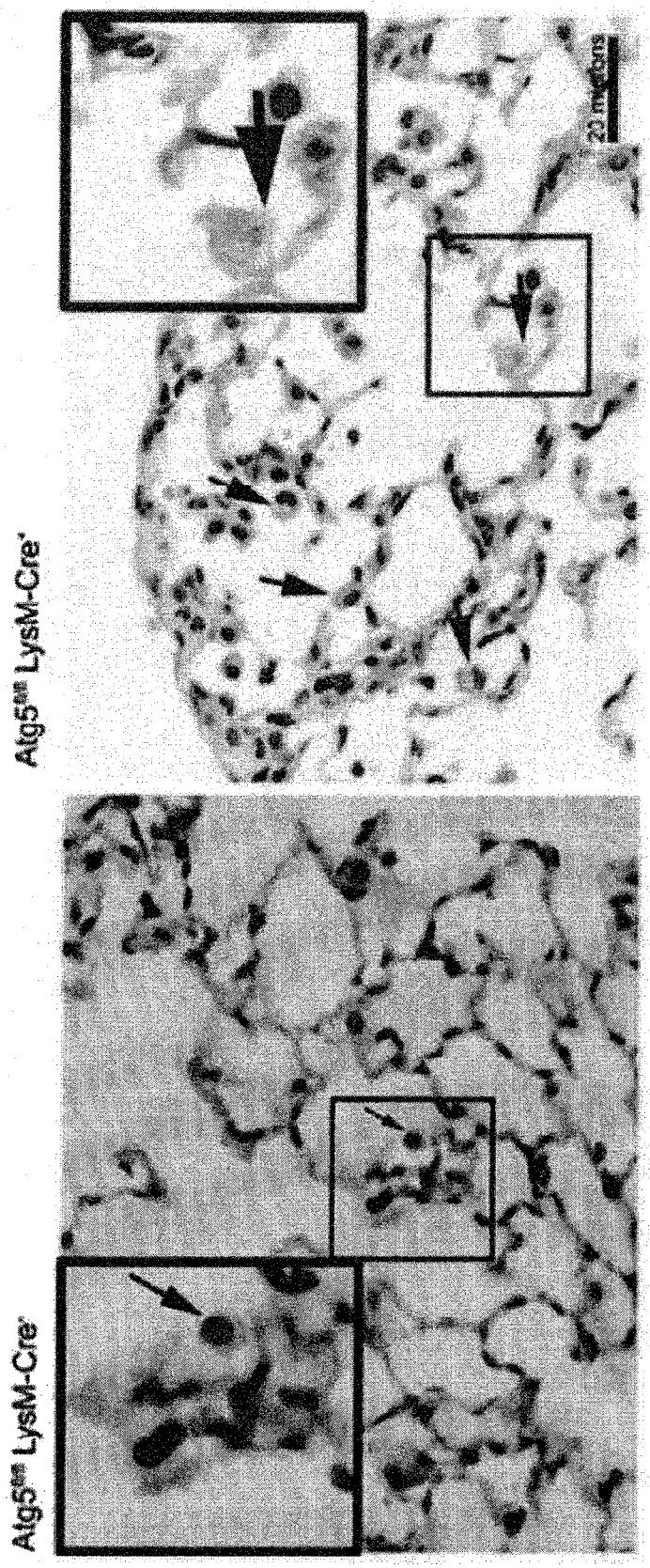
Supplementary Figure 2

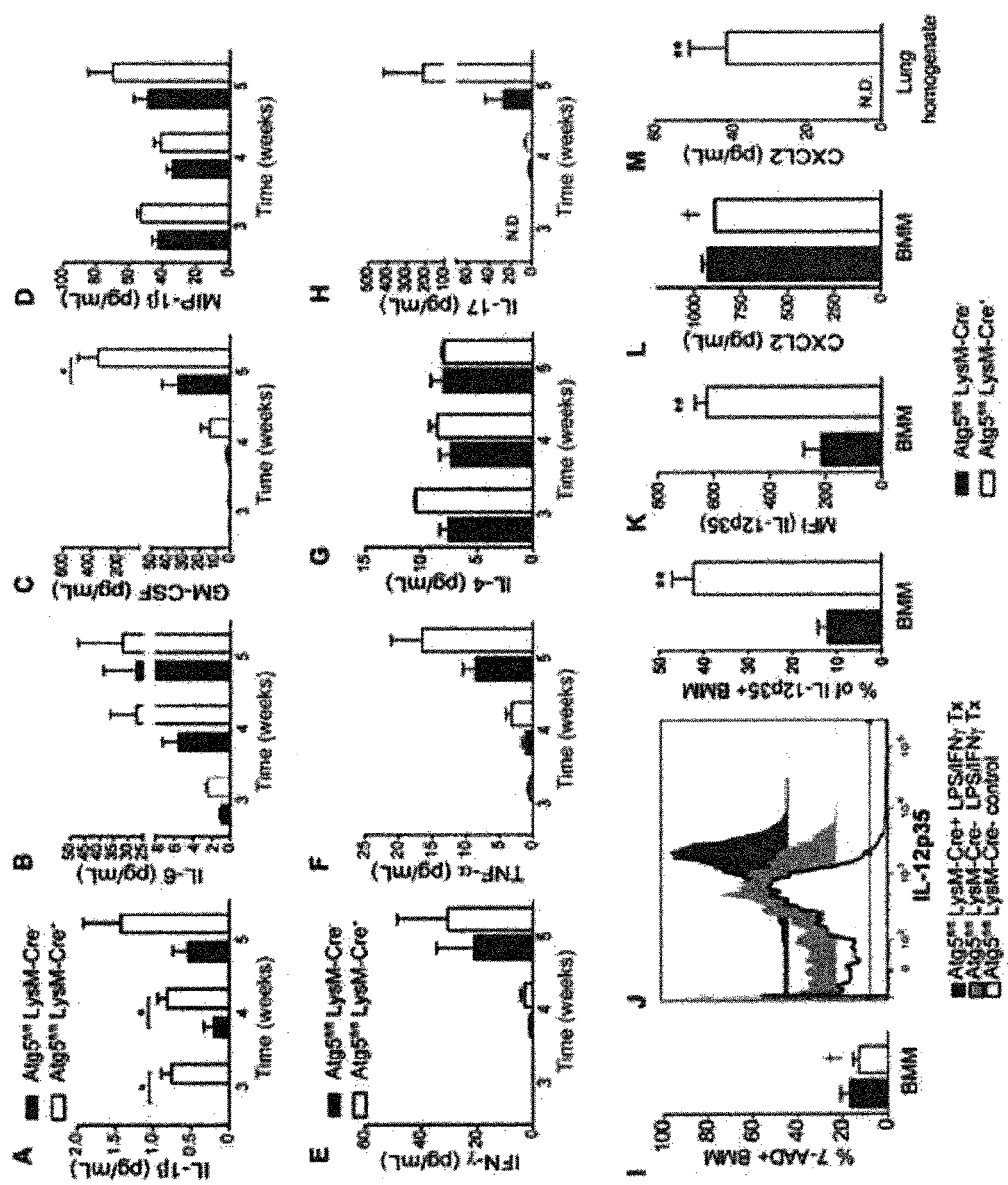
Supplementary Figure 3

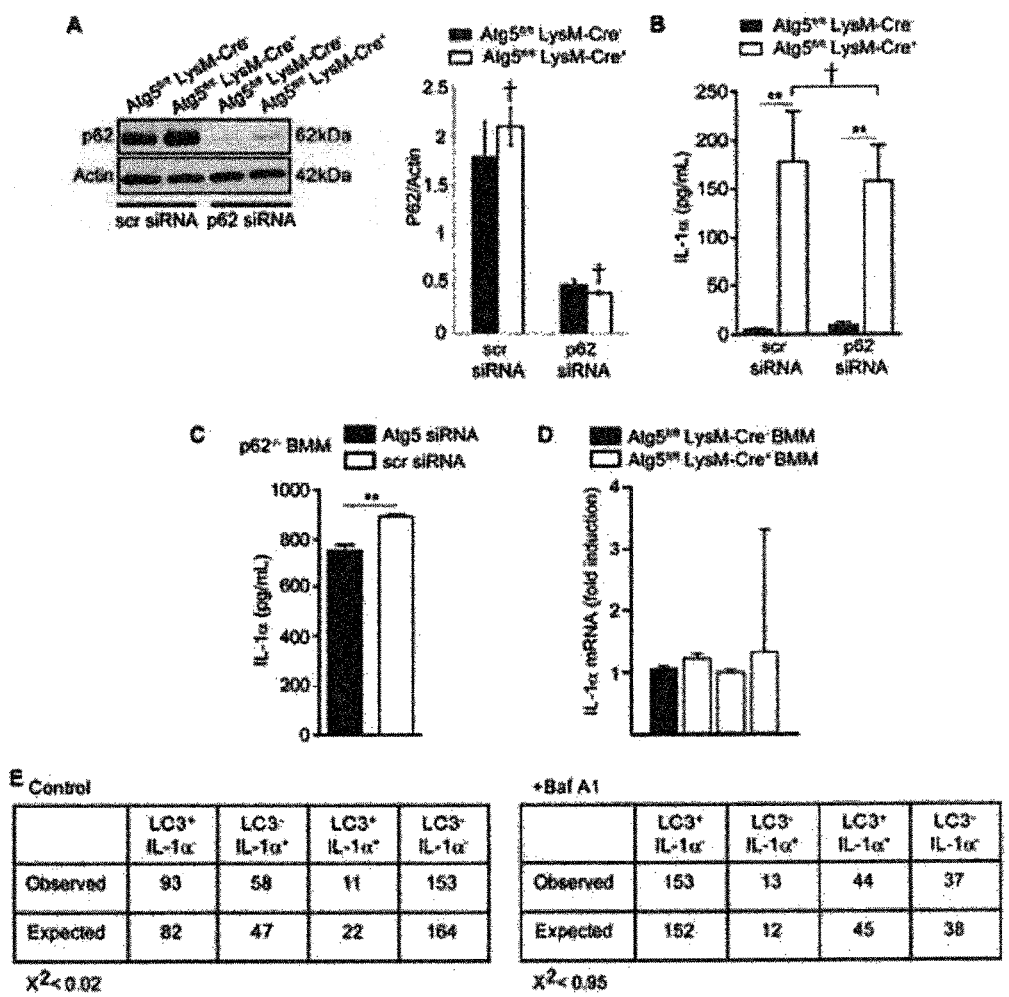
Supplementary Figure 4

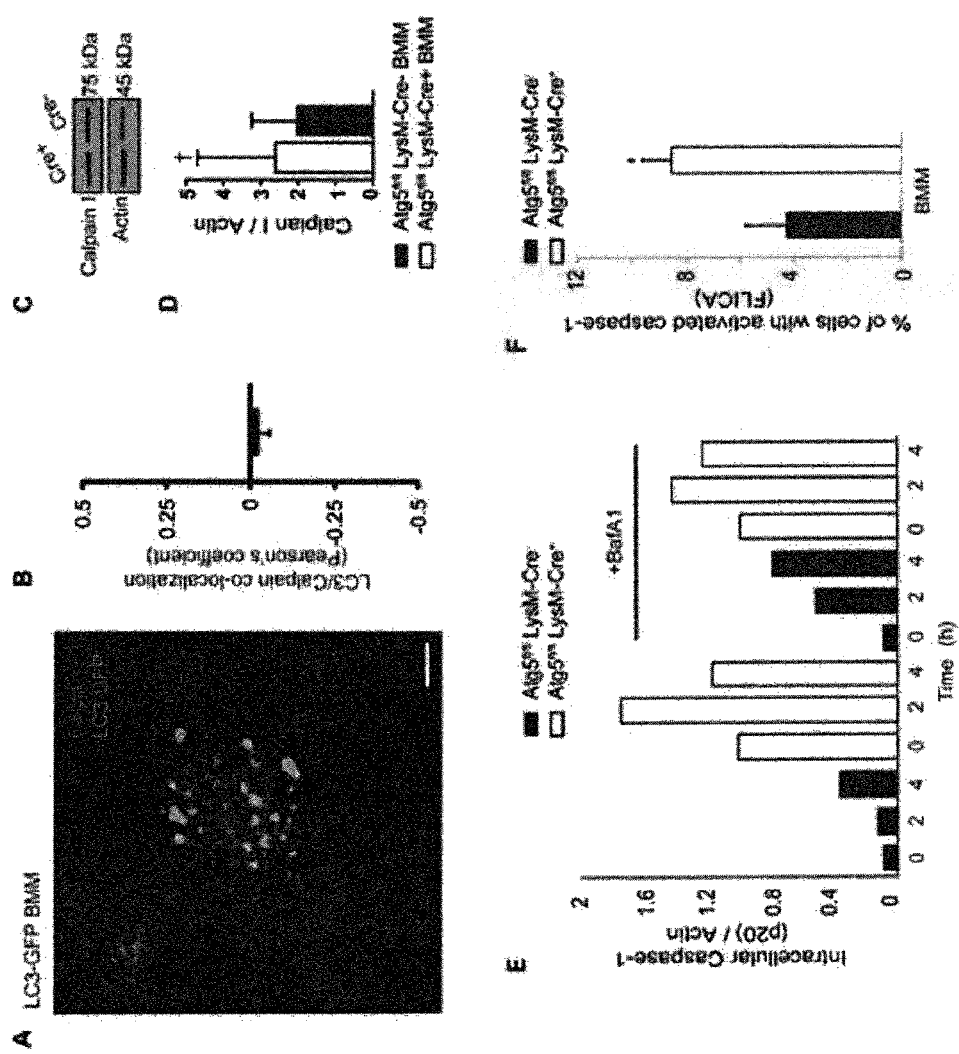
Supplementary Figure 5

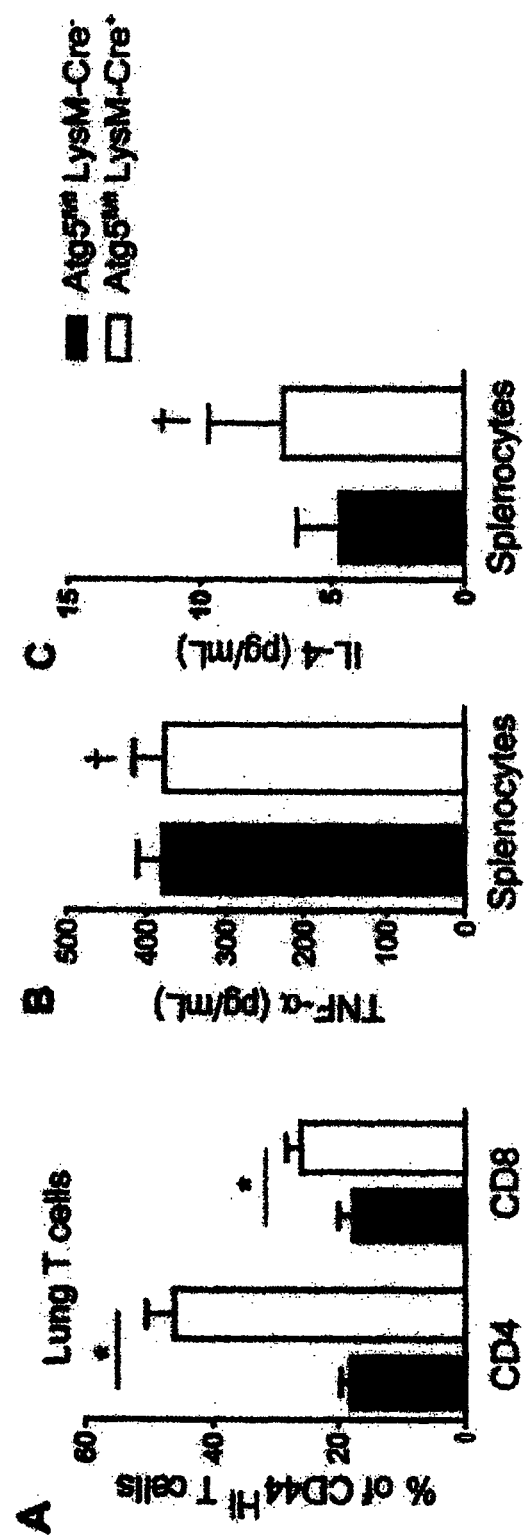
Supplementary Figure 6

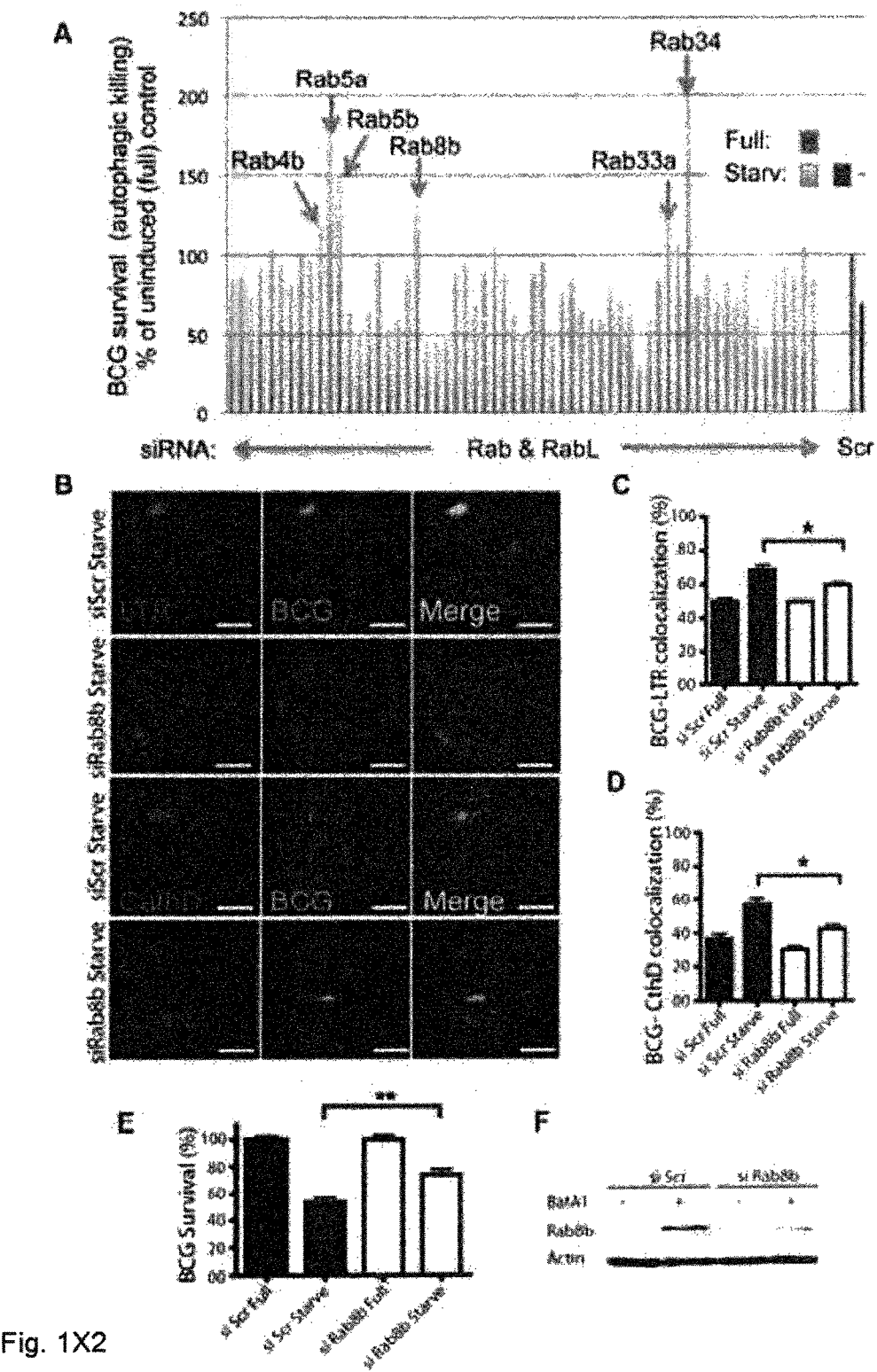
Fig. 1X2

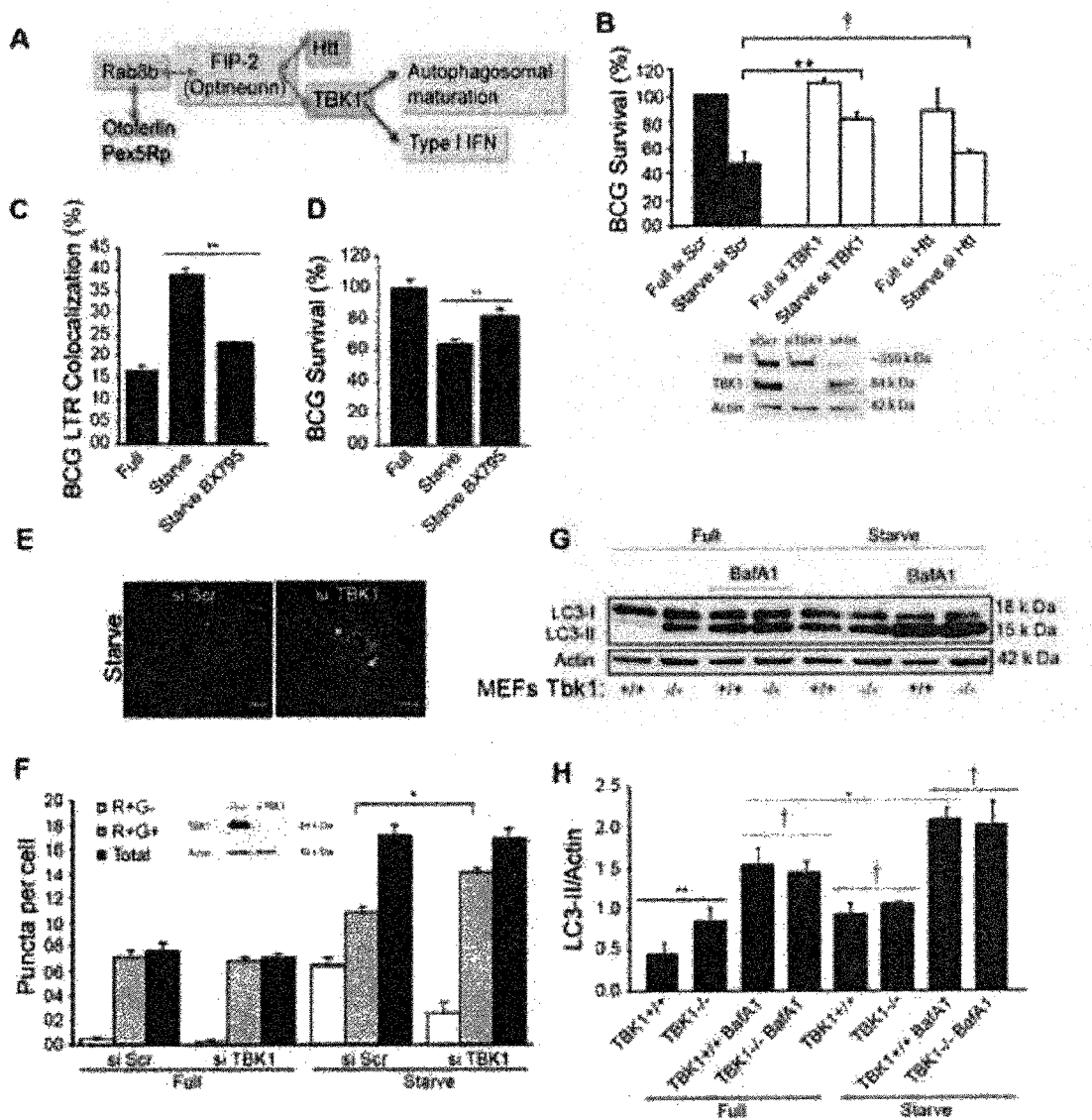
Fig. 2X2

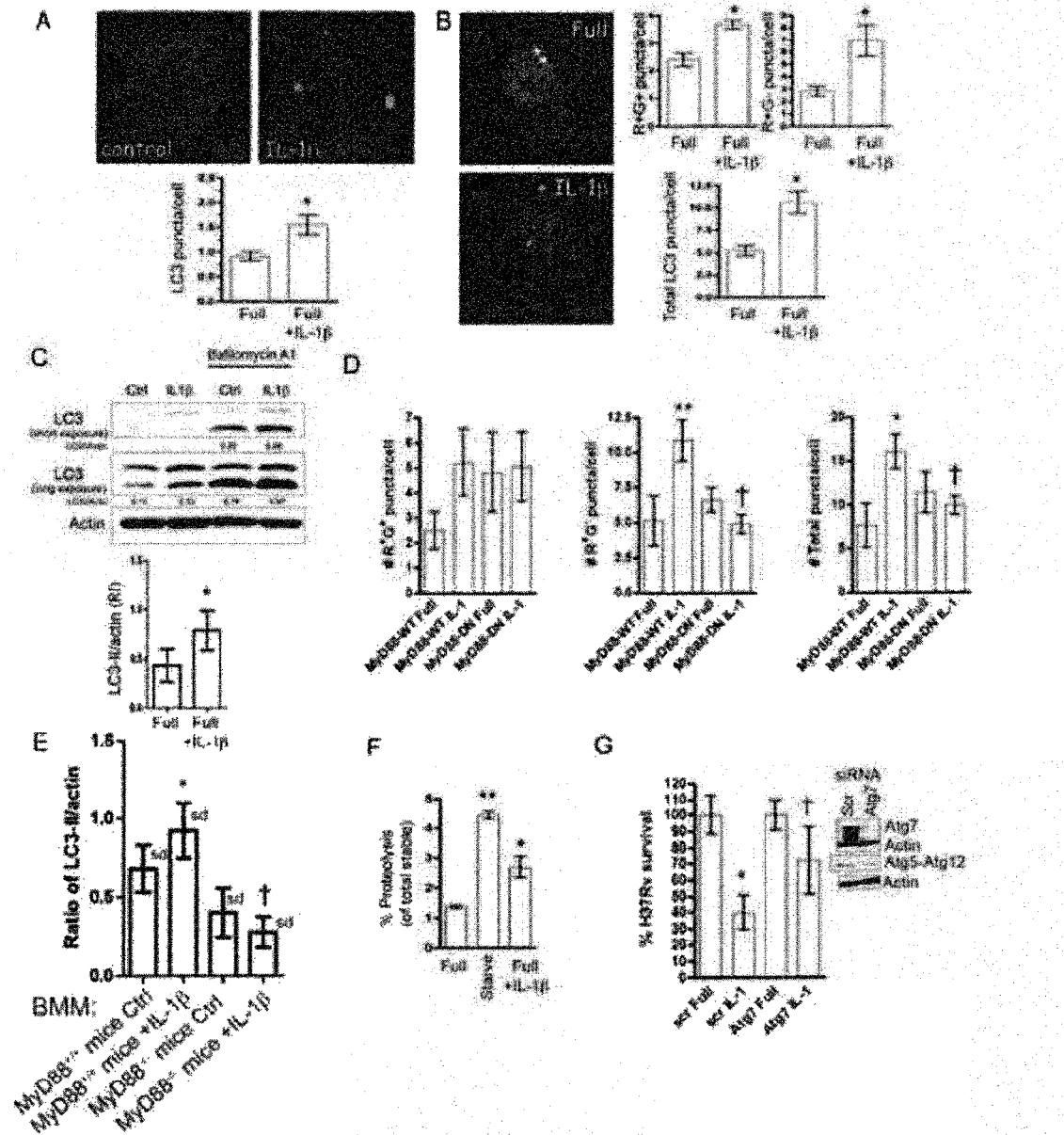
Fig. 3X2

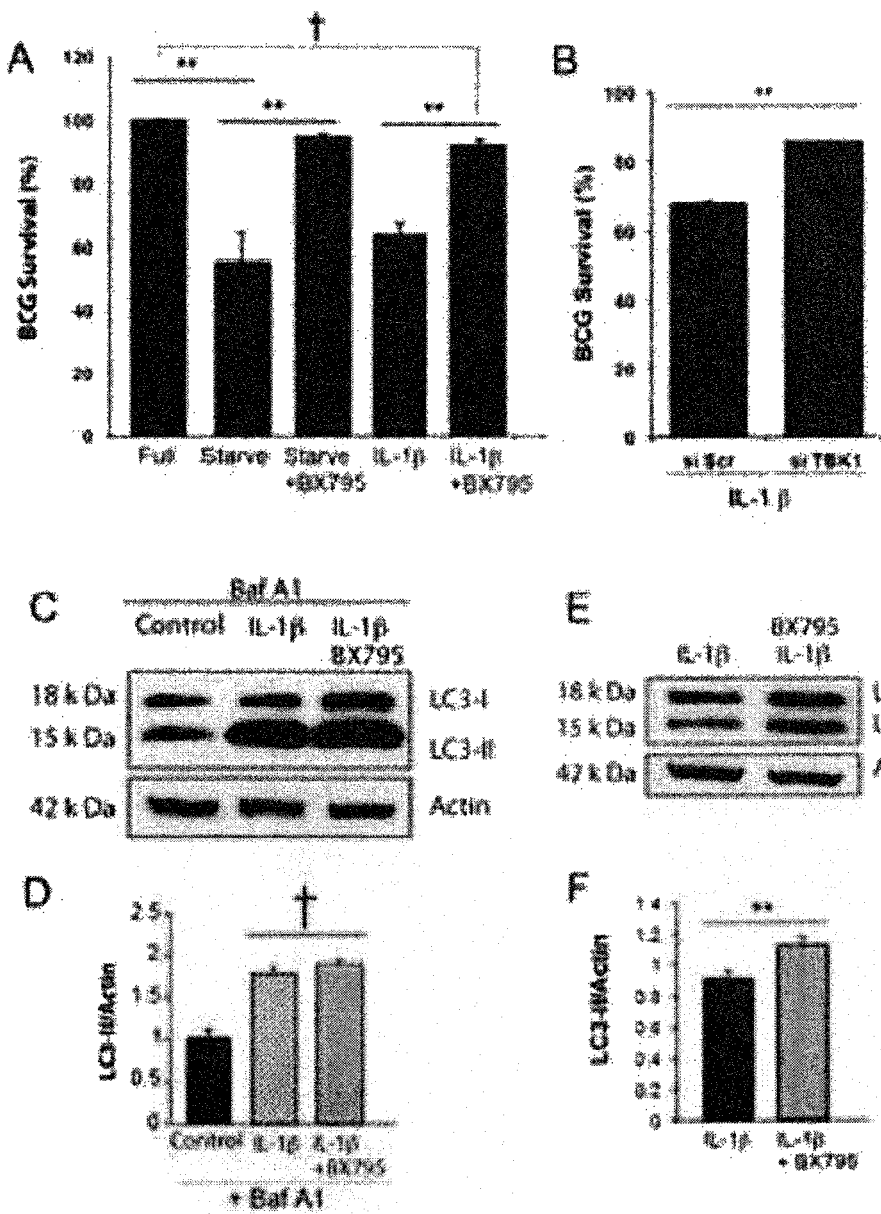
Fig 4X2

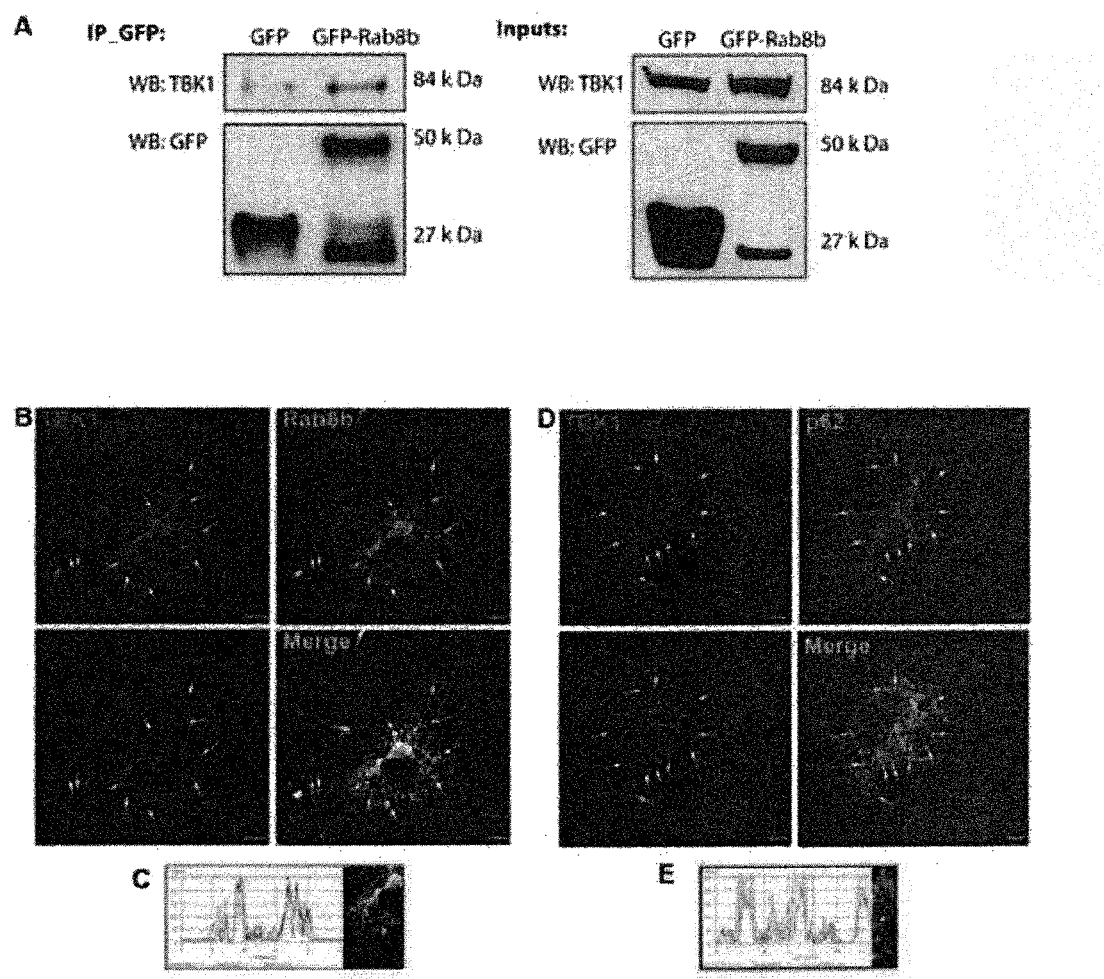
Fig. 5X2

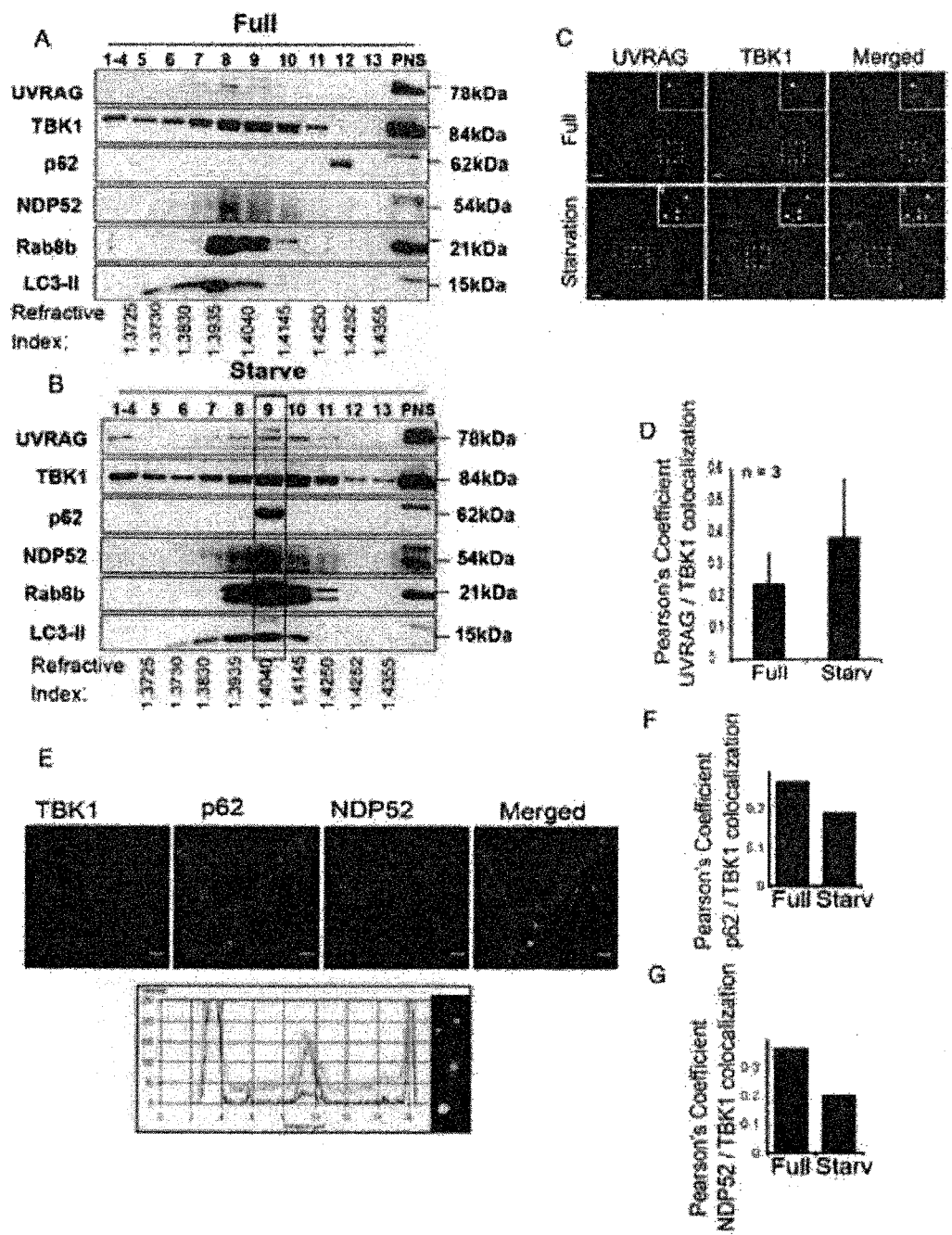
Fig. 6X2

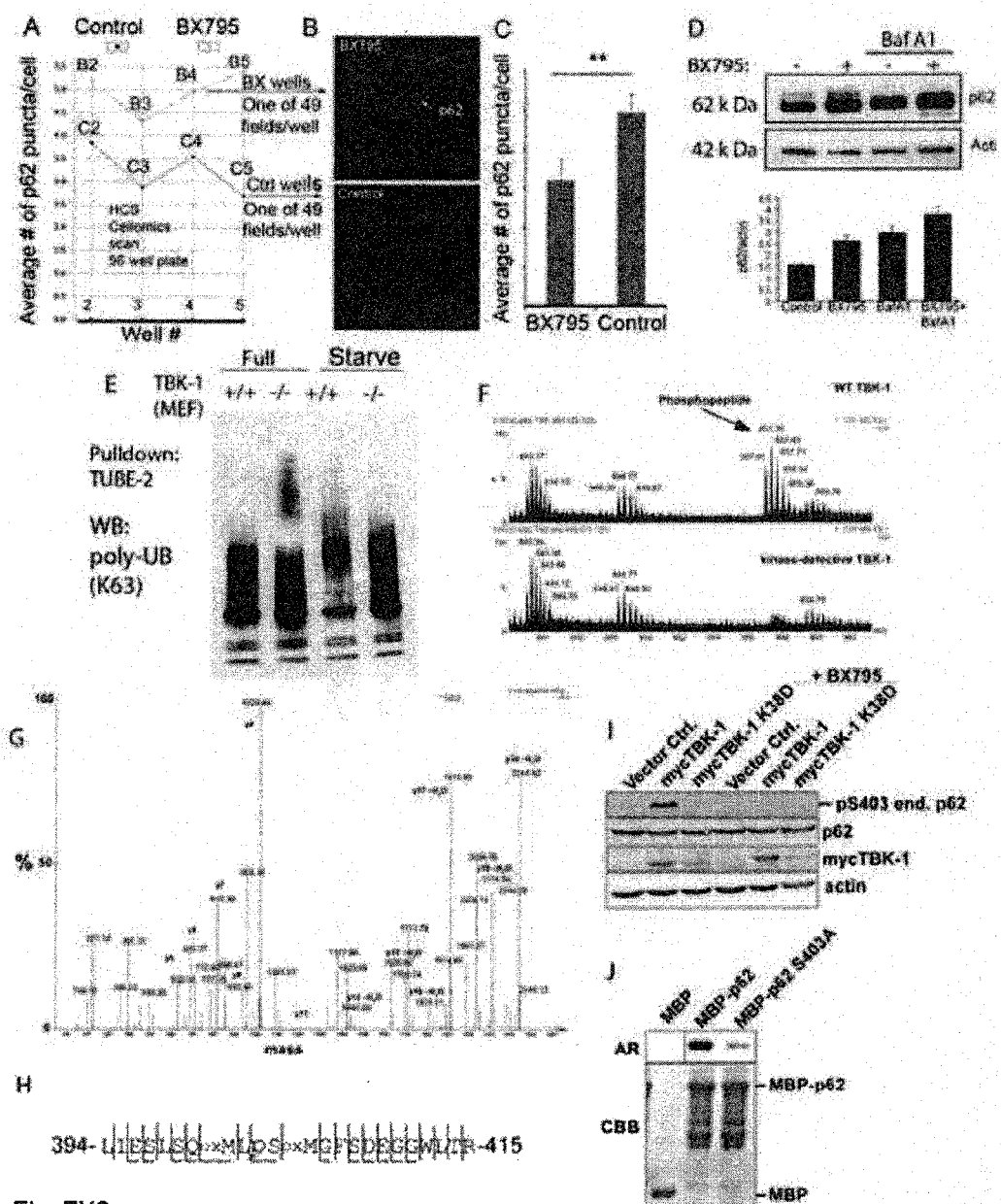
Fig. 7X2

| Rab | Dharmacon Mouse catalog # | Mouse Accession numbers | Mouse mRNA NM hyperlink | Mouse Web links | Mouse Genome Informatics | GeneID | BCG survival (%) | SE | Knockdown verified by |
|---|---|---|---|---|---|---|---|---|---|
| 1A | M-040850-00 | NM_008996 | NM_008996 | RAb1A | MGI:97842 | GeneID:19324 | 84.56 | 47.9 | RT-PCR |
| 1B | Custom | NM_029576 | NM_029576 | Rab1B | MGI:1923558 | GeneID: 76308 | 86.79 | 23.1 | RT-PCR |
| 2A | M-040851-00 | NM_021518 | NM_021518 | Rab2A | MGI:1926750 | GeneID: 59021 | 73.63 | 30.9 | RT-PCR |
| 2B | M-055076-00 | NM_172601 | NM_172601 | Rab2B | MGI:1923588 | GeneID:76338 | 94.34 | 16.1 | RT-PCR |
| 3A | M-060407-00 | NM_009001 | NM_009001 | Rab3A | MGI:97843 | GeneID 19339 | 103.2 | 64.4 | RT-PCR |
| 3B | M-059841-00 | NM_023537 | NM_023537 | Rab3b | MGI:1917158 | GeneID:69908 | 94.2 | 55.9 | RT-PCR |
| 3C | M-061032-00 | NM_023852 | NM_023852 | Rab3C | MGI:1914545 | GeneID:67295 | 81.51 | 46.4 | RT-PCR |
| 3D | M-040852-00 | NM_031874 | NM_031874 | Rab3D | MGI:97844 | GeneID:19340 | 101.8 | 63.9 | RT-PCR |
| 4A | M-040853-00 | NM_009003 | NM_009003 | Rab4a | MGI:105069 | GeneID: 19341 | 97.17 | 4.32 | RT-PCR, WB |
| 4B | M-040854-00 | NM_029391 | NM_029391 | Rab4B | MGI:105071 | GeneID: 19342 | 119.8 | 5.89 | RT-PCR |
| 5A | M-040855-00 | NM_025887 | NM_025887 | Rab5A | MGI:105926 | GeneID: 271457 | 173.1 | 28.8 | WB |
| 5B | M-040856-00 | NM_011229 | NM_011229 | Rab5B | MGI:105938 | GeneID: 9344 | 150 | 25.5 | RT-PCR |
| 5C | M-040857-00 | NM_024456 | NM_024456 | Rab5C | MGI:105306 | GeneID: 19345 | 67.19 | 5.9 | RT-PCR |
| 6A | M-040858-00 | NM_024287 | NM_024287 | Rab6A | MGI:894313 | GeneID: 19346 | 47.25 | 12.5 | RT-PCR |
| 6B | Custom | NM173781 | NM173781 | Rab6B | MGI:107283 | GeneID: 270192 | 64.84 | 16.6 | RT-PCR |
| 7 | M-040859-00 | NM_009005 | NM_009005 | Rab7 | MGI:105068 | GeneID: 19349 | 75.49 | 3.58 | WB |
| 7L1 | M-053101-00 | NM_144875 | NM_144875 | Rab7L1 | MGI:2385107 | GeneID: 22642 | 52.34 | 21.8 | RT-PCR |
| 7B | Custom | NM_145509 | NM_145509 | Rab7B | MGI:2442295 | GeneID: 226421 | 60.16 | 10.6 | RT-PCR |
| 8A | M-040860-00 | NM_023126 | NM_023126 | Rab8A | MGI:96960 | GeneID: 17274 | 87.9 | 3.58 | WB |
| 8B | M-053301-00 | NM_173413 | NM_173413 | Rab8B | MGI:2442982 | GeneID: 23544 | 130.15 | 16.6 | WB |
| 9A | M-040861-00 | NM_019773 | NM_019773 | Rab9A=Rab9 | MGI:1890695 | GeneID: 56382 | 45.05 | 3.58 | RT-PCR, WB |
| 9B | Custom | NM_176971 | NM_176971 | Rab9B | MGI:2442454 | GeneID: 319642 | 46.88 | 12.5 | RT-PCR |
| 10 | M-040862-00 | NM_016676 | NM_016676 | Rab10 | MGI:105066 | GeneID: 19325 | 50.55 | 6.2 | RT-PCR |
| 11A | M-040863-00 | NM_017382 | NM_017382 | Rab11A | MGI:1358202 | GeneID: 53869 | 90 | 22.4 | WB |
| 11B | M-040864-00 | NM_008997 | NM_008997 | Rab11B | MGI:99425 | GeneID: 19326 | 95.63 | 11.4 | RT-PCR |
| 12 | M-040865-00 | XM_126792 | XM_126792 | Rab12 | MGI:894284 | GeneID: 19328 | 68.45 | 29.3 | RT-PCR |
| 13 | M-045749-00 | NM_026677 | NM_026677 | Rab13 | MGI:1927232 | GeneID: 68328 | 90.97 | 25.8 | RT-PCR |
| 14 | Custom | NM_026697.3 | NM_026697.3 | Rab14 | MGI:1915615 | GeneID: 68365 | 104.8 | 53.1 | WB |
| 15 | M-061135-00 | NM_134050 | NM_134050 | Rab15 | MGI:1916865 | GeneID: 104886 | 89.26 | 33 | RT-PCR |
| 17 | M-058833-00 | NM_008998 | NM_008998 | Rab17 | MGI:104640 | GeneID: 19329 | 63.28 | 6.56 | RT-PCR |
| 18 | M-040867-00 | NM_011225 | NM_011225 | Rab18 | MGI:102790 | GeneID: 19330 | 50.85 | 22.8 | RT-PCR |
| 19 | M-042333-00 | NM_011226 | NM_011226 | Rab19 | MGI:103292 | GeneID: 19331 | 88.75 | 23.3 | RT-PCR |
| 20 | M-063804-00 | NM_011227 | NM_011227 | Rab20 | MGI:102789 | GeneID: 19332 | 95.52 | 5.73 | RT-PCR |
| 21 | M-044489-00 | NM_024454 | NM_024454 | Rab21 | MGI:894308 | GeneID: 216344 | 52.54 | 56.1 | RT-PCR |
| 22A | Custom | NM_024436.3 | NM_024436.3 | Rab22a | MGI:105072 | GeneID: 19334 | 76.66 | 41.1 | WB |
| 22B (31) | Custom | NM_133685 | NM_133685 | Rab22B(Rab31) | MGI:1914603 | GeneID: 106577 | 86.55 | 19.1 | RT-PCR |
| 23 | M-040868-00 | NM_008999 | NM_008999 | Rab23 | MGI:98833 | GeneID: 19335 | 66.25 | 2.91 | RT-PCR |
| 24 | M-040869-00 | NM_009000 | NM_009000 | Rab24 | MGI:105065 | GeneID: 19336 | 60.8 | 7.81 | RT-PCR |
| 25 | M-040870-00 | NM_016899 | NM_016899 | Rab25 | MGI:1858203 | GeneID: 53868 | 58.75 | 21.9 | RT-PCR |
| 26 | M-054468-00 | XM_283428 | XM_283428 | Rab26 | MGI:2443284 | GeneID: 328778 | 79.3 | 7.58 | RT-PCR |
| 27A | M-060970-00 | NM_023635 | NM_023635 | Rab27A | MGI:1861441 | GeneID: 11891 | 70.63 | 36.2 | WB |
| 27B | M-050808-00 | NM_030554 | NM_030554 | Rab27B | MGI:1931295 | GeneID: 80718 | 62.94 | 7.37 | RT-PCR |
| 28 | Custom | NM_027295 | NM_027295 | Rab28 | MGI:1917285 | GeneID: 100972 | 30.77 | 13.8 | RT-PCR |
| 30 | M-057666-00 | NM_029494 | NM_029494 | Rab30 | MGI:1923235 | GeneID: 75985 | 59.44 | 9.69 | RT-PCR |
| 32 | M-063539-00 | NM_026405 | NM_026405 | Rab32 | MGI:1915094 | GeneID: 67844 | 85.12 | 12.3 | RT-PCR |
| 33A | M-042315-00 | NM_011228 | NM_011228 | Rab33A | MGI:109493 | GeneID: 19337 | 119.8 | 27.7 | RT-PCR |
| 33B | M-049255-00 | NM_016858 | NM_016858 | Rab33B | MGI:1330805 | GeneID: 19338 | 106.6 | 10.4 | RT-PCR |
| 34 | M-040872-00 | NM_033475 | NM_033475 | Rab34 | MGI:104606 | GeneID: 19376 | 198.3 | 7.44 | RT-PCR |

Figure 8X2

| | | | | | | |
|---|---|---|---|---|---|---|
| 35 | Custom | NM_198163 | Rab35 | MGI:1924657 | GeneID: 77407 | 74.73 | 9.72 | RT-PCR |
| 36 | M-062928-00 | NM_029781 | Rab36 | MGI:1924127 | GeneID: 76877 | 88.71 | 5.82 | RT-PCR |
| 37 | M-059382-00 | NM_021411 | Rab37 | MGI:1929945 | GeneID: 58222 | 73.85 | 41.9 | RT-PCR |
| 38 | M-040873-00 | NM_028238 | Rab38 | MGI:1919683 | GeneID: 72433 | 84.75 | 33.9 | RT-PCR |
| 39A | M-057236-00 | NM_175562 | Rab39A | MGI:2442855 | GeneID: 270160 | 71.51 | 11.3 | RT-PCR |
| 39B | M-063919-00 | NM_175122 | Rab39B | MGI:1915040 | GeneID: 67790 | 89.78 | 11.9 | RT-PCR |
| 40B | M-051754-00 | NM_139147 | Rab40B | MGI:2183451 | GeneID: 217371 | 60.75 | 4.93 | RT-PCR |
| 40C | M-051719-00 | NM_139154 | Rab40C | MGI:2183454 | GeneID: 224624 | 42.47 | 8.88 | RT-PCR |
| 43 | Custom | NM_133717 | "Rab43" | MGI:1917084 | Gene!: 69834 | 87.65 | 19 | RT-PCR |
| L2A | M-056257-00 | NM_026817 | RabL2A | MGI:1915958 | GeneID: 68708 | 92.59 | 7.41 | RT-PCR |
| L3 | M-049684-00 | NM_026297 | RabL3 | MGI:1914907 | GeneID: 67657 | 86.42 | 11.9 | RT-PCR |
| L4 | M-055277-00 | NM_025931 | RabL4 | MGI:1914292 | | 104.9 | 18.6 | RT-PCR |
| L5 | M-055293-00 | NM_026073 | RabL5 | MGI:1914536 | GeneID: 67286 | 85.19 | 9.8 | RT-PCR |

| | | | | |
|---|---|---|---|---|
| Control Full | Control | Scr. Cont. Full | uninduced | 99.89 | 2.9 |
| Control Starve | | Scr. Cont. Starv | autophagy induced | 68.88 | 5.3 |

*BCG survival relative to uninduced control with Scr siRNA

**Min: 50% KD

Figure 8X2 (cont.)

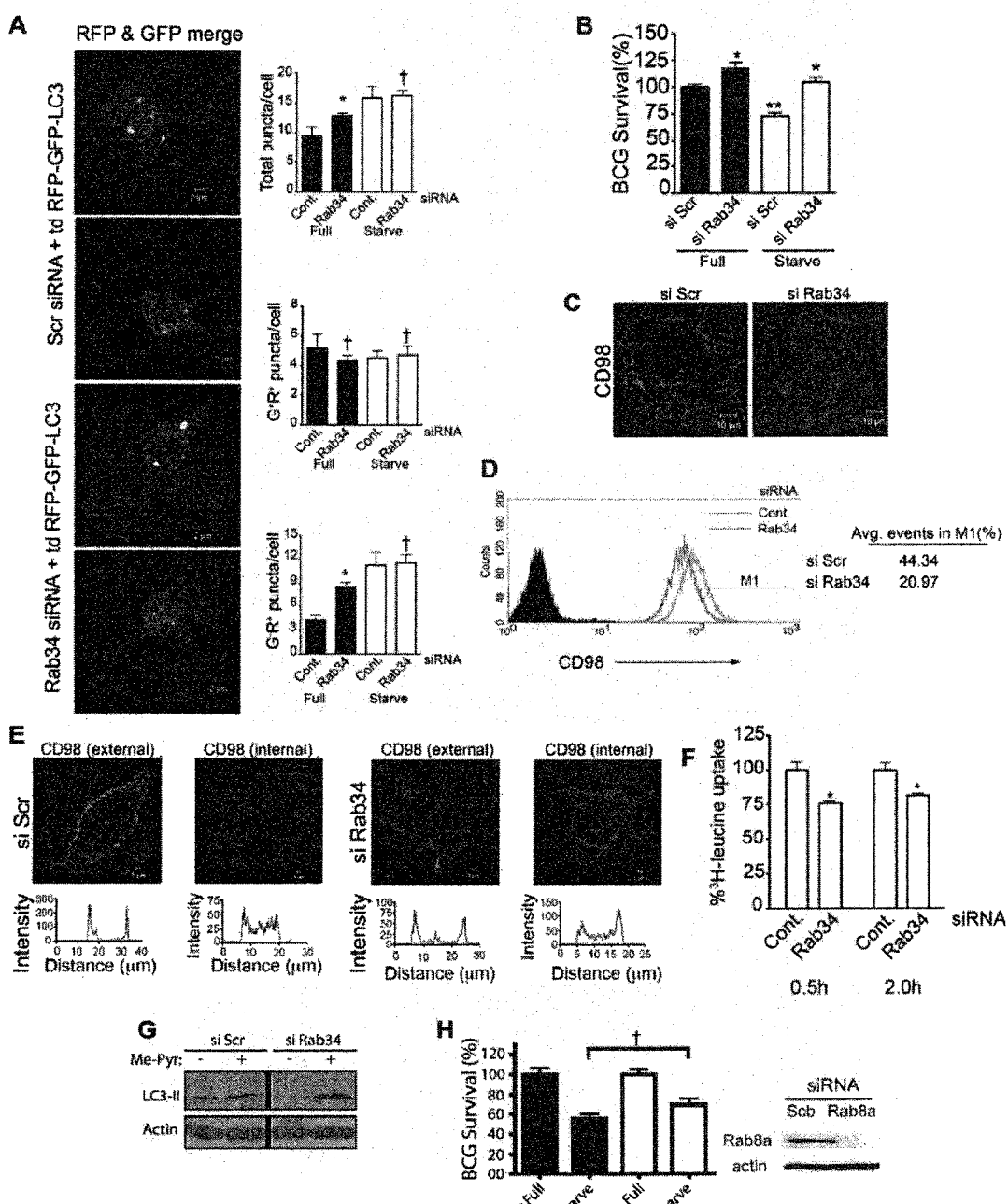
Suppl. Fig. 1S

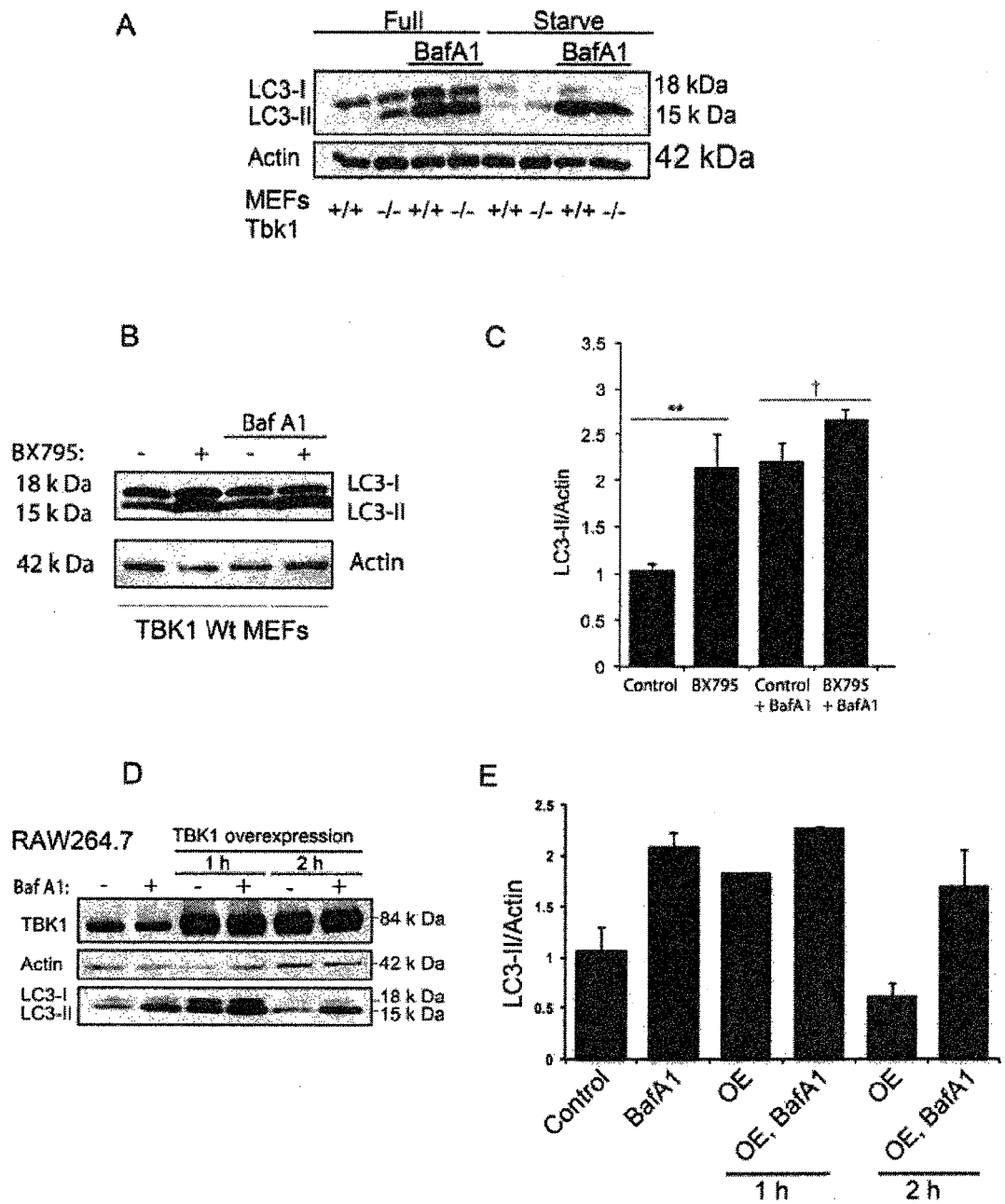
Suppl. Fig. 2S

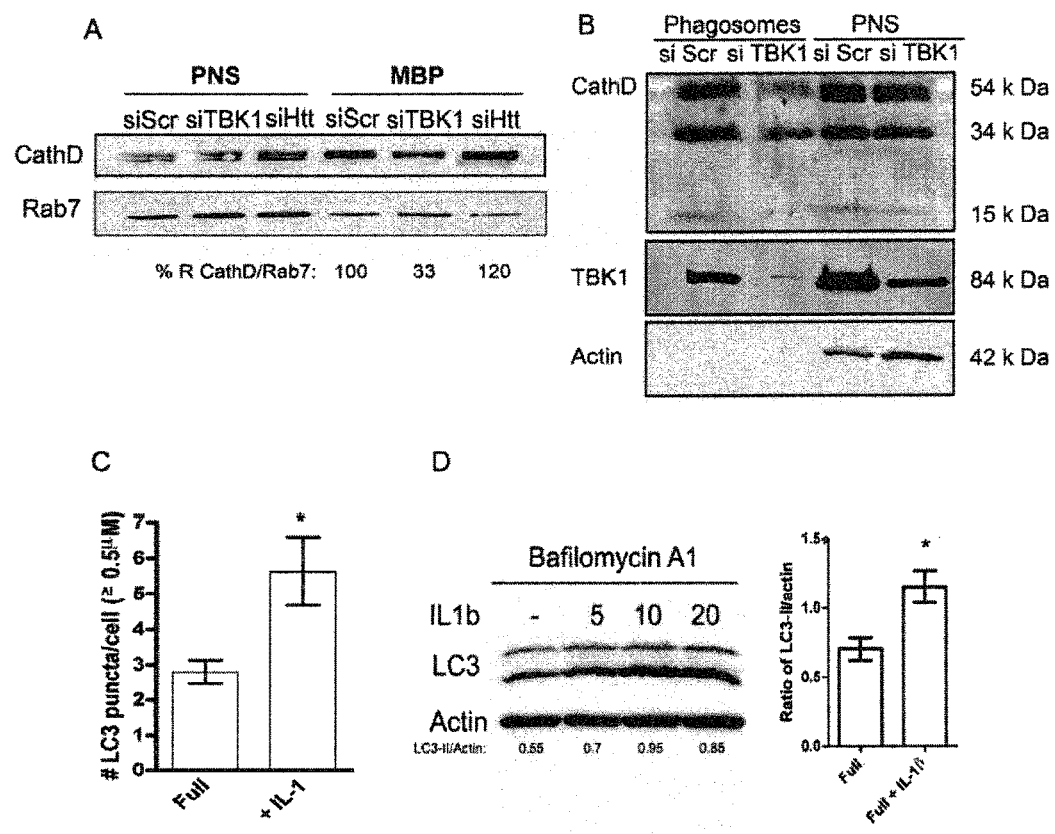
Suppl. Fig. 3S

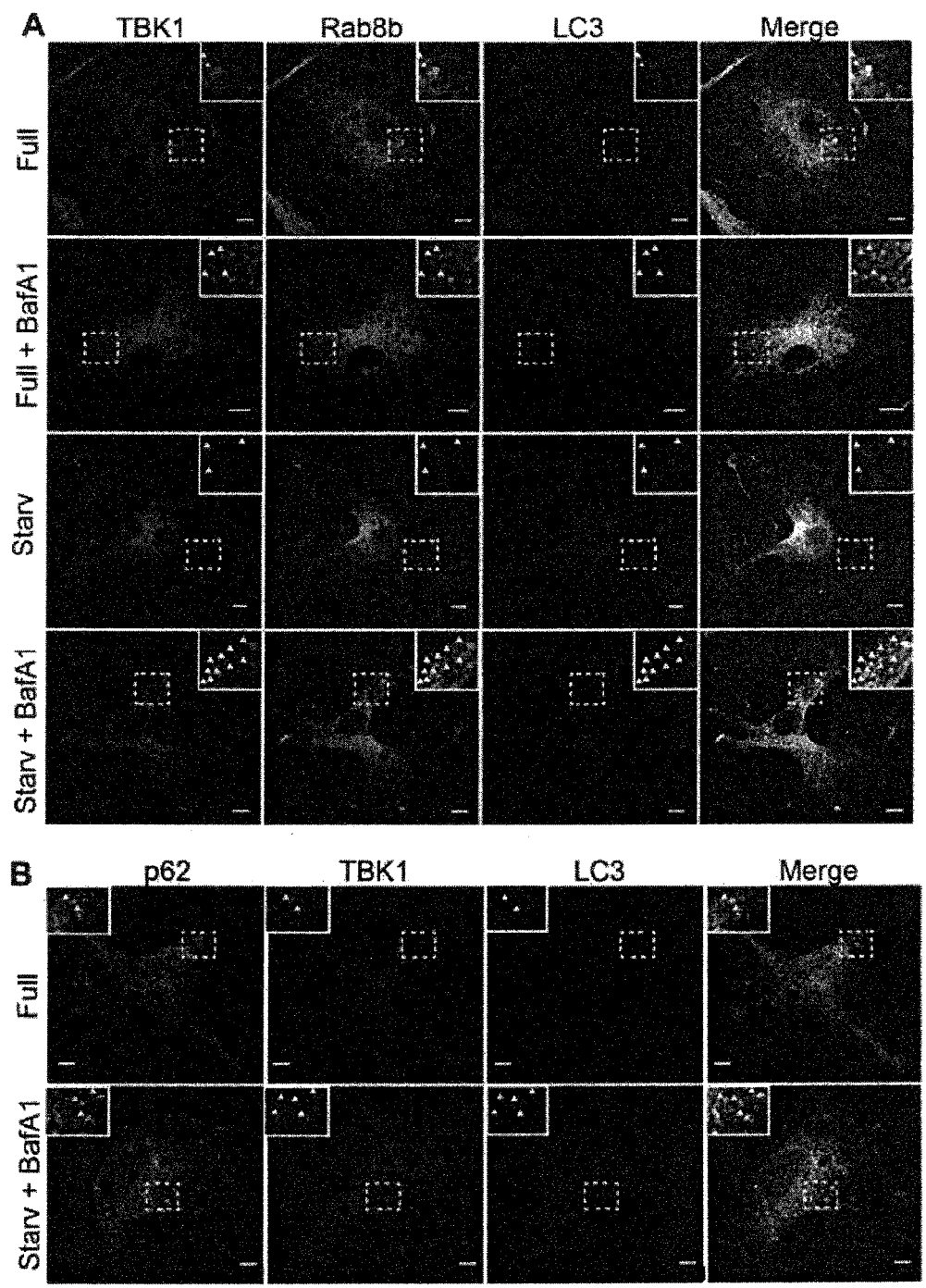
Suppl. Fig. 4S

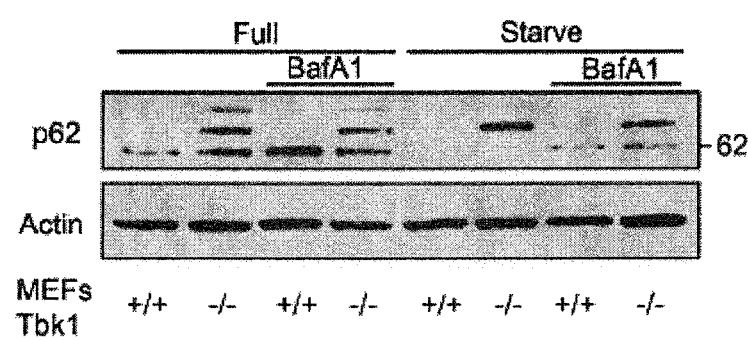
Suppl. Fig. 5S

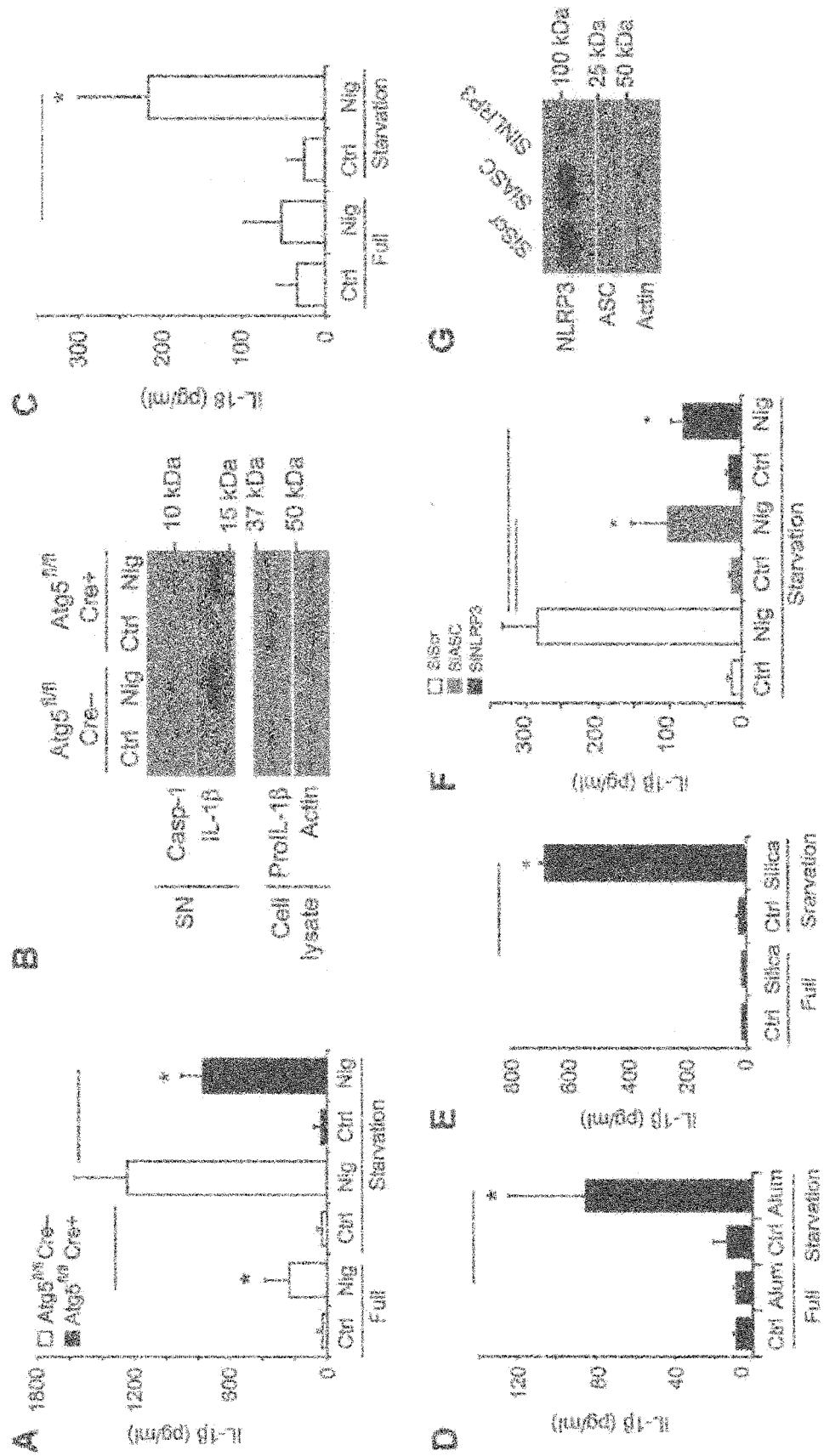
FIGURE 1X3 (A-G)

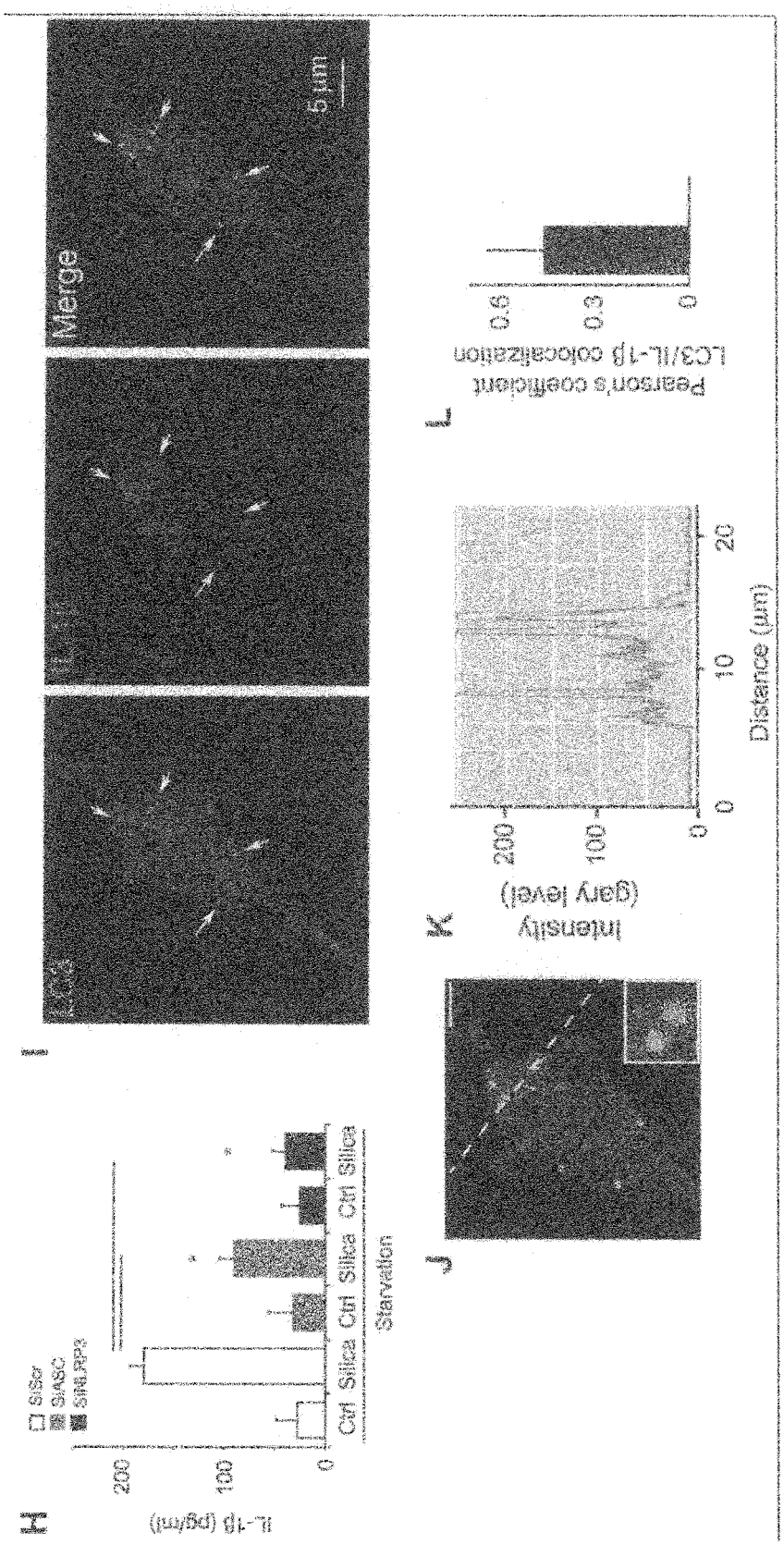

FIGURE 2X3
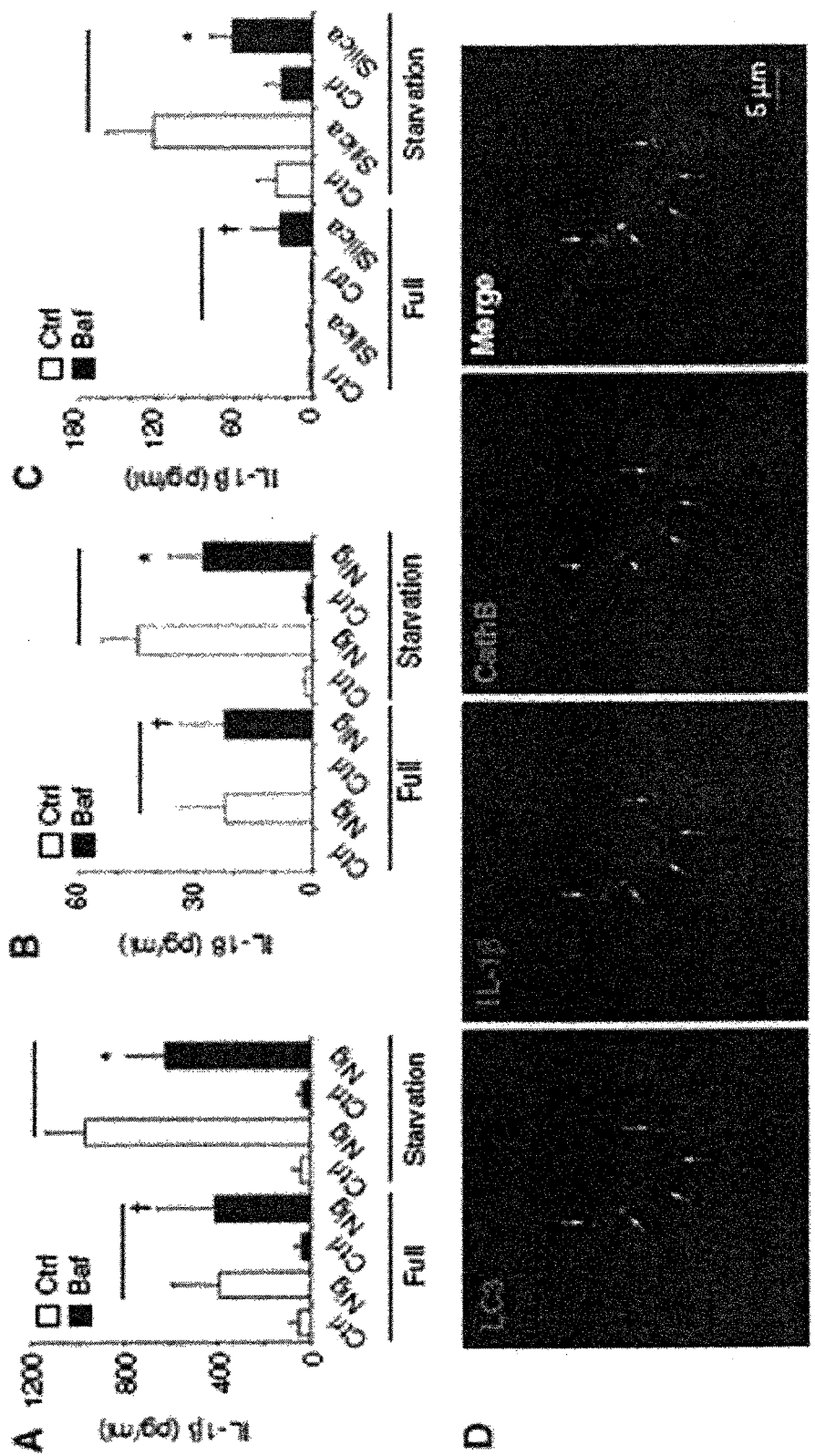

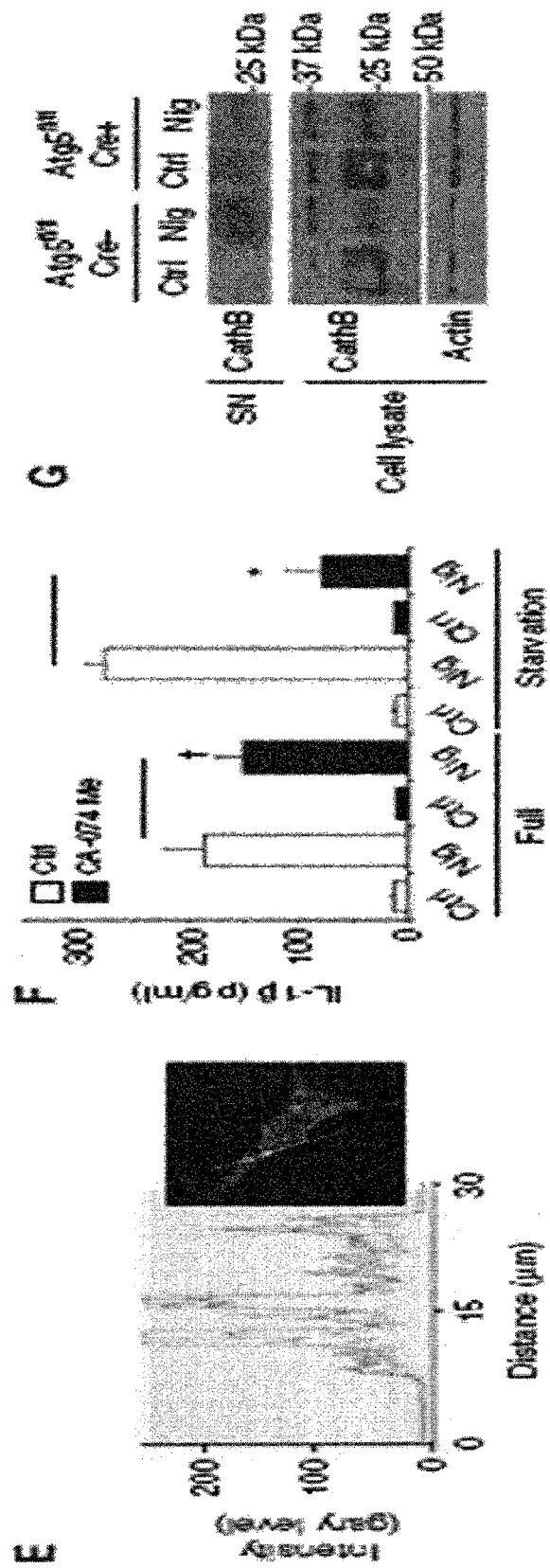
FIGURE 2X3 (CONT'D)

FIGURE 3X3
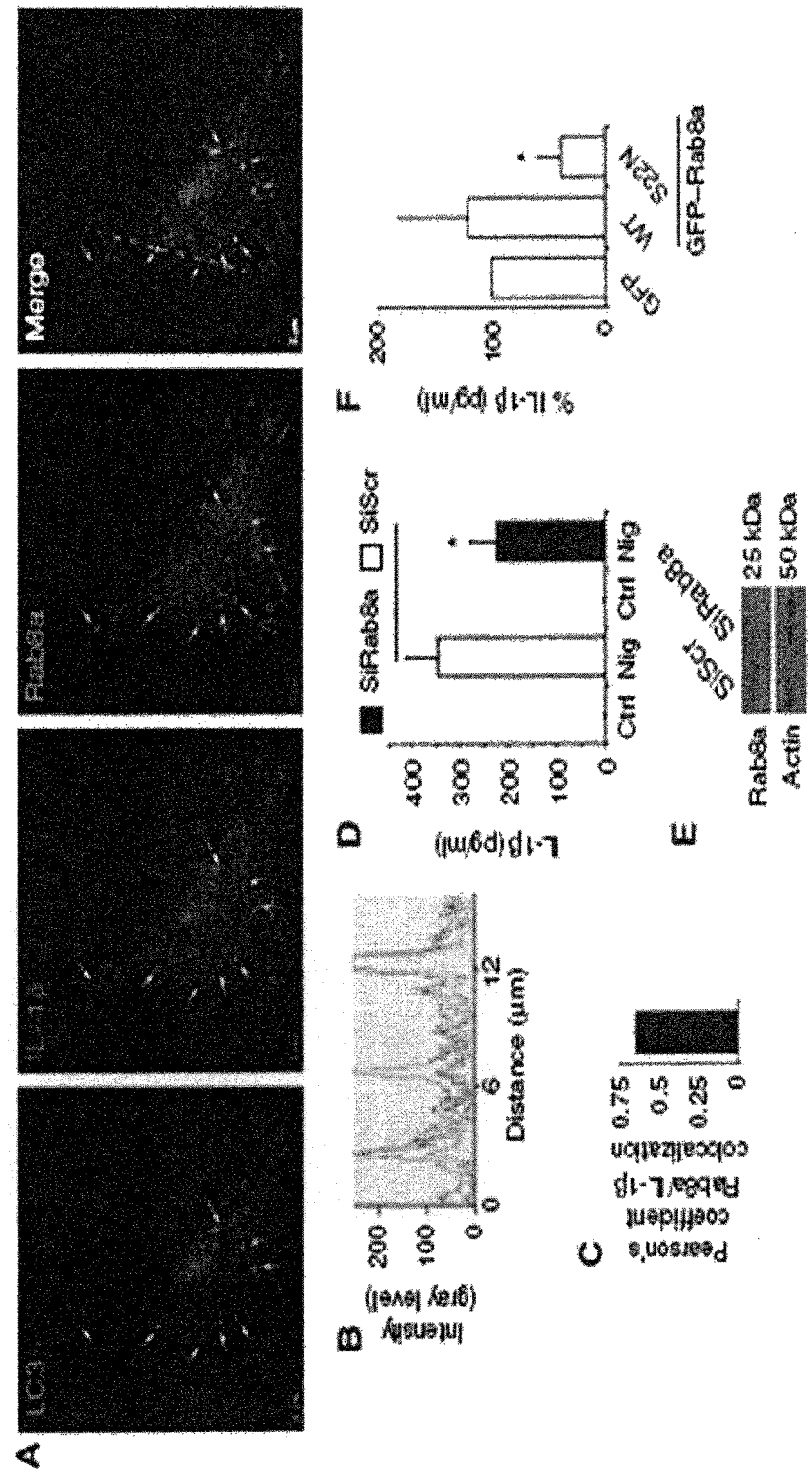

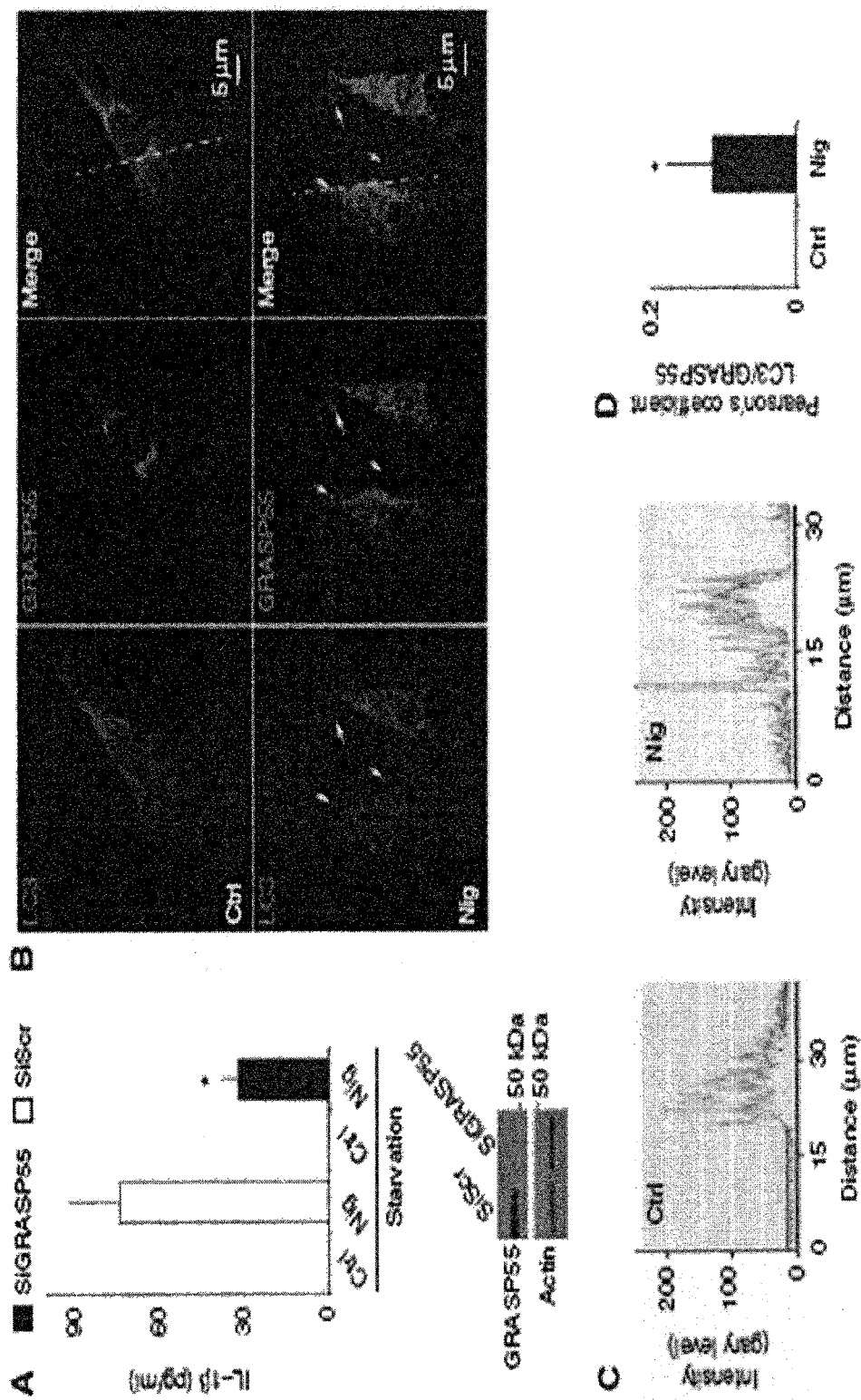
FIGURE 4X3

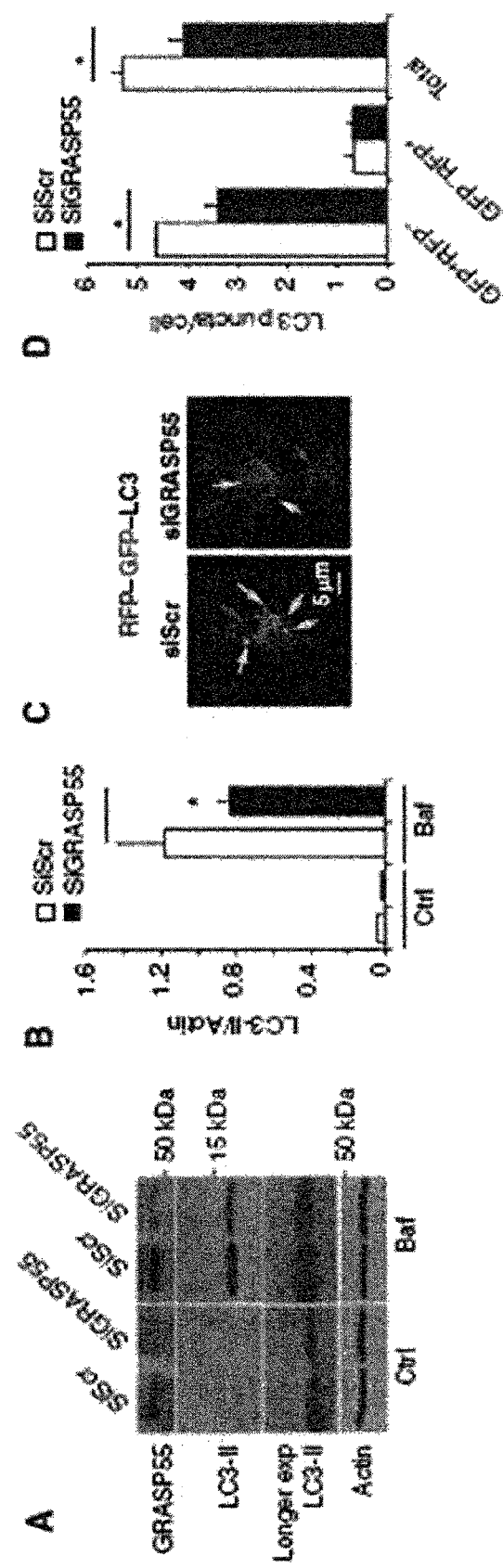
FIGURE 5X3

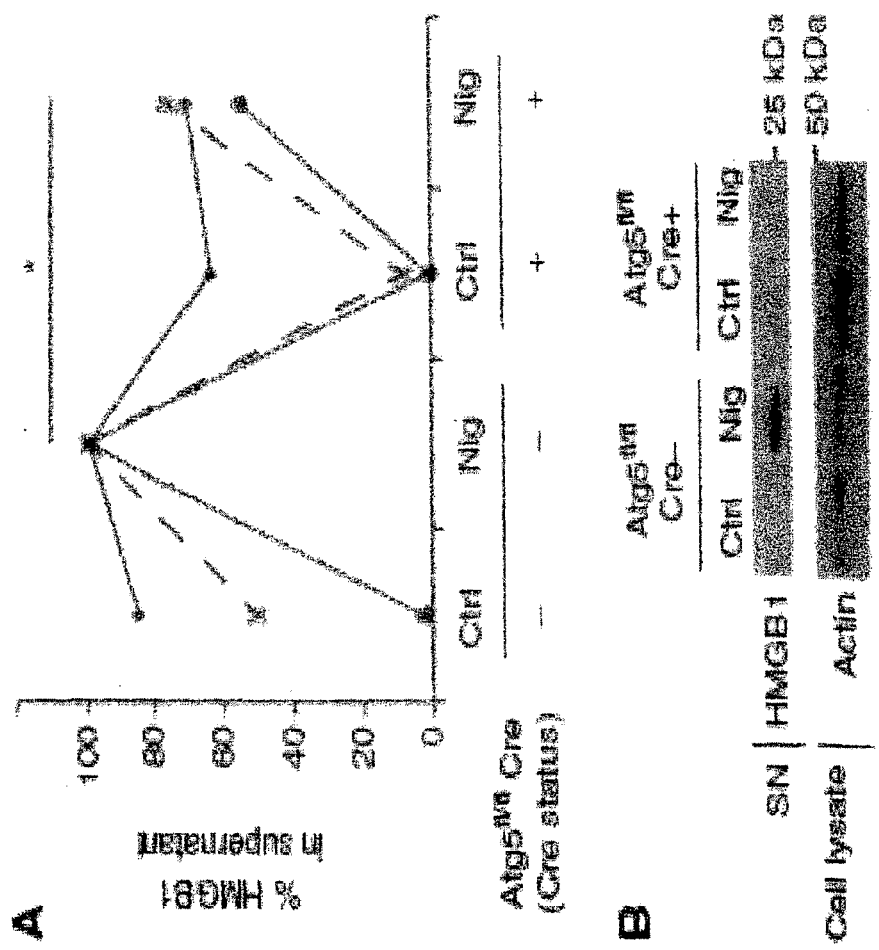
FIGURE 6X3

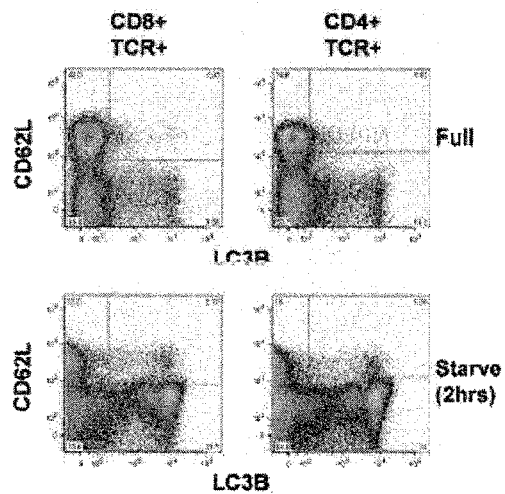
FIGURE 1X4
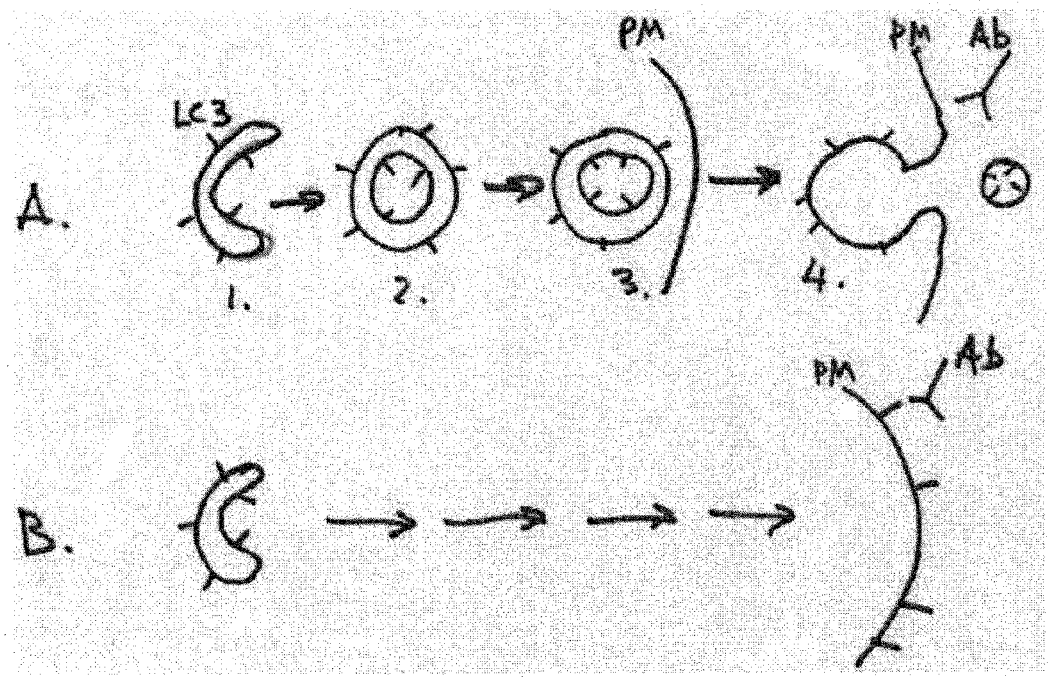
FIGURE 2X4

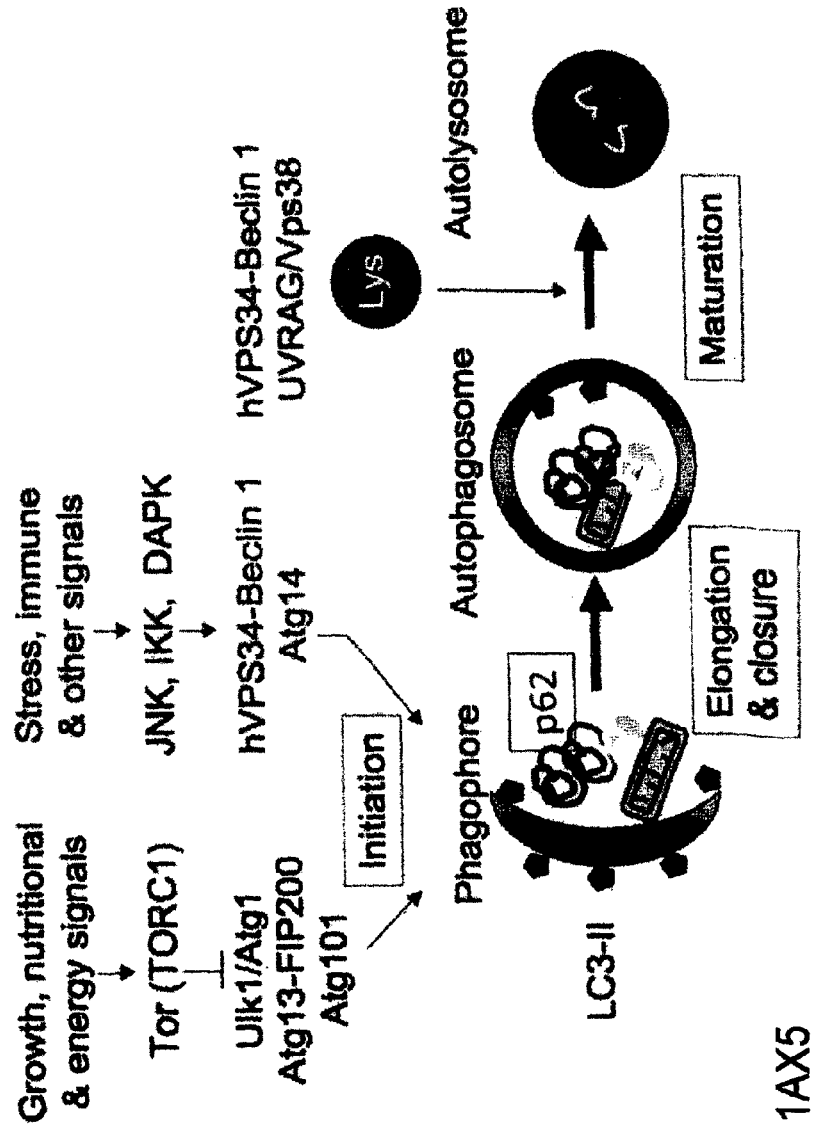
FIGURE 1AX5

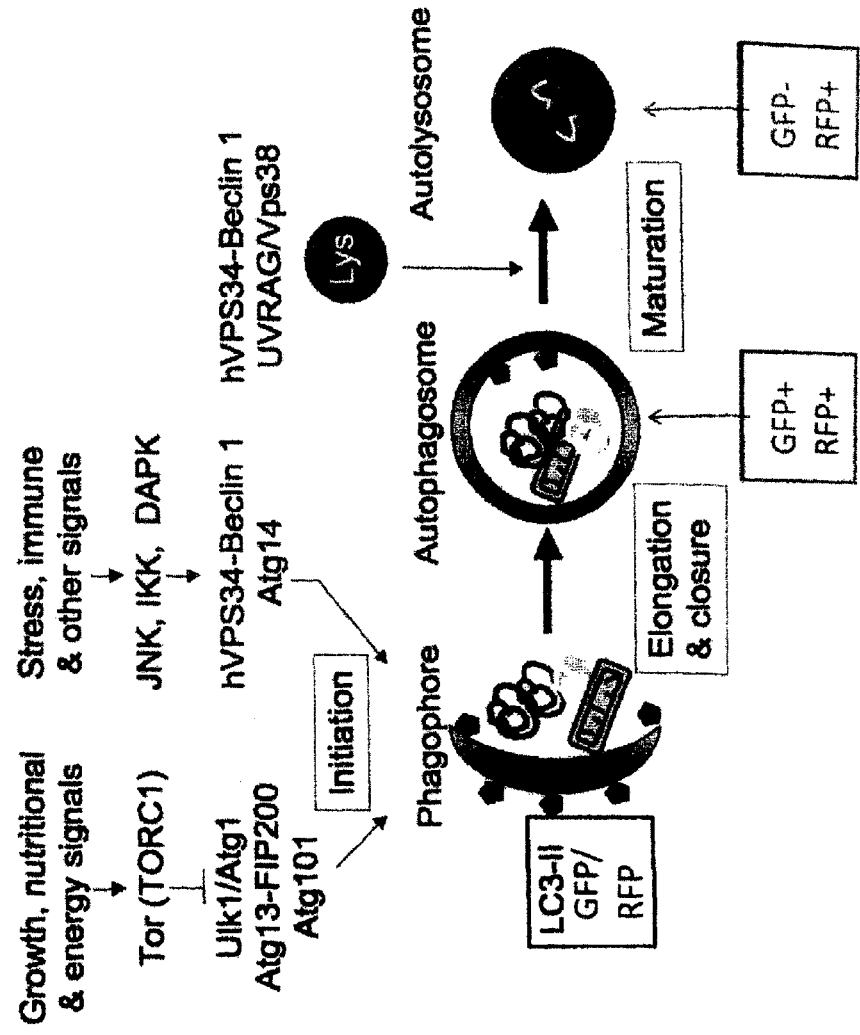
FIGURE 1BX5

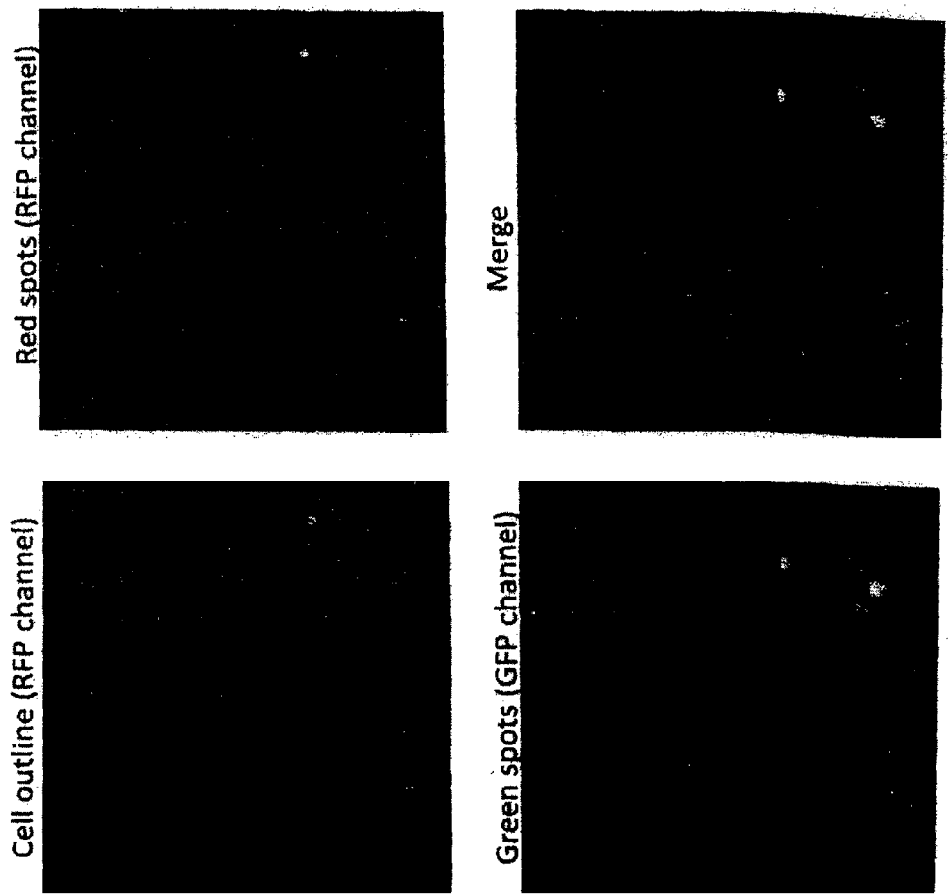
FIGURE 2X5

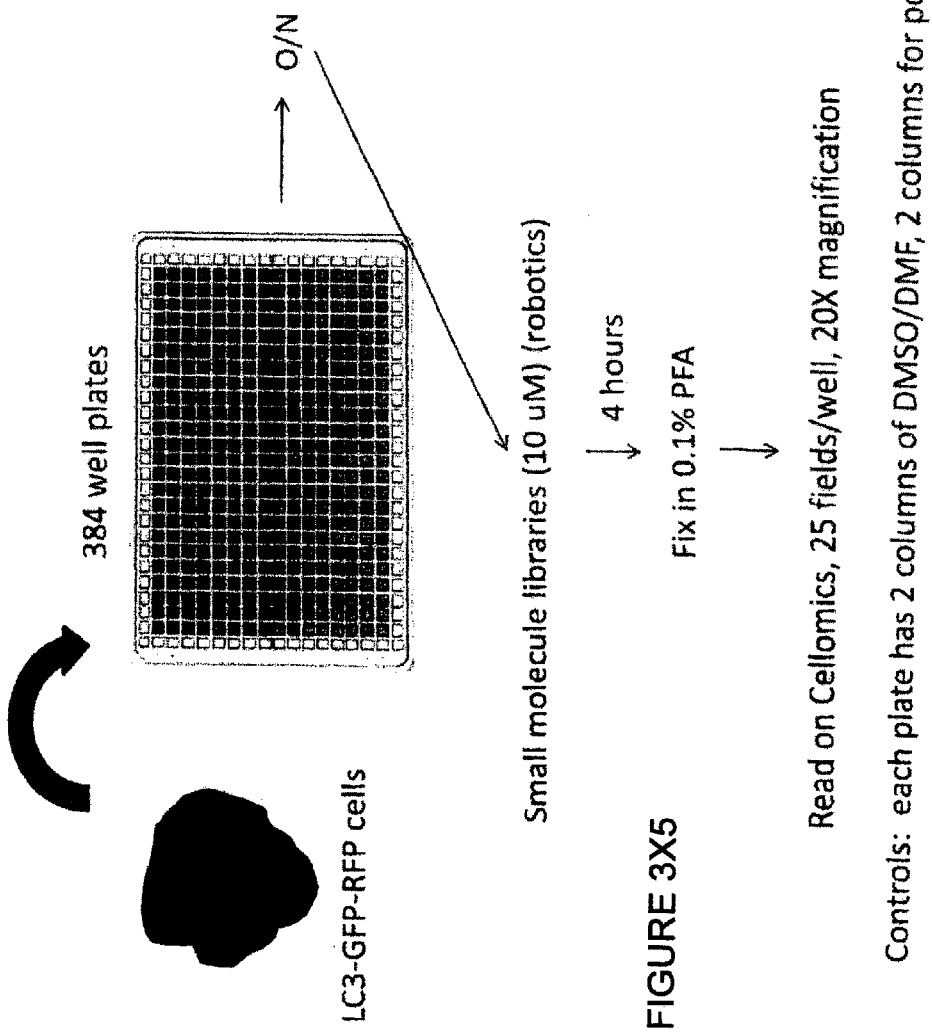
FIGURE 3X5

Positive and negative controls
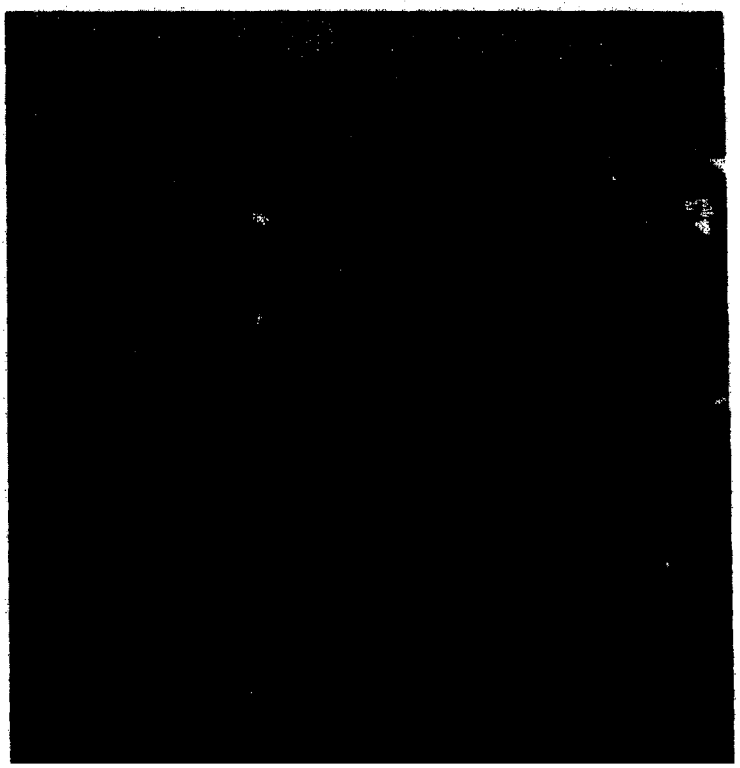
Rapamycin
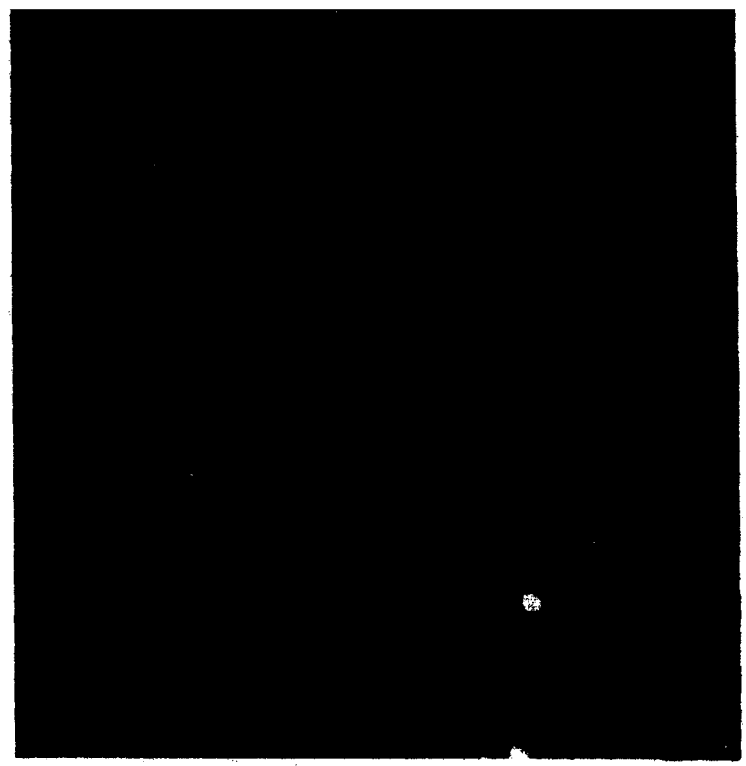
DMSO
FIGURE 4X5

Lessons learned from Prestwick and TPIMS Screens

- Positive controls: pp242 > rapamycin > starvation
- Read time for 384-well plate
  - 11-13 hours for 25 reads/well at 20X for ~70% confluent plate
  - 5-8 hours for 25 reads/well at 20X for ~95% confluent plate
  - Shifting read pattern helps in non-confluent plates

FIGURE 5X5

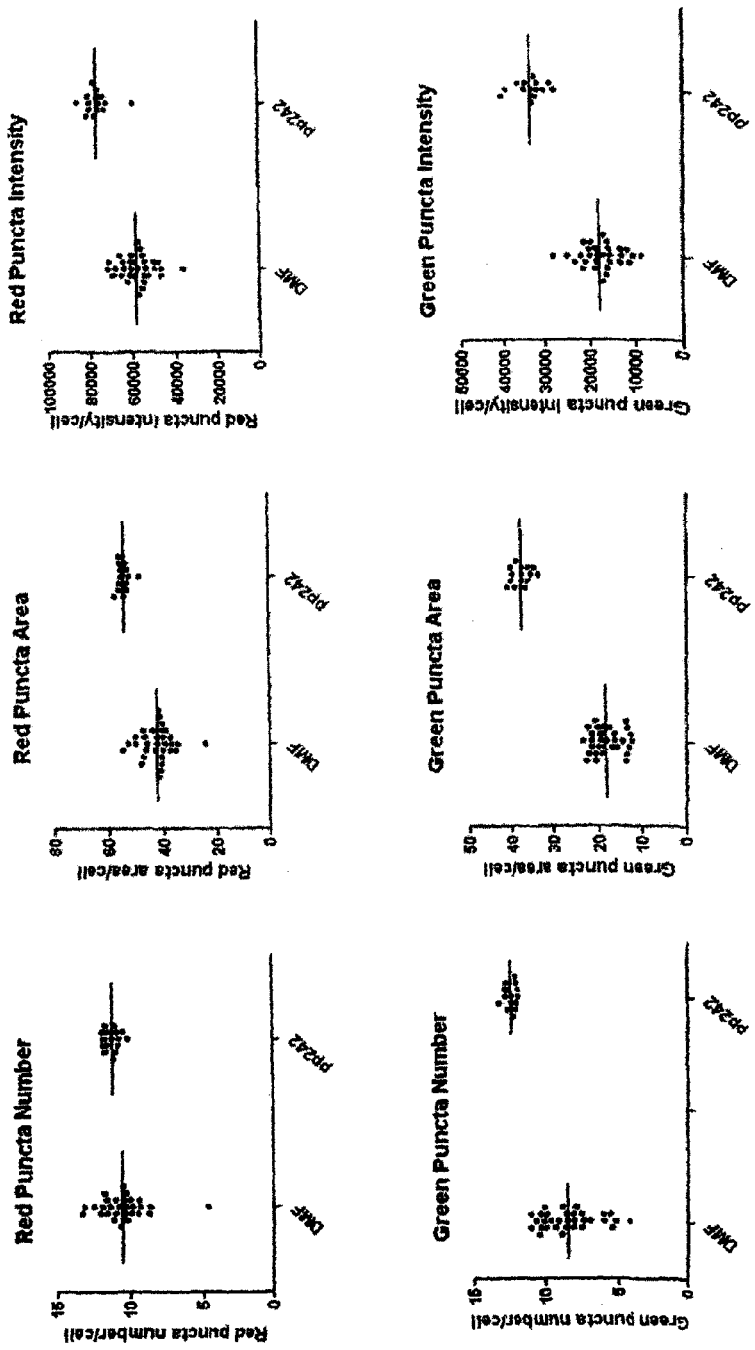
FIGURE 6X5

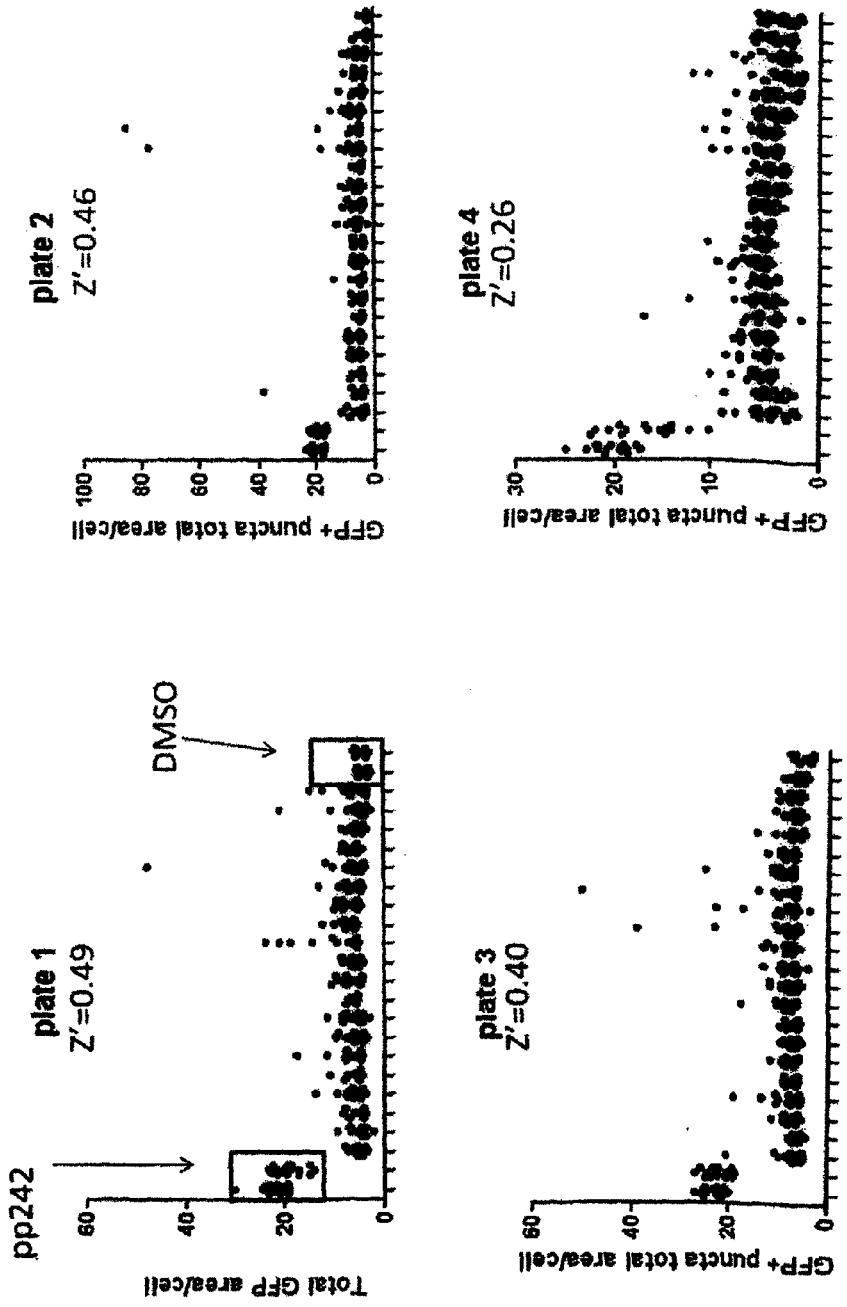
FIGURE 7AX5

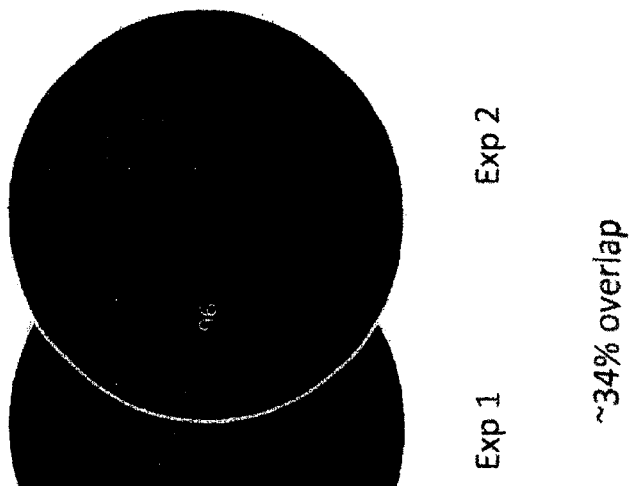
FIGURE 8X5

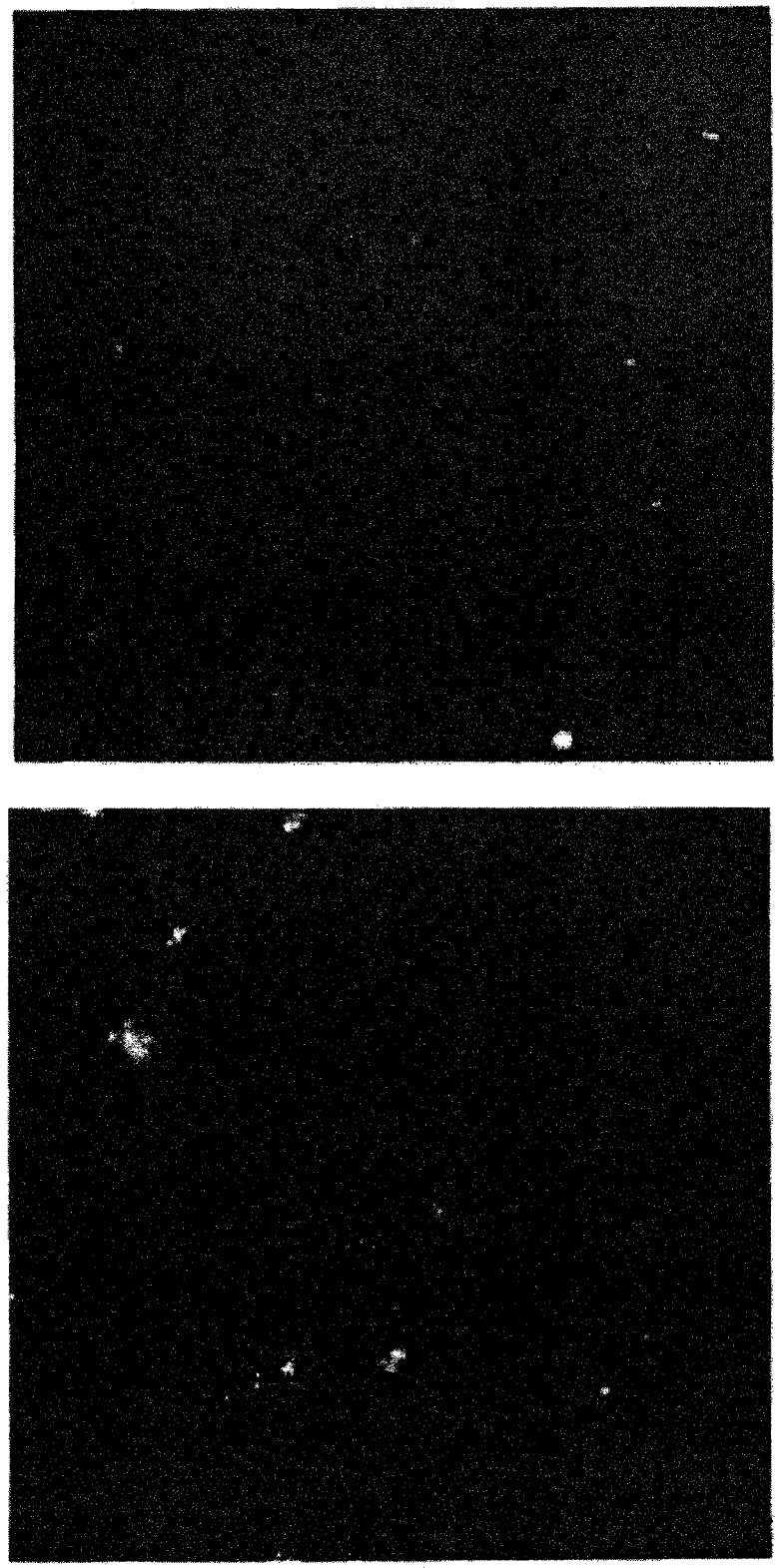
FIGURE 9X5

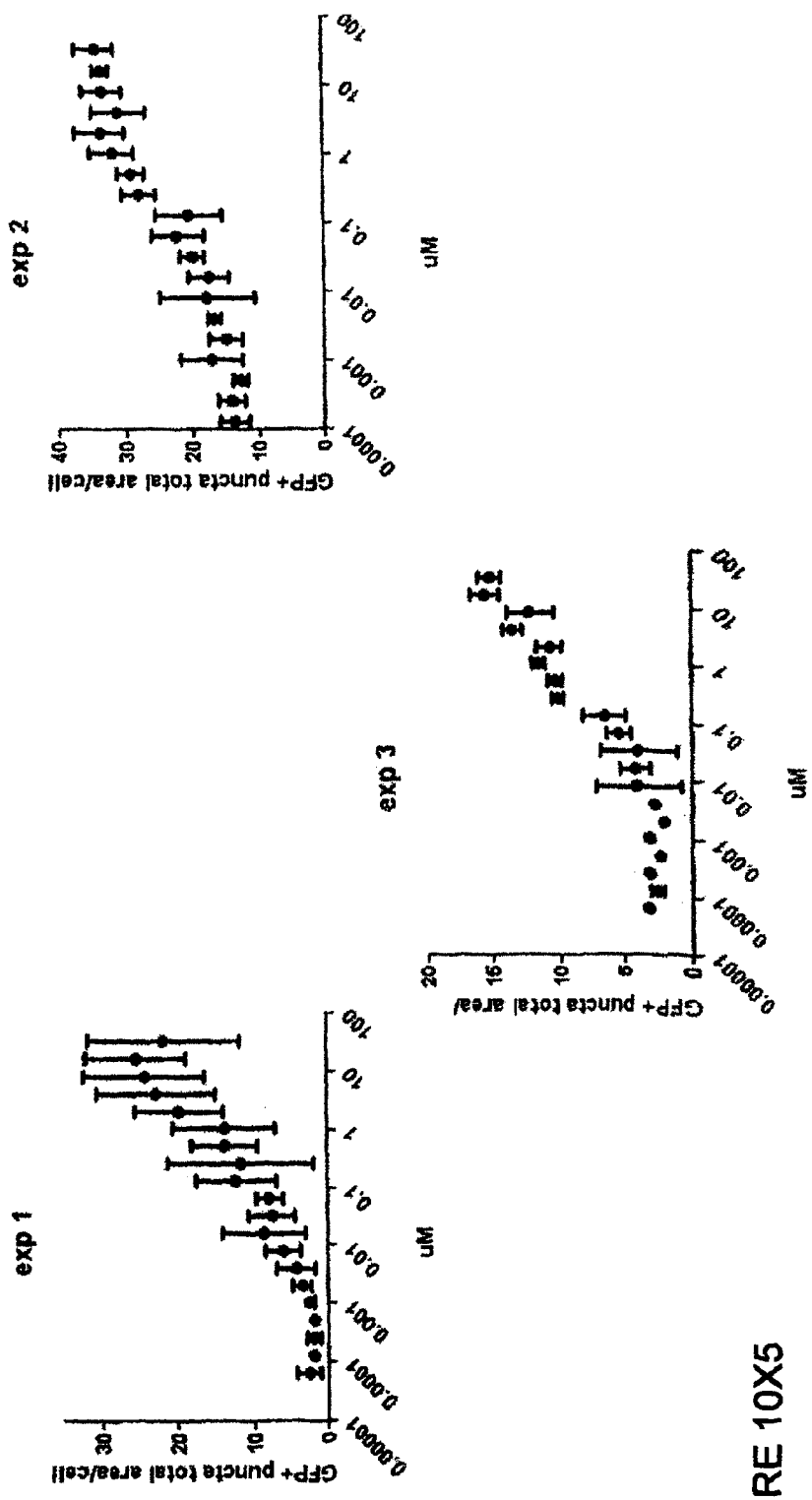
FIGURE 10X5

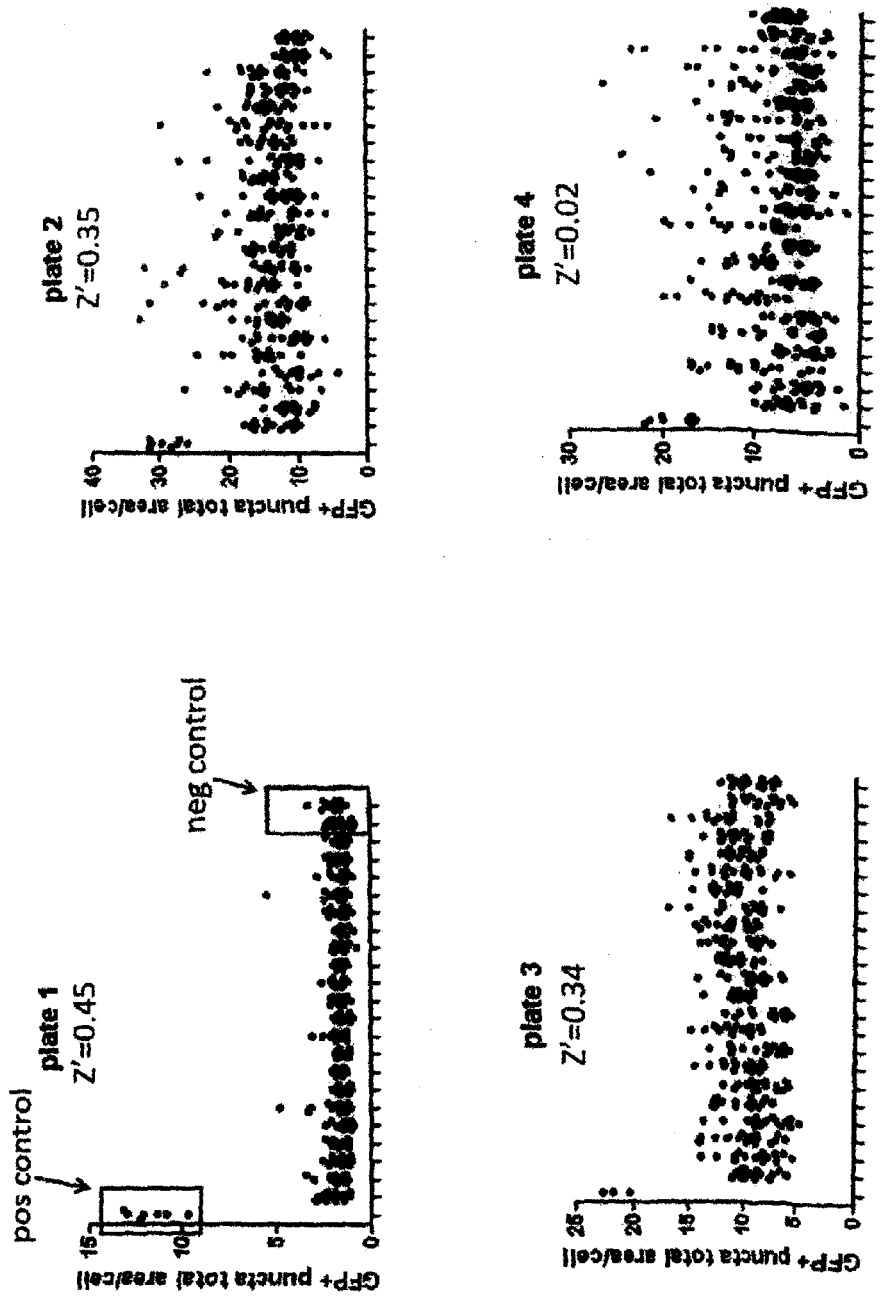
FIGURE 11X5

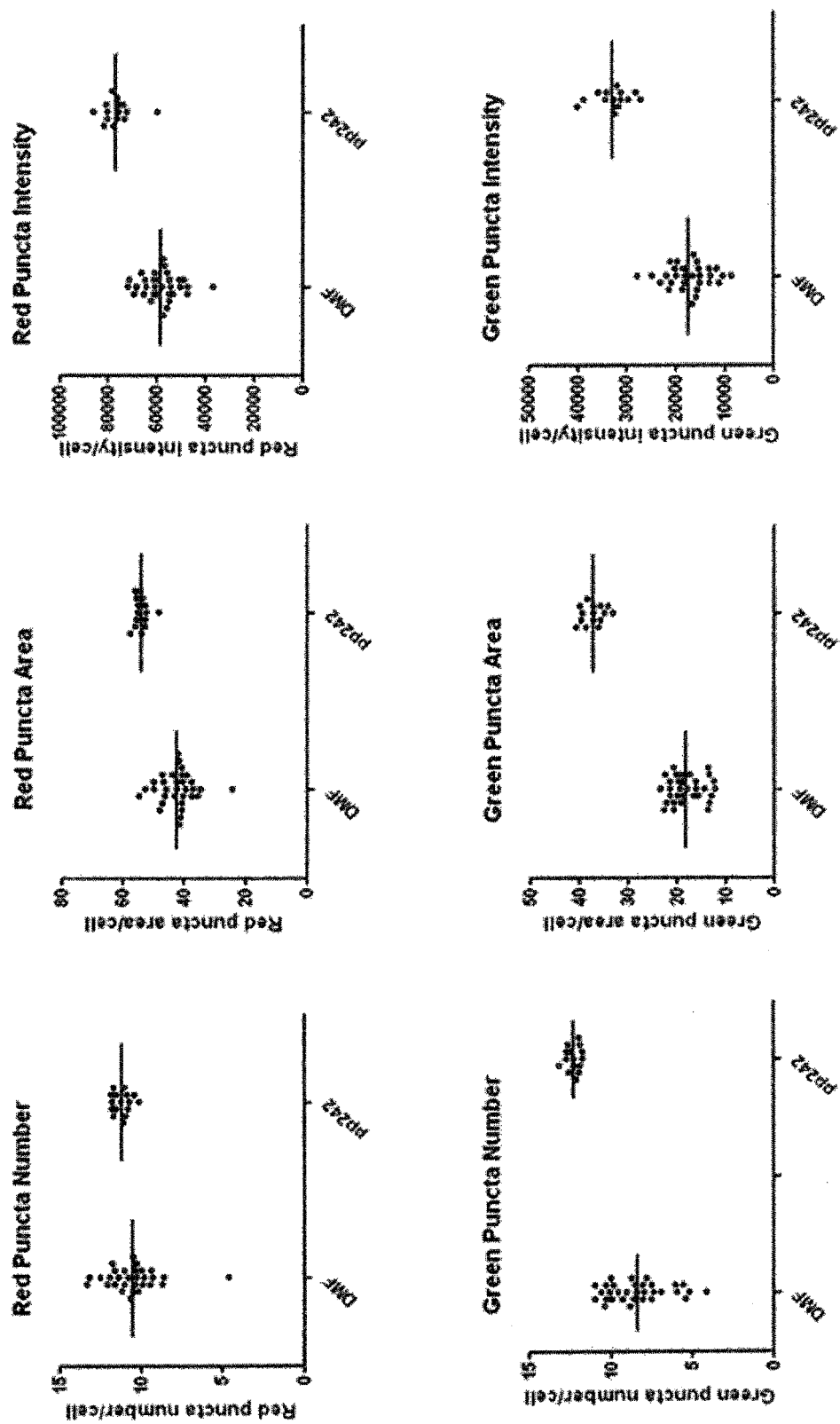
FIGURE 1X6

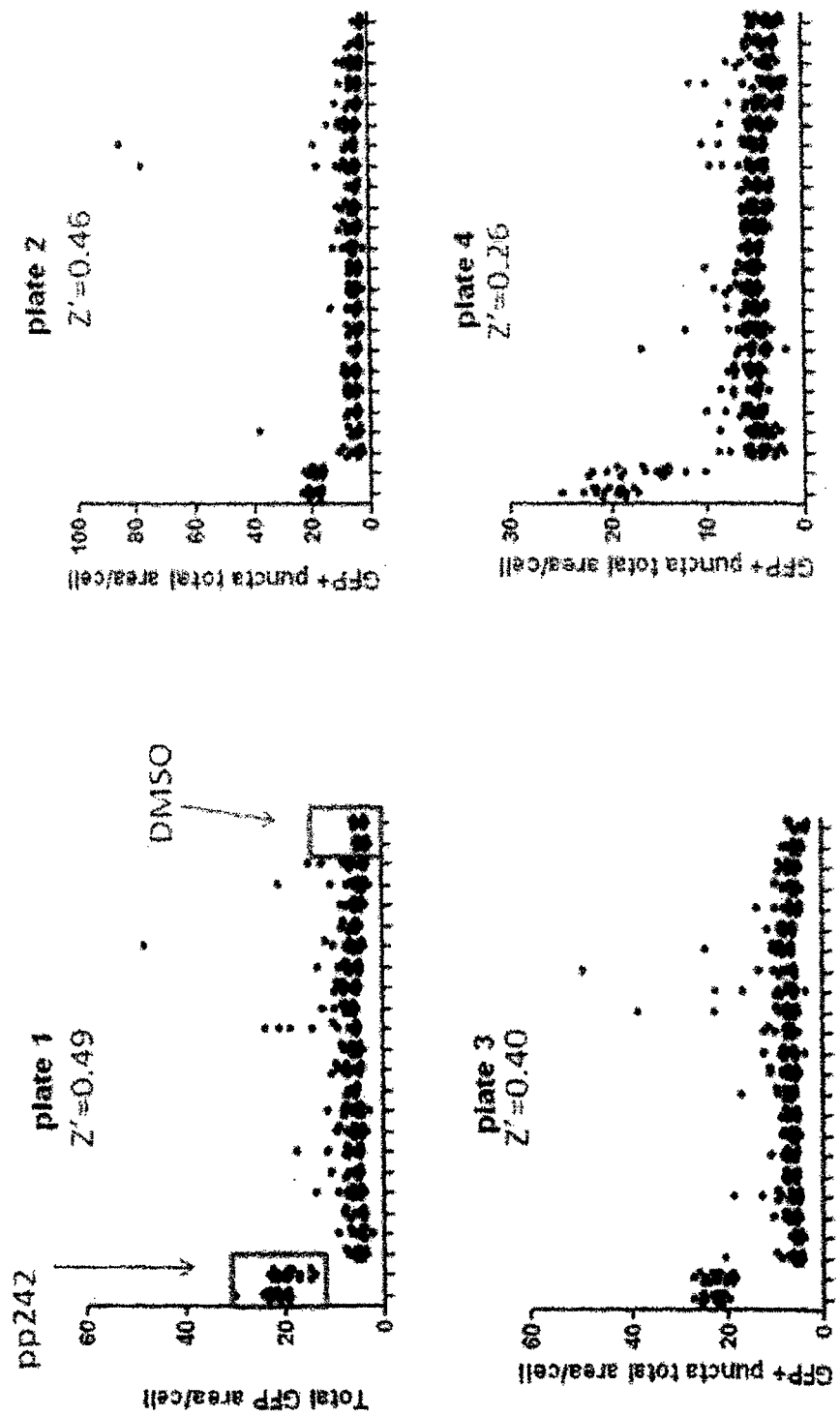
FIGURE 2X6

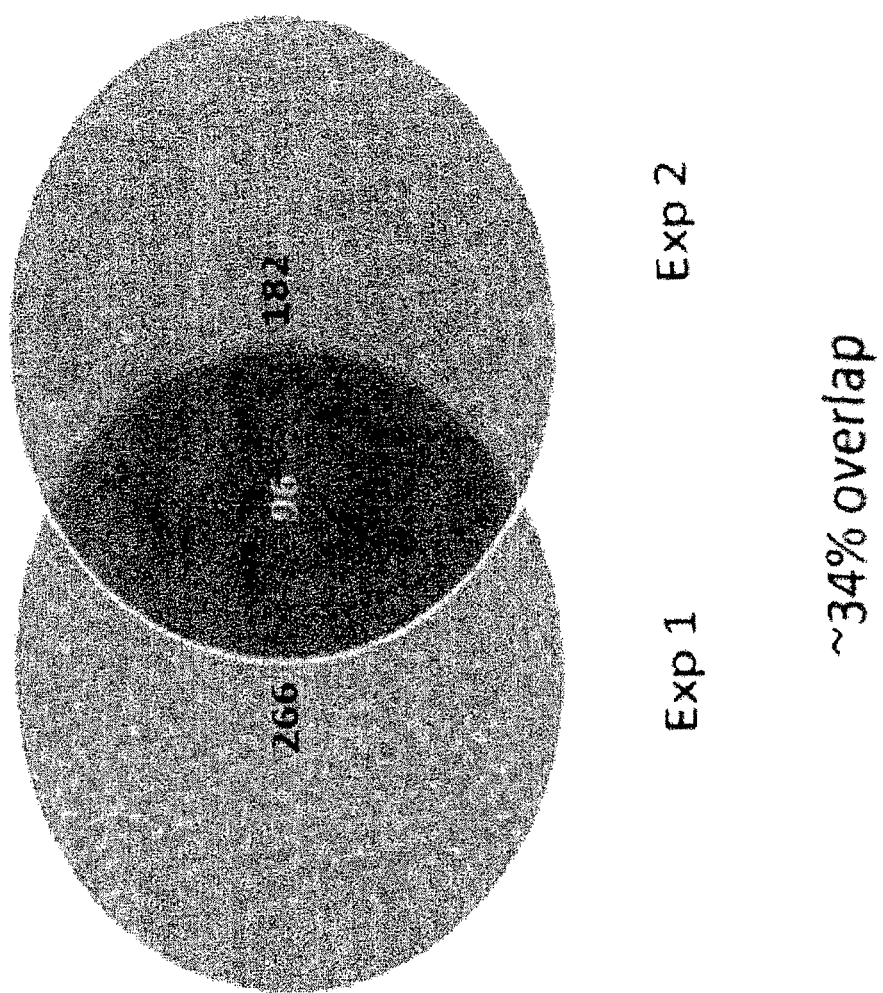
FIGURE 3X6

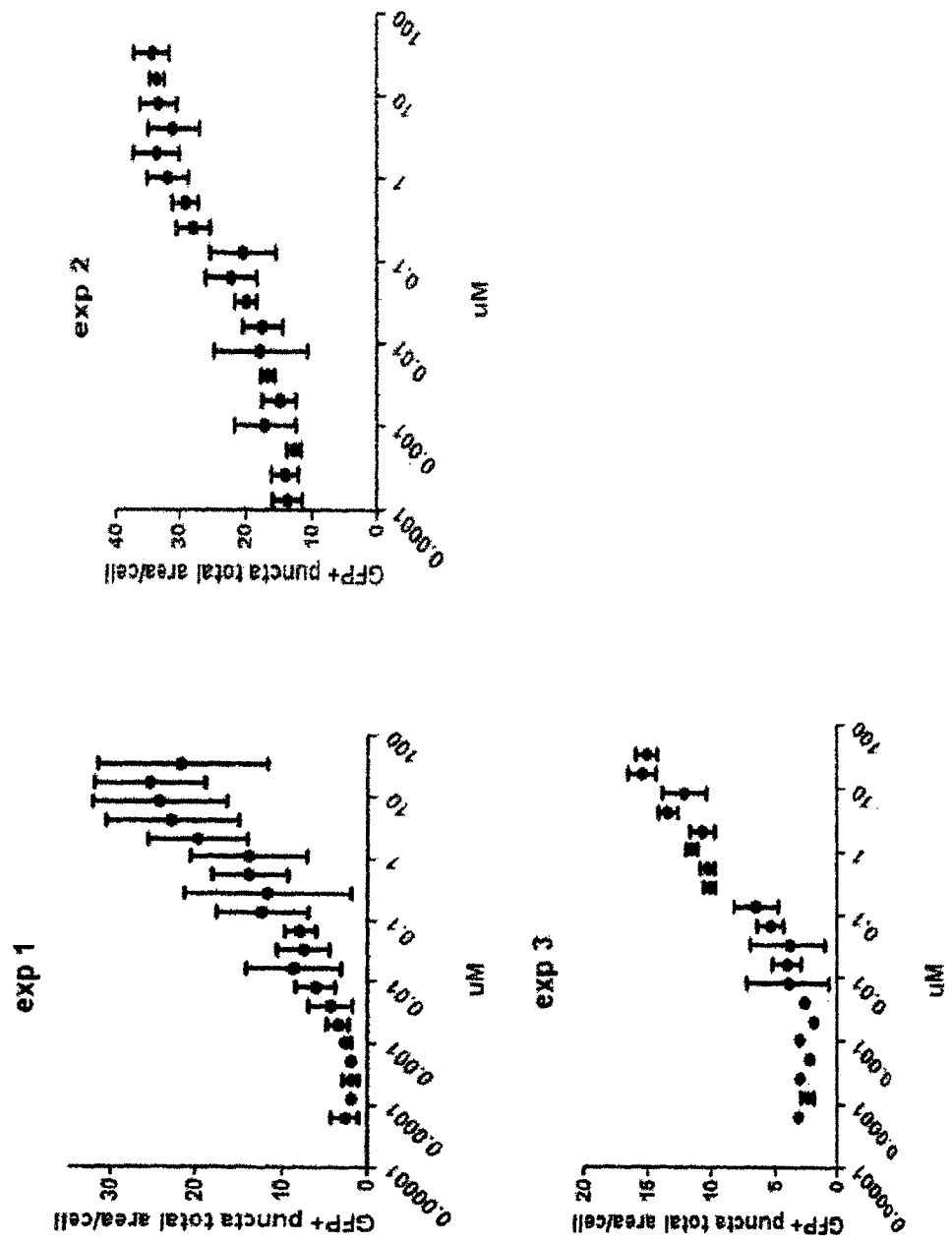
FIGURE 4X6

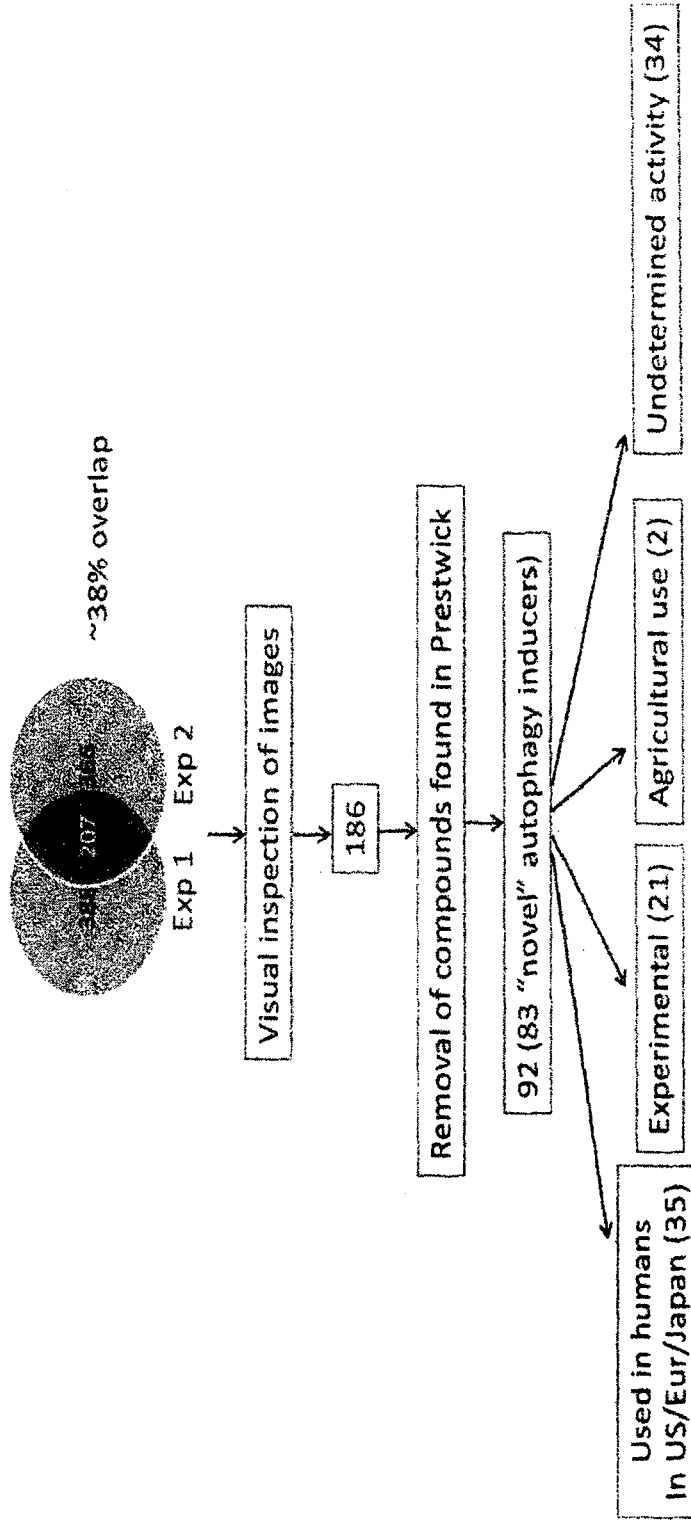
FIGURE 5X6

METHODS OF TREATING AUTOPHAGY-ASSOCIATED DISORDERS AND RELATED PHARMACEUTICAL COMPOSITIONS, DIAGNOSTICS, SCREENING TECHNIQUES AND KITS

RELATED APPLICATIONS

This application claims priority from and is a United States national phase application of International Patent Application No. PCT/US2012/037300 filed May 10, 2012 entitled "Methods of Treating Autophagy-Associated Disorders and Related Pharmaceutical Compositions, Diagnostics, Screening Techniques and Kits", which claims priority from U.S. Provisional Application Ser. No. US61/484,653 filed May 10, 2011, entitled "Autophagy Diagnostics, Screening, and Therapeutics", the complete disclosure of which two applications is hereby incorporated by reference in its entirety.

GOVERNMENT SUPPORT

The invention described herein was funded in part by National Institute of Health Grant No. R01 AI069345. Accordingly, the United States has certain rights in the invention.

FIELD OF THE INVENTION

The invention provides methods of treating autophagy-associated disorders, and related pharmaceutical compositions, diagnostics, screening techniques and kits.

BACKGROUND OF THE INVENTION

Autophagy is a homeostatic process highly conserved in eukaryotic cells where it acts as a cytoplasmic biomass quantity and quality control system (Mizushima et al., 2008; Yang and Klionsky, 2010). Its functions encompass programmed cell survival and cell death, normally skewed toward cell survival (Kroemer and Levine, 2008) through provision of energy and nutrients and ridding the cytoplasm of toxic macromolecular aggregates, faulty organelles (Mizushima et al., 2008; Yang and Klionsky, 2010) and invading microorganisms (Deretic and Levine, 2009; Levine et al., 2011).

The cell-autonomous antimicrobial defense functions of autophagy, demonstrated initially in the case of streptococci (Nakagawa et al., 2004) and *Mycobacterium tuberculosis* (Gutierrez et al., 2004; Harris et al., 2007; Ponpuak et al., 2010), have been extended to a wide variety of microbes with a caveat that most highly adapted pathogens have evolved specific protective mechanisms against autophagic elimination of microbes (Deretic and Levine, 2009; Gannage et al., 2009; Kyei et al., 2009; Lee et al., 2009; Orvedahl et al., 2007; Yoshikawa et al., 2009). Other studies have uncovered orderly intersections between autophagy and innate (Chaturvedi et al., 2008; Cooney et al., 2010; Delgado et al., 2008; Huang et al., 2009; Sanjuan et al., 2007; Shi and Kehrl, 2010; Tang et al., 2010; Travassos et al., 2009; Xu et al., 2007; Yano et al., 2008) and adaptive immunity (Blanchet et al., 2010; Lee et al., 2010; Munz, 2009; Nedjic et al., 2008; Paludan et al., 2005; T cell development, differentiation and homeostasis (Jia and He, 2011; Nedjic et al., 2008), and inflammatory responses (Cadwell et al., 2010; Jounai et al., 2007; Levine et al., 2011; Saitoh and Akira, 2010). Autophagy suppresses endogenous, cell-autonomous promoters of inflammation (Mathew et al., 2009; Orvedahl et al., 2010).

Specific autophagic factors, such as Atg5-Atg12, have been shown to inhibit RIG-I signaling (Jounai et al., 2007) whereas Atg9, have been reported to negatively regulate trafficking, assembly and activation of TBK-1 (TANK-binding kinase 1), which, among its key functions, controls type I interferon response elicited by intracellular double stranded DNA (Saitoh et al., 2009). In the context of anti-inflammatory function, recent studies indicate that autophagy plays an inhibitory role in inflammasome and IL-1β activation by mechanisms that involve mitochondrial homeostasis (Nakahira et al., 2010; Zhou et al., 2011) or potentially direct effects (Harris et al., 2011). Finally, a number of genetic links have been found in human populations between autophagy and idiopathic inflammatory (Consortium, 2007; Craddock et al., 2010) or infectious diseases such as tuberculosis (Che et al., 2010; Intemann et al., 2009; Singh et al., 2006; Singh et al., 2010), with significant inflammatory components and tissue damage.

Given the interconnectedness of autophagy and immunity, it is likely that the immune manifestations of autophagy are affected not only by the induction of autophagy but also by the completion of the autophagic pathway. The formation of the autophagic organelles of the sensu stricto autophagy pathway (also referred to as macroautophagy) depends on multiple sources of membrane or regulatory factors (Tooze and Yoshimori, 2010). The key stages of autophagy however are not restricted to the formation of autophagosomal membranes and include the sequestration of the earmarked cargo by the autophagic adaptors (Bjorkoy et al., 2005; Kirkin et al., 2009; Thurston et al., 2009; Wild et al., 2011), and the less understood process of the maturation of autophagic organelles into autolysosomes where the captured material is degraded (Korolchuk et al., 2011; Liang et al., 2008; Matsunaga et al., 2009; Zhong et al., 2009).

Thus, autophagy is directly implicated in cancer, type II diabetes, neurodegenerative syndromes such as Alzheimer's, Huntington's and Parkinson's diseases, chronic inflammatory diseases (e.g. Crohn's disease), type II diabetes, infections (such as tuberculosis and HIV (I and II)/AIDS, hepatitis B, hepatitis C), and a variety of disorders associated with aging. A better understanding of how autophagic mechanisms are implicated in the aforementioned diseases could prove critical to preventing or treating these maladies.

The references which are cited above are presented after Example 2 of the present specification.

SUMMARY OF THE INVENTION

The elucidation of certain autophagic processes involved in the onset and progression of a variety of infectious and inflammatory-related disorders has led to the discovery of methods of treating and diagnosing such ailments. Further, the discovered novel methods have led to our being able to identify compounds that are effective as modulators of autophagy in the treatment of infectious and inflammatory-related disorders, as well as versatile techniques that enable the high through-put analyses of autophagic processes, including the disease state in a patient for diagnosis and/or monitoring therapy of the disease state. The present invention is directed to a method of identifying compounds which exhibit biological activity as modulators (inhibitors or agonists) of autophagy and consequently, can be used in the treatment of diseases which occur or are mediated through autophagy as a mechanism.

In one embodiment, the present invention provides a method of modulating autophagy in a biological system, in particular a patient or subject. In this aspect of the invention, a compound identified herein as an autophagy modulator (inhibitor or agonist, also referred to generically as an "autostatin") is presented to the biological system, including administration to a patient or subject in need, in order to modulate (often enhance or up-regulate but in certain instances, for example cancer, inhibit) autophagy and effect a favorable result in the biological system, often a patient or subject. The resulting modulation may be monitored or applied in the biological system to effect a favorable result, including the inhibition, treatment and/or prevention of cancer, including metastasis of cancer, or the inhibition, treatment (including the amelioration of symptoms) and/or prevention of one or more disease states or conditions in which the modulation, especially including upregulation or inhibition of autophagy provides a favorable result in numerous disease states and/or conditions including neurodegeneration (including, for example, Alzheimer's disease, Parkinson's disease; other ataxias), chronic inflammatory diseases (including, for example, inflammatory bowel disease, including Crohn's disease, rheumatoid arthritis, lupus, multiple sclerosis, chronic obstructive pulmonary disease/ COPD, pulmonary fibrosis, cystic fibrosis, Sjogren's disease), diabetes and metabolic syndrome, muscle degeneration and atrophy, frailty in aging, stroke and spinal cord injury, arteriosclerosis, infectious diseases (HIV I and II, HBV, HCV, including secondary disease states or conditions associated with infectious diseases, including AIDS) and tuberculosis, among others. The common principle of this embodiment of the invention is that compounds, including autostatins which are autophagy modulators (i.e., inhibitors or activators of autophagy), depending upon the disease state, condition or symptom to be treated, may cure, prevent (including reducing the likelihood of), improve prognosis, ameliorate symptoms and/or improve the quality of the patient's or subject's life. In addition, in the therapeutic aspects of the invention, the administration of an autophagy modulator (autostatin) may prolong the life of the patient, as well as improve the quality of life in the aging patient or subject.

In one embodiment the method of treating an autophagy-mediated disease state or condition comprising administering at least one autostatin alone or optionally in combination with at least one additional bioactive agent. In this method an autostatin selected from the group consisting of flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon and nortriptyline, tetrachlorisophthalonitrile and phenylmercuric acetate, pharmaceutically acceptable salts thereof and mixtures thereof, alone or in combination with at least one additional bioactive agent, optionally in combination with a pharmaceutically acceptable carrier, additive or excipient, may be administered to a patient or subject in need to treat an autophagy-mediated disease state and/or condition. It is noted that flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline and their pharmaceutically acceptable salts show activity as agonists or inducers of autophagy in the treatment of an autophagy-mediated disease, tetrachlorisophthalonitrile, phenylmercuric acetate and their pharmaceutically acceptable salts, find use as antagonists or inhibitors of autophagy. All of these compounds will find use as modulators of autophagy in the various autophagy-mediated disease states and conditions described herein, with the agonists being preferred in most disease states other than cancer and in the case of the treatment of cancer, the inhibitors described above are preferred, alone or in combination with an autophagy agonist as described above and/or an additional anticancer agent as otherwise described herein.

Pharmaceutical compositions according to the present invention comprise an effective amount of at least one autophagy modulator selected from the group consisting of flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, tetrachlorisophthalonitrile, phenylmercuric acetate and their pharmaceutically acceptable salts, optionally in combination with a pharmaceutically acceptable carrier, additive and/or excipient and further optionally, in combination with at least one additional bioactive agent (e.g., an anticancer agent, antibiotic, anti-tuberculosis agent, antiviral agent such as an anti-HIV agent, anti-HBV agent or anti-HCV agent, etc.), preferably at least one anticancer agent as otherwise disclosed herein or at least one additional autophagy modulator as otherwise described herein. In the present invention, an additional autophagy modulator (autostatin) is selected from the group consisting of may be combined with an additional autophagy modulator selected from the group consisting of benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene and mixtures thereof.

In an additional embodiment, the invention provides a method of monitoring or determining whether a subject is responding to therapy with an autophagy modulator (autostatin) suffers from, or is at risk of developing a disease or condition which is an autophagy-mediated disease or condition, the method comprising measuring LC3 levels in a blood sample of the patient or subject, measuring the LC3 levels in said sample and comparing the LC3 levels with a control, wherein a measurement of LC3 levels in said sample which is higher or lower than the control (the control may be derived from a sample of tissue from healthy, disease-free individuals or individuals known to have a disease state or condition being identified) is evidence of the likelihood of the existence of said disease state or condition in said tissue of said patient. It unexpectedly has been discovered that LC3 polypeptide is expressed on blood cells, in particular, mononuclear cells This discovery makes analysis readily amenable to immunohistochemistry, immunostaining, immunofluorescence and western blot assay. Also, the method can use monoclonal or polyclonal antibodies. In one embodiment, the assay is a sandwich assay for point of care or home use.

In another embodiment, the present disclosure provides a clinically usable assay that can be applied for diagnostics and monitoring the progression of therapy of an autophagy mediated disease using an easy to obtain blood sample from a patient or subject. It is based upon the unexpected discovery that LC3 polypeptides are expressed on the surface of blood cells, in particular, peripheral blood mononuclear cells (PBMC) in particular, primary lymphocytes. Counterintuitively, given the engagement of autophagy and intracellular membranes, the expectation is that LC3 polypeptides are found exclusively intracellularly, yet, it has been discovered by the present inventor that LC3 as an autophagy marker can be detected on the surface of cells, in particular primary lymphocytes. The inventors find surprisingly that LC3 polypeptide (which has heretofore been found only on intracellular membranes detectable by complicated methods of microscopy) is detected by simple antibody staining on the cell surface of primary lymphocytes using antibodies and flow cytometry or other simple assays of detection, including antibody assays such as an ELISA assay. This makes the quantification of LC3 in blood/plasma samples of patients relatively facile. This information (i.e., the relative level of LC3 expressed in the blood of a patient) is useful for diagnosis, prognosis and monitoring of the effective of therapy of disease states and/or conditions which are mediated through authophagy.

Based on prior art understanding regarding autophagy, one could not predict that LC3 polypeptide, including LC3B, would be exposed on the surface of the plasma membrane of the cell, such as a blood lymphocyte and be amenable to identification with surface based assays, including antibody-based assays or flow cytometry. This is due to the accepted topology of the LC3 distribution on the intracellular membranes. According to prior art convention, even if the intracellular membranes were to fuse with the plasma membrane (PM), LC3 would not be exposed to the outside (the surface of the cell); according to conventional understanding, LC3 would always be shielded from the exposure to the outside and not accessible to antibodies, unless the cells were permeabilized). In one embodiment, in the present invention, it has been discovered unexpectedly that LC3 is exposed on the external cell surface (i.e., on the external side of the plasma membrane facing the outside of the cell, rather than the inside surface) and thus is accessible to the exogenously added antibody to recognize LC3. In one embodiment, the assay method takes advantage of this discovery and can conduct assays of LC3 in blood samples of cells quickly, accurately and without permeabilization of the cell (which can lead to inaccuracies). In this method, LC3 in a blood sample, including a plasma sample, is quantified and compared to a control or standard. The results can be used to evidence the existence or absence of an autophagy mediated disease state or condition, provide an indication of the prognosis of treating a disease state (for example, by comparing the results to a control which is obtained from a population of patients or subjects who have had favorable or unfavorable therapeutic results) or monitor therapy of an autophagy-mediated disease state with an autophagy modulator (autostatin) over a period of therapeutic intervention. This discovery makes analysis readily amenable to immunohistochemistry, immunostaining, immunofluorescence and western blot assay. Also, the method can use monoclonal or polyclonal antibodies, including especially in a sandwich assay in point of care facilities and/or home use.

Pursuant to this embodiment, blood from patients or subjects can be drawn, and white blood cells (or more specifically different mononuclear cell populations, e.g. primary lymphocytes including CD4 and CD8 cells and their subsets) untreated or exposed to starvation in a buffer (simple PBS or EBSS) for a period of time (between 10 minutes and several hours, often about an hour to an hour and a half) and LC3 is detected on the surface preferably by antibody staining (the antibody preferably being conjugated to a reporter moiety which provides a fluorescent or other signal which can be readily observed and optionally, quantitated) without specifically permeabilizing the cells. Alternatively, in the assay method described above, the amount of LC3 can be determined by a variety of techniques, including immunohistochemistry, immunostaining, immunofluorescence and western blot assay. Also, the method can use monoclonal or polyclonal antibodies. In certain embodiments, the assay is a sandwich assay, an ELISA assay or other antibody based assay, including a fluorometric and/or colorimetric assay which can be used at point of care facilities or at home.

Thus, the discovery related to external cell surface expressed LC3 forms the basis for one or more of the following: (i) clinical tests for patients (blood drawing and staining for LC3 on lymphocytes or whole white blood cells), (b) biomarkers in clinical studies (same as above), including providing a prognosis for therapy with a particular autostatin for a particular autophagy-mediated disease state or condition, (iii) drug screening and development of approaches for the induction and/or inhibition of autophagy, and (iv) a target for treatment with blocking antibodies should LC3 on the cell surface show biological functions. Additional information may be found in the present specification as described in detail herein. This discovery makes analysis is readily amenable to immunohistochemistry, immunostaining, immunofluorescence and western blot assay. Also, the method can use monoclonal or polyclonal antibodies.

In one embodiment, the invention provides a method for identifying the existence of compounds which exhibit activity consistent with modulation of autophagy such that the compounds may be useful in treating disease states or conditions which are mediated through autophagy. In this embodiment of the invention, the method comprises exposing cells expressing LC3 to one or more compounds, including a library of compounds, and determining whether a compound or compounds bind to LC3 wherein a compound which binds to LC3 is a potential modulator of LC3. In an alternative embodiment, the assay comprises determining whether the compound is an inhibitor or agonist of LC3 and therefore autophagy, for example, by determining whether the compound induces or inhibits the formation of LC3 puncta (as evidenced by the signal provided by a fluorescent reporter such as green fluorescent green protein/FGP or red fluorescent protein/FRP as described in greater detail in the examples herein), wherein a compound which induces the formation of LC3 punta is evidence that a tested compound is a potential therapeutic compound as a modulator (in this case, an agonist) of autophagy and a compound which inhibits the formation of LC3 punta is evidence that a tested compound is a potential therapeutic compound as a modulator (in this case, an antagonist) of autophagy. Once identified and further tested, the compounds may be used as therapeutic agents in the treatment of disease states and/or conditions which are mediated through an autophagy mechanism as otherwise described herein. In the assay method described above, the amount of LC3 can be determined by a variety of techniques, including immunohistochemistry, immunostaining, immunofluorescence and western blot assay. Also, the method can use monoclonal or polyclonal antibodies.

The present invention also relates to compounds which have been identified as modulators of autophagy (autostatins) which can be used for the treatment of an autophagy mediated disease state or condition. Thus, the present invention is also directed to pharmaceutical compositions which comprise an effective amount of at least one compound identified as an autophagy modulator in the assay described above, optionally in combination with a pharmaceutically acceptable carrier, additive or excipient and further optionally, at least one additional bioactive agent. Such disease states or conditions, include, for example, cancer, including metastasis of cancer, lysosomal storage diseases (discussed in detail hereinbelow), neurodegeneration (including, for example, Alzheimer's disease, Parkinson's disease; other ataxias), immune response, chronic inflammatory diseases, including inflammatory bowel disease, including Crohn's disease, rheumatoid arthritis, lupus, multiple sclerosis, chronic obstructive pulmonary disease/COPD, pulmonary fibrosis, cystic fibrosis, Sjogren's disease; diabetes (I and II) and metabolic syndrome, liver disease, renal disease (including glomerular disease), cardiovascular disease (especially including ischemia, stroke, pressure overload and complications during reperfusion), muscle degeneration and atrophy, symptoms of aging (including amelioration or the delay in onset or severity or frequency of aging-related symptoms and chronic conditions including muscle atrophy, frailty, metabolic disorders, low grade inflammation, atherosclerosis and associated conditions such as cardiac and neurological both central and peripheral manifestations including stroke, age-associated dementia and sporadic form of Alzheimer's disease, pre-cancerous states, and psychiatric conditions including depression.), stroke and spinal cord injury, arteriosclerosis, infectious diseases (microbial infections, including bacterial, fungal, cellular, viral (including influenza, herpes virus, HIV, HBV and HCV, among others) and parasitic infections, including protozoal and helminthic, including secondary disease states or conditions associated with infectious diseases), including AIDS and tuberculosis, among others, including in periodontal disease, development, both overly mature and immature development (including erythrocyte differentiation), embryogenesis/fertility and ageing/progeria. The common principle of this embodiment of the invention is that compounds, including autostatins which are modulators (i.e., inhibitors or activators) of autophagy (depending upon the disease) may be used alone or in combination with other agents, including other agents in a cocktail for the treatment of the disease state and/or condition which is mediated through autophagy.

In still other aspects of the invention, in one embodiment, the invention provides a method of determining whether a subject suffers from, or is at risk of developing tuberculosis as defined hereinafter, including *M. tuberculosis*, the method comprising determining a caspase-1 level in a sample obtained from the subject and comparing the determined caspase-1 level to a control caspase-1 level (from a sample of one or more healthy patients without tuberculosis or a sample of wherein an increase or decrease in caspase-1 level indicates an increased likelihood that the subject suffers from or is at risk of developing tuberculosis. For example, this method can comprise the steps of:

(a) contacting a biological test sample obtained from the subject with an antibody or an antigen binding fragment thereof having specific binding affinity for caspase-1, under conditions such that a complex can form between caspase-1 and the antibody or the antigen binding fragment thereof;

(b) measuring the amount of said complex, thereby determining the amount of caspase-1 in said biological test sample; and (c) comparing the amount of caspase-1 in said biological test sample to a standard or control sample;

wherein an increased amount of caspase-1 in said biological test sample relative to the standard or control sample is indicative of tuberculosis in said test sample.

The amount of caspase-1 in a biological sample can be determined by a variety of techniques, including immunohistochemistry, immunostaining, immunofluorescence and western blot assay. Antibodies used in the methods of the invention can be monoclonal or polyclonal antibodies.

In another embodiment, the invention provides a method of determining whether a subject suffers from, or is at risk of developing an inflammation-associated metabolic disorder as defined hereinafter, the method comprising determining the level of one or more autophagy-related immunomodulatory cytokines, alarmins or their regulators in a sample obtained from the subject and comparing determined autophagy-related immunomodulatory cytokine levels to control autophagy-related immunomodulatory cytokine levels, wherein a decrease in autophagy-related immunomodulatory cytokine levels indicates an increased likelihood that the subject suffers from or is at risk of developing an inflammation-associated metabolic disorder. For example, this method can comprise the steps of:

(a) contacting a biological test sample obtained from the subject with an antibody or an antigen binding fragment thereof having specific binding affinity for an autophagy-related immunomodulatory cytokine as defined hereinafter, under conditions such that a complex can form between the autophagy-related immunomodulatory cytokine and the antibody or the antigen binding fragment thereof;

(b) measuring the amount of said complex, thereby determining the amount of autophagy-related immunomodulatory cytokine in said biological test sample; and (c) comparing the amount of autophagy-related immunomodulatory cytokine in said biological test sample to a standard or control sample;

wherein a decreased amount of autophagy-related immunomodulatory cytokine in said biological test sample relative to the standard or control sample is indicative of an inflammation-associated metabolic disorder in said test sample. This assay may be used alone or in combination with other assays in order to identify a particular disease state or condition to be treated.

In the assay method described above, the amount of autophagy-related immunomodulatory cytokine can be determined by a variety of techniques, including immunohistochemistry, immunostaining, immunofluorescence and western blot assay. Also, the method can use monoclonal or polyclonal antibodies.

In a preferred embodiment of the method described above:

(1) the inflammation-associated metabolic disorder is selected from the group consisting of a hyperglycemic disorder (e.g. Type I and Type II diabetes, severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), and elevated triglycerides);

(2) the autophagy-related immunomodulatory cytokine is selected from the group consisting of IL-1α, IL-1β, IL-18, IL-12 p40 subunit, IL-4, IL13, LMP1, EBNA2, IFN-γ, ATG16L1, IRGM1, LC3B-II, HMGB1, TBK-1, GRASP-55 and GRASP-65, exocyst components regulating secretion of the said cytokines and alarmins and mixtures thereof and (3) the method is conducted in a high-throughput, high-content imaging format as described hereinafter.

In still another embodiment, the invention provides a method of screening for a composition useful in the treatment of tuberculosis (e.g. *M. tuberculosis*), the method comprising contacting a sample of a tuberculosis-infected lung cell population with a candidate composition and determining the extent to which the candidate composition down-regulates translation of caspase-1, wherein the candidate composition is identified as being potentially useful in the treatment of tuberculosis if translation levels of caspase-1 in the sample are less than the comparable control values for an untreated tuberculosis-infected lung cell population. For example, this method can comprise the steps of:

(a) contacting a first sample of a tuberculosis-infected lung cell population with a candidate composition;

(b) determining one or more values representing the extent to which the candidate composition down-regulates translation of caspase-1 in the first sample; and (c) comparing the determined one or more values to control values based on translation levels of caspase-1 in a second, untreated sample of the cell population, wherein the candidate composition is identified as being potentially useful in the treatment of tuberculosis if translation levels of caspase-1 in the first sample are less than the comparable control values in the second sample.

In still another embodiment, the invention provides method of screening for a composition useful in the treatment of an inflammation-associated metabolic disorder, the method comprising contacting a sample of a cell population evidencing a inflammation-associated metabolic disorder morphology with a candidate composition and determining the extent to which the candidate composition up-regulates translation of one or more autophagy-related immunomodulatory cytokines, wherein the candidate composition is identified as being potentially useful in the treatment of an inflammation-associated metabolic disorder if translation levels of the one or more autophagy-related immunomodulatory cytokines in the sample are less than the comparable control values for an untreated sample of the cell population. For example, this method can comprise the steps of:

(a) contacting a first sample of a cell population evidencing an inflammation-associated metabolic disorder morphology with a candidate composition;

(b) determining one or more values representing the extent to which the candidate composition down-regulates translation of one or more autophagy-related immunomodulatory cytokines in the first sample; and (c) comparing the determined one or more values to control values based on translation levels of one or more autophagy-related immunomodulatory cytokines in a second, untreated sample of the cell population, wherein the candidate composition is identified as being potentially useful in the treatment of an inflammation-associated metabolic disorder if translation levels of one or more autophagy-related immunomodulatory cytokines in the first sample are greater than the comparable control values in the second sample.

In still another embodiment, the invention provides method of determining whether a subject suffers from, or is at risk of developing an inflammation-associated metabolic disorder, the method comprising:

(a) contacting a biological test sample obtained from the subject with an antibody or an antigen binding fragment thereof having specific binding affinity for LC3B-I or LC3B-II, under conditions such that a complex can form between the autophagy-related immunomodulatory cytokine and the antibody or the antigen binding fragment thereof;

(b) measuring the amount of said complex, thereby determining the amount of LC3B-I or LC3B-II in said biological test sample; and (c) comparing the amount of LC3B-I or LC3B-II in said biological test sample to a standard or control sample;

wherein a difference in the amount of LC3B-I or LC3B-II in said biological test sample relative to the standard or control sample is indicative of an inflammation-associated metabolic disorder in said test sample. In this method, the biological test sample preferably is a sample of white blood cells and the antibody is a purified monoclonal antibody (e.g. LC3B (D11) XP® Rabbit mAb #3868 from Cell Signalling Technology, Inc., Danvers, Mass., USA), and wherein the antibody fragment is a fragment of such antibody. Also, the antibody or fragment thereof may also be used.

In still another embodiment, the invention provides a method of determining whether a subject suffers from, or is at risk of developing tuberculosis (e.g. *M. tuberculosis*), the method comprising determining TBK-1 levels in a sample obtained from the subject and comparing determined TBK-1 levels to control TBK-1 levels, wherein a decrease in TBK-1 levels indicates an increased likelihood that the subject suffers from or is at risk of developing tuberculosis (e.g. *M. tuberculosis*). For example, this method can comprise the steps of:

(a) contacting a biological test sample obtained from the subject with an antibody or an antigen binding fragment thereof having specific binding affinity for TBK-1, under conditions such that a complex can form between TBK-1 and the antibody or the antigen binding fragment thereof;

(b) measuring the amount of said complex, thereby determining the amount of TBK-1 in said biological test sample; and (c) comparing the amount of TBK-1 in said biological test sample to a standard or control sample;

wherein a decreased amount of TBK-1 in said biological test sample relative to the standard or control sample is indicative of tuberculosis in said test sample.

In the method described above, the amount of TBK-1 can be determined by a variety of techniques, including immunohistochemistry, immunostaining, immunofluorescence and western blot assay and the antibody can be a monoclonal or polyclonal antibody.

In still another embodiment, the invention provides method of screening for a composition useful in the treatment of tuberculosis (e.g. *M. tuberculosis*), the method comprising contacting a sample of a tuberculosis-infected lung cell population with a candidate composition and determining the extent to which the candidate composition up-regulates translation of TBK-1, wherein the candidate composition is identified as being potentially useful in the treatment of tuberculosis if translation levels of TBK-1 in the sample are greater than the comparable control values for an untreated tuberculosis-infected lung cell population. For example, this method can comprise the steps of:
(a) contacting a first sample of a tuberculosis-infected lung cell population with a candidate composition;
(b) determining one or more values representing the extent to which the candidate composition up-regulates translation of TBK-1 in the first sample; and
(c) comparing the determined one or more values to control values based on translation levels of TBK-1 in a second, untreated sample of the cell population, wherein the candidate composition is identified as being potentially useful in the treatment of tuberculosis if translation levels of TBK-1 in the first sample are greater than the comparable control values in the second sample.

In still another embodiment, the invention provides a method of screening a composition for an autophagy-associated effect on cytoplasmic puncta of either (1) tuberculosis-infected lung cells, or (2) cells implicated in a lipid-related metabolic disorder, the method comprising:
(a) culturing a sample of the cells;
(b) plating the cell sample on multi-well plates;
(c) contacting the cell sample with the composition; and
(d) using high-content imaging to examine the cell sample for an autophagy-associated effect on cytoplasmic puncta, wherein the method is conducted using a high-throughput format.

In a preferred embodiment of the high-content imaging method described above (any embodiment, especially including those embodiments related to identifying autostatins as otherwise described herein), the multi-well plates are 384-well plates, the cells are transfected with RFP-LC3 or GFP-LC3 prior to plating, the cytoplasmic puncta are RFP-LC3 puncta or GFP-LC3 puncta, and the composition is selected from a chemical library such as Prestwick chemical library or the Torrey Pines Institute library. In another preferred embodiment, this method includes comparing the autophagy-associated effect on cytoplasmic puncta in cell samples that have been contacted with the composition and the morphology of positive control cell samples that have been contacted with either pp242, rapamycin or other mTor inhibitor as described herein, or that have been starved.

In still another embodiment, the invention provides a method of treating a subject who has been infected with tuberculosis (e.g. *M. tuberculosis*) or who is at risk of such infection, the method comprising administering to the subject a pharmaceutically effective amount of a caspase-1 inhibitor as defined hereinafter.

In still another embodiment, the invention provides a method of treating a subject who suffers from an inflammation-associated metabolic disorder or who is at risk of developing such a disorder, the method comprising administering to the subject a pharmaceutically effective amount of a TBK-1 agonist as defined hereinafter.

In still another embodiment, the invention provides a method of treating a subject who has been infected with tuberculosis (e.g. *M. tuberculosis*) or who is at risk of such infection, the method comprising administering to the subject a pharmaceutically effective amount of a TBK-1 agonist (e.g. a vascular disrupting agent (VDA) such as lavone acetic acid and its derivatives, e.g., 5,6-dimethylxanthenone-4-acetic acid (DMXAA)).

In still another embodiment, the invention provides a kit comprising:
(a) at least one reagent which is selected from the group consisting of (i) reagents that detect a transcription product of the gene coding for a TBK-1 protein marker or autophagy-related immunomodulatory cytokine as described herein (ii) reagents that detect a translation product of the gene coding for TBK-1 or an autophagy-related immunomodulatory cytokine, and/or reagents that detect a fragment or derivative or variant of said transcription or translation product;
(b) instructions for diagnosing, or prognosticating either an infection by tuberculosis (e.g. *M. tuberculosis*) or the presence of an inflammation-associated metabolic disorder, or determining the propensity or predisposition of a subject to develop either tuberculosis (e.g. *M. tuberculosis*) or an inflammation-associated metabolic disorder or of monitoring the effect of a treatment of a tuberculosis (e.g. *M. tuberculosis*)-related infection or an inflammation-associated metabolic disorder.

In still another embodiment, the invention provides a kit comprising:
(a) at least one reagent which is selected from the group consisting of (i) reagents that detect a transcription product of the gene coding for caspase-1 marker or an autophagy-related immunomodulatory cytokine as described herein (ii) reagents that detect a translation product of the gene coding for caspase-1 or an autophagy-related immunomodulatory cytokine, and/or reagents that detect a fragment or derivative or variant of said transcription or translation product;
(b) instructions for diagnosing, or prognosticating either an autophagy-related immunomodulatory cytokine or infection by tuberculosis (e.g. *M. tuberculosis*), or determining the propensity or predisposition of a subject to develop an autophagy-related immunomodulatory cytokine or to contract a tuberculosis (e.g. *M. tuberculosis*)-associated infection or of monitoring the effect of a treatment of a tuberculosis (e.g. *M. tuberculosis*)-associated infection.

In still another embodiment, the invention provides a pharmaceutical composition comprising:
(a) an autophagy-related immunomodulatory cytokine antagonist; and optionally
(b) a pharmaceutically-acceptable excipient.

In still another embodiment, the invention provides a pharmaceutical composition comprising:
(a) an autophagy-related immunomodulatory cytokine agonist; and optionally
(b) a pharmaceutically-acceptable excipient.

In still another embodiment, the invention provides a pharmaceutical composition comprising:
(a) a caspase-1 or TBK-1 antagonist; and optionally
(b) a pharmaceutically-acceptable excipient.

The autophagy-related methods disclosed herein therefore provide versatile approaches to the diagnosis and treatment of a wide variety of diseases that to date have remained difficult to identify and treat. These and other aspects of the invention are explained further in the Detailed Description of the Invention.

BRIEF DESCRIPTION OF THE FIGURES

Figures for Example 1

(A) Weight loss in Atg5$^{fl/fl}$ LysM-Cre+ and Atg5$^{fl/fl}$ LysM-Cre− mice infected with *M. tuberculosis* H37Rv ($e^3$ dose; see Suppl. Table 1). (B) Gross lung pathology ($e^3$ dose). (C) Lung histological sections ($e^3$ dose, day 36). Panels: i-iv, H&E stain (arrows, necrotic lesions); v and vi, acid-fast staining (arrows, bacilli; insets enlarged area). (D) Survival of Atg5$^{fl/fl}$ LysM-Cre+ and Atg5$^{fl/fl}$ LysM-Cre− mice infected with *M. tuberculosis* H37Rv (e4 dose). (E) Weight loss in Atg5$^{fl/fl}$ LysMCre+ and Atg5$^{fl/fl}$ LysM-Cre− mice infected with *M. tuberculosis* H37Rv (e4 dose). Data, means±SE, **p<0.01 (t test). Mouse survival statistics: Kaplan-Meier survival analysis with the Log-Rank method.

Figure 2:
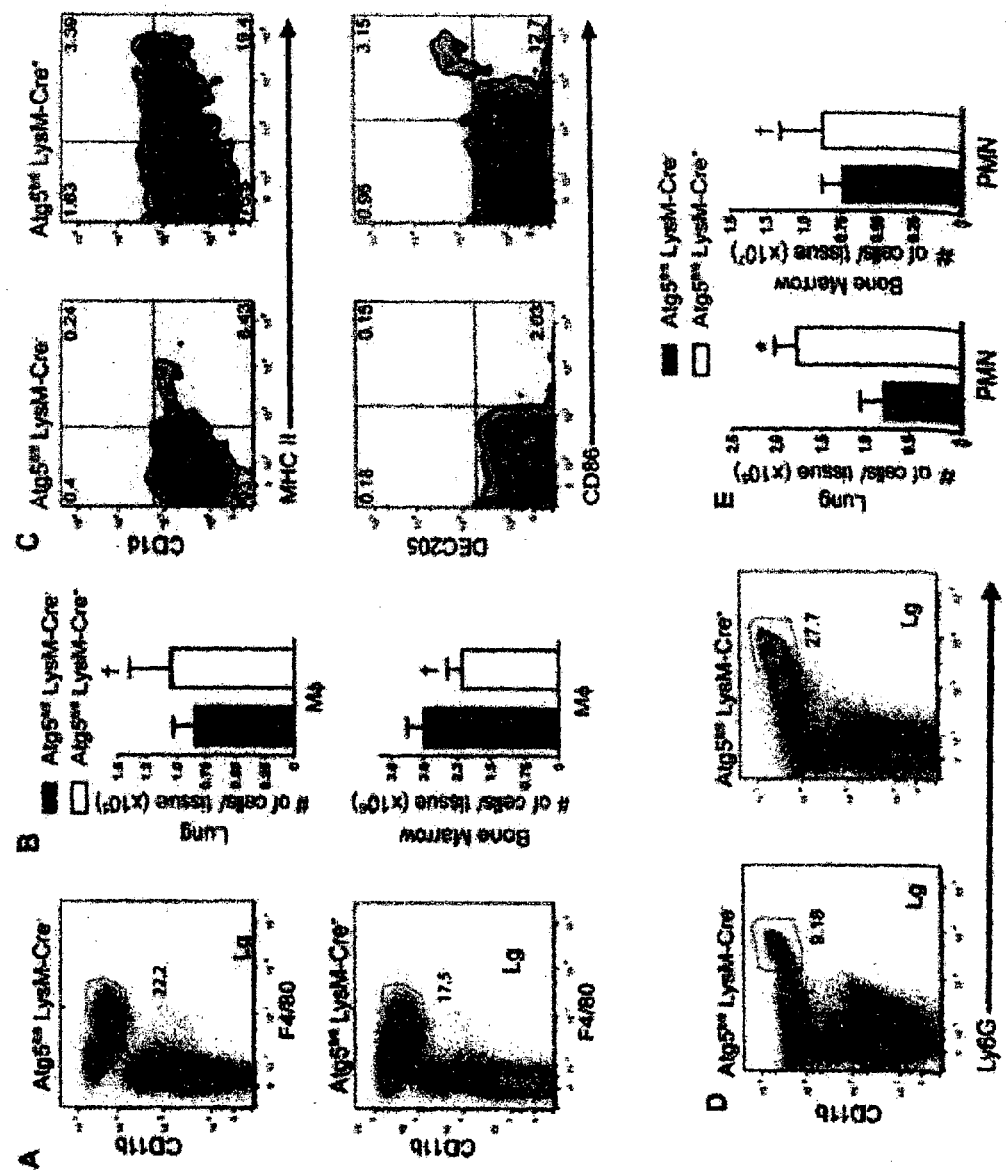

FIG. 2. Intrinsically Activated Phenotype of Lung Macrophages and Neutrophilic Infiltration in Uninfected Atg5fl/fl LysM-Cre+ Mice.

(A, B) Flow cytometric quantification of macrophages per organ tissues in uninfected Atg5$^{fl/fl}$ LysM-Cre+ and Atg5$^{fl/fl}$ LysM-Cre− mice. (C) Activation state of macrophages measured by surface markers CD1d, MHC II, DEC205 and CD86 in the lungs of uninfected Atg5$^{fl/fl}$ LysM-Cre− (left plots) and Atg5$^{fl/fl}$ LysM-Cre+ mice (right plots). (D, E) PMN quantification in the lungs and bone marrow of uninfected Atg5fl/fl LysM-Cre+ and Atg5$^{fl/fl}$ LysM-Cre− mice. Data, means±SE, n≥3, *p<0.05, †>0.05 (t test).

Figure 3:
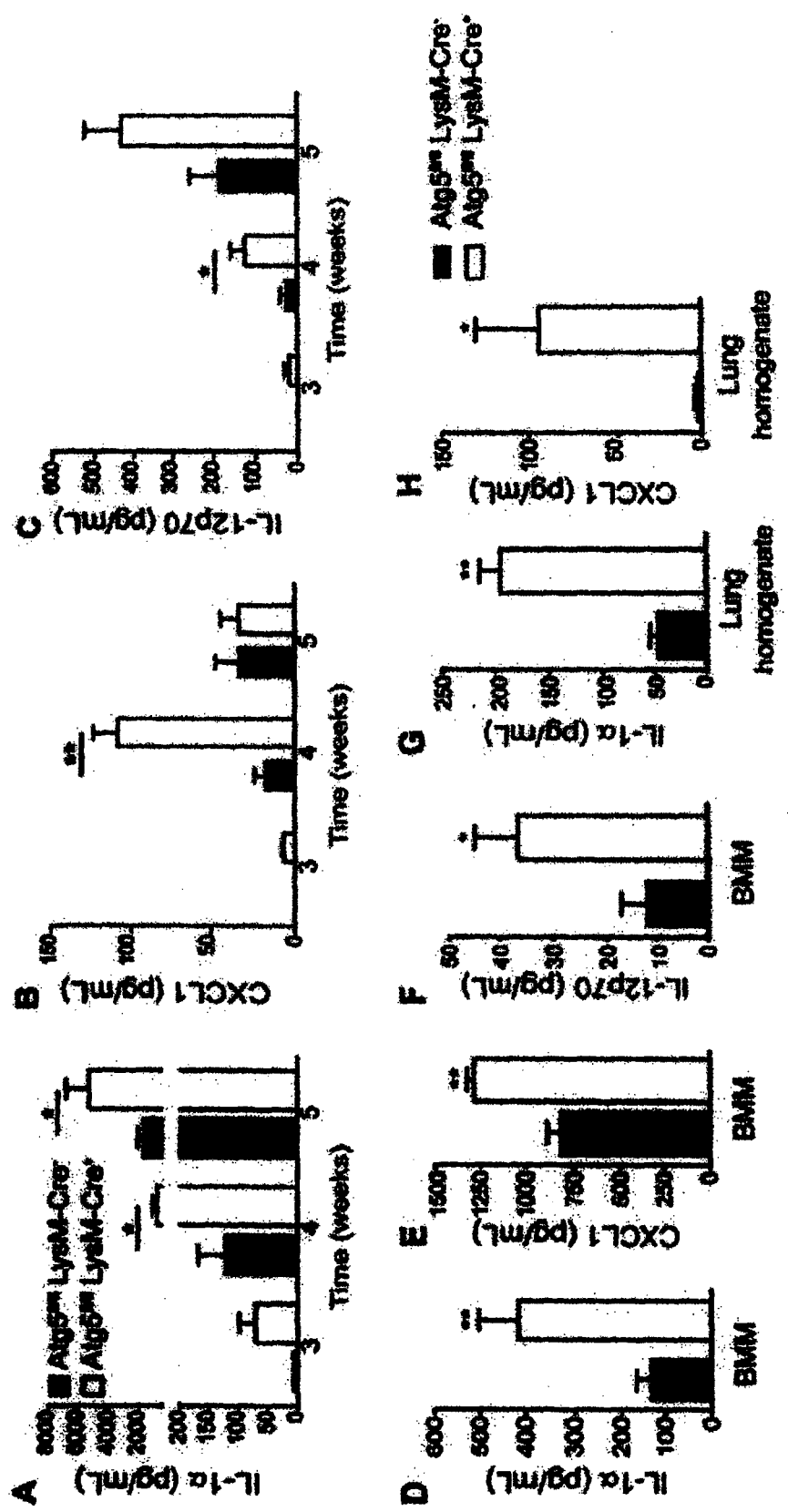

FIG. 3. Excess Cytokine Secretion is a Cell-Autonomous Property of Autophagy-Deficient Macrophages.

(A-C) Multiplex cytokine detection by Luminex in the lungs of *M. tuberculosis* H37Rv infected Atg5$^{fl/fl}$ LysM-Cre+ and Cre− mice (e2 dose, 102 CFU); shown: IL-1α, CXCL1, and IL-12p70 (see Suppl. FIG. S3 for additional cytokines). (D-F) In vitro cytokine (IL-1α, CXCL1, and IL-12p70) release (ELISA) from LPS+IFN-γ-stimulated Atg5$^{fl/fl}$ LysM-Cre+ and Cre− bone marrow-derived macrophages (BMM). (G,H) IL-1α and CXCL1 levels (ELISA) in lung homogenates of uninfected Atg5fl/fl LysM-Cre+ and Cre− mice. Data, means±SE, n≥3, *p<0.05, **p<0.01 (t test).

Figure 4:
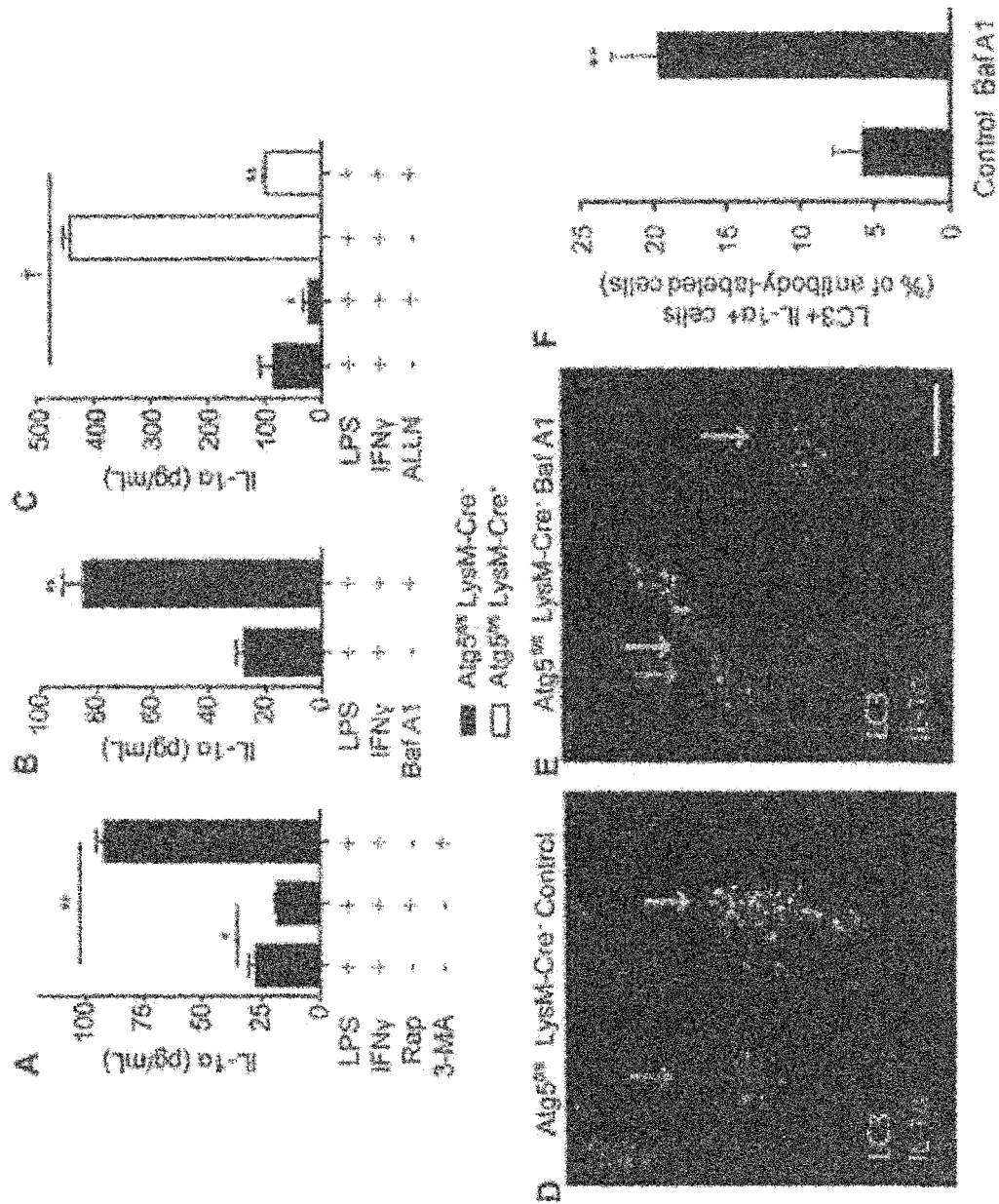

FIG. 4. Autophagy Regulates IL-1α Release.

(A,B) IL-1α (ELISA) released from LPS+IFN-γ stimulated Atg5$^{fl/fl}$ LysM-Cre+ and Atg5$^{fl/fl}$ LysM-Cre− BMM in the presence of 50 µg/ml rapamycin (Rap), 10 mM 3-MA, or 100 nM Bafilomycin A1 (Baf A1) after 12 h of stimulation. (C) IL-1α (ELISA) in culture supernatants of cells as in A, treated with calpain inhibitor, ALLN (100 µM). (D-F) Images and quantification of cells positive for LC3-only, IL-1α-only or LC3+IL-1α. Cells, wild type (Atg5+) BMM stimulated with LPS+IFN-γ and incubated for 90 min in EBSS in the absence (D, control) or presence (E, Baf A1) of bafilomycin A1. Cutoff for cells to be considered positive: >6 red or green puncta. Red arrowheads, IL-1α+ LC3− cells; green arrowheads, IL-1α− LC3+ cells; 10 µm. Data, means±SE; n≥3; *p<0.05, **p<0.01, †>0.05 (t test).

Figure 5:
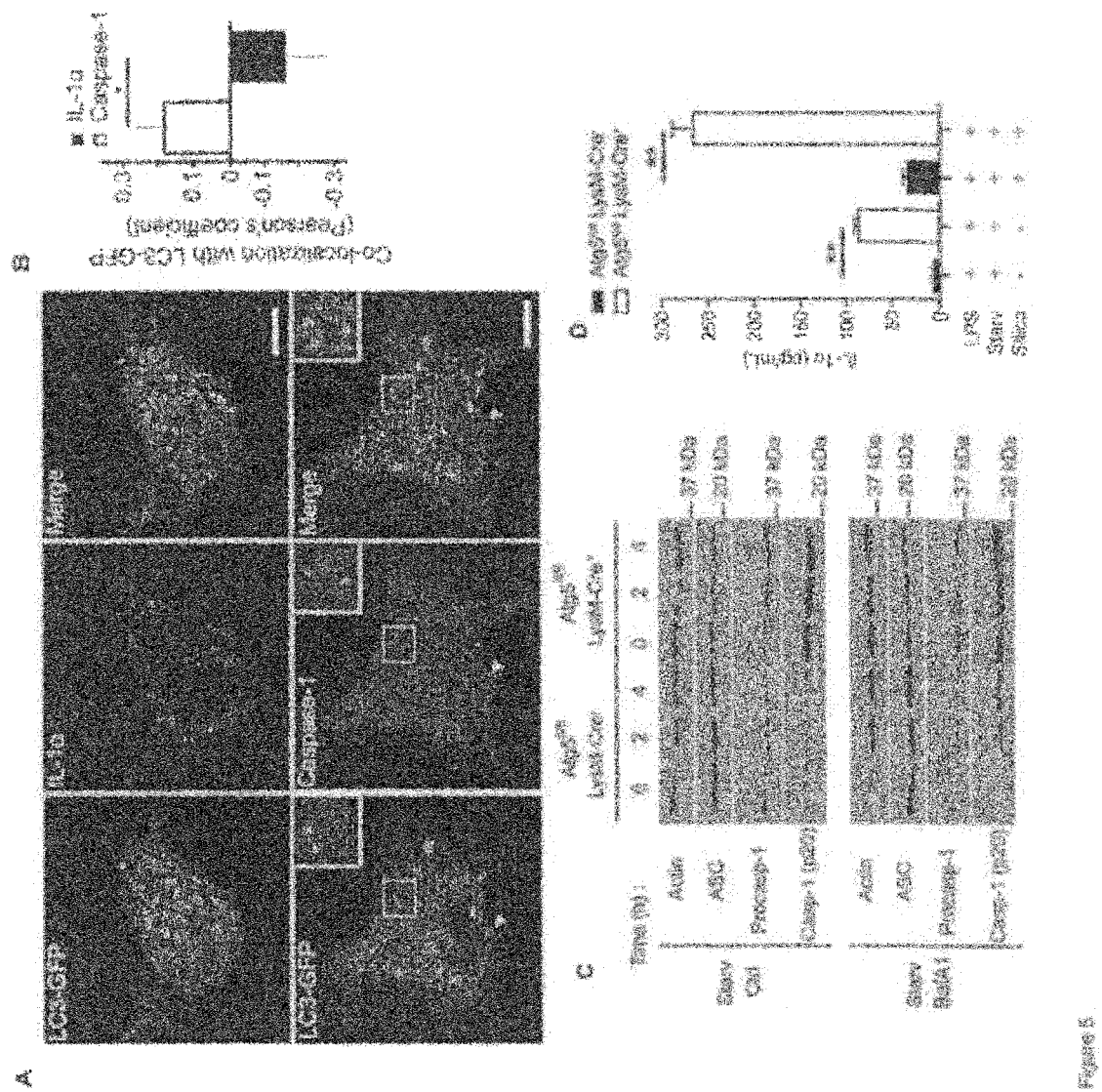

FIG. 5. Active Caspase-1 is a Target for Autophagy.

(A) Confocal microcopy analysis of caspase-1 colocalization relative to LC3 in GFP-LC3 expressing BMM induced for autophagy by starvation (EBSS) in the presence of bafilomycin A1 for 90 minutes. Scale bar, 5 µM; Arrowheads and insets, LC3+ caspase-1+ positive profiles (colocalization). (B) Pearson's colocalization coefficient for caspase-1 vs. LC3 and IL-1α vs. LC3. (C) Caspase-1 accumulation in Atg5$^{fl/fl}$ LysM-Cre− or Atg5$^{fl/fl}$ LysM-Cre+ BMM induced for autophagy in EBSS with or without bafilomycin A1 (BafA1) and subjected to Western blot analysis. (D) IL-1α (culture supernatant ELISA) released from Atg5fl/fl LysM-Cre+ and Atg5fl/fl LysM-Cre− BMM incubated overnight with 100 ng/ml LPS and exposed for 1 h to inflammasome agonist silica (250 µg/ml) in EBSS. Data, means±SE, n≥3; **p<0.01 (t test).

Figure 6:
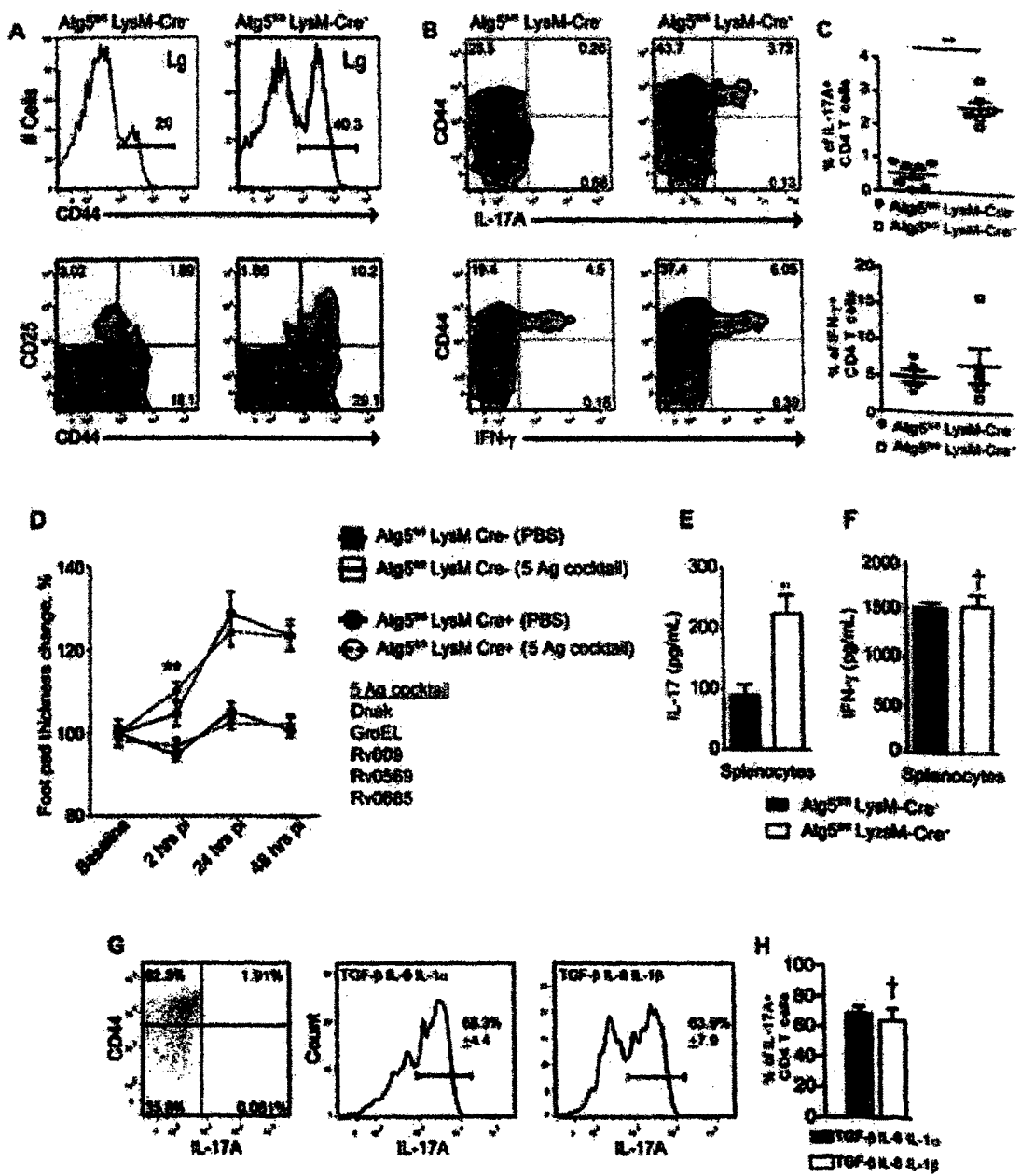

FIG. 6. IL-17 Phenotype in CD4 T Cells from Atg5fl/fl LysM-Cre+ Mice.

(A) CD44 and CD25 expression on CD4 T cells from lungs of uninfected Atg5$^{fl/fl}$ LysM-Cre+ and Atg5$^{fl/fl}$ LysM-Cre− mice. (B,C) Intracellular levels of IL-17A (top panel) and IFN-γ (bottom panel) in CD4 T cells isolated from lungs of uninfected Atg5$^{fl/fl}$ LysM-Cre+ and Cre− mice and stimulated with phorbol 12-myristate 13-acetate and ionomycin ex vivo in the presence of brefeldin A and monensin. (D) DTH reaction (footpad induration) in BCG-infected Atg5$^{fl/fl}$ LysM-Cre+ and Atg5$^{fl/fl}$ LysM-Cre− mice footpad-injected with the synthetic PPD at day 21 postinfection. Data, percent change (footpad thickness) upon challenge with the synthetic PPD relative to the contralateral PBS-challenged footpad. (E,F) Cytokine production (IL-17A and IFN-γ; ELISA) by splenocytes from Atg5$^{fl/fl}$ LysM-Cre+ and Atg5$^{fl/fl}$ LysM-Cre− mice (day 23 post-infection with BCG) re-stimulated for 3 days ex vivo with the synthetic PPD. (G) Intracellular IL-17A production (day 4; release blocked with monensin) by naïve CD4 T cells polarized in the presence of cytokine cocktails: 5 ng/ml TGF-β and 20 ng/ml IL-6, plus 20 ng/ml IL-1α or 20 ng/ml IL-1β. Dot plot, levels of IL-17A in unstimulated cells (starting material). Histograms, IL-17A in naïve CD4 T cells polarized in the presence of TGF-β, IL-6 and IL-1α or TGF-β, IL-6 and IL-1β. (H) Percent of IL-17A+ CD4 T cells under respective polarizing conditions. Data: means±SE; n≥3; **p<0.01; †, p>0.05 (t test).

FIG. 1T. Tabular summary of results of mouse tuberculosis experiment of Example 1.

FIGS. 1-6 (Supplementary). Pathology, immunoblotting, detection assay and flow cytometry results of mouse tuberculosis experiment of Example 1.

Figures for Example 2

FIG. 1X2. analysis of the complete set of murine rab and rab-like factors for effects on cell-autonomous autophagic elimination of *mycobacteria* and the role of Rab8b. A. Sixty-two Rab or Rab-like factors encoded by the *Mus musculus* genome were knocked down by siRNA in RAW264.7 macrophages (details and identity of each bar in Supple Table 1S), macrophages infected with *M. tuberculosis* var. Bovis BCG, autophagy induced by starvation (Starv), and autophagic killing of BCG quantified. Increase in BCG survival indicates decrease in autophagic killing. Scr, scrambled (control) siRNA. B-D. Effect of Rab8b knockdown on maturation of BCG phagosomes into autophagolysosomes. LTR, Lysotracker Red (acidotropic dye); CathD, cathepsin D. E-F. Validation of the role for Rab8b in autophagic killing of BCG. BCG survival, % of BCG CFU recovered from RAW 264.7 macrophages pretreated with siRNAs; si Scr, conrol scrabled siRNA; si Rab8b, Rab8bsiRNA; Full, full medium; Starve, autophagy induced by starvation. Data, means±se (n≥3; †, p≥0.05*, p<0.05; **, p<0.01; ANOVA).

FIG. 2X2. Role of TBK-1, a Rab8b downstream effector, in autophagic maturation. A. Rab8b effector cascade. Double headed arrows, protein interactions. Arrows, processes downstream of TBK-1 (autophagy connection established here). Htt, Huntingtin (normal, without expanded Glu repeats). B. Role of downstream effectors of Rab8b in autophagic killing of BCG. BCG survival, % of BCG CFU recovered from RAW 264.7 macrophages pretreated with siRNAs. Full, full medium (control conditions); si Scr, scrambled siRNA (control siRNA); Starve, autophagy induced by starvation; si TBK1, siRNA to TBK1. C. Effect of TBK-1 inhibitor BX795 on acidification of BCG-containing organelles following induction of autophagy. RAW 264.7 macrophages were pretreated with 10 nM BX795, infected, and induced for autophagy by starvation (Starve). D. Autophagic killing of BCG in RAW 264.7 macrophages pretreated with BX795. BCG survival, % CFU recovered from RAW 264.7 cells. E,F. RAW 264.7 expressing RFP-GFP-LC-3 and pretreated with scrambled or TBK-1 siRNAs were untreated (Full) or induced (Starv) for autophagy. Puncta; R+G+(RFP+GFP+), early autophagic organelles; R+G− (RFP+GFP−), late autophagic organelles. Images, merged red and green channels. G,H. Effects of TBK-1 on LC3-II levels and degradation during autophagic maturation. Tbk-1−/− and Tbk-1+/+ MEFs were uninduced and induced for autophagy, treated or not treated with bafilomycin A1 (BafA1) to inhibit autophagic degradation of LC3-II. Data, means±se (n≥3; †, p≥0.05*, p<0.05; **, p<0.01; ANOVA).

FIG. 3X2. IL-1β-induced autophagy eliminates intracellular *mycobacteria* in a process dependent on TBK-1. A. RAW264.7 macrophages were transiently transfected with EGFP-LC3 and treated with 10 ng/ml murine IL-1β for 2 h, and 27 assayed for LC3 puncta formation by confocal microscopy (only puncta≥1 μm were scored as positive). B. RAW264.7 macrophages transfected with mRFPGFP-LC3 tandem probe, treated with 10 ng/ml IL-1β for 2 h were scored for number (per transfected cell) of RFP+GFP+ puncta (R+G+; early autophagosomes), RFP+GFP− (R+G−; autolysosomes), and total LC3 puncta. C. Immunoblot analysis of endogenous LC3 conversion to lipidated form (LC3-II) in RAW 264.7 murine macrophages upon treatment with 10 ng/ml IL-1β for 2 h, in the absence or presence of bafilomycin A1. Graph, ratio of LC3-II to actin intensity in immunoblots from bafilomycin A1-treated samples. D. RAW264.7 murine macrophages were co-transfected with tandem mRFP-GFP-LC3 probe and expression constructs containing either wild-type MyD88 (MyD88-WT) or a dominant-negative mutant of MyD88 (MyD88-DN). Following stimulation with 10 ng/ml IL-1β for 2 h, LC3 puncta were quantified as in B. E. Induction of autophagy in response to IL-1β is abrogated in bone marrow-derived macrophages (BMM) from MyD88 knockout (MyD88−/−) mice, measured by ratios of LC3-II band relative to actin following treatments of BMMs and immunoblotting of cellular extracts. F. Proteolysis of stable proteins (radiolabeled by a pulsechase protocol) upon stimulation of RAW264.7 cells with 10 ng/ml IL-1β for 2 h (Full+IL-1β) relative to control (Full) or starvation-induced autophagy (Starve). G. Mycobacterial killing as a measure of autophagic endpoint is induced by IL-1β. RAW264.7 macrophages were knocked down for Atg7 (by Atg7 siRNA transfection 48 h prior to infection), infected with *M. tuberculosis* H37Rv for 1 h, washed and then left untreated or treated with 10 ng/ml recombinant murine IL-1b for 2 h after which they were lysed and plated for colony forming units determination, and survival expressed relative to sample transfected with control scrambled siRNA and not treated with IL-1β. Immunoblots, Atg7 knockdown and levels of Atg5-Atg12 complexes. Data, means±se, except in E where data are means±sd (n≥3; †, p≥0.05*, p<0.05; **, p<0.01; ANOVA).

FIG. 4X2. Requirement for TBK1 in IL-1β mediated autophagic killing of BCG. A. BCG survival, % CFU recovered from RAW264.7 macrophages pretreated with IL-1β with and without 10 nM BX795 treatment. B. BCG survival in infected RAW264.7 (and knocked down or not for TBK-1) macrophages stimulated with IL-1β.C-F. Requirement for TBK-1 in IL-1β induced autophagy. RAW264.7 macrophages were incubated in full medium (Control) or induced by adding IL-1β to full medium. Cells were pretreated with 10 nM BX795 where indicated. Macrophages were treated with or without bafilomycin A1 (BafA1) to inhibit autophagic degradation of LC3-II, and cellular extracts analyzed by immunoblotting. Graphs, densitometric analyses of LC3-II levels normalized to actin levels (LC3-II/Actin) were plotted. Data, means±se (n=3; †, p≥0.05; **, p<0.01; ANOVA).

FIG. 5X2. Rab8b and its downstream effector TBK-1 co-immunoprecipitate and colocalize with autophagic organelles. A.

HEK 293T cell extracts, transiently transfected with control (EGFP), GFP-Rab8b (Wt, wild type) and GFP-Rab8b Q67L (Q67L, constitutively active) expression constructs were immunoprecipitated with anti-GFP antibody; immunoblots for immune complexes and inputs were probed with anti-TBK-1 and anti-GFP antibodies. B. Colocalization of Rab8b and its downstream effector, TBK-1 with the basal autophagic machinery factor LC3. Fluorescence; endogenous TBK-1 (red, Alexa568), Rab8B (green, Alexa488), LC3 (blue, Alexa633). Cells (mouse primary bone marrow macrophages; BMM) were induced for autophagy by starvation in the presence of bafilomycin A1 to inhibit autophagic maturation and degradation. Arrows, colocalization of Rab8b, TBK-1, and LC3. C. Representative line tracing of three fluorescence channels in images in A. D. TBK-1 colocalization with the autophagic adaptor sequestosome 1/p62 and LC3. Cells (BMM), treatments, labels and graphs as in a and b. Arrows, colocalization of TBK-1, p62 and LC3. Cells (BMM) were induced for autophagy by starvation in the presence of bafilomycin A1 to inhibit autophagic maturation. E. Representative line tracing of fluorescence channels in images in C. Data, representative of ≥3 independent experiments.

FIG. 6X2. TBK-1 co-fractionates and colocalizes on intracellular membranous organelles with autophagic adaptors and machinery. Analysis by subcellular fractionation of the assembly of Rab8b-TBK-1 and autophagic machinery in resting cells or upon induction of autophagy (by starvation). RAW 264.7 macrophages uninduced (A) or induced (B) for autophagy were subjected to subcellular fractionation of organelles by isopycnic sucrose density gradient centrifugation. PNS, postnuclear supernatant. 1-4, pooled fractions. Rectangle over fraction 9, convergence in autophagic organelles (LC3-II) of: Rab8b, TBK-1, UVRAG (Beclin 1 interacting protein specific for autophagosomal maturation), and autophagic adapters p62 and NDP52. Refractive indexes below the lanes reflect sucrose density of each fraction. C. Images; endogenous UVRAG (Alexa568), endogenous TBK-1 (Alexa488). Cells, BMM, uninduced (Full) and induced (Starvation) for autophagy. D. Pearson's coefficient of TBK-1 and UVRAG colocalization. E. TBK-1 colocalization with autophagic adaptors in BMM. Images: endogenous TBK-1 (Alexa568; red), p62 (Alexa488; green), NDP52 (Alexa633; blue) and merged. Line tracing, analysis of colocalization of TBK-1 (red tracing), p62 (green tracing) and NDP52 (blue tracing). F,G. Pearson's colocalization coefficients for TBK-1-p62 and TBK-1-NDP52. Data, means±se (n=3, three independent experiments with at least 5 images analyzed per experiment; †, p≥0.05; **, p<0.01; ANOVA).

FIG. 7X2. TBK-1 controls p62 phosphorylation, and affects autophagic clearance of p62 and its cargo capture, delivery and degradation. A-C. High content imaging analysis (using Cellomics high-content microscopy system) of p62 puncta (endogenous, revealed by immunofluorescence) in BMM with or without treatment with TBK-1 inhibitor BX795. Panel A shows output from Cellomics high-content microscopy and analysis software comparing the number 29 of p62 puncta between TBK-1 inhibitor-treated (BX795) and control (DMSO) BMM. Vertical axis denotes the mean number of p62 puncta per cell and horizontal axis denotes the position of the well (B, BX795 series; C, control series)

on the plate. Between 754 and 2395 cells were analyzed per well. Panel C shows t test (data, means±se; **, p<0.01) from cumulative data treating only whole wells as independent samples (n=4). D. Effects of TBK1 pharmacological inhibitor, BX795 on p62 levels. Tbk-1+/+ MEFs were treated with BX795; bafilomycin A1 (BafA1) to inhibit autophagic degradation. Densitometric analyses of p62 levels normalized against actin levels were plotted (n=2; error bars, range). E. TBK-1 is necessary for efficient autophagic clearance of poly ubiquitinated proteins. Cell lysates from Tbk-1+/+ and Tbk-1−/− MEFs uninduced and induced for autophagy by starvation were incubated with TUBE2 agarose beads and bound material pulled down. Western blots were probed for K63 polyubiquitin chains. F-H. Identification of TBK-1-dependent S403 phosphorylation of the UBA domain of p62. In vivo phosphorylation of p62 UBA domain following cotransfection of GFP-p62D69A (D69A mutation prevents oligomerization with endogenous p62) and expression constructs of TBK-1 wild type or kinase defective form. Immunoprecipitated (GFP-p62) material was subjected to tandem mass spectrometry. A triply charged ion with the mass 857.01 was selected for fragmentation. This ion was identified as the phosphorylated LIESLSQMLpSMGFSDEGG-WLTR peptide (shown in panel H) from p62. Panel G shows MS spectra from LC-MS, showing the phosphopeptide of 857.01 m/z observed in p62 phosphorylated by TBK1. The peptide was not observed when GFP-p62 was co-transfected with the kinase-defective K38D mutant of TBK1. Spectra are taken from the same retention time in both runs, confirmed by the unspecific peaks observed in both spectra. I. HEK293 cells transfected with vector control, myc-TBK-1 or myc-TBK-1 K38D were left untreated or were treated for 2 h with 1 μm BX795. Cell extracts were immunoblotted with antibodies against phospho-p62 (S403), p62, myc and actin. Abbreviations: end. p62, endogenous p62. J. MBP or MBP-tagged p62 proteins were expressed and affinity-purified from *E. coli*. TBK-1 mediated phosphorylation was assessed by incubating recombinant MBP, MBP-p62 or MBP-p62 S403A with recombinant active TBK-1 in the presence of [γ-32P] ATP for 10 min at 30° C. The reaction products were analyzed by autoradiography (AR). CBB, Coomassie Brilliant Blue staining.

FIG. 8X2. Additional Rabs displayed a range of effects on autophagic killing of BCG, including those Rabs previously implicated in autophagy.

Suppl. FIG. 1S. Analysis of the effect of Rab34 on autophagy. A. Rab34 knockdown elevates proportion of autolysosomes under basal conditions. RAW264.7 macrophages, knocked down for Rab34 by siRNA and expressing RFP-GFP-LC3, were quantified for early (G+R+) and acidified late (G-R+) autophagic organelles. Note an increase in G-R+LC3 puncta under uninduced (Full) conditions and no increase relative to scramble siRNA control under induced (starvation) conditions. B. Rab34 increases BCG survival (relative to Full control) under both uninduced (Full) and induced (Starve) conditions. C. A monolayer of cells (unpermeabilized) stained for CD98. D. Flow cytometry analysis of CD98 expression. E. Rab34 is required for CD98 (amino acid importer) expression on plasma membrane. CD98 was stained in unpermeabilized (external) and permeabilized (internal) cells and fluorescence examined by imaging and quantified by line tracing intensity. F. Uptake of [3H] Leu by cells knocked down for Rab34. RAW264.7 macrophages were transfected with control (Scr) and Rab34 siRNA (for 48 h) and DMEM supplemented with 1 μCi/ml tritiated L-Leucine was added to cells. Samples for uptake were taken at 0.5 and 2 h. At each time point, cells were washed quickly three times in PBS, hypotonically lysed and measured for total radioactivity using liquid scintillation. Uptake was normalized to control siRNA treated cells. G. Membrane permeant form of pyruvate (methyl pyruvate) employed as previously described (Lum et al., 2005) for nutritional bypass restores LC3-II levels in cells knocked down for Rab34. H. Role of Rab8a in autophagic killing of BCG. Knockdown of Rab8a shows a trend but no statistical significance in protecting BCG form autophagic killing. Rab8a knockdown analyzed by immunoblotting. Data, means and standard errors (n=3); *, p<0.05; †, p≥0.5 (ANOVA).

Suppl. FIG. 2S. TBK-1 is required for autophagic maturation. A. Effects of TBK-1 absence or presence on LC3-II levels in mouse embryonic fibroblasts (MEFs). Tbk-1−/− and Tbk-1+/+ MEFs were uninduced and induced for autophagy, treated or not treated with 100 nM bafilomycin A1 (BafA1) to inhibit autophagic degradation of LC3-II under basal conditions (Full) or during 90 min of starvation in EBSS (Starve). B,C. Effects on LC3-II levels of BX795, a pharmacological inhibitor of TBK-1. Tbk-1+/+ MEFs, untreated or treated with 10 nM BX795 (16 h) in the presence or absence of 100 nM bafilomycin A1 (BafA1; 2 h) were subjected to immunoblotting analysis. Ratio of LC3-II/actin band intensity. Data, means±se (n=3; †, *, p<0.05; , p<0.01; t-test). ). D,E. Although attempts to complement the absence of TBK-1 in Tbk1-/-MEFs by transfection with Tbk-1 expression constructs was hampered by low transfection efficiency, overexpresion of Tbk-1 transgene in RAW 264.7 cells caused alterations in LC3**-II levels, which diminished faster with time in Tbk-1 transgeneexpressing cells relative to untransfected cells.

Suppl. FIG. 3S. TBK1 is required for cathepsin D delivery to autophagolysosmes and conventional phagosomes and IL-1β induces autophagy in primary murine and human macrophages. A,B. RAW 264.7 macrophages pretreated with siRNAs, after ingestion of 1 μm magnetic beads were either induced (A) or uninduced (B) for autophagy by starvation. MBP, previously characterized magnetic bead autophagolysosomal organelles 2 (Ponpuak et al., 2010). Delivery of cathepsin D was determined by immunoblotting. PNS, post-nucelar supernatant. C. Macrophages derived from bone marrows obtained from femurs of EGFP-LC3 knock-in mice were treated with 10 ng/ml recombinant murine IL-1β and LC3 puncta quantified. D. Immunoblot analysis of LC3-II formation, in human monocyte-derived macrophages treated with 10 ng/ml human recombinant IL-1β. Data, means±se (n=3; *, p<0.05; t-test).

Suppl. FIG. 4S. Rab8b and TBK1 colocalize with autophagic machinery. A,B. Endogenous proteins in BMM as in FIG. 5 were imaged in cells incubated in indicated conditions: Full, complete medium; Full+BafA1, complete medium supplemented with bafilomycin A1; Starv, autophagy induced by starvation (EBSS); Starv+BafA1, autophagy induced by starvation in the presence of bafilomycin A1. When treated with BafA1, the purpose was to inhibit autophagic maturation and degradation. Triangles in insets, colocalization of all three fluorescent probes.

Suppl. FIG. 5S. TBK-1 renders p62 competent for entry into the autophagy pathway. Immunoblot of cell lysates from Tbk-1−/− and Tbk-1+/+ MEFs, uninduced (Full) and induced (Starve) for autophagy, untreated or treated with bafilomycin A1 (BafA1). Immunoblot was developed using p62 antibody.

Figures for Example 3

FIG. 1X3. induction of autophagy enhances IL-1β secretion. (A) Atg5fl/fl Cre− and Atg$5^{fl/fl}$ Cre+ bone marrow-derived macrophages (BMMs), pretreated overnight with 100 ng/ml LPS, were stimulated for 1 h with the inflammasome agonist nigericin (20 mM) with (Starvation; EBSS) or without (Full; full medium) autophagic induction. Cell culture supernatants were assayed for murine IL-1β by ELISA. Data represent mean values±s.d. (nX3); *Po0.05. (B) LPS-pretreated Atg5fl/fl Cre$^-$ and Atg$^{5fl/fl}$ Cre$^+$ BMMs were stimulated with 20 mM nigericin for 1 h in OptiMEM and the release of active caspase-1 and IL-1β was determined by immunoblotting. (C) As in (A), assayed for IL-18. Data represent mean values±s.d. (nX3); *Po0.05. (D) LPS-pretreated BMMs were exposed to alum (250 mg/ml) for 1 h with or without autophagic induction by starvation. Secreted IL-1β was measured as in (A). Data represent mean values±s.d. (nX3); *Po0.05. (E) LPS-pretreated BMMs were exposed to silica (250 mg/ml) for 1 h with or without autophagic induction by starvation. Secreted IL-1β was measured as in (A). Data represent mean values±s.d. (nX3); *Po0.05. (F) BMMs were transfected with scramble (Scr) control siRNA or siRNAs against ASC and NLRP3. After 48 h following transfection, cells were treated overnight with LPS and subjected to nigericin (20 mM) and starvation for 1 h. Data represent mean values±s.d. (nX3); *Po0.05. (G) Immunoblot analysis of ASC and NLRP3 knockdowns. (H) BMMs were transfected with scramble (Scr) control siRNA or siRNAs against ASC and NLRP3. After 48 h following transfection, cells were treated overnight with LPS and subjected to silica (250 mg/ml) and starvation for 1 h. Data represent mean values±s.d. (nX3); *Po0.05. (I) Colocalization of IL-1β with the basal autophagic machinery factor LC3. Fluorescence: LC3 (green, Alexa488); IL-1β (red, Alexa568). BMMs were from GFP-LC3 knock-in mice, treated with LPS then prepared for immunofluorescence microscopy using fluorescently labelled antibodies against GFP and IL-1b. (J, K) A line fluorescence tracing from images in (I). (L) Pearson's colocalization coefficient for IL-1β and LC3. Pearson's coefficient was derived from three independent experiments with five fields per experiment, for a total of 15 fields contributing to the cumulative result.

FIG. 2X3 Autophagic pathway progression promotes secretion of inflammasome substrates. (A, B) LPS-pretreated BMMs were treated with 20 mM nigericin (Nig) and 100 nM bafilomycin A1 (Baf) with (Starvation) or without (Full) autophagic induction for 1 h and secreted IL-1β (A) and IL-18 (B) were measured. Data represent mean values+s.d. (nX3); *Po0.05. (C) LPS-pretreated BMMs were treated with 250 mg/ml of silica and 100 nM bafilomycin A1 (Baf) with (Starvation) or without (Full) autophagic induction for 1 h and secreted IL-1β were measured. Data represent mean values±s.d. (nX3); *Po0.05. (D) Colocalization of cathepsin B with the basal autophagic machinery factor LC3 and IL-1b. Fluorescence; LC3 (green, Alexa488), IL-1β (red, Alexa568), and cathepsin B (blue, Alexa633). BMMs from GFP-LC3 knockin mice were treated with LPS and then analysed for immunofluorescence. (E) Colocalization line tracing analysis from images in (D). (F) LPS-pretreated BMMs were treated with 20 mM nigericin and cathepsin B inhibitor CA-074 Me (10 mM), with (Starvation) or without (Full) autophagic induction, for 1 h and secreted IL-1β was measured. Data represent mean values±s.d. (nX3); *Po0.05. (G) LPS-pretreated Atg$^{5fl/fl}$ Cr$^+$ and Atg$^{5fl/fl}$ Cre$^-$ BMMs were stimulated with 20 mM nigericin for 1 h in OptiMEM and release of cathepsin B was determined by immunoblotting.

FIG. 3X3. Rab8a is required for autophagy-activated IL-1β secretion. (A) Colocalization of Rab8a with the basal autophagic machinery factor LC3 and IL-1b. Fluorescence; LC3 (green, Alexa488), IL-1β (red, Alexa568), Rab8a (blue, Alexa633). BMMs from GFP-LC3 knock-in mice were pretreated with LPS and analysed by immunofluorescence microscopy. Arrows indicate triple colocalization. (B) Line tracing analysis of fluorescence signal intensity. (C) Pearson's colocalization coefficient for IL-1β and Rab8a. Pearson's coefficients were derived from three completely independent experiments with 45 fields per experiment, for a total of X15 fields contributing to the cumulative result. (D) BMMs were transfected with siRNAs against Rab8a or scramble (Scr) control. At 24 h after the first transfection, cells were transfected again with siRNA, treated with LPS and the day after subjected to nigericin in full medium for 1 h, and IL-1β secretion measured. (E) Immunoblot analysis of Rab8a knockdown in BMMs. (F) RAW264.7 macrophages were transfected with GFP-tagged Rab8a constructs (WT, wild type; S22N, dominant-negative mutant), treated overnight with LPS and stimulated for 1 h with 20 mM nigericin along with induction of autophagy by starvation. IL-1β secretion was measured by ELISA. Data represent mean values±s.d. (nX3); *Po0.05.

FIG. 4X3. GRASP55 is required for autophagy-activated IL-1β secretion. (A) BMM cells were transfected with scramble (Scr) control siRNA or siRNA against GRASP55. After 48 h of transfection, cells were treated with LPS and the day after subjected to 20 mM nigericin in EBSS, and secreted IL-1β was measured by ELISA. Data represent mean values±s.d. (nX3); *Po0.05. Inset: Immunoblot analysis of GRASP55 knockdown. (B) Immunofluorescence confocal microscopy analysis of LC3 and GRASP55 distribution. LC3 (green, Alexa488), GRASP55 (red, Alexa568). BMMs were pretreated overnight with 100 ng/ml LPS and either not stimulated (Ctrl) or stimulated (Nig) for 30 min with the inflammasome agonist nigericin (20 mM) in full medium. (C) Line tracings, analysis of fluorescence signal intensity from images in (B). (D) Pearson's coefficients for LC3 and GRASP55 were quantified using SlideBook morphometric analysis software as a measure of adjacency between GRASP55 and LC3 profiles. Pearson's coefficients were derived from three independent experiments with five fields per experiment, for a total of 15 fields contributing to the cumulative result.

FIG. 5X3. GRASP55 controls autophagy initiation. (A, B) Effect of GRASP55 on autophagy induction by measuring LC3-II. BMM cells were transfected with GRASP55 siRNAs or scramble (Scr) control. At 72 h post transfection, cells were induced for autophagy, treated or not with Bafilomycin A1 (Baf) to inhibit autophagic degradation and LC3-II/actin ratios determined by immunoblotting (A) followed by densitometry (B). Data represent mean values±s.d. (nX3); *Po0.05. (C, D) RAW 264.7 was transfected with GRASP55 siRNAs or scramble (Scr) siRNA control. Following 48 h of siRNA treatment, cells were transfected with RFP-GFP-LC3 plasmid (GFP is sensitive to acidification, whereas RFP is not), after 24 h induced for autophagy in EBSS for 1 h and autophagic induction and flux quantified (graph in D) by determining the number of early autophagic organelles (GFP$^+$ RFP$^+$ puncta) and autolysosomal organelles (GFP$^-$ RFP$^+$ puncta) per cell as illustrated in fluorescent images (yellow arrows, GFP$^+$RFP$^+$; red arrows, GFP$^-$ RFP$^+$). Total, yellow+red puncta per cell. Data represent mean values±s.d. (nX3); *Po0.05.

FIG. 6X3. HMGB1 is an autophagy-based alternative secretion substrate. (A) Atg$^{5fl/fl}$ Cre$^-$ and Atg$^{5fl/fl}$ Cre$^+$ BMMs, pretreated overnight with 100 ng/ml LPS, were stimulated for 1 h with 20 mM nigericin (Nig; inflammasome agonist) while incubated in EBSS for induction of autophagy by starvation. Cell culture supernatants were assayed for murine HMGB1 by ELISA. Data (normalized to sample with maximum HMGB1 secretion in each experimental repeat; Cre– and Nig) represent mean values±s.d. (nX3);*P₀0.05. (B) LPS-pretreated $Atg5^{fl/fl}$ Cre⁻ and $Atg5^{fl/fl}$ Creþ BMMs were stimulated with 20 mM nigericin for 1 h in OptiMEM and the release of HMGB1 was determined by immunoblotting.

Figure for Example 4

FIG. 1X4. LC3B-II autophagy marker is detected on the surface of cells (see Example 4).

FIG. 2X4 shows that even if the intracellular membranes were to fuse with the plasma membrane (PM), LC3 would not be exposed to the outside according to the current Knowledge. Instead, LC3 would always be shielded from the exposure to the outside and not accessible to antibodies in a sandwich assay, unless the cells were permeabilized. Scheme 1 process B, depicts what is experimentally detected pursuant to the present invention, i.e. LC3 is exposed on the cell surface on the side of the plasma membrane facing the outside of the cell and thus being accessible to the exogenously added antibody to recognize LC3.

Figures for Example 5

FIG. 1AX5. Depiction of autophagic processes.

FIG. 1BX5. Further depiction of autophagic processes.

FIG. 2X5. Detection of puncta as observed in the experiment of Example 5.

FIG. 3X5. High-content imaging experimental design used to examine cell samples for an autophagy-associated effect on cytoplasmic puncta in the experiment of Example 5.

FIG. 4X5. Positive and negative controls used in high-content imaging experiment of Example 5.

FIG. 5X5. Summary of Prestwick and TPIMS screens used in the high-content imaging experiment of Example 5.

FIG. 6X5. Comparison of autophagy-associated effects on cytoplasmic puncta in the experiment of Example 5.

FIG. 7AX5. Prestwick screen data determined in the high-content imaging experiment of Example 5.

FIG. 8X5. Overlap of hits from two separate Prestwick screens for induction of autophagy as determined in the experiment of Example 5.

FIG. 9X5. Hits, real and imagined, as determined in the high-content imaging experiment of Example 5.

FIG. 10X5. Dose response curves to pp242 as determined in the high-content imaging experiment of Example 5.

FIG. 11X5. TIPMS library screen conducted in the high-content imaging experiment of Example 5.

Figures for Example 6

FIG. 1X6. Use of Cellomics ArrayScan to detect induction of authophagy. LC3-RFP/RGP HeLa cells were incubated with the known inducer of autophagy pp242, an mTOR inhibitor, for 4 hours then fixed in 0.1% PFA. Wells were scanned for number, area, or intensity of GFP+ or RFP+ puncta per cell using a Cellomics ArrayScan. Negative control (DMF-treated) wells were also measured. Each dot represents the data from a single well.

FIG. 2X6. Chemical library screen for modulation of autophagy. LC3-RFP/GFP HeLa cells were incubated with compounds from the chemical library for 4 hours, then fixed in 0.1% PFA. Wells were scanned using a Cellomics ArrayScan. Negative control (DMSO-treated) and positive control (pp242) wells were also measured. Each dot represents the data from a single well.

FIG. 3X6. Shows comparison of replicate chemical library screens for modulation of autophagy. Two different chemical library screens were performed as in FIG. 2 on separate days. The data was combined, and compounds that were hits in both screens were picked for further experimentation.

FIG. 4X6. Dose response measurement of pp242 and induction of autophagy. LC3-RFP/GFP HeLa cells were incubated with different concentrations of pp242 for 4 hours, then fixed in 0.1% PFA. Wells were scanned using a Cellomics ArrayScan. Negative control (DMSO-treated) and positive control (pp242) wells were also measured. Each dot represents the data from four separate wells, and error bars are standard deviation.

FIG. 5X6. Overview of chemical screens for modulation of autophagy. Two different chemical library screens were performed on separate days. The data was combined, and compounds that were hits in both screens were picked for further experimentation.

DETAILED DESCRIPTION OF THE INVENTION

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound disclosed herein and includes tautomers, regioisomers, geometric isomers as applicable, and also where applicable, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation of autophagy within the context of a particular treatment or alternatively, the effect of a bioactive agent which is coadministered with the autophagy modulator (autotoxin) in the treatment of disease.

The terms "treat", "treating", and "treatment", etc., as used herein, refer to any action providing a benefit to a patient at risk for or afflicted by an autophagy mediated disease state or condition as otherwise described herein. The benefit may be in curing the disease state or condition, inhibition its progression, or ameliorating, lessening or suppressing one or more symptom of an autophagy mediated disease state or condition. Treatment, as used herein, encompasses both prophylactic and therapeutic treatment.

As used herein, the term "autophagy mediated disease state or condition" refers to a disease state or condition that results from disruption in autophagy or cellular self-digestion. Autophagy is a cellular pathway involved in protein and organelle degradation, and has a large number of connections to human disease. Autophagic dysfunction is associated with cancer, neurodegeneration, microbial infection and ageing, among numerous other disease states and/or conditions. Although autophagy plays a principal role as a protective process for the cell, it also plays a role in cell death. Disease states and/or conditions which are mediated through autophagy (which refers to the fact that the disease state or condition may manifest itself as a function of the increase or decrease in autophagy in the patient or subject to be treated and treatment requires administration of an inhibitor or agonist of autophagy in the patient or subject) include, for example, cancer, including metastasis of cancer, lysosomal storage diseases (discussed hereinbelow), neurodegeneration (including, for example, Alzheimer's disease, Parkinson's disease, Huntington's disease; other ataxias), immune response (T cell maturation, B cell and T cell homeostasis, counters damaging inflammation) and chronic inflammatory diseases (may promote excessive cytokines when autophagy is defective), including, for example, inflammatory bowel disease, including Crohn's disease, rheumatoid arthritis, lupus, multiple sclerosis, chronic obstructive pulmonary disease/COPD, pulmonary fibrosis, cystic fibrosis, Sjogren's disease; hyperglycemic disorders, diabetes (I and II), affecting lipid metabolism islet function and/or structure, excessive autophpagy may lead to pancreatic β-cell death and related hyperglycemic disorders, including severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), and elevated triglycerides) and metabolic syndrome, liver disease (excessive autophagic removal of cellular entities—endoplasmic reticulum), renal disease (apoptosis in plaques, glomerular disease), cardiovascular disease (especially including ischemia, stroke, pressure overload and complications during reperfusion), muscle degeneration and atrophy, symptoms of aging (including amelioration or the delay in onset or severity or frequency of aging-related symptoms and chronic conditions including muscle atrophy, frailty, metabolic disorders, low grade inflammation, atherosclerosis and associated conditions such as cardiac and neurological both central and peripheral manifestations including stroke, age-associated dementia and sporadic form of Alzheimer's disease, pre-cancerous states, and psychiatric conditions including depression), stroke and spinal cord injury, arteriosclerosis, infectious diseases (microbial infections, removes microbes, provides a protective inflammatory response to microbial products, limits adapation of authophagy of host by microbe for enhancement of microbial growth, regulation of innate immunity) including bacterial, fungal, cellular and viral (including secondary disease states or conditions associated with infectious diseases), including AIDS and tuberculosis, among others, development (including erythrocyte differentiation), embryogenesis/fertility/infertility (embryo implantation and neonate survival after termination of transplacental supply of nutrients, removal of dead cells during programmed cell death) and ageing (increased autophagy leads to the removal of damaged organelles or aggregated macromolecules to increase health and prolong lire, but increased levels of autophagy in children/young adults may lead to muscle and organ wasting resulting in ageing/progeria).

The term "lysosomal storage disorder" refers to a disease state or condition that results from a defect in lysosomomal storage. These disease states or conditions generally occur when the lysosome malfunctions. Lysosomal storage disorders are caused by lysosomal dysfunction usually as a consequence of deficiency of a single enzyme required for the metabolism of lipids, glycoproteins or mucopolysaccharides. The incidence of lysosomal storage disorder (collectively) occurs at an incidence of about 1:5,000-1:10,000. The lysosome is commonly referred to as the cell's recycling center because it processes unwanted material into substances that the cell can utilize. Lysosomes break down this unwanted matter via high specialized enzymes. Lysosomal disorders generally are triggered when a particular enzyme exists in too small an amount or is missing altogether. When this happens, substances accumulate in the cell. In other words, when the lysosome doesn't function normally, excess products destined for breakdown and recycling are stored in the cell. Lysosomal storage disorders are genetic diseases, but these may be treated using autophagy modulators (autostatins) as described herein. All of these diseases share a common biochemical characteristic, i.e., that all lysosomal disorders originate from an abnormal accumulation of substances inside the lysosome. Lysosomal storage diseases mostly affect children who often die as a consequence at an early stage of life, many within a few months or years of birth. Many other children die of this disease following years of suffering from various symptoms of their particular disorder.

Examples of lysosomal storage diseases include, for example, activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM! Ganliosidosis, including infantile, late infantile/juvenile and adult/chronic), Hunter syndrome (MPS II), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, Pompe disease, pycnodysostosis, Sandhoff disease, Schindler disease, Tay-Sachs and Wolman disease, among others.

The term "modulator of autophagy", "regulator of autophagy" or "autostatin" is used to refer to a compound which functions as an agonist (inducer or up-regulator) or antagonist (inhibitor or down-regulator) of autophagy. Depending upon the disease state or condition, autophagy may be upregulated (and require inhibition of autophagy for therapeutic intervention) or down-regulated (and require upregulation of autophagy for therapeutic intervention). In most instances, in the case of cancer treatment with a modulator of autophagy as otherwise described herein, the autophagy modulator is often an antagonist of autophagy. In the case of cancer, the antagonist (inhibitor) of autophagy may be used alone or combined with an agonist of autophagy The following compounds have been identified as autophagy modulators according to the present invention and can be used in the treatment of an autophagy mediated disease state or condition as otherwise described herein. It is noted that an inhibitor of autophagy is utilized where the disease state or condition is mediated through upregulation or an increase in autophagy which causes the disease state or condition and an agonist of autophagy is utilized where the disease state or condition is mediated through downregulation or a decrease in autophagy. The following compounds have been identified as autophagy modulators (autotaxins) in autophagy assays according to the present invention: flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon and nortriptyline, tetrachlorisophthalonitrile, phenylmercuric acetate and pharmaceutically acceptable salts thereof. It is noted that flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline and their pharmaceutically acceptable salts show activity as agonists or inducers of autophagy in the treatment of an autophagy-mediated disease, whereas tetrachlorisophthalonitrile, phenylmercuric acetate and their pharmaceutically acceptable salts, find use as antagonists or inhibitors of autophagy. All of these compounds will find use as modulators of autophagy in the various autophagy-mediated disease states and conditions described herein, with the agonists being preferred in most disease states other than cancer (although inhibitors may also be used alone, or preferably in combination with the agonists) and in the case of the treatment of cancer, the inhibitors described above are preferred, alone or in combination with an autophagy agonist as described above and/or an additional anticancer agent as otherwise described herein.

Other compounds which may be used in combination with the autophagy modulators which are described above, include for example, other "additional autophagy modulators" or "additional autostatins" which are known in the art. These can be combined with one or more of the autophagy modulators which are disclosed above to provide novel pharmaceutical compositions and/or methods of treating autophagy mediated disease states and conditions which are otherwise described herein. These additional autophagy modulators including benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene and mixtures thereof.

The term "co-administration" or "combination therapy" is used to describe a therapy in which at least two active compounds in effective amounts are used to treat an autophagy mediated disease state or condition as otherwise described herein, either at the same time or within dosing or administration schedules defined further herein or ascertainable by those of ordinary skill in the art. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes an administration in which one active agent (especially an autophagy modulator) is administered at approximately the same time (contemporaneously), or from about one to several minutes to about 24 hours or more than the other bioactive agent coadministered with the autophagy modulator. The additional bioactive agent may be any bioactive agent, but is generally selected from an additional autophagy mediated compound, an additional anticancer agent, or another agent, such as a mTOR inhibitor such as pp242, rapamycin, envirolimus, everolimus or cidaforollimus, among others including epigallocatechin gallate (EGCG), caffeine, curcumin or reseveratrol (which mTOR inhibitors find particular use as enhancers of autophagy using the compounds disclosed herein and in addition, in the treatment of cancer with an autophagy modulator (inhibitor) as described herein, including in combination with tetrachlorisophthalonitrile, phenylmercuric acetate and their pharmaceutically acceptable salts, which are inhibitors of autophagy. It is noted that in the case of the treatment of cancer, the use of an autophagy inhibitor is preferred, alone or in combination with an autophagy inducer (agonist) as otherwise described herein and/or a mTOR inhibitor as described above. In certain embodiments, an mTOR inhibitor selected from the group consisting of pp242, rapamycin, envirolimus, everolimus, cidaforollimus, epigallocatechin gallate (EGCG), caffeine, curcumin, reseveratrol and mixtures thereof may be combined with at least one agent selected from the group consisting of digoxin, xylazine, hexetidine and sertindole, the combination of such agents being effective as autophagy modulators in combination.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer (especially basal cell carcinoma or squamous cell carcinoma), acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. In certain aspects, the cancer which is treated is lung cancer, breast cancer, ovarian cancer and/or prostate cancer.

The term "tumor" is used to describe a malignant or benign growth or tumefacent.

The term "additional anti-cancer compound", "additional anti-cancer drug" or "additional anti-cancer agent" is used to describe any compound (including its derivatives) which may be used to treat cancer. The "additional anti-cancer compound", "additional anti-cancer drug" or "additional anti-cancer agent" can be an anticancer agent which is distinguishable from a CIAE-inducing anticancer ingredient such as a taxane, vinca alkaloid and/or radiation sensitizing agent otherwise used as chemotherapy/cancer therapy agents herein. In many instances, the co-administration of another anti-cancer compound according to the present invention results in a synergistic anti-cancer effect. Exemplary anti-cancer compounds for co-administration with formulations according to the present invention include anti-metabolites agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and tyrosine kinase inhibitors or ABL kinase inhibitors (e.g. imatinib).

Anti-cancer compounds for co-administration include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

Co-administration of one of the formulations of the invention with another anticancer agent will often result in a synergistic enhancement of the anticancer activity of the other anticancer agent, an unexpected result. One or more of the present formulations comprising an autophagy modulator (autostatin) may also be co-administered with another bioactive agent (e.g., antiviral agent, antihyperproliferative disease agent, agents which treat chronic inflammatory disease, among others as otherwise described herein).

The term "antiviral agent" refers to an agent which may be used in combination with authophagy modulators (autostatins) as otherwise described herein to treat viral infections, especially including HIV infections, HBV infections and/or HCV infections. Exemplary anti-HIV agents include, for example, nucleoside reverse transcriptase inhibitors (NRTI), non-nucleoeoside reverse transcriptase inhibitors (NNRTI), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Anti-HCV agents include, for example, interferon, pegylated interferon, ribavirin, NM 283, VX-950 (telaprevir), SCH 50304, TMC435, VX-500, BX-813, SCHSO3034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9Agonist, PHX1766, SP-30 and mixtures thereof.

As used herein, "antibody" includes, but is not limited to, monoclonal antibodies. The following disclosure from U.S. Patent Application Document No. 20100284921, the entire contents of which are hereby incorporated by reference, exemplifies techniques that are useful in making antibodies employed in formulations of the instant invention.

As described in U.S. Patent Application Document No. 20100284921, "antibodies . . . may be polyclonal or monoclonal. Monoclonal antibodies are preferred. The antibody is preferably a chimeric antibody. For human use, the antibody is preferably a humanized chimeric antibody.

An anti-target-structure antibody . . . may be monovalent, divalent or polyvalent in order to achieve target structure binding. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

The invention also includes [use of] functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application Nos. WO 1993/21319 and WO 1989/09622. Functional equivalents include polypeptides with amino acid sequences substantially the same as the amino acid sequence of the variable or hypervariable regions of the antibodies raised against target integrins according to the practice of the present invention.

Functional equivalents of the anti-target-structure antibodies further include fragments of antibodies that have the same, or substantially the same, binding characteristics to those of the whole antibody. Such fragments may contain one or both Fab fragments or the F(ab').sub.2 fragment. Preferably the antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Preferred constant regions are gamma 1 (IgG1), gamma 2 (IgG2 and IgG), gamma 3 (IgG3) and gamma 4 (IgG4). The light chain constant region can be of the kappa or lambda type.

The monoclonal antibodies may be advantageously cleaved by proteolytic enzymes to generate fragments retaining the target structure binding site. For example, proteolytic treatment of IgG antibodies with papain at neutral pH generates two identical so-called "Fab" fragments, each containing one intact light chain disulfide-bonded to a fragment of the heavy chain (Fc). Each Fab fragment contains one antigen-combining site. The remaining portion of the IgG molecule is a dimer known as "Fc". Similarly, pepsin cleavage at pH 4 results in the so-called F(ab')2 fragment.

Single chain antibodies or Fv fragments are polypeptides that consist of the variable region of the heavy chain of the antibody linked to the variable region of the light chain, with or without an interconnecting linker. Thus, the Fv comprises an antibody combining site.

Hybrid antibodies may be employed. Hybrid antibodies have constant regions derived substantially or exclusively from human antibody constant regions and variable regions derived substantially or exclusively from the sequence of the variable region of a monoclonal antibody from each stable hybridoma.

Methods for preparation of fragments of antibodies (e.g. for preparing an antibody or an antigen binding fragment thereof having specific binding affinity for either caspase-1 or an autophagy-related immunomodulatory cytokine) are either described in the experiments herein or are otherwise known to those skilled in the art. See, Goding, "Monoclonal Antibodies Principles and Practice", Academic Press (1983), p. 119-123. Fragments of the monoclonal antibodies containing the antigen binding site, such as Fab and F(ab')2 fragments, may be preferred in therapeutic applications, owing to their reduced immunogenicity. Such fragments are less immunogenic than the intact antibody, which contains the immunogenic Fc portion. Hence, as used herein, the term "antibody" includes intact antibody molecules and fragments thereof that retain antigen binding ability.

When the antibody used in the practice of the invention is a polyclonal antibody (IgG), the antibody is generated by inoculating a suitable animal with a target structure or a fragment thereof. Antibodies produced in the inoculated animal that specifically bind the target structure are then isolated from fluid obtained from the animal. Anti-target-structure antibodies may be generated in this manner in several non-human mammals such as, but not limited to, goat, sheep, horse, rabbit, and donkey. Methods for generating polyclonal antibodies are well known in the art and are described, for example in Harlow et al. (In: Antibodies, A Laboratory Manual, 1988, Cold Spring Harbor, N.Y.).

When the antibody used in the methods used in the practice of the invention is a monoclonal antibody, the antibody is generated using any well known monoclonal antibody preparation procedures such as those described, for example, in Harlow et al. (supra) and in Tuszynski et al. (Blood 1988, 72:109-115). Generally, monoclonal antibodies directed against a desired antigen are generated from mice immunized with the antigen using standard procedures as referenced herein. Monoclonal antibodies directed against full length or fragments of target structure may be prepared using the techniques described in Harlow et al. (supra).

The effects of sensitization in the therapeutic use of animal-origin monoclonal antibodies in the treatment of human disease may be diminished by employing a hybrid molecule generated from the same Fab fragment, but a different Fc fragment, than contained in monoclonal antibodies previously administered to the same subject. It is contemplated that such hybrid molecules formed from the anti-target-structure monoclonal antibodies may be used in the present invention. The effects of sensitization are further diminished by preparing animal/human chimeric antibodies, e.g., mouse/human chimeric antibodies, or humanized (i.e. CDR-grafted) antibodies. Such monoclonal antibodies comprise a variable region, i.e., antigen binding region, and a constant region derived from different species. By 'chimeric' antibody is meant an antibody that comprises elements partly derived from one species and partly derived form at least one other species, e.g., a mouse/human chimeric antibody.

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, the antibodies produced are largely human but contain antigen-binding specificities generated in mice. As demonstrated by Morrison et al., 1984, Proc. Natl. Acad. Sci. USA 81:6851-6855, both chimeric heavy chain V region exon (VH)-human heavy chain C region genes and chimeric mouse light chain V region exon (VK)-human K light chain gene constructs may be expressed when transfected into mouse myeloma cell lines. When both chimeric heavy and light chain genes are transfected into the same myeloma cell, an intact H2L2 chimeric antibody is produced. The methodology for producing such chimeric antibodies by combining genomic clones of V and C region genes is described in the above-mentioned paper of Morrison et al., and by Boulianne et al. (Nature 1984, 312:642-646). Also see Tan et al. (J. Immunol. 1985, 135:3564-3567) for a description of high level expression from a human heavy chain promotor of a human-mouse chimeric K chain after transfection of mouse myeloma cells. As an alternative to combining genomic DNA, cDNA clones of the relevant V and C regions may be combined for production of chimeric antibodies, as described by Whitte et al. (Protein Eng. 1987, 1:499-505) and Liu et al. (Proc. Natl. Acad. Sci. USA 1987, 84:3439-3443). For examples of the preparation of chimeric antibodies, see the following U.S. Pat. Nos. 5,292,867; 5,091,313; 5,204,244; 5,202,238; and 5,169,939. The entire disclosures of these patents, and the publications mentioned in the preceding paragraph, are incorporated herein by reference. Any of these recombinant techniques are available for production of rodent/human chimeric monoclonal antibodies against target structures.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., 1986, Nature 321:522-525; Verhoeyen et al., 1988, Science 239:1534-1536; Hale et al., 1988, Lancet 2:1394-1399; Queen et al., 1989, Proc. Natl. Acad. Sci. USA 86:10029-10033). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-target structure antibodies of reduced human immunogenicity."

Further, standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

High-content imaging techniques and diagnostic methods described herein can use fluorescence-inducing compounds, e.g. a fluorescent moiety such as a fluorescein dye or a rhodamine dye. In some embodiments, the fluorescent moiety comprises two or more fluorescent dyes that can act cooperatively with one another, for example by fluorescence resonance energy transfer ("FRET"). The fluorescent moiety may be any fluorophore that is capable of producing a detectable fluorescence signal in an assay medium; the fluorescence signal can be "self-quenched" and capable of fluorescing in an aqueous medium. "Quench" refers to a reduction in the fluorescence intensity of a fluorescent group as measured at a specified wavelength, regardless of the mechanism by which the reduction is achieved. As specific examples, the quenching may be due to molecular collision, energy transfer such as FRET, a change in the fluorescence spectrum (color) of the fluorescent group or any other mechanism. The amount of the reduction is not critical and may vary over a broad range. The only requirement is that the reduction be measurable by the detection system being used. Thus, a fluorescence signal is "quenched" if its intensity at a specified wavelength is reduced by any measurable amount.

Examples of fluorophores include xanthenes such as fluoresceins, rhodamines and rhodols, cyanines, phtalocyanines, squairanines, bodipy dyes, pyrene, anthracene, naphthalene, acridine, stilbene, indole or benzindole, oxazole or benzoxazole, thiazole or benzothiazole, carbocyanine, carbostyryl, prophyrin, salicylate, anthranilate, azulene, perylene, pyridine, quinoline, borapolyazaindacene, xanthene, oxazine or benzoxazine, carbazine, phenalenone, coumarin, benzofuran, or benzphenalenone. Examples of rhodamine dyes include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichlorotetramethylrhodamine (dTAMRA).

Examples of fluorescein dyes include, but are not limited to, 4,7-dichlorofluoresceins, 5-carboxyfluorescein (5-FAM) and 6-carboxyfluorescein (6-FAM).

For example, cells can be transfected with green fluorescent protein-tagged autophagic marker protein light chain 3 (GFP-LC3) (see e.g., Gonzalez-Polo R-A, et al. (2005) J. Cell Sci. 118:3091-3102), which is a fluorescent fusion protein that is incorporated into autophagosomes (also called autophagic vesicles, or AV); confocal microscopy can be used to score the number of autophagosomes (LC3-GFP dots) per cell. Although this can be done using robotics and automated microscopy Detection and spatial localization in a biological sample as described herein may be based on, but not restricted to fluorescence in the ultra-violet, visible, infrared spectral regions, or may report via radiofrequencies (MRI/NMR) and well as radioactive detection. In addition, a reporter group containing heavy atoms is employed for detection using electron microscopy (EM or TEM), scanning EM (SEM) or mass spectral or equivalent techniques. In alternative embodiments, the reporter (domains or moieties) comprise functional groups that either turn off or on its reporting function from its native state, but in the presence of a biological sample (for example; pH change, presence of a specific enzyme, metal etc.) changes its state, giving further details to the biological environment in an autophagic vesicle.

In one embodiment of the invention, "sandwich" type immunoassays are utilized to measure LC3 in a sample, preferably a blood sample, to facilitate an ease of analysis of LC3 activity in the blood of a patient or subject. In one embodiment, the methods of the invention utilize a capture antibody that specifically binds to LC3. The capture antibody may be coupled to a solid substrate or solid phase. Examples of suitable substrates include, but are not limited to, wells of microtiter plates or cuvettes, or nitrocellulose or nylon membranes. In one embodiment of the invention, the capture antibodies are coupled to paramagnetic particles in wells of microtiter plates or cuvettes. For example, biotin-coupled capture antibodies can couple to streptavidin coated paramagnetic particles via the well known avidin-biotin binding reaction. Other methods of coupling the capture antibody to the solid phase of the assays are known to those skilled in the art. LC3 antibodies, including monoclonal antibodies are available in the art (available from Cell Signalling Technology, Danvers, Massachussetts, USA). The use of these and/or other antibodies which are otherwise described herein or are well known in the art and may be readily adapted to the present invention.

In practicing the sandwich immunoassay, LC3 may also be exposed to a detection antibody that is coupled to a detectable label. Examples of suitable labels are described above, one example of a label is an acridinium ester. Methods of coupling labels to antibodies are well known in the art. For example, acridinium, as a "sulfonyl chloride ester" can be crosslinked to the detection antibody by the reaction of the lysly moiety of the epsilon amino group of lysine in proteins, such as antibodies, to the acridinium ester. The reaction products may then be separated by size exclusion chromatography on Sepharose beads or otherwise.

In certain embodiments of the invention, the sandwich immunoassays may be chemiluminescent immunoassays, but colorimetric assays may be preferred for point of care applications, including home applications. Although specific monoclonal antibodies are disclosed herein and are commercially available, other monoclonal antibodies that could be used as capture and detection antibodies for LC3 as described herein can be produced using conventional methods known in the art. See, for example, Kohler and Milstein, (1975) Nature, 256:495-97; or Sambrook et al. (2001) Molecular Cloning: A Laboratory Manual, 3rd edition, Cold Spring Harbor Laboratory Press. Briefly, animals, such as mice, are injected with an antigen, such as LC3 or fragments thereof, that may be coupled to a carrier protein. The animals are boosted with one or more antigen injections, and are hyperimmunized by an intravenous (IV) booster about three days before fusion. Spleen cells from the mice are isolated and are fused by standard methods to myeloma cells. Hybridomas are selected in standard hypoxanthine/aminopterin/thymine (HAT) medium, according to standard methods. Hybridomas secreting antibodies which recognize different epitopes of the antigen are identified, cultured, and subcloned using standard immunological techniques. The antibodies are then screened for the desired specificity or cross reactivity using methods known in the art.

Although one embodiment of the invention employs colorimetric or chemiluminescent sandwich inumunoassays to practice the methods of the invention, other immunoassays, such as ELISAs and RIAs may be used. The parameters and components of the assays are determined and optimized as is well known to those skilled in the art such that the assays provide measurement of LC3 levels in the biological samples being assayed. In addition, although certain embodiments of the invention utilize antibodies as the agents capturing LC3, LC3 may be captured in the assays of the invention using other chemical agents or molecules that are not antibodies. For example, such an agent may recognize carbohydrate profiles of LC3 and thereby bind the LC3 to a solid phase in a similar manner as the capture antibodies described herein.

In some embodiments of the invention, it may be desirable to automate the methods as much as practical in order to improve replicability of the results and reduce the time and costs required to conduct the assays. Automated assays used to practice the methods of the invention permit users to conduct at least about 80 tests per hour, and preferably more than about 100 test per hour.

One may also use any conventional, non-automated, assay device to practice the methods of the invention. For example, a conventional microtiter plate can be used to store the various solutions used in performing the assay. The device should permit the biological sample to be exposed to a combination of antibodies. The antibodies may recognize different epitopes of the antigen(s) being assayed. The device should also cause the bound antigen to be retained to a substrate as solutions are added and removed during the assay.

By way of example, and not by way of limitation, wells of a microtiter plate can be loaded with a solution containing streptavidin coated magnetic particles, as described herein. A solution containing biotin coupled capture antibodies (e.g., biotin coupled mAb) is added to the well to enable the coupling of the capture antibodies to the magnetic particles. A concentration of capture antibody is empirically selected (based on expected antigen concentrations) as discussed herein, to permit binding of all, or essentially all, of the test antigen that is available in the sample. In that regard, typical antigen concentrations in biological samples are in the nanogram to low microgram range (e.g. less than 1 ng/ml-5 µg/ml) so that the capture antibody concentrations are in the low to high microgram range (e.g. 1-100 µg/ml). The sample is added to the well. If the sample contains the antigens of interest (e.g., LC3), the antigen will bind to the capture antibodies. The plate is exposed to a magnetic field to immobilize the magnetic particles, and the solution is removed from the well; but the antigen will not be removed because it is bound to the antibodies that are bound to the magnetic particles that are immobilized by the magnetic field. A solution containing the detection antibody coupled to a label (e.g., acridinium labeled mAb) is added to the well containing the bound antigen. As indicated elsewhere herein, the concentration of the detection antibody is preferably selected so that all, or essentially all, of the test antigen molecules (e.g., LC3) are bound by the detection antibody. Thus, the detection antibody can be provided at concentrations at least an order of magnitude greater than the expected concentration of the test antigen. For example, if a test antigen has an expected concentration of 2 ng/ml, the detection antibody concentration can be at least 20 ng/ml (0.02 µg/ml). After a sufficient amount of time (from about 10 minutes to about 8 or more hours, which is determined in a calibration step), determined and optimized empirically as described herein, the plate is exposed to a magnetic field, the solution is then removed, and the sample is washed. The amount of label remaining in the well is then measured (e.g., by a luminometer). The measured values can be quantitative or qualitative. Quantitative results are usually preferred. The measured values may then be compared to a standard or a threshold.

One immunoassay system which may be used in the present invention is the Nichols Advantage® immunoassay system, which is a fully automated chemiluminescent system. The system is a bench-top instrument that performs solid phase chemiluminescent immunoassays. Streptavidin-coated magnetic particles and biotinylated antibodies may be employed in the assay system. Acridinium ester is typically the chemiluminescence label for signal detection. Other assay systems may also be employed in the present method.

In practicing the methods of the invention, a control may be provided in the assay to ensure that the reactions have been successful. For example, a control could be provided with a polyclonal antibody solution for other analytes present in the biological sample or the same analytes present in other control samples.

In point of care applications, and in home assay tests, the following exemplary colorimetric assay may be used. The assay may also be chemiluminescent, but is preferably colorimetric in nature (for ease of use). The test device for determining concentration levels of LC3 may be a nitrocellulose-based (or other appropriate polymeric material) colorimetric sandwich assay (nitrocellulose-based sandwich assay) or two antibody test based upon a capture antibody and a detection antibody (at least one) wherein the capture and detection antibodies recognize and bind different epitopes of LC3, and wherein one of the antibodies (the detection antibody) is coupled to a label that produces a detectable or colorimetric signal (through a dye such as a gold-based dye) and the other antibody, the capture antibody, is anchored to a support, preferably a polymeric material, preferably a nitrocellulose or other film layer, wherein the capture antibody is fixed in a line in the film layer. In this preferred assay, both the capture antibody and the detection antibody are specific for different epitopes on LC3, such that the LC3 may be measured. In preferred aspects, the capture antibody is specific for a particular epitope on LC3 and the detection antibody may be much less specific provided that the antibody binds, and consequently labels, essentially all of the LC3 which is bound to the capture antibody. In this assay the capture antibody is specific for a different epitope on LC3 than is the detection antibody although both the capture and detection antibodies (in the case of the detection antibody, either singly or collectively) are specific for LC3 to maximize accuracy.

In this point of home or point of care diagnostic test, the detection antibody is linked to dye (gold-based or other) and initially is in an upper layer material which is porous to liquid and is free to move to a lower layer when it comes into contact with liquid, such as blood, serum, plasma or urine, which contains LC3. The detection antibody of the upper layer is free to move from the upper layer (preferably a porous sponge material) to the lower layer. The other antibody (the capture antibody) is anchored in the nitrocellose matrix or other similar material in a shape like a line. The LC3 containing cells in serum would enter the device and bind to the antibody-dye. There can an opening in the device case called the "result window", exposing any color from the dye. The LC3 antibody-dye would then move into or through the nitrocellulose matrix until it reaches the anchored captured antibody. The result ("result line") would be a colored line in the "result window". A further line of die could be shown in the "result window". This is the "control dye line" or line generated by a dye that corresponds to the color and intensity that would be observed in the line in the "result window" from the antibody-dye: LC3: anchored antibody sandwich if blood/serum/urine concentration was formed by at least about a certain concentration of LC3 containing cells. If the "result line" was not as intense as the "control dye line" then LC3 are at which evidence that autophagy was not responsible for the patient's illness or condition. If the "result line" was similar or more intense than the "control dye line" then the patient is predicted to have an autophagy-mediated disease state and/or condition with a high accuracy. The aim would be for a test of high sensitivity calibrated preferably to a level of LC3 predictive of a disease state.

"Cells implicated in a lipid-related metabolic disorder" include any cell manifesting a disruption of cellular lipid homeostasis. For example, familial hypercholesterolemia (FH) is caused by mutations in the LDL receptor. Although LDL receptors are expressed ubiquitously, the hepatic LDL receptor has the greatest quantitative effect in controlling plasma LDL levels. Hence hepatocytes are type of cells implicated in a lipid-related metabolic disorder. Lipoprotein lipase (LPL) deficiency is a rare autosomal recessive disorder characterized by markedly elevated plasma levels of triglycerides. Most LPL expression is in muscle and adipose tissue. Muscle (e.g. skeletal muscle) and adipose tissue cells are therefore another type of useful cell implicated in metabolic disorders. ApoE serves as a ligand that mediates the clearance of chylomicron and VLDL remnant lipoproteins by binding to the LDL receptor and related members of the same gene family. Most apoE in plasma is derived from the liver. A genetic deficiency of apoE results in substantially elevated levels of lipoprotein remnants and is associated with an increased risk for atherosclerotic vascular disease. Hepatocytes can be used in the evaluation of this disorder using techniques described herein.

Unesterified cholesterol is esterified to cholesteryl ester in the blood by the lipoprotein-associated enzyme lecithin: cholesterol acyltransferase (LCAT). Complete LCAT deficiency is characterized by markedly reduced HDL cholesterol levels (less than 10 mg/dl), corneal opacities, anemia, and progressive proteinuria and renal insufficiency eventually leading to end-stage renal disease. Although LCAT is normally synthesized in the liver, because it is a secreted protein it could theoretically be made in other tissues such as muscle. Hepatocytes and muscle cells can therefore be used in the evaluation of this disorder using techniques described herein. Tangier disease is a rare genetic disorder associated with markedly reduced HDL cholesterol levels (less than 5 mg/dl), the accumulation of cholesterol in macrophages and related cells, neuropathy, and premature atherosclerosis. Macrophages or bone marrow stem cells can therefore be used in the evaluation of this disorder using techniques described herein. ApoA-I is the major protein in HDL; a genetic deficiency of apoA-I results in markedly reduced HDL and seems, at least in some kindreds, to increase the risk for coronary artery disease. Hepatocytes and muscle cells can be used in the evaluation of this disorder using techniques described herein.

Cell samples used in methods of the invention can be stem cells. Stem cells are cells capable of differentiation into other cell types, including those having a particular, specialized function (i.e., terminally differentiated cells, such as erythrocytes, macrophages, etc.), progenitor (i.e., "multipotent") cells which can give rise to any one of several different terminally differentiated cell types, and cells that are capable of giving rise to various progenitor cells. Cells that give rise to some or many, but not all, of the cell types of an organism are often termed "pluripotent" stem cells, which are able to differentiate into any cell type in the body of a mature organism, although without reprogramming they are unable to de-differentiate into the cells from which they were derived. "Multipotent" stem/progenitor cells (e.g., neural stem cells) have a more narrow differentiation potential than do pluripotent stem cells. Another class of cells even more primitive (i.e., uncommitted to a particular differentiation fate) than pluripotent stem cells are the so-called "totipotent" stem cells (e.g., fertilized oocytes, cells of embryos at the two and four cell stages of development), which have the ability to differentiate into any type of cell of the particular species. For example, a single totipotent stem cell could give rise to a complete animal, as well as to any of the myriad of cell types found in the particular species (e.g., humans). In this specification, pluripotent and totipotent cells, as well as cells with the potential for differentiation into a complete organ or tissue, are referred as "primordial" stem cells.

"The morphology of positive control cell samples" can be determined using techniques that are well-known to those or ordinary skill in the art. For example, microtubule associated protein light chain 3(LC3) is a ubiquitin-like protein that binds to autophagosomes (AVs). Mammalian cells can be transfected with GFP tagged LC3 to track and follow the fate of AVs in the cell and to measure autophagic flux. Also, GFP-LC3 puncta that colocalize with mitochondria is a way to measure the initiation of mitochondrial autophagy, the catabolic process by which mitochondria are targeted for lysosomal degradation. See e.g. Chu, C. T., Plowey, E. D., Dagda, R. K., Hickey, R. W., Cherra III, S. J., and Clark, R. S. Autophagy in Neurite Injury and Neurodegeneration: in vitro and in vivo models. Meth. Enzymol: 453:217-49, 2009; Dagda, R. K., Zhu, J., Kulich, S. M., and Chu, C. T. Mitochondrially localized ERK2 regulates mitophagy and autophagic cell stress. Autophagy. 4 (6): 770-82, 2008. PMID: 18594198; and Zhu J, Dagda R K, Chu C T. Monitoring mitophagy in neuronal cell cultures. Department of Pathology, University of Pittsburgh School of Medicine, Pittsburgh, Pa., USA. Methods Mol. Biol. 2011; 793:325-39, 2011.

As disclosed herein the invention enables the use of high-throughput format, high-content imaging to examine the cell sample for an autophagy-associated effect on cytoplasmic puncta.

In one embodiment, determination of an autophagy-associated effect on cytoplasmic puncta involves detecting the amount of autophagy, or the amount of autophagosomes (AV) or AV activity, in a sample (e.g. a cell) both in the absence and presence of a candidate composition and an increase or a decrease in the amount of autophagy as compared to control indicates that the candidate composition is a modulator of autophagy in a cell extract, cell, tissue, organ, organism or individual. Fluorescence microscopy or a fluorescence imaging can be used to determine the amount of and/or the location of the detectable composition or moiety in a sample cell. The screening, e.g., high-throughput screening, method can comprise high-content imaging on a multi-well plate. The screening can be constructed and practiced on a multi-well plate. (Typically, wells are arranged in two-dimensional linear arrays on the multi-well platform. However, the wells can be provided in any type of array, such as geometric or non-geometric arrays. Commonly used numbers of wells include 24, 96, 384, 864, 1,536, 3,456, and 9,600.) Transmission electron microscopy (TEM) can be used to determine the amount of and/or the location of the detectable composition or moiety in the cell extract, cell, tissue, organ, organism or individual. This technique can be adapted to a plate-reader format for high-throughput screening of drugs that modulate autophagy, i.e., high-throughput detection of autophagic (autophagosome) levels and/or activity in cells or tissues. Compositions disclosed in U.S. Patent Application Document No. 20120042398 (e.g., cadaverine derivatives) can localize into or detect autophagosomes (AV) or AV subpopulations, and these compositions can comprise any detectable moiety or group, e.g., cadaverine derivative(s), or fluorescent-, bioluminescent, radioactive- and/or paramagnetic-conjugated cadaverine reagents.

For generally applicable methods and materials that can be employed in the use of high-throughput format, high-content imaging to examine a cell sample for an autophagy-associated effect on cytoplasmic puncta, see: Eils et al., Concurrent detection of autolysosome formation and lysosomal degradation by flow cytometry in a high-content screen for inducers of autophagy. BMC Biology 2011, 9:38; Carragher, et al., Combining imaging and pathway profiling: an alternative approach to cancer drug discovery, *Drug Discovery Today*, Volume 17, Issues 5-6, March 2012, Pages 203-214; and *Methods in Enzymology Volume* 506 *Imaging and Spectrascopic Analysis of Living Cells* (Conn ed.) (2012).

In preferred embodiments, the methods of the invention are conducted in a high-throughput format.

Exemplary high-throughput assay systems include, but are not limited to, an Applied Biosystems plate-reader system (using a plate with any number of wells, including, but not limited to, a 96-well plate, a-384 well plate, a 768-well plate, a 1,536-well plate, a 3,456-well plate, a 6,144-well plate, and a plate with 30,000 or more wells), the ABI 7900 Micro Fluidic Card system (using a card with any number of wells, including, but not limited to, a 384-well card), other microfluidic systems that exploit the use of TaqMan probes (including, but not limited to, systems described in WO 04083443 A1, and published U.S. Patent Application Nos. 2003-0138829 A1 and 2003-0008308 A1), other micro card systems (including, but not limited to, WO04067175 A1, and published U.S. Patent Application Nos. 2004-083443 A1, 2004-0110275 A1, and 2004-0121364 A1), the Invader® system (Third Wave Technologies), the OpenArray™ system (Biotrove), systems including integrated fluidic circuits (Fluidigm), and other assay systems known in the art. In certain embodiments, multiple different labels are used
in each multiplex amplification reaction in a high-throughput multiplex amplification assay system such that a large number of different target nucleic acid sequences can be analyzed on a single plate or card. In certain embodiments, a high-throughput multiplex amplification assay system is capable of analyzing most of the genes in a genome on a single plate or card. In certain embodiments, a high-throughput multiplex amplification assay system is capable of analyzing all genes in an entire genome on a single plate or card. In certain embodiments, a high-throughput multiplex amplification assay system is capable of analyzing most of the nucleic acids in a transcriptome on a single plate or card. In certain embodiments, a high-throughput multiplex amplification assay system is capable of analyzing all of the nucleic acids in a transcriptome on a single plate or card.

The practice of the present invention may also employ conventional biology methods, software and systems. Computer software products of the invention typically include computer readable medium having computer-executable instructions for performing the logic steps of the method of the invention. Suitable computer readable
medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing information over networks such as the Internet. For example, the components of the system may be interconnected via any suitable means including over a network, e.g. the ELISA plate reader to the processor or computing device. The processor may take the form of a portable processing device that may be carried by an individual user e.g. lap top, and data can be transmitted to or received from any device, such as for example, server, laptop, desktop, PDA, cell phone capable of receiving data, BLACKBERRY™, and the like. In some embodiments of the invention, the system and the processor may be integrated into a single unit. In another example, a wireless device can be used to receive information and forward it to another processor over a telecommunications network, for example, a text or multi-media message.

The functions of the processor need not be carried out on a single processing device. They may, instead be distributed among a plurality of processors, which may be interconnected over a network. Further, the information can be encoded using encryption methods, e.g. SSL, prior to transmitting over a network or remote user. The information required for decoding the captured encoded images taken from test objects may be stored in databases that are accessible to various users over the same or a different network.

In some embodiments, the data is saved to a data storage device and can be accessed through a web site. Authorized users can log onto the web site, upload scanned images, and immediately receive results on their browser. Results can also be stored in a database for future reviews.

In some embodiments, a web-based service may be implemented using standards for interface and data representation, such as SOAP and XML, to enable third parties to connect their information services and software to the data. This approach would enable seamless data request/response flow among diverse platforms and software applications.

The term "compound" is used herein to refer to any specific chemical compound disclosed herein. Within its use in context, the term generally may refer to a single compound, such as a polypeptide or other molecular entity used in the present invention.

In certain non-limiting embodiments, an increase or a decrease in a subject or test sample of the level of measured protein or gene expression or autophagic change as compared to a comparable level of measured protein or gene expression or autophagic change in a control subject or sample can be an increase or decrease in the magnitude of approximately ±5,000-10,000%, or approximately ±2,500-5,000%, or approximately ±1,000-2,500%, or approximately ±500-1,000%, or approximately ±250-500%, or approximately ±100-250%, or approximately ±50-100%, or approximately ±25-50%, or approximately ±10-25%, or approximately ±10-20%, or approximately ±10-15%, or approximately 5-10%, or approximately ±1-5%, or approximately ±0.5-1%, or approximately ±0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control", as used herein, can mean a sample of preferably the same source (e.g. blood, serum, tissue etc.) which is obtained from at least one healthy subject to be compared to the sample to be analyzed. In order to receive comparable results the control as well as the sample should be obtained, handled and treated in the same way. In certain examples, the number of healthy individuals used to obtain a control value may be at least one, preferably at least two, more preferably at least five, most preferably at least ten, in particular at least twenty. However, the values may also be obtained from at least one hundred, one thousand or ten thousand individuals.

A level and/or an activity and/or expression of a translation product of a gene and/or of a fragment, or derivative, or variant of said translation product, and/or the level or activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Standard techniques for growing cells, separating cells, and where relevant, cloning, DNA isolation, amplification and purification, for enzymatic reactions involving DNA ligase, DNA polymerase, and restriction endonucleases as disclosed above can be employed.

In exemplary embodiments of the invention which comprise detecting the presence of antibodies that are reactive to caspase-1, antibodies are found in a sample from a subject. The antibodies can be detected by an immunoassay wherein an antibody-protein complex is formed. The antibodies are found in the sample of the subject, e.g. serum. The subject is a human and the implicated disease (e.g. tuberculosis) is idiopathic. Healthy individuals have minimal or undetectable anti-caspase-1 by conventional ELISA or Western blots. Individuals with idiopathic tuberculosis have significant amount of detectable anti-caspase-1 auto-antibodies, at least 10% more anti-caspase-1 auto-antibodies detected over that from a healthy non-tuberculosis individual or the level obtained for a population of healthy non-tuberculosis individuals by conventional ELISA or Western blots as described herein. Moreover the levels of auto-antibodies correspond with the clinical features of the disease condition. Patients in remission after effective treatment have minimal or undetectable anti-caspase-1 auto-antibodies by conventional ELISA or Western blots. As an example, by undetectable amount of anti-caspase-1 auto-antibodies, it means that no visible band is observed in a Western Blot analysis performed as described in Example 1, wherein human serum is diluted 1:100 and used in blot assays described herein. In one embodiment, the amount of anti-caspase-1 auto-antibodies in a healthy non-tuberculosis individual or the average amount in a population of healthy non-tuberculosis individuals as determined by conventional ELISA or Western blot can be considered as the background, reference or the control level. The collected samples of serum from the healthy non-tuberculosis individuals are diluted 1:100 and used in Western blot assays. The intensity of the visible band is quantified by densitometry. The densitometry intensity can be calibrated with a range of known titer of anti-caspase-1 antibodies reacting with a fixed amount of antigen caspase-1. For example, the range of known antibody titer can be 0. mu.g/ml, 0.5. mu.g/ml, 1.0 .mu.g/ml, 1.5. mu.g/ml, 2.0. mu.g/ml, 2.5. mu.g/ml, 3.0. mu.g/ml, 5. mu.g/ml, 7.5. mu.g/ml, 10. mu.g/ml, and 15.

mu.g/ml and the fixed amount of caspase-1 can be 0.5. mu.g on a blot. By comparing the densitometry intensity of a human sample with the calibration curve, it is possible to estimate the titer of the anti-caspase-1 in the sample. For the data collected for a population of individuals, the average value and one order of standard deviation is computed. Ideally, a population has about 25 healthy non-tuberculosis individuals, preferably more. The statistics, the average value and one order of standard deviation can be uploaded to the computer system and data storage media. Patients having at least 10% more than this average amount of anti-caspase-1 auto-antibodies is likely to have tuberculosis, especially if the patient is also presents the clinical significant features of the disease. Methodologies that are similar to those described above can be used to evaluate other targets and disorders described herein.

In one embodiment, the auto-antibodies in the sample are reactive against the caspase-1 that has been extracted from mammalian tissues or recombinant mammalian caspase-1, e.g. the human caspase-1. The sample from the subject can be a blood sample. In other embodiments, the sample is a serum or plasma sample. In one embodiment, the auto-antibodies are detected by a serological immunoassay, such as an enzyme-linked immunosorbant assay or a nephelometric immunoassay.

The term "patient" or "subject" refers to an animal, such as a mammal, or a human, in need of treatment or therapy to which compounds according to the present invention are administered in order to treat a condition or disease state associated with a tuberculosis infection or inflammation-associated metabolic disorder, for instance, a particular stage of an obesity-related disorder, using compounds according to the present invention.

An "inflammation-associated metabolic disorder" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia or a lipid-related metabolic disorder (e.g. hyperlipidemia (e.g., as expressed by obese subjects), elevated low-density lipoprotein (LDL), depressed high-density lipoprotein (HDL), and elevated triglycerides) and insulin-resistant diabetes, such as Mendenhall's Syndrome, Werner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased CD4+ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth.

An "inflammation-associated metabolic disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequela of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment, "inflammation-associated metabolic disorder" includes: central obesity, dyslipidemia including particularly hypertriglyceridemia, low HDL cholesterol, small dense LDL particles and postpranial lipemia; glucose intolerance such as impaired fasting glucose; insulin resistance and hypertension, and diabetes. The term "diabetes" is used to describe diabetes mellitus type I or type II. The present invention relates to a method for improving renal function and symptoms, conditions and disease states which occur secondary to impaired renal function in patients or subjects with diabetes as otherwise described herein. It is noted that in diabetes mellitus type I and II, renal function is impaired from collagen deposits, and not from cysts in the other disease states treated by the present invention.

Mycobacterial infections often manifest as diseases such as tuberculosis. Human infections caused by *mycobacteria* have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686, (1999); and 2000 WHO/OMS Press Release).

*Mycobacteria* other than *M. tuberculosis* are increasingly found in opportunistic infections that plague the AIDS patient. Organisms from the *M. avium*-intracellular complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

In many countries the only measure for TB control has been vaccination with *M. bovis bacille* Calmette-Guerin (BCG). The overall vaccine efficacy of BCG against TB, however, is about 50% with extreme variations ranging from 0% to 80% between different field trials. The widespread emergence of multiple drug-resistant *M. tuberculosis* strains is also a concern.

*M. tuberculosis* belongs to the group of intracellular bacteria that replicate within the phagosomal vacuoles of resting macrophages, thus protection against TB depends on T cell-mediated immunity. Several studies in mice and humans, however, have shown that *Mycobacteria* stimulate antigen-specific, major histocompatibility complex (MHC) class II- or class I-restricted CD4 and CD8 T cells, respectively. The important role of MHC class I-restricted CD8 T cells was convincingly demonstrated by the failure of β2-microglobulin) deficient mice to control experimental *M. tuberculosis* infection.

As used herein, the term "tuberculosis" comprises disease states usually associated with infections caused by *mycobacteria* species comprising *M. tuberculosis* complex. The term "tuberculosis" is also associated with mycobacterial infections caused by *mycobacteria* other than *M. tuberculosis*. Other mycobacterial species include *M. avium-intracellulare, M. kansarii, M. fortuitum, M. chelonae, M. leprae, M. africanum*, and *M. microti, M. avium paratuberculosis*, M. intracellulare, M. scrofulaceum, M. xenopi, M. marinum, M. ulcerans.

An "infectious disease" includes but is limited to those caused by bacterial, mycological, parasitic, and viral agents. Examples of such infectious agents include the following: *staphylococcus, streptococcaceae, neisseriaaceae, cocci, enterobacteriaceae, pseudomonadaceae, vibrionaceae, campylobacter, pasteurellaceae, bordetella, francisella, brucella, legionellaceae, bacteroidaceae*, gram-negative *bacilli, clostridium, corynebacterium, propionibacterium*, gram-positive *bacilli, anthrax, actinomyces, nocardia, mycobacterium, treponema, borrelia, leptospira, mycoplasma, ureaplasma, rickettsia, chlamydiae*, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picornaviruses, reoviruses, togaviruses, flaviviruses, bunyaviridae, rhabdoviruses, human immunodeficiency virus and retroviruses.

In certain embodiments, an "infectious disease" is selected from the group consisting of tuberculosis, leprosy, Crohn's Disease, acquired immunodeficiency syndrome, Lyme disease, cat-scratch disease, Rocky Mountain spotted fever and influenza or a viral infection selected from HIV (I and/or II), hepatitis B virus (HBV) or hepatitis C virus (HCV).

"Autophagy-related immunomodulatory cytokines" include, but are not limited to, IL-1α, IL-1β, IL-18, IL-12 p40 subunit, IL-4, IL13, LMP1, EBNA2, IFN-γ, ATG16L1, IRGM1, LC3B-II, HMGB1 and TBK-1, among others.

"TBK-1 agonists" include, but are not limited to, a vascular disrupting agent (VDA) such as lavone acetic acid and its derivatives, e.g., 5,6-dimethylxanthenone-4-acetic acid (DMXAA)).

"Caspase-1 inhibitors" include, but are not limited to, minocycline, VX-765, IL-18BP, Ac-YVAD.cmk, acetyl-Tyr-Val-Ala-Asp-chloromethylketone, N-benzyloxycarbonyl-Val-Ala-Asp-fluoromethylketone, zVAD-fmk, Z-Val-Ala-DL-Asp-fluoromethylketone, ML132 (CID-4462093; NCGC-00183434), (−)-berkeleyamide A (1), NCGC00185682, VRT-043198, the capsase-1 inhibitors identified in Boxer, et al., ChemMedChem, 2010 May 3; 5(5):730-8, and N-Ac-Tyr-Val-Ala-Asp-chloromethyl ketone (Ac-YVAD-CMK).

"Autophagy-related immunomodulatory cytokine antagonists" include but are not limited to interleukin-1 receptor antagonist (IL-1RA), human recombinant forms of IL-1RA, a vascular disrupting agent (VDA) such as lavone acetic acid and its derivatives, e.g., 5,6-dimethylxanthenone-4-acetic acid (DMXAA).

The term "biological sample" encompasses a variety of sample types obtained from an organism and can be used in a diagnostic or monitoring assay. The term encompasses blood and/or plasma and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "body fluid" and "bodily fluid," used interchangeably herein, refer to a biological sample of liquid from a mammal, e.g., from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts. Particular bodily fluids that are interest in the context of the present invention include serum, plasma, and blood.

According to various embodiments, the compounds according to the present invention may be used for treatment or prevention purposes in the form of a pharmaceutical composition. This pharmaceutical composition may comprise one or more of an active ingredient as described herein.

As indicated, the pharmaceutical composition may also comprise a pharmaceutically acceptable excipient, additive or inert carrier. The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrolidone, polyvinylpolypyrolidone, sodium acetate, magnesium stearate, sodium laurylsulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive.

The pharmaceutical composition may be in a form chosen from sterile isotonic aqueous solutions, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intestinal, parenteral, oral, buccal, nasal, intramuscular, transcutaneous, transdermal, intranasal, intraperitoneal, and topical. The pharmaceutical compositions may be immediate release, sustained/controlled release, or a combination of immediate release and sustained/controlled release depending upon the compound(s) to be delivered, the compound(s), if any, to be coadministered, as well as the disease state and/or condition to be treated with the pharmaceutical composition. A pharmaceutical composition may be formulated with differing compartments or layers in order to facilitate effective administration of any variety consistent with good pharmaceutical practice.

The subject or patient may be chosen from, for example, a human, a mammal such as domesticated animal, or other animal. The subject may have one or more of the disease states, conditions or symptoms associated with autophagy as otherwise described herein.

The compounds according to the present invention may be administered in an effective amount to treat or reduce the likelihood of an autophagy-mediated disease and/or condition as well one or more symptoms associated with the disease state or condition. One of ordinary skill in the art would be readily able to determine an effective amount of active ingredient by taking into consideration several variables including, but not limited to, the animal subject, age, sex, weight, site of the disease state or condition in the patient, previous medical history, other medications, etc.

For example, the dose of an active ingredient which is useful in the treatment of an autophagy mediated disease state, condition and/or symptom for a human patient is that which is an effective amount and may range from as little as 100 µg or even less to at least about 500 mg or more, which may be administered in a manner consistent with the delivery of the drug and the disease state or condition to be treated. In the case of oral administration, active is generally administered from one to four times or more daily. Transdermal patches or other topical administration may administer drugs continuously, one or more times a day or less frequently than daily, depending upon the absorptivity of the active and delivery to the patient's skin. Of course, in certain instances where parenteral administration represents a favorable treatment option, intramuscular administration or slow IV drip may be used to administer active. The amount of active ingredient which is administered to a human patient preferably ranges from about 0.05 mg/kg to about 10 mg/kg, about 0.1 mg/kg to about 7.5 mg/kg, about 0.25 mg/kg to about 6 mg/kg., about 1.25 to about 5.7 mg/kg.

The dose of a compound according to the present invention may be administered at the first signs of the onset of an autophagy mediated disease state, condition or symptom. For example, the dose may be administered for the purpose of lung or heart function and/or treating or reducing the likelihood of any one or more of the disease states or conditions which become manifest during an inflammation-associated metabolic disorder or tuberculosis or associated disease states or conditions, including pain, high blood pressure, renal failure, or lung failure. The dose of active ingredient may be administered at the first sign of relevant symptoms prior to diagnosis, but in anticipation of the disease or disorder or in anticipation of decreased bodily function or any one or more of the other symptoms or secondary disease states or conditions associated with an autophagy mediated disorder to condition.

These and other aspects of the invention are described further in ther following illustrative examples.

EXAMPLE 1

Autophagy is a barrier against excessive inflammation and active tuberculosis

Here we show that autophagy plays a dual role against tuberculosis: anti-bacterial and anti-inflammatory. Autophagy defect in Atg5$^{fl/fl}$ LysM-Cre+ mice, infected with *M. tuberculosis*, resulted in increased bacillary burden and excessive pulmonary inflammation, neutrophilic infiltration, and necrosis. This response was in part due to a cell-autonomous pro-inflammatory phenotype. Autophagy-deficient macrophages released excessive amounts of cytokines delivered by conventional and unconventional secretory pathways. The mechanism for excessive secretion was determined for the cytosolic alarmin IL-1α: caspase 1, required for unconventional secretion of IL-1α, was downregulated by autophagy. IL-1α induced IL-17 in CD4 T cells in keeping with neutrophilic inflammatory state. Thus, autophagy protects against *M. tuberculosis* and prevents uncontrolled inflammation leading to tissue necrosis characteristic of active tuberculosis disease.

Introduction

Despite *M. tuberculosis* being one of the first recognized microbes subject to elimination by immunological autophagy in ex vivo systems in murine and human macrophages (Alonso et al., 2007; Gutierrez et al., 2004; Harris et al., 2007; Kim et al., 2011; Xu et al., 2007; Yuk et al., 2009a), the in vivo role of autophagy in control of *M. tuberculosis* has not been reported, although genetic evidence nevertheless indicates that at least one of the autophagic factors (Singh et al., 2006; Singh et al., 2010) involved in Crohn's disease (Craddock et al., 2010; McCarroll et al., 2008) may predispose human populations to tuberculosis (Intemann et al., 2009). Given the compelling reasons to test whether autophagy matters for control of *M. tuberculosis* in vivo, here we used a mouse model of tuberculosis and employed transgenic mice deficient in Atg5 in macrophages, the cell type parasitized by *M. tuberculosis* (Vergne et al., 2004). We demonstrate that autophagy controls tuberculosis infection in vivo and uncover a potentially key role of autophagy in containing the inflammatory reactions of the host. When autophagy is deficient in the macrophages of infected mice, not only does this permit bacterial growth but also leads to an excessive proinflammatory response, with partial roots in sterile inflammation, leading to lung tissue destruction, necrosis and active tuberculosis. Thus, in addition to the demonstration that autophagy controls *M. tuberculosis* in vivo, our data indicate that autophagy represents a barrier against tissue destruction, the hallmark of active disease and the necessary infection stage for the propagation of tuberculosis in human populations.

Results

Autophagy protects mice from excessive lung pathology following aerogenic infection with *M. Tuberculosis*

The in vivo role of autophagy was investigated by selective genetic deletion of Atg5 in myeloid cells, with macrophages being of principal interest as the cells both successfully parasitized by intracellular *M. tuberculosis* (Vergne et al., 2004) and targeted by protective immune responses. We used the previously reported conditional gene knockout mouse model Atg5$^{fl/fl}$ LysM-Cre+ with Atg5 deletion in myeloid lineage (Zhao et al., 2008). The Atg5+ mice (Atg5fl/fl LysM-Cre−) and their Atg5$^{fl/fl}$ LysM-Cre+ littermates, previously characterized for lack of Atg5 and autophagy in macrophages (Dupont et al., 2011), were subjected to aerogenic infection with virulent *M. tuberculosis* H37Rv. A major weight loss was observed in the infected Atg5-deficient mice compared to Atg5-proficient mice (FIG. 1A) when mice were infected with 103 *M. tuberculosis* cfu (lung deposition infectious dose termed e3; Supplementary Table 1). This was accompanied by lung pathology remarkable for gross tubercle lesions in contrast to smaller infected foci in the lungs of Atg5+ animals (FIG. 1B). Microscopic examination of Atg5$^{fl/fl}$ LysM-Cre+ lung tissue revealed massive lesions showing poor cellular organization and extensive necrotic centers, with veterinary pathologist findings described in Supplementary Materials (FIG. 1C). Acid fast bacilli, with prominence of extracellular bacteria, were notable in Atg5$^{fl/fl}$ LysM-Cre+ compared to Atg5$^{fl/fl}$ LysM-Cre− lung sections (FIG. 1C). Unlike the infected Atg5$^{fl/fl}$ LysM-Cre+ lungs, the lungs from the infected Atg5fl/fl LysM-Cre− mice had fewer intracellular bacilli with little to no extracellular bacilli present in the lung sections (FIG. 1C).

In keeping with the well-known general resistance of mice to tuberculosis, neither group of mice succumbed to the infection in short term (36 days) experiments (Supplementary Table 1). When a higher infection dose (e4; lung disposition of 104 cfu Supplementary Table 1) was employed, this resulted in animal mortality with accelerated deaths (along with weight loss) among Atg5fl/fl LysM-Cre+ mice relative to their Atg5fl/fl LysM-Cre− littermates, starting 20 days post infection (FIG. 1D,E). With the most commonly used low infectious dose (e2; lung disposition of 102 cfu), the Atg5fl/fl LysM-Cre+ mice displayed increased lung gross pathology and organ size/weight of both lungs and spleens (Suppl. FIG. S1A-C), poorer cellular organization and more necrosis (Suppl. FIG. S1D), increased infiltration of innate immune cells into the lungs (Suppl. FIG. S1E-G), and more acid fast bacilli in lung sections (Suppl. FIG. S1H). The lungs of e2 infected animals showed a ten-fold increase in cfu recovered from Atg5fl/fl LysM-Cre+ mice relative to their Atg5 fl/fl LysM-Crelittermates (FIG. S1H).

These data collectively show that Atg5$^{fl/fl}$ LysM-Cre+ mice are more susceptible to *M. tuberculosis* infection and display increased inflammation and lung pathology over a range of infectious doses Atg5 deficiency increases basal immune activation state in the uninfected lung Given the large differences in lung gross and histopathology and a relatively small detectable difference in bacterial loads between infected Atg5fl/fl LysM-Cre+ and Atg5$^{fl/fl}$ LysM-Cre− mice (FIG. S1H), we considered the possibility that, apart from the direct effects in eliminating *mycobacteria* from macrophages as previously established in vitro (Alonso et al., 2007; Gutierrez et al., 2004; Harris et al., 2007; Kim et al., 2011; Xu et al., 2007; Yuk et al., 2009a), autophagy in myeloid cells may be necessary for innate immune cellular homeostasis or function to prevent an excessive response to infection. We tested whether indications of such alterations may be detectable in animals not infected with *M. tuberculosis*, since infection would complicate interpretations. Similar numbers of cells expressing macrophage markers, F4/80+ CD11b+ (Lineage-negative: CD3− CD19−), were detected in the lungs and bone marrow of uninfected Atg5fl/fl LysMCre+ and Cre− mice (FIG. 2A,B). However, lung macrophages obtained from uninfected. Atg5$^{fl/fl}$ LysM-Cre+ mice displayed an activated phenotype (FIG. 2C), in keeping with their general in situ morphology (Suppl. FIG. S2A; inset). Specifically, Atg5$^{fl/fl}$ LysM-Cre+ cells had increased expression of MHC class II, DEC205, and CD86. An increase in the numbers of CD11b+ F4/80− cells was observed in uninfected Atg5$^{fl/fl}$ LysM-Cre+ mice (FIG. 2A). Further examination revealed that these cells were Ly6G+ (1a8 clone) polymorphonuclear granulocytes (PMN; neutrophils) (FIG. 2D). This increase in PMN total number was only observed in the lungs, as bone marrow PMN numbers were comparable for both groups of mice (FIG. 2E). These data indicate that autophagy in myeloid cells of peripheral organs such as lungs, where continual immune surveillance is necessary, maintains a homeostatic balance of immune cells and their activations states under normal physiological conditions.

Atg5-deficiency in myeloid lineage results in excessive inflammatory cytokine response to infection We examined cytokine profiles (using Luminex technology) during the course of e$^2$ infection in the lungs of Atg5$^{fl/fl}$ LysM-Cre+ and Atg5fl/fl LysM-Cre− littermates. Within the broad panel of cytokines and chemokines tested, the e$^2$-infected Atg5fl/fl LysM-Cre+ lungs displayed a significant increase in the cytokines IL-1α and IL-12 and a chemokine, CXCL1, at different time points of infection (FIG. 3A-C). Additional increases were observed for IL-1β (albeit the absolute levels were low) and GM-CSF with no differences in IL-6 and the chemokine MIP-1β (FIG. S3A-D). We did not see a major difference in IFN-γ and TNFα the well established anti-tuberculosis cytokines (Flynn and Chan, 2001), or IL-4, an intracellular pathogen-permissive cytokine known to inhibit autophagy ex vivo (Harris et al., 2007) (FIG. S3E-G). A difference in IL-17 levels was detected (Suppl. FIG. S3H). To test whether cytokine increases in the lungs of infected Atg5$^{fl/fl}$ LysM-Cre+ animals had cell-autonomous and infection-independent roots based on defective autophagy in relevant cell types, we compared bone marrow macrophages (BMM) from uninfected Atg5$^{fl/fl}$ LysM-Cre+ mice and Atg5fl/fl LysM-Cre− littermate controls. Uninfected BMM were stimulated with IFN-γ and the TNF-α mimetic LPS, with IFN-γ and TNF-α being two key cytokines driving the responses to *M. tuberculosis* infection. Remarkably, Atg5$^{fl/fl}$ LysM-Cre+ BMM recapitulated the in vivo pattern of elevated cytokine secretion and displayed increased release of IL-1α, IL-12p70 and CXCL1 relative to Atg5$^{fl/fl}$ LysM-Cre− BMM (FIG. 3D-F). Differential IL-1α release was not due to changes in cell death or membrane permeability since in vitro activated. BMM from Atg5$^{fl/fl}$ LysM-Cre+ and Atg5$^{fl/fl}$ LysM-Cre− mice showed no difference in staining with 7-AAD (Suppl. FIG. S3I). Furthermore, Atg5$^{fl/fl}$ LysM-Cre+ and Atg5$^{fl/fl}$ LysM-Cre− showed differential release of only a subset of cytokines, including IL-12p70 and CXCL1 that, unlike IL-1α, utilize the biosynthetic pathway and traffic through the lumen of ER-Golgi-post-Golgi organelles for active secretion from the cells. Intracellular IL-12p35 was also shown via flow cytometry to be increased in stimulated BMM lacking Atg5 relative to Atg5-proficient BMM (Suppl. FIG. S3J,K). A subset of the above in vitro findings showing elevated cytokine secretion were corroborated in vivo using lung homogenates of uninfected Atg5fl/fl LysM-Cre+ and Cre− mice (FIG. 3D-F). Atg5$^{fl/fl}$ LysM-Cre+ lung samples had significantly increased amounts of IL-1α and CXCL1 compared to Atg5$^{fl/fl}$ LysM-Cre− lungs (FIG. 3G,H). IL-12p70 was below the limit of detection in uninfected lung homogenates and could not be assessed in this way. Conversely, the chemokine, CXCL2, which was expressed at similar levels in the presence or absence of an intact autophagy pathway in BMM examined in vitro; was increased in Atg5fl/fl LysM-Cre+ lung homogenate (Suppl. FIG. S3L,M). These results revealed additional complexities in vivo, but nevertheless validated both in vivo and in vitro the elevated IL-1α and CXCL1 phenotype in Atg5fl/fl LysM-Cre+ lungs and macrophages.

Autophagy is essential for the regulation of IL-1α Ssecretion

We next focused on the cell-autonomous IL-1α hypersecretion phenotype in Atg5$^{fl/fl}$ LysM-Cre+ macrophages. IL-1α is a cytosolic protein, produced as a proform processed during activation by proteases such as calpain or alternative proteolytic enzymes (Afonina et al., 2011) and actively exported out of the cell (Yazdi et al., 2010) or passively released upon cell death (Chen et al., 2007). We first confirmed that autophagy was a negative regulator of IL-1α release by pharmacologically manipulating autophagy in autophagy-competent macrophages. When autophagy was induced with rapamycin in Atg5fl/fl LysM-Cre− BMM this reduced the amount of IL-1α being secreted (FIG. 4A). Conversely, when Atg5fl/fl LysM-Cre− BMM were treated with 3-methyladenine, an inhibitor of autophagosome formation, the levels of IL-1α were significantly increased (FIG. 4A) mimicking a condition observed upon genetic disabling of autophagy. A similar trend was observed when bafilomycin A1, an inhibitor of autophagic flux was added during stimulation (FIG. 4B). The results of pharmacological modulation of autophagy in normal BMM validated the conclusions derived with Atg5$^{fl/fl}$ LysM-Cre+ BMM that autophagy negatively regulates IL-1α activation and secretion.

Cell-autonomous IL-1α hypersecretion phenotype in autophagy-deficient macrophages is not secondary to autophagic effects on p62 or calpain To delineate the mechanism of how autophagy controls IL-1α activation and secretion we considered several levels and factors that could potentially mediate the effects of the absence of autophagy. The autophagic adaptor protein p62, which is consumed during autophagy (Jam et al., 2010) and is the founding member of the SLR family of PRR functions in innate immunity signaling (Deretic, 2011), accumulates in the absence of autophagy pathway and has been shown to perturb NF-κB responses (Mathew et al., 2009; Moscat and Diaz-Meco, 2009). As IL-1α expression is induced by NF-κB (Xia et al., 1999), p62 accumulation could be the cause of elevated IL-1α expression. However, knocking down p62 via siRNA in Atg5$^{fl/fl}$ LysM-Cre+ BMM (FIG. S4A) did not abrogate the elevated IL-1α secretion by these cells (FIG. S4B). A converse experiment was also carried out. Atg5 was knocked down in BMM from p62−/− knockout mice and this still caused more (albeit less pronounced likely due to residual Atg5 levels) IL-1α secretion than in the scrambled siRNA control (FIG. S4C). Finally, no increase in IL-1α mRNA levels were detected in Atg5$^{fl/fl}$ LysM-Cre+ BMM relative to Atg5fl/fl LysM-Cre− BMM (FIG. S4D), thus establishing that Atg5-deficient cells are neither transcriptionally pre-activated for IL-1α expression nor that p62 contributes to the IL-1α phenotype. Since calpain activates IL-1α, we used ALL, a calpain inhibitor, to test whether calpain was involved in the IL-1α hypersecretion phenotype of Atg5fl/fl LysM-Cre+ cells. ALLN treatment of Atg5fl/fl LysM-Cre+ completely abrogated the excess IL-1α production normalizing its secretion to the levels seen with Atg5fl/fl LysM-Crecells (FIG. 4C). Hence, we considered the possibility that calpain was involved in mediating differences between Atg5fl/fl LysM-Cre+ and Atg5fl/fl LysM-Cre+ cells, and that it could be a substrate for autophagic removal. However, calpain and LC3 did not colocalize in the cytoplasm, as indicated by a negative Pearson's colocalization coefficient in bafilomycin A1-treated cells that would have preserved calpain in autophagic organelles due to inhibition of autophagic flux and degradation (Suppl. FIG. S5A,B). Most importantly, the intracellular levels of calpain were similar in Atg5fl/fl LysM-Cre+ and Atg5fl/fl LysM-Cre BMM (FIG. S5C, D).

Factor X is responsible for hypersecretion of IL-1α in the absence of autophagy

Next we studied whether IL-1α is a direct target for removal in autophagic organelles. When autophagy-competent BMM (Atg5$^{fl/fl}$ LysM-Cre−) were examined by fluorescent confocal microscopy, cells fell into two categories— those that were positive for IL-1α punctate staining and those that were positive for LC3 puncta (FIG. 4D) with very few cells that were positive for both IL-1α established by a χ2 test (χ2<0.02; Suppl. FIG. S4E). This observation was initially taken as an indication that IL-1α may be targeted by autophagy for degradation, so we proceeded by examining whether bafilomycin A1 treatment could spare IL-1α. Indeed, bafilomycin A1 treatment increased the number of cells positive for both IL-1α and LC3 (FIGS. 4E and F) with nonrandom distribution (Suppl. FIG. S4E; χ2<0.95). However, LC3 and IL-1α did not colocalize (FIGS. 4E and 5A,B), suggesting that it is not IL-1α that is a direct substrate for autophagic elimination. This led us to postulate the existence of a putative factor, dubbed factor X, regulating IL-1α in some way, e.g. amounts or secretion, was a substrate for autophagy.

Factor X is caspase 1

In considering the candidates for factor X, we were aided by the recent reports that alarmins, including IL-1α, that are not conventional substrates for inflammasome can nevertheless be affected by a platform similar to that which controls the conventional caspase 1 substrate IL-1β (Fettelschoss et al., 2011; Keller et al., 2008; Yazdi et al., 2010). In contrast to the negative Pearson's colocalization coefficient for IL-1α and LC3, caspase 1 and LC3 showed positive colocalization (FIG. 5A,B). Next, BMM were tested for caspase 1 levels and activation. Atg5fl/fl LysM-Cre+ BMM showed increased levels of activated caspase 1 (p20) in comparison to Atg5$^{fl/fl}$ LysM-Cre− BMM, whereas pro-caspase 1 levels did not differ (FIG. 5C and Suppl. FIG. S5E). Bafilomycin A1 treatment resulted in abnormally higher levels of caspase 1 p20 in Atg5fl/fl LysM-Cre− BMM mimicking the state of Atg5$^{fl/fl}$ LysM-Cre+ cells (FIG. 5C and Suppl. FIG. S5E). Furthermore, caspase 1 activity measured by FLICA assay demonstrated increased enzymatically active Caspase 1 in Atg5fl/fl LysM-Cre+ BMM compared to Atg5fl/fl. LysM-Cre− BMM (Suppl. FIG. S5F). Finally, IL-1α secretion was further increased from autophagy-defective BMM in response to silica, which is a conventional inflammasome agonist (FIG. 5D). We conclude that factor X is caspase 1 and that it is normally targeted by autophagy for downregulation. Caspase 1 is increased in amounts and activity in autophagy-defective macrophages, and is a contributor to the cell-autonomous phenotype of elevated IL-1α secretion observed in our experiments with Atg5$^{fl/fl}$ LysM-Cre+macrophages.

Functional autophagic machinery in macrophages dictates CD4 T cell polarization and regulates IL-17 response The activated macrophages, PMN infiltrates, cytokines and chemokines present in the lung of uninfected Atg5$^{fl/fl}$ LysM-Cre+ mice suggested features of a Th17 response (Chung et al., 2009; Korn et al., 2009). We considered this further. First, we determined the proportion of CD8 and CD4 T cells displaying an activated/memory phenotype. CD44 and CD25 expression was examined on both CD8 and CD4 T cells. The proportion of T cells displaying an activated/ memory phenotype (CD44high) was significantly increased for both CD8 and CD4 populations in Atg5$^{fl/fl}$ LysM-Cre+ mice (FIG. 6A, Suppl. FIG. S6A). A portion of the CD44high CD4 T cells were also positive for CD25 suggesting that these cells were recently activated (FIG. 6A). To determine if these T cells were polarized to a certain subset of helper T cells we stimulated total lung leukocytes with PMA/ionomycin (plus protein transport inhibitors) and then assessed intracellular levels of IL-17A and IFN-γ expressed by CD4 T cells. CD4 T cells from Atg5fl/fl LysM-Cre+ lungs but not those from Atg5$^{fl/fl}$ LysM-Cre− lungs produced IL-17A (FIG. 6B,C). There was no marked difference between the same cells from two sources in their ability to mount IFN-α response (FIG. 6B.C). These findings indicate a propensity of CD4 T cells from Atg5$^{fl/fl}$ LysM-Cre+ CD4 T cells to produce IL-17A upon stimulation.

Defective autophagy in myeloid lineage of Atg5fl/fl LysM-Cre+ mice promotes IL-17 response to defined *M. tuberculosis* antigens by T cells The cells from the lungs of *M. tuberculosis* infected Atg5$^{fl/fl}$ LysM-Cre+ and Cremice revealed little difference in key Th1 and Th2 cytokines as described above. However, a trend was observed for more IL-17 in infected Atg5$^{fl/fl}$ LysM-Cre+ mice (FIG. S3E-H). We followed up on this lead using a cocktail of 5 well defined. *M. tuberculosis* protein antigens (DnaK, GroEL, Rv009, Rv0569, Rv0685), collectively referred to as synthetic PPD (Yang et al., 2011) in reference to the purified protein derivative (PPD) used clinically as tuberculin skin test for evidence of recent tuberculosis infection or BCG vaccination. This synthetic reagent contains the dominant antigens present in the conventional PPD, includes additional key immunogenic proteins. Synthetic PPD reproduces the anatomical and molecular properties of the tuberculin skin test and eliminates false positive inflammatory reactions (seen in uninfected hosts) caused by the contaminating lipoglycans and carbohydrates resident in conventional PPD, thus enabling monitoring of specific responses to infection with the *M. tuberculosis* complex organisms in a model system (Yang et al., 2011). Atg5 fl/fl LysM-Cre+ and Cre– mice were infected with live *M. bovis* BCG and then evaluated for their ability to mount a delayed type hypersensitivity response (DTH) to synthetic PPD (Yang et al., 2011). Three weeks postinfection, mice were injected with the synthetic PPD or PBS in the hind footpad and swelling was measured at 0, 2, 24 and 48 h postinoculation (FIG. 6C). No measurable difference was observed at 24 and 48 h time point between the autophagy competent and mutant mice. However, when splenocytes were re-stimulated ex vivo with the synthetic PPD, IL-17A was detected at a significantly higher levels with Atg5$^{fl/fl}$ LysM-Cre+ splenocyte supernatant whereas no differences were observed for typical Th1 and Th2 cytokine signatures (FIG. 6D,E; Suppl. FIG. S6B,C) indicating polarization to IL-17 producing phenotype in Atg5$^{fl/fl}$ LysM-Cre+ mice. Finally, we tested whether IL-1α, observed in excess in Atg5$^{fl/fl}$ LysM-Cre+ lungs or with Atg5fl/fl LysM-Cre+ BMM could act similarly to IL-1β in promoting Th17 polarization (Chung et al., 2009). Naïve CD4 T cells were treated in the presence of TGF-β, IL-6 and IL-1α or IL-1β and then stimulated in the presence of protein transport inhibitors. The intracellular levels of IL-17A were elevated whether IL-1α or IL-1β were used to promote Th17 differentiation (FIG. 6F).

These data sets indicate that a dysregulation in the autophagic pathway in macrophages can result in an in situ generation of IL-17-producing T cells via the excess production of IL-1α.

Discussion

This work demonstrates the in vivo role for autophagy in protection against tuberculosis. Along with the previous in vitro studies (Alonso et al., 2007; Gutierrez et al., 2004; Harris et al., 2007; Hartman and Kornfeld, 2011; Kim et al., 2011; Xu et al., 2007; Yuk et al., 2009a) this establishes that autophagy is an antimycobacterial effector mechanism. Autophagy also protects against excessive tissue necrosis and lung pathology, the hallmarks of active tuberculosis. This effect is not a trivial consequence of increased bacillary loads but reflects a cell-autonomous action of autophagy as shown in vitro with macrophages from uninfected animals. In addition to the expected immune activation commensurate with bacterial loads, autophagy-defective macrophages have an intrinsic propensity to release excessive amounts of inflammatory mediators IL-1α and CXCL1, shown in vitro and mirrored in vivo in uninfected lungs. A model emerges whereby these mediators pivot inflammation with features of Th17 response, neutrophilic infiltration, tissue necrosis and organ damage, the main features of active tuberculosis and contagious state of the host.

The mechanisms of cell-autonomous elimination of *M. tuberculosis* by autophagy have been extensively studied in vitro and include direct microbial digestion in autophagolysosomes (Gutierrez et al., 2004), delivery of neoantimicrobial peptides generated in autolysosomes to compartments harboring intracellular mycobacteria (Alonso et al., 2007; Kim et al., 2011; Ponpuak et al., 2010) and an interplay of autophagy with conventional antimicrobial peptides (Yuk et al., 2009b). Our previous work (Ponpuak et al., 2010) has highlighted the role of the SLR p62 in these processes, along with the examples of other SLRs engaging an array of intracellular bacteria (Deretic, 2011; Dupont et al., 2009; Thurston et al., 2009; Wild et al., 2011; Yoshikawa et al., 2009) and viruses (Orvedahl et al., 2010). The work presented in the accompanying study by J. Cox and colleagues extends this further and places the role of SLRs in the context of the ESXdependent interactions between *M. tuberculosis* and the host cell cytosol. In contrast to a preponderance of studies in vitro, autophagic control of microbes remains to be fully understood in vivo (Orvedahl et al., 2010; Zhao et al., 2008). Altered intestinal tissue and Paneth cell function has been noted in response to microbial flora and viral co-infection in an Atg16L1 hypomorph mouse model of Crohn's disease, a chronic inflammatory condition [Cadwell, 2010 #13743]. In the animal model of protection against lethal Sindbis virus infection, the dominant contribution of autophagy was in preventing tissue damage independently of viral loads (Orvedahl et al., 2010). This dovetails with the aspect of our study that shows autophagic protection against excessive inflammation and necrosis in the murine model of tuberculosis.

The finding that a loss of autophagy in macrophages results in increased release of IL-1α and CXCL1 and fosters an environment where T cells produce IL-17A production links for the first time autophagy with elements of the Th17 response. The increased presence of neutrophils in the lungs of Atg5$^{fl/fl}$ LysM-Cre+ mice infected with *M. tuberculosis* was consistent with lung tissue damage and progressive disease. The role of neutrophils in tuberculosis has been both highlighted in recent patient cohort studies (Berry et al., 2010) and may be associated with the paradoxical Koch effect (Koch, 1891), whereby administration of *M. tuberculosis* antigens to pre-infected subjects increases granulocyte influx and necrosis in the preexisting stabilized lesions in the lung (Moreira et al., 2002; Taylor et al., 2003; Turner et al., 2000). Neutrophils contribute to tuberculosis pathogenesis (Eruslanov et al., 2005), support lymphatic mycobacterial dissemination (Abadie et al., 2005), and promote person-to-person transmission via cavitary disease or other routes of bacillary delivery into patients' sputa (Eum et al., 2010), outweighing potential antibacterial actions of neutrophils. Our data indicate that autophagy, when functional, curbs neutrophilic response.

A specific dysregulated cytokine response in Atg5$^{fl/fl}$ LysM-Cre+ mice for which a cell-autonomous molecular mechanism has been determined in this work is the excessive release of IL-1α. IL-1 signaling has been implicated in defense against *M. tuberculosis* but presents a host of non-trivial relationships. IL-1β and its receptor IL-1RI have been associated with the powerful antimycobacterial role of MyD88 (Fremond et al., 2007; Mayer-Barber et al., 2010), an adaptor downstream of IL-1R1 and other pattern recognition receptors. Mycobacterial products can induce inflammasome, caspase 1, and IL-1β production (Mishra et al., 2010) and virulent *M. tuberculosis* actively suppresses inflammasome activation and IL-1β production in vivo (Master et al., 2008). The effector mechanisms downstream of IL-1 signaling include autophagy as a mycobactericidal mechanism activated by IL-1β via MyD88 (Pilli et al., submitted). Nevertheless, not all aspects of IL-1 signaling are protective. IL-1β suppresses IFN-γ production and Th1 polarization by inducing COX-2 and promotes Th17 responses causing neutrophil-dominated inflammation (van de Veerdonk et al., 2011). Whereas beneficial in control of extracellular bacteria, these features may not be desirable against *M. tuberculosis* as discussed above and instead may contribute to immunopathology. This is in keeping with the findings that excess IL-17A and potentially other Th17 cytokines and neutrophil chemokines can deleteriously enhance lung pathology during *M. tuberculosis* infection (Cruz et al., 2010). As observed in present study, IL-1α can affect aspects of Th17 polarization as effectively as IL-1β. It has been reported that the abundant presence of IL-1α in IL-1β-deficient mice (Mayer-Barber et al., 2010) cannot compensate for the lack of IL-1β, arguing that IL-1α may not have the anti-mycobacterial potency or bioavailability as IL-1β, which suggest that IL-1α may be primarily pathogenic. Nevertheless, the results of two recent studies (Guler et al., 2011; Mayer-Barber et al., 2011) indicate that IL-1α is required to control tuberculosis at a yet to be defined stage during immune response or tissue remodeling. Thus, any therapeutic strategies aiming at neutralizing IL-1α specifically to curb tissue destruction and neutrophilic contribution to contagious state in active disease will have to await further studies.

IL-1α is produced as a cytosolic pro-form that can be processed by calpain or other proteases (Afonina et al., 2011) and actively exported out of the cell as shown here and elsewhere (Yazdi et al., 2010) or be passively released upon cell death (Chen et al., 2007). The IL-1α secretion, normally suppressed by basal autophagy as detected here was an active process of unconventional secretion from macrophages, in keeping with macrophages being one of the major sources of secreted IL-1α in certain forms of inflammation (Kono et al., 2010). The cellular mechanism of excessive IL-1α release was linked to increased intracellular active caspase-1 in $Atg5^{fl/fl}$ LysM-Cre+ macrophages. Although surprising, this is in keeping with the growing evidence (Fettelschoss et al., 2011; Keller et al., 2008; Lamkanfi, 2011; Lamkanfi et al., 2010; Willingham et al., 2009; Yazdi et al., 2010) that various inflammasome components contribute to extracellular release of substrates other than the canonical caspase-1-processed targets such as IL-1β (Dinarello, 2009). Like IL-1β, the alarmins HGMB1 (Keller et al., 2008; Lamkanfi, 2011; Lamkanfi et al., 2010; Willingham et al., 2009) and IL-1α (Fettelschoss et al., 2011; Keller et al., 2008; Yazdi et al., 2010) are subject to unconventional secretion and are affected by inflammasome components although they are not proteolytically processed by caspase-1 (Johansen et al., 2011; Keller et al., 2008; Lamkanfi, 2011; Lamkanfi et al., 2010; Willingham et al., 2009; Yazdi et al., 2010). The mechanism for hypersecretion of IL-12 and CXCL1 by Atg5fl/fl LysM-Cre+ macrophages was not determined. We favor the possibility that these cytokines, which utilize the conventional secretory pathway, are influenced by the recently described specific intersections between the organelles of the biosynthetic secretory pathway and autophagy as shown in the case of IL-6 (Narita et al., 2011).

Tuberculosis has been and remains one of the main global public health hazards further augmented by the HIV co-pandemic (Nunn et al., 2005). The classical presentation of disease is often masked by the untreated HIV co-infection (Nunn et al., 2005), but in principle the majority of humans have a well developed capacity to contain the infection so that the majority of the world's population infected with the tubercle bacillus is asymptomatic and only approximately 10% of individuals develop active disease. This tip of the iceberg is nevertheless key to continuing the tuberculosis contagion in human populations, since active disease is necessary for the transmission of tuberculosis. We propose that autophagy plays a dual role: it both protects against the microbe and guards against host-inflicted tissue destruction and active disease. In this model autophagy curbs tuberculosis transmission by helping maintain the majority of the infected population asymptomatic. Strategies aimed at pharmacological manipulation of autophagy may diminish tuberculosis spread, which may prove vital in containing the spread of the increasingly drug-resistant tuberculosis strains.

Experimental Procedures

Mice, infection, cells, flow cytometry and immunodetection methods

The transgenic $Atg5^{fl/fl}$ LysM-Cre+ (myeloid specific Atg5 deletion) and $Atg5^{fl/fl}$ LysM-Cre– mice have been previously characterized [Zhao, 2008 #6094] and the autophagy defect in BMM extensively documented [Dupont, 2011 #14374]. LC3-GFP knock-in transgenic mice [Mizushima, 2004 #17] and p62–/– knockout mice [Komatsu, 2007 #5273] have been previously described. Mice were maintained under specific pathogen-free conditions. F1 progeny from $Atg5^{fl/fl}$ LysM-Cre×$Atg5^{fl/fl}$ crosses were genotyped for presence (LysM-Cre+) or absence (LysMCre) of the LysM-Cre allele by Transnetyx Inc. (Cordova, Tenn.). Infection studies were carried out using murine respiratory infection model [Flynn, 2008 #5138] and virulent *M. tuberculosis* H37Rv with modifications [Talaat, 2004 #14428] [Zahrt, 2001 #1633] described in supplementary materials. All cells were pretreated with Stain. FcX (anti-CD16/32) (Biolegend) before being stained for: CD14 (Sa14-2), F4/80 (BM8), IFN-γ (XMG1.2), IL-17A (TC11-18H10.1), CD11b (M1/70), DEC205 (NLDL-145), CD8 (53-6.7), CD86 (GL-1), Ly6G (1A8), CD25 (PC61), MHC II (M5/114.15.2) (Biolegend). CD19 (eBio1D3), TCRβ (H57-597), CD3e (145-2C11), CD44 (IM7), CD4 (GK1.5), CD1d (1B1), DEC205 (205yekta), CD4 (RM4-5), CD45 (30-F11), CD3 (17A2), F4/80 (BM8), CD11b (M1/70), B220 (RA3-6B2), CD8α (53-6.7), IL-12p35 (4D10p35), IL-1α (ALF-161), MCH II (M5/114.15.2), CD25 (PC61.5) (eBioscience), Ly6G (1a8) (BD Biosciences). Caspase 1 activity was measured by flow cytometry using the FLICA caspase 1 reagent (FAM-YVAD-FMK) (Immunochemistry Technologies). Cells were incubated with 7-AAD for viability assessment. Secreted cytokines (IL-1α, CXCL1, CXCL2 and IL-12p70) were measured by ELISA (R&D Systems). For cytokine secretion, murine BMM, prepared as described [Ponpuak, 2010 #13020], were stimulated with 5 ng/ml mIFN-γ and 100 μg/ml LPS, with autophagy agonist and antagonists rapamycin (Invivogen), 3-MA, bafilomycin A1, and ALLN (Sigma) added 30 minutes prior to LPS and IFN-γ stimulation. For autophagy-dependent unconventional secretion of cytosolic cytokines as described [Dupont, 2011 #14374], BMM were stimulated for 1 h with 250 μg/ml silica (MIN-U-SIL-15, US Silica) with starvation (EBSS) to induce autophagy.

Microscopy and Image Analysis

For confocal microscopy, BMM were stained with mouse anti-GFP (Abeam, 10 μg/ml) to enhance LC3-GFP visualization, rabbit anti-caspase 1 (Santa Cruz Biotechnology), rabbit anti-calpain 1 (Cell Signaling Technology), or hamster anti-IL-1α (eBioscience) followed by secondary antibodies. Pearson's colocalization coefficients were derived using SLIDEBOOK 5.0 (Intelligent Imaging Innovations) applying the SLIDEBOOK 5 default algorithm command 'AND'. All Pearson's coefficients were derived from three independent experiments with five fields or more per experiment, for a total of 15 fields contributing to the cumulative result.

Delayed-type hypersensitivity and cell-mediated immunity

Mice were infected intranasally with $5\times10^6$ BCG for 21 days, and then injected with the synthetic PPD (a five antigens cocktail: Dnak, GroEL, Rv009, Rv0569, and Rv0685) at 1.0 µg/ml in PBS, or PBS control, 50 µl in separate footpads. DTH was assessed as described [Yang, 2011 #14416] by comparing swelling to a baseline value immediately after injection. Splenocytes ($5.0\times10^5$ cells/well) were restimulated with the synthetic PPD adjusted for 2.0 µg/ml (Dnak and GroEL), and 4.0 µg/ml (Rv009, Rv0569 and Rv0685) and culture supernatants assayed for IFN-γ, TNF-α, IL-4 and IL-17 secretion by ELISA (R&D Systems).

T Cell Assays

Single cell suspensions from whole lungs isolated from naïve Atg5fl/fl LysM-Cre+ and Cre− mice were cultured in RPMI 10% FBS and Cell Stimulation Cocktail (phorbol 12-myristate 13-acetate and ionomycin plus brefeldin A and monensin; eBioscience) for 4 h and analyzed by flow cytometry. For in vitro polarization, naïve CD4+ T cell from spleens were sorted CD44lowCD4+TCRβ+ cells in a MoFlo high speed cell sorter (BeckmanCoulter), sorted cells ($5\times10^5$ cells/well), incubated with plate-bound anti-CD3 antibody (Hu et al., 2011) and stimulated with 20 ng/ml IL-6, 5 ng/ml TGF-β, 20 ng/ml IL-1α or 20 ng/ml IL-1β (R&D Systems) in the presence of anti-CD28 (37.51), anti-IFN-β (R4.6A2), anti-IL-4 (11B11), anti-IL-2 (JE56-1A12) (eBioscience). After 4 days, cells were stimulated with 1× Cell Stimulation Cocktail in the presence of protein transport inhibitors for 5 hours at 37° C. and analyzed by flow cytometry.

Other experimental procedures. Additional methods are described in Supplementary Materials.

Supplementary Results

Histopathology findings in Atg5fl/fl LysM-Cre+ mice infected with *M. tuberculosis* H37Rv At necropsy the veterinary pathologist's findings were as follows: the Atg5-deficient mice exhibited extensive, discreet multinodular to coalescing foci of lung inflammation (granulomas), whereas the Atg5fl/fl LysM-Cre− mice exhibited more subtle lung lesions characterized by mild, patchy foci of white discoloration without nodule formation (FIG. 1B). Microscopic examination revealed that the lungs from the Atg$^{5fl/fl}$ LysMCre+ mice exhibited marked pulmonary inflammation resembling the caseating granulomas found in cases of human TB, characterized by nodular, often coalescing foci consisting of peripheral infiltrates of lymphocytes, macrophages, plasma cells and occasional neutrophils, surrounding central foci of necrotic debris containing dead and dying neutrophils (FIG. 1C; FIG. S1D). Acid-fast staining of the lungs from these mice revealed abundant intracellular and extracellular bacilli. In contrast, lungs from the infected Atg$^{5fl/fl}$ LysM-Cre− mice exhibited only irregular, mild to moderate, bronchioalveolar and interstitial infiltrates of lymphocytes, macrophages and plasma cells without organization into discreet nodules. Acid-fast staining of lungs from these mice revealed very sparse intracellular bacilli, and no apparent extracellular bacilli (FIG. 1C; FIG. S1H).

Supplementary Experimental Procedures

*M. tuberculosis* infection of Atg$^{5fl/fl}$ LysM-Cre mice

*M. tuberculosis*, strain H37Rv, inoculum was prepared by diluting a frozen stock of known titer in sterile PBS/0.05% Tween 80. Mice were anesthetized with isofluorane (Abbott Laboratories, Chicago, Ill.) and 50 µl of fluid containing *M. tuberculosis* were placed on the nostrils of mice, after which mice were allowed to inhale the inoculum under direct observation. The mice awoke approximately 1 minute after sedation. The mice were kept warm with a heat lamp and allowed to recover under direct observation. One hour after inoculation, 3 randomly selected mice from the infected cohort were harvested to determine lung depositions. Bacterial burden was determined using homogenized organs. Samples were serially diluted and duplicated, and 50 µl aliquots of each dilution were spread on Selective Mitchinson 7H11 agar plates (Remel) and placed into humidified incubator at 37° C. for 12 days. Mice were weighted twice prior to infection on days −3 and −1 for baseline. Upon infection, mice were monitored daily for survival and weighted semi-weekly. At the indicated times, mice were sacrificed by CO2 overdose, and lungs were harvested and homogenized in 1 ml of PBS/0.05% Tween 80. For histopathological examination, lungs were insufflated with 10% neutral buffered formalin via tracheal cannulation and removed en bloc. At the same time, spleens were harvested and all organs were placed into 10% buffered formalin for further processing in histological studies. Paraffin embedded sections were stained with hematoxylin and eosin (H&E stain) or acid fast stain and evaluated by a board certified veterinary pathologist. Samples were subjected to a freeze/thaw cycle, sonicated for 30 sec, allowed to sit on ice for 30 min, centrifuged at 12,000 rpm for 10 min, supernatants collected and filtered through a 0.45 µm syringe filter and assayed for cytokines using the Luminex Multiplex System (Luminex Corp, Austin Tex.). Beads for cytokine quantification were from Invitrogen and used according to the manufacturer's instruction.

Cells and tissue preparation

Lungs were perfused with sterile saline in order to remove peripheral blood cells. Lungs were then minced and enzymatically (DNAse/collagenase solution) treated at 37o C for 60 min. The digested lung tissue was then mechanically disrupted using a pestle and wire screen. Cells were then filtered over a nylon wool column to remove particulate and remaining red blood cells were lysed and cells were then centrifuged through a layer of 30% percoll to remove debris and dead cells. Spleens were homogenized in HBSS containing HEPES, L-glutamine and pen-strep (HGPG) using frosted slides. For lung homogenate, lungs were minced, homogenized, homogenate resuspended in a total volume of 1 ml PBS, pressed through a 70-mm cell strainer, centrifuged and clarified supernatant collected for analysis.

Antibodies, immunoblotting, detection assays, siRNA knockdowns and flow cytometry Cells were washed with PBS and lysed with RIPA buffer containing protease inhibitor cocktail (Roche). Cells extracts were analyzed by standard immunoblotting techniques with antibodies to ASC (Enzo Life Science, AL177), procaspase-1 and active caspase-1 (P20) (Cell Signaling, 2225), GFP (Abeam), calpain I (Cell Signaling), p62 (Abeam) and actin (Sigma). Proteins were resolved on a 12% SDS-polyacrylamide gels and transferred to nitrocellulose membranes. The membrane was blocked for 1 h in 5% nonfat dried milk in PBS/Tween 20 (0.1%) and probed with primary antibody overnight at 4° C. After washing with PBS/Tween, the blot was probed with appropriate anti-mouse HRP-conjugated secondary antibody for 1 h at room temperature and stained with SuperSignal West Dura chemiluminescent substrate (Thermo Fisher Scientific). Actin was used as standardization control. For siRNA knockdowns, BMM were transfected by nucleoporation using Nucleofector Reagent Kit Mouse Macrophage (Amaxa/Lonza Biosystems). For murine p62 or Atg5 knockdowns, cells were transfected with siGENOME SMARTpool reagents (Dharmacon). p62-(GCATTGAAGTGGATATTGA; GACGATGACTGGACCCATT; TCGGAGGATCCCAGTGTGA; CAGCAAGCCGGGTGGGAAT), Atg5-(CCAAUUGGUUUACUAUUUG; CGAAUUCCAACUUGCUUUA; UUAGUGAGAUAUGGUUUGA; GCAUAAAAGUCAAGUGAUC). Non-targeting siRNA pool (Scramble) was used as a control—(UAGCGACUAAACACAUCAA; UAAGGCUAUGAAGAGAUAC; AUGUAUUGGCCUGUAUUAG; AUGAACGUGAAUUGCUCAA).

At 48 h post transfection, cells were stimulated overnight with LPS and IFN-γ (1 µg/ml and 5 ng/ml, respectively) and the supernatants were collected for further analysis. Cells were collected and analyzed for targeted protein expression by immunoblotting as described above. Flow cytometry was carried out on a LSRFortessa or FACSCalibur (BD Biosciences) and data analyzed using FlowJo software (TreeStar).

Quantitative RT PCR

Total RNA was isolated from BMM using RNeasy kit (Qiagen) and cDNA was generated using QuantiTect Reverse Transcription kit (Qiagen). RT-PCR was performed using SYBR Green I QuantiFast SYBR Green Kit (Qiagen) using the following amplification conditions: PCR initial activation step: 95OC-5 min; Two-step cycling: Denaturation: 95OC-10 sec; Combined annealing/extension: 60OC-10 sec; Number of cycles 40. The primers for IL-1a: (F) 5'-GCA ACG GGA AGA TTC TGA AG-3'; (R) 5'-TGA CAA ACT TCT GCC TGA CG-3'. The results were analyzed using relative quantification by comparing the ratios of the target gene and the reference housekeeping gene, actin.

REFERENCES FOR EXAMPLE 1

Abadie, V., Badell, E., Douillard, P., Ensergueix, D., Leenen, P. J., Tanguy, M., Fiette, L., Saeland, S., Gicquel, B., and Winter, N. (2005). Neutrophils rapidly migrate via lymphatics after Mycobacterium bovis BCG intradermal vaccination and shuttle live bacilli to the draining lymph nodes. Blood 106, 1843-1850.

Afonina, I. S., Tynan, G. A., Logue, S. E., Cullen, S. P., Bots, M., Luthi, A. U., Reeves, E. P., McElvaney, N. G., Medema, J. P., Lavelle, E. C., et al. (2011). Granzyme B-dependent proteolysis acts as a switch to enhance the proinflammatory activity of IL-1alpha. Molecular cell 44, 265-278.

Alonso, S., Pethe, K., Russell, D. G., and Purdy, G. E. (2007). Lysosomal killing of Mycobacterium mediated by ubiquitin-derived peptides is enhanced by autophagy. Proc Natl Acad Sci USA 104, 6031-6036.

Axe, E. L., Walker, S. A., Manifava, M., Chandra, P., Roderick, H. L., Habermann, A., Griffiths, G., and Ktistakis, N. T. (2008). Autophagosome formation from membrane compartments enriched in phosphatidylinositol 3-phosphate and dynamically connected to the endoplasmic reticulum. J Cell Biol 182, 685-701.

Berry, M. P., Graham, C. M., McNab, F. W., Xu, Z., Bloch, S. A., Oni, T., Wilkinson, K. A., Banchereau, R., Skinner, J., Wilkinson, R. J., et al. (2010). An interferoninducible neutrophil-driven blood transcriptional signature in human tuberculosis. Nature 466, 973-977.

Blanchet, F. P., Moris, A., Nikolic, D. S., Lehmann, M., Cardinaud, S., Stalder, R., Garcia, E., Dinkins, C., Leuba, F., Wu, L., et al. (2010). Human immunodeficiency virus-1 inhibition of immunoamphisomes in dendritic cells impairs early innate and adaptive immune responses Immunity 32, 654-669.

Chen, C. J., Kono, H., Golenbock, D., Reed, G., Akira, S., and Rock, K. L. (2007). Identification of a key pathway required for the sterile inflammatory response triggered by dying cells. Nat Med 13, 851-856.

Chung, Y., Chang, S. H., Martinez, G. J., Yang, X. O., Nurieva, R., Kang, H. S., Ma, L., Watowich, S. S., Jetten, A. M., Tian, Q., et al. (2009). Critical regulation of early Th17 cell differentiation by interleukin-1 signaling. Immunity 30, 576-587.

Craddock, N., Hurles, M. E., Cardin, N., Pearson, R. D., Plagnol, V., Robson, S., Vukcevic, D., Barnes, C., Conrad, D. F., Giannoulatou, E., et al. (2010). Genomewide association study of CNVs in 16,000 cases of eight common diseases and 3,000 shared controls. Nature 464, 713-720.

Criollo, A., Niso-Santano, M., Malik, S. A., Michaud, M., Morselli, E., Marino, G., Lachkar, S., Arkhipenko, A. V., Harper, F., Pierron, G., et al. (2011). Inhibition of autophagy by TAB2 and TAB3. Embo J 30, 4908-4920.

Criollo, A., Senovilla, L., Authier, H., Maiuri, M. C., Morselli, E., Vitale, I., Kepp, O., Tasdemir, E., Galluzzi, L., Shen, S., et al. (2010). The IKK complex contributes to the induction of autophagy. Embo J 29, 619-631.

Cruz, A., Fraga, A. G., Fountain, J. J., Rangel-Moreno, J., Torrado, E., Saraiva, M., Pereira, D. R., Randall, T. D., Pedrosa, J., Cooper, A. M., et al. (2010). Pathological role of interleukin 17 in mice subjected to repeated BCG vaccination after infection with Mycobacterium tuberculosis. J Exp Med 207, 1609-1616.

Delgado, M. A., Elmaoued, R. A., Davis, A. S., Kyei, G., and Deretic, V. (2008). Toll-like receptors control autophagy. Embo J 27, 1110-1121.

Deretic, V. (2005). Autophagy in innate and adaptive immunity. Trends Immunol 26, 523-528.

Deretic, V. (2011). Autophagy as an innate immunity paradigm: expanding the scope and repertoire of pattern recognition receptors. Curr Opin Immunol.

Deretic, V., and Levine, B. (2009). Autophagy, immunity, and microbial adaptations. Cell Host Microbe 5, 527-549.

Dinarello, C. A. (2009). Immunological and inflammatory functions of the interleukin-1 family. Annu Rev Immunol 27, 519-550.

Dupont, N., Jiang, S., Pilli, M., Ornatowski, W., Bhattacharya, D., and Deretic, V. (2011). Autophagy-based unconventional secretory pathway for extracellular delivery of IL-1beta. Embo J 30, 4701-4711.

Dupont, N., Lacas-Gervais, S., Bertout, J., Paz, I., Freche, B., Van Nhieu, G. T., van der Goot, F. G., Sansonetti, P. J., and Lafont, F. (2009). Shigella phagocytic vacuolar membrane remnants participate in the cellular response to pathogen invasion and are regulated by autophagy. Cell Host Microbe 6, 137-149.

Duran, J. M., Anjard, C., Stefan, C., Loomis, W. F., and Malhotra, V. (2010). Unconventional secretion of Acb1 is mediated by autophagosomes. J Cell Biol 188, 527-536.

Egan, D. F., Shackelford, D. B., Mihaylova, M. M., Gelino, S., Kohnz, R. A., Mair, W., Vasquez, D. S., Joshi, A., Gwinn, D. M., Taylor, R., et al. (2011). Phosphorylation of ULK1 (hATG1) by AMP-activated protein kinase connects energy sensing to mitophagy. Science 331, 456-461.

Eruslanov, E. B., Lyadova, I. V., Kondratieva, T. K., Majorov, K. B., Scheglov, I. V., Orlova, M. O., and Apt, A. S. (2005). Neutrophil responses to *Mycobacterium tuberculosis* infection in genetically susceptible and resistant mice. Infect Immun 73, 1744-1753.

Eum, S. Y., Kong, J. H., Hong, M. S., Lee, Y. J., Kim, J. H., Hwang, S. H., Cho, S. N., Via, L. E., and Barry, C. E., 3rd (2010). Neutrophils are the predominant infected phagocytic cells in the airways of patients with active pulmonary TB. Chest 137, 122-128.

Fettelschoss, A., Kistowska, M., LeibundGut-Landmann, S., Beer, H. D., Johansen, P., Senti, G., Contassot, E., Bachmann, M. F., French, L. E., Oxenius, A., et al. (2011). Inflammasome activation and IL-1beta target IL-1 alpha for secretion as opposed to surface expression. Proc Natl Acad Sci USA 108, 18055-18060.

Flynn, J. L., and Chan, J. (2001). Immunology of tuberculosis. Annu Rev Immunol 19, 93-129.

Fremond, C. M., Togbe, D., Doz, E., Rose, S., Vasseur, V., Maillet, I., Jacobs, M., Ryffel, B., and Quesniaux, V. F. (2007). IL-1 receptor-mediated signal is an essential component of MyD88-dependent innate response to *Mycobacterium tuberculosis* infection. J Immunol 179, 1178-1189.

Fujita, N., Hayashi-Nishino, M., Fukumoto, H., Omori, H., Yamamoto, A., Noda, T., and Yoshimori, T. (2008). An Atg4B mutant hampers the lipidation of LC3 paralogues and causes defects in autophagosome closure. Mol Biol Cell 19, 4651-4659.

Guler, R., Parihar, S. P., Spohn, G., Johansen, P., Brombacher, F., and Bachmann, M. F. (2011). Blocking IL-1alpha but not IL-1beta increases susceptibility to chronic *Mycobacterium tuberculosis* infection in mice. Vaccine 29, 1339-1346.

Gutierrez, M. G., Master, S. S., Singh, S. B., Taylor, G. A., Colombo, M. I., and Deretic, V. (2004). Autophagy is a defense mechanism inhibiting BCG and *Mycobacterium tuberculosis* survival in infected macrophages. Cell 119, 753-766.

Harris, J., De Haro, S. A., Master, S. S., Keane, J., Roberts, E. A., Delgado, M., and Deretic, V. (2007). T helper 2 cytokines inhibit autophagic control of intracellular *Mycobacterium tuberculosis*. Immunity 27, 505-517.

Hartman, M. L., and Kornfeld, H. (2011). Interactions between Naive and Infected Macrophages Reduce *Mycobacterium tuberculosis* Viability. PLoS One 6, e27972.

He, C., and Levine, B. (2010). The Beclin 1 interactome. Curr Opin Cell Biol 22, 140-149.

Intemann, C. D., Thye, T., Niemann, S., Browne, E. N., Amanua Chinbuah, M., Enimil, A., Gyapong, J., Osei, I., Owusu-Dabo, E., Helm, S., et al. (2009). Autophagy gene variant IRGM-261T contributes to protection from tuberculosis caused by *Mycobacterium tuberculosis* but not by *M. africanum* strains. PLoS Pathog 5, e1000577.

Itakura, E., and Mizushima, N. (2011). p62 Targeting to the autophagosome formation site requires self-oligomerization but not LC3 binding. The Journal of cell biology 192, 17-27.

Jain, A., Lamark, T., Sjottem, E., Larsen, K. B., Awuh, J. A., Overvatn, A., McMahon, M., Hayes, J. D., and Johansen, T. (2010). p62/SQSTM1 is a target gene for transcription factor NRF2 and creates a positive feedback loop by inducing antioxidant response element-driven gene transcription. J Biol Chem 285, 22576-22591.

Jia, W., Pua, H. H., Li, Q. J., and He, Y. W. (2011). Autophagy regulates endoplasmic reticulum homeostasis and calcium mobilization in T lymphocytes. J Immunol 186, 1564-1574.

Johansen, P., Fettelschoss, A., Amstutz, B., Selchow, P., Waeckerle-Men, Y., Keller, P., Deretic, V., Held, L., Kundig, T. M., Bottger, E. C., et al. (2011). Relief from Zmp1-mediated arrest of phagosome maturation is associated with facilitated presentation and enhanced immunogenicity of mycobacterial antigens. Clin Vaccine Immunol 18, 907-913.

Jounai, N., Kobiyama, K., Shiina, M., Ogata, K., Ishii, K. J., and Takeshita, F. (2011). NLRP4 negatively regulates autophagic processes through an association with beclin1. J Immunol 186, 1646-1655.

Keller, M., Ruegg, A., Werner, S., and Beer, H. D. (2008). Active caspase-1 is a regulator of unconventional protein secretion. Cell 132, 818-831.

Kim, B. H., Shenoy, A. R., Kumar, P., Das, R., Tiwari, S., and MacMicking, J. D. (2011). A family of IFN-gamma-inducible 65-kD GTPases protects against bacterial infection. Science 332, 717-721.

Koch, R. (1891). A Further Communication on a Remedy for Tuberculosis. Br Med J 1, 125-127.

Kono, H., Karmarkar, D., Iwakura, Y., and Rock, K. L. (2010). Identification of the cellular sensor that stimulates the inflammatory response to sterile cell death. J Immunol 184, 4470-4478.

Korn, T., Bettelli, E., Oukka, M., and Kuchroo, V. K. (2009). IL-17 and Th17 Cells. Annu Rev Immunol 27, 485-517.

Kyei, G. B., Dinkins, C., Davis, A. S., Roberts, E., Singh, S. B., Dong, C., Wu, L., Kominami, E., Ueno, T., Yamamoto, A., et al. (2009). Autophagy pathway intersects with HIV-1 biosynthesis and regulates viral yields in macrophages. J Cell Biol 186, 255-268.

Lamkanfi, M. (2011). Emerging inflammasome effector mechanisms. Nature reviews Immunology 11, 213-220.

Lamkanfi, M., Sarkar, A., Vande Walle, L., Vitari, A. C., Amer, A. O., Wewers, M. D., Tracey, K. J., Kanneganti, T. D., and Dixit, V. M. (2010). Inflammasomedependent release of the alarmin HMGB1 in endotoxemia. J Immunol 185, 4385-4392.

Lee, H. K., Lund, J. M., Ramanathan, B., Mizushima, N., and Iwasaki, A. (2007). Autophagy-dependent viral recognition by plasmacytoid dendritic cells. Science 315, 1398-1401.

Lee, H. K., Mattei, L. M., Steinberg, B. E., Alberts, P., Lee, Y. H., Chervonsky, A., Mizushima, N., Grinstein, S., and Iwasaki, A. (2010). In vivo requirement for Atg5 in antigen presentation by dendritic cells. Immunity 32, 227-239.

Levine, B., Mizushima, N., and Virgin, H. W. (2011). Autophagy in immunity and inflammation. Nature 469, 323-335.

Manjithaya, R., Anjard, C., Loomis, W. F., and Subramani, S. (2010). Unconventional secretion of *Pichia pastoris* Acb1 is dependent on GRASP protein, peroxisomal functions, and autophagosome formation. J Cell Biol 188, 537-546.

Master, S. S., Rampini, S. K., Davis, A. S., Keller, C., Ehlers, S., Springer, B., Timmins, G. S., Sander, P., and Deretic, V. (2008). *Mycobacterium tuberculosis* prevents inflammasome activation. Cell Host Microbe 3, 224-232.

Mathew, R., Karp, C. M., Beaudoin, B., Vuong, N., Chen, G., Chen, H. Y., Bray, K., Reddy, A., Bhanot, G., Gelinas, C., et al. (2009). Autophagy suppresses tumorigenesis through elimination of p62. Cell 137, 1062-1075.

Mayer-Barber, K. D., Andrade, B. B., Barber, D. L., Hieny, S., Feng, C. G., Caspar, P., Oland, S., Gordon, S., and Sher, A. (2011). Innate and Adaptive Interferons Suppress IL-1alpha and IL-1beta Production by Distinct Pulmonary Myeloid Subsets during *Mycobacterium tuberculosis* Infection. Immunity 35, 1023-1034.

Mayer-Barber, K. D., Barber, D. L., Shenderov, K., White, S. D., Wilson, M. S., Cheever, A., Kugler, D., Hieny, S., Caspar, P., Nunez, G., et al. (2010). Caspase-1 independent IL-1beta production is critical for host resistance to *mycobacterium tuberculosis* and does not require TLR signaling in vivo. J Immunol 184, 3326-3330.

McCarroll, S. A., Huett, A., Kuballa, P., Chilewski, S. D., Landry, A., Goyette, P., Zody, M. C., Hall, J. L., Brant, S. R., Cho, J. H., et al (2008). Deletion polymorphism upstream of IRGM associated with altered IRGM expression and Crohn's disease. Nat Genet. 40, 1107-1112.

Mishra, B. B., Moura-Alves, P., Sonawane, A., Hacohen, N., Griffiths, G., Moita, L. F., and Anes, E. (2010). *Mycobacterium tuberculosis* protein ESAT-6 is a potent activator of the NLRP3/ASC inflammasome. Cell Microbiol 12, 1046-1063.

Mizushima, N., Levine, B., Cuervo, A. M., and Klionsky, D. J. (2008). Autophagy fights disease through cellular self-digestion. Nature 451, 1069-1075.

Mizushima, N., Yoshimori, T., and Ohsumi, Y. (2011). The role of atg proteins in autophagosome formation. Annu Rev Cell Dev Biol 27, 107-132.

Moreira, A. L., Tsenova, L., Aman, M. H., Bekker, L. G., Freeman, S., Mangaliso, B., Schroder, U., Jagirdar, J., Rom, W. N., Tovey, M. G., et al. (2002). Mycobacterial antigens exacerbate disease manifestations in *Mycobacterium tuberculosis*-infected mice. Infect Immun 70, 2100-2107.

Moscat, J., and Diaz-Meco, M. T. (2009). p62 at the crossroads of autophagy, apoptosis, and cancer. Cell 137, 1001-1004.

Nakagawa, I., Amano, A., Mizushima, N., Yamamoto, A., Yamaguchi, H., Kamimoto, T., Nara, A., Funao, J., Nakata, M., Tsuda, K., et al. (2004). Autophagy defends cells against invading group A *Streptococcus*. Science 306, 1037-1040.

Narita, M., Young, A. R., Arakawa, S., Samarajiwa, S. A., Nakashima, T., Yoshida, S., Hong, S., Berry, L. S., Reichelt, S., Ferreira, M., et al. (2011). Spatial coupling of mTOR and autophagy augments secretory phenotypes. Science 332, 966-970.

Nedjic, J., Aichinger, M., Emmerich, J., Mizushima, N., and Klein, L. (2008). Autophagy in thymic epithelium shapes the T-cell repertoire and is essential for tolerance. Nature 455, 396-400.

Nunn, P., Williams, B., Floyd, K., Dye, C., Elzing a, G., and Raviglione, M. (2005). Tuberculosis control in the era of HIV. Nat Rev Immunol 5, 819-826.

Orvedahl, A., Macpherson, S., Sumpter, R., Jr., Talloczy, Z., Zou, Z., and Levine, B. (2010). Autophagy Protects against Sindbis Virus Infection of the Central Nervous System. Cell Host Microbe 7, 115-127.

Paludan, C., Schmid, D., Landthaler, M., Vockerodt, M., Kube, D., Tuschl, T., and Munz, C. (2005). Endogenous MHC class II processing of a viral nuclear antigen after autophagy. Science 307, 593-596.

Ponpuak, M., Davis, A. S., Roberts, E. A., Delgado, M. A., Dinkins, C., Zhao, Z., Virgin, H. W. t., Kyei, G. B., Johansen, T., Vergne, I., et al. (2010). Delivery of cytosolic components by autophagic adaptor protein p62 endows autophagosomes with unique antimicrobial properties. Immunity 32, 329-341.

Pua, H. H., Guo, J., Komatsu, M., and He, Y. W. (2009). Autophagy is essential for mitochondrial clearance in mature T lymphocytes. J Immunol 182, 4046-4055.

Saitoh, T., and Akira, S. (2010). Regulation of innate immune responses by autophagy-related proteins. J Cell Biol 189, 925-935.

Sancak, Y., Bar-Peled, L., Zoncu, R., Markhard, A. L., Nada, S., and Sabatini, D. M. (2010). Ragulator-Rag complex targets mTORC1 to the lysosomal surface and is necessary for its activation by amino acids. Cell 141, 290-303.

Singh, S. B., Davis, A. S., Taylor, G. A., and Deretic, V. (2006). Human IRGM induces autophagy to eliminate intracellular *mycobacteria*. Science 313, 1438-1441.

Singh, S. B., Ornatowski, W., Vergne, I., Naylor, J., Delgado, M., Roberts, E., Ponpuak, M., Master, S., Pilli, M., White, E., et al. (2010). Human IRGM regulates autophagy and cell-autonomous immunity functions through mitochondria. Nat Cell Biol 12, 1154-1165.

Taylor, J. L., Turner, O. C., Basaraba, R. J., Belisle, J. T., Huygen, K., and Orme, I. M. (2003) Pulmonary necrosis resulting from DNA vaccination against tuberculosis. Infect Immun 71, 2192-2198.

Thurston, T. L., Ryzhakov, G., Bloor, S., von Muhlinen, N., and Randow, F. (2009). The TBK1 adaptor and autophagy receptor NDP52 restricts the proliferation of ubiquitin-coated bacteria. Nat Immunol 10, 1215-1221.

Tooze, S. A., and Yoshimori, T. (2010). The origin of the autophagosomal membrane. Nat Cell Biol 12, 831-835.

Travassos, L. H., Carneiro, L. A., Ramjeet, M., Hussey, S., Kim, Y. G., Magalhaes, J. G., Yuan, L., Soares, F., Chea, E., Le Bourhis, L., et al. (2010). Nod1 and Nod2 direct autophagy by recruiting ATG16L1 to the plasma membrane at the site of bacterial entry. Nat Immunol 11, 55-62.

Turner, J., Rhoades, E. R., Keen, M., Belisle, J. T., Frank, A. A., and Orme, I. M. (2000). Effective preexposure tuberculosis vaccines fail to protect when they are given in an immunotherapeutic mode. Infect Immun 68, 1706-1709.

van de Veerdonk, F. L., Netea, M. G., Dinarello, C. A., and Joosten, L. A. (2011). Inflammasome activation and IL-1beta and IL-18 processing during infection. Trends Immunol 32, 110-116.

Vergne, I., Chua, J., Singh, S. B., and Deretic, V. (2004). Cell biology of *mycobacterium tuberculosis* phagosome. Annu Rev Cell Dev Biol 20, 367-394.

Weidberg, H., Shvets, E., Shpilka, T., Shimron, F., Shinder, V., and Elazar, Z. (2010). LC3 and GATE-16/GABARAP subfamilies are both essential yet act differently in autophagosome biogenesis. Embo J 29, 1792-1802.

Wild, P., Farhan, H., McEwan, D. G., Wagner, S., Rogov, V. V., Brady, N. R., Richter, B., Korac, J., Waidmann, O., Choudhary, C., et al. (2011). Phosphorylation of the autophagy receptor optineurin restricts *Salmonella* growth. Science 333, 228-233.

Willingham, S. B., Allen, I. C., Bergstralh, D. T., Brickey, W. J., Huang, M. T., Taxman, D. J., Duncan, J. A., and Ting, J. P. (2009). NLRP3 (NALP3, Cryopyrin) facilitates in vivo caspase-1 activation, necrosis, and HMGB1 release via inflammasome-dependent and -independent pathways. J Immunol 183, 2008-2015.

Xia, Y., Chen, S., Wang, Y., Mackman, N., Ku, G., Lo, D., and Feng, L. (1999). RelB modulation of IkappaBalpha stability as a mechanism of transcription suppression of interleukin-1alpha (IL-1alpha), IL-1beta, and tumor necrosis factor alpha in fibroblasts. Mol Cell Biol 19, 7688-7696.

Eissa, N. T. (2007). Toll-like receptor 4 is a sensor for autophagy associated with innate immunity. Immunity 27, 135-144.

Yang, H., Troudt, J., Grover, A., Arnett, K., Lucas, M., Cho, Y. S., Bielefeldt-Ohmann, H., Taylor, J., Izzo, A., and Dobos, K. M. (2011). Three protein cocktails mediate delayed-type hypersensitivity responses indistinguishable from that elicited by purified protein derivative in the guinea pig model of *Mycobacterium tuberculosis* infection. Infect Immun 79, 716-723.

Yang, Z., and Klionsky, D. J. (2010). Eaten alive: a history of macroautophagy. Nat Cell Biol 12, 814-822.

Yazdi, A. S., Guarda, G., Riteau, N., Drexler, S. K., Tardivel, A., Couillin, I., and Tschopp, J. (2010). Nanoparticles activate the NLR pyrin domain containing 3 (Nlrp3) inflammasome and cause pulmonary inflammation through release of IL-1alpha and IL-1beta. Proc Natl Acad Sci USA 107, 19449-19454.

Yoshikawa, Y., Ogawa, M., Hain, T., Yoshida, M., Fukumatsu, M., Kim, M., Mimuro, H., Nakagawa, I., Yanagawa, T., Ishii, T., et al. (2009). *Listeria monocytogenes* ActA-mediated escape from autophagic recognition. Nat Cell Biol 11, 1233-1240.

Yuk, J. M., Shin, D. M., Lee, H. M., Yang, C. S., Jin, H. S., Kim, K. K., Lee, Z. W., Lee, S. H., Kim, J. M., and Jo, E. K. (2009a). Vitamin D3 induces autophagy in human monocytes/macrophages via cathelicidin. Cell Host Microbe 6, 231-243.

Yuk, J. M., Shin, D. M., Lee, H. M., Yang, C. S., Jin, H. S., Kim, K. K., Lee, Z. W., Lee, S. H., Kim, J. M., and Jo, E. K. (2009b). Vitamin D3 induces autophagy in human monocytes/macrophages via cathelicidin. Cell Host Microbe 6, 231-243.

Zhao, Z., Fux, B., Goodwin, M., Dunay, I. R., Strong, D., Miller, B. C., Cadwell, K., Delgado, M. A., Ponpuak, M., Green, K. G., et al. (2008). Autophagosomeindependent essential function for the autophagy protein Atg5 in cellular immunity to intracellular pathogens. Cell Host Microbe 4, 458-469.

EXAMPLE 2

TBK-1 Controls autophagy pathway in cell-autonomous antimicrobial defense

We screened the Rab family of membrane trafficking regulators for effects on autophagic elimination of *Mycobacterium tuberculosis* var. bovis BCG and found that Rab8b and its downstream effector, innate immunity regulator TBK-1, are required for autophagic elimination of *mycobacteria* in macrophages. TBK-1 was necessary for proper autophagic flux via coordinated assembly and function of the autophagic machinery. TBK-1 phosphorylated the autophagic adaptor p62/sequestosome 1 on Ser-403, a residue essential for its role in autophagic clearance. TBK-1 was required for the execution of IL-1β-induced autophagy and IL-1β-dependent autophagic killing of *mycobacteria*. Thus, TBK-1 is a key regulator of immunological autophagy and is responsible for the maturation of atophagosomes into lytic bactericidal organelles.

We approached the far less studied processes governing autophagic flux by a systematic screening of Rabs, the central regulators of membrane trafficking and organellar identity in eukaryotic cells (Stenmark, 2009). We show that Rab8b and its downstream effector TBK-1 play a key role in orchestrating autophagic maturation and cell-autonomous defense against *mycobacteria*. We furthermore show that the major proinflammatory cytokine IL-1β induces autophagy, that the IL-1β-stimulated autophagy can eliminate intracellular *Mycobacterium tuberculosis*, and that TBK-1 was responsible for maturation of autophagosomes into mycobactericidal organelles. Finally, we show that TBK-1 phosphorylates a key autophagy adapter p62/sequestosome 1 (Bjorkoy et al., 2005), the founding member of a new subfamily of pattern recognition receptors (PRRs) termed Sequestosome-like receptors (SLRs) (Deretic, 2011), at the Ser-403 residue essential for its autophagic clearance function.

Results

Rab screen for autophagic killing of *M. tuberculosis* var. bovis BCG reveals a role for Rab8b. We screened a library of siRNAs to all murine Rabs and Rablike factors (FIG. 1A and Suppl. Table S1) for effects on the previously characterized (Gutierrez et al., 2004; Harris et al., 2007; Singh et al., 2006; Singh et al., 2010) autophagic killing of *Mycobacterium tuberculosis* var. bovis BCG (BCG), as a demonstrated (Ponpuak et al., 2010) measure of the function of the entire autophagy pathway (from initiation to maturation) in a biologically, immunologically, and medically significant system. The previously implicated endocytic Rabs (e.g. Rab5) showed a role in accordance with observations in other autophagy-dependent systems (Ravikumar et al., 2008). Additional Rabs displayed a range of effects on autophagic killing of BCG, including those Rabs previously implicated in autophagy, e.g., Rab7, Rab32, Rab33b, (Hirota and Tanaka, 2009; Itoh et al., 2011; Jager et al., 2004) with the notable exception of Rab2, (Olkkonen et al., 1993). We focused in subsequent studies on two Rabs, Rab8b and Rab34, which had no immediately predictable function whereas our preliminary observations indicated that they affected autophagic maturation. A knockdown of Rab34 caused premature formation of autolysosomes (Suppl. FIG. S1A) associated with a decline in the ability to kill BCG (Suppl. FIG. S1B), reduced plasma membrane expression of CD98 (Suppl. FIG. S1C-E), a subunit of amino acid transporters that import amino acids including leucine. A knockdown of Rab34 diminished [3H] Leu uptake by the cells (Suppl. FIG. S1F), and its effects on autophagy measured by LC3-II could be reversed by addition of methyl-pyruvate to the medium (Suppl FIG. S1G). The action of Rab34 was complementary to the previously reported effects of Rab7 (Edinger et al., 2003) and although indirect was informative regarding how cellular energetics governs autophagy in cell-autonomous defense against microbes.

Rab8b knockdown caused a decrease in conversion of BCG phagosomes to degradative compartments following induction of autophagy (Gutierrez et al., 2004; Harris et al., 2007; Ponpuak et al., 2010) (FIG. 1X2B-D) and autophagic killing of *mycobacteria* (FIG. 1X2E). In side-by-side comparisons, we observed only a trend with Rab8a (Suppl. FIG. S1H), whereas Rab8b siRNA reproducibly diminished autophagic killing of BCG in a statistically significant fashion (FIG. 1X2E). We concluded that both Rab8a and Rab8b likely play a role in autophagy but that Rab8b had a dominant effect at least in our model system measuring autophagic killing of *mycobacteria*.

TBK-1 is a downstream effector of Rab8b contributing to autophagic elimination of *mycobacteria* by affecting autophagic maturation. How might Rab8b affect autophagic killing of *mycobacteria*? Among the few known interacting partners of Rab8b is FIP-2 (also known as optineurin; FIG. 2X2A). FIP-2 in turn associates with the wild type (non-pathogenic) huntingtin (Htt) (Hattula and Peranen, 2000), and TBK-1 (Morton et al., 2008), a protein broadly conserved within Coelomata. TBK-1 is a pivotal regulator of innate immunity strategically positioned at the interface with cellular pro-survival pathways (Ou et al., 2011). Htt and TBK-1 have been thus far implicated as an autophagic degradation substrate (mutant Htt aggregates (Ravikumar et al., 2008; Sarkar et al., 2007)) and, in the case of TBK-1, as being indirectly inhibited by intracellular trafficking imposed by the autophagy factor Atg9 (Saitoh et al., 2009) or playing a role in modifying an autophagic adaptor for *Salmonella* (Wild et al., 2011). Here we considered a model, whereby these factors could play an active role in the regulation of the autophagic pathway. The role of the wild type Htt is not well understood although it has been implicated in cargo trafficking from the trans-Golgi network (TGN) to lysosomal compartments (del Toro et al., 2009). We first tested whether the Rab8b phenotype was exerted via Htt as a putative effector (known to functionally affect peripheral myeloid cells in Huntington's disease patients (Bjorkqvist et al., 2008)). However, an Htt knockdown in macrophages did not result in a statistically significant loss of autophagic killing of BCG (FIG. 2B). Thus, we concluded that Htt was not critical for autophagic elimination of *mycobacteria* and turned our attention to TBK-1.

In contrast to Htt, a knockdown of TBK-1 caused a deficit in autophagic killing of BCG (FIG. 2X2B), indicating that Rab8b effects on autophagy and elimination of *mycobacteria* may be exerted via TBK-1. This was confirmed using the TBK-1 inhibitor BX795 (Clark et al., 2009). When macrophages were treated with BX795, this abrogated starvation-induced BCG phagosome maturation (FIG. 2X2C) and autophagic killing of BCG (FIG. 2X2D).

TBK-1 is necessary for autophagosome maturation. We next tested how TBK-1 affected autophagy and found that TBK-1 knockdown did not affect formation of autophagosomes but suppressed their maturation (autophagic flux) into autolysosomes, as revealed by the tandem RFP-GFP-LC3 reporter (FIG. 2X2E,F), which identifies early autophagic organelles as RFP+GFP+ and matured autolysosomal organelles as RFP+GFP− since GFP (but not RFP) fluorescence is sensitive to lumenal acidification (Kimura et al., 2007; Pankiv et al., 2007). A loss of TBK-1 reduced the number of RFP+GFP− acidified autophagic organelles and increased RFP+GFP+ puncta, consistent with inhibition of autophagic maturation (FIG. 2 X2E,F). A positive role of TBK-1 in autophagosomal maturation was confirmed by LC3 immunoblots in TBK-1−/− MEFs (FIG. 2 X2G,H). MEFs lacking TBK-1 showed accumulation of LC3-II (a marker of early autophagic organelles) under both basal (full medium) and induced (starvation) conditions. The increase in LC3-II in the absence of TBK-1 cannot be explained by de-repression of autophagy initiation since the levels of LC3-II protected from degradation by bafilomycin A1 were slightly lower in or equal to TBK-1 knockout cells (FIG. 2G,H and Suppl. FIG. S2A).

To confirm that the phenotype was due to TBK-1 deficiency, we inhibited with BX795 TBK-1 in wild type (TBK-1+/+) MEFs and tested effects of BX795 on starvation induced autophagy. As with genetically deficient TBK-1−/− MEFs, pharmacological inhibition of TBK-1 led to diminished autophagic maturation as determined by LC3-II blots (Suppl. FIG. S2B,C). Although attempts to complement the absence of TBK-1 in Tbk1−/− MEFs by transfection with Tbk-1 expression constructs was hampered by low transfection efficiency, overexpression of Tbk-1 transgene in RAW 264.7 cells caused alterations in LC3-II levels, which diminished faster with time in Tbk-1 transgeneexpressing cells relative to untransfected cells (Suppl. FIG. S2D,E). The LC3-II immunoblot experiments and the assays using RFP-GFP-LC3 reporter collectively established that TBK-1 was key for autophagic flux and maturation. TBK-1 was also important for delivery of the lysosomal hydrolase Cathepsin D to autophagolysosomal compartments, purified from macrophages induced for autophagy by starvation using magnetic beads as previously described (Ponpuak et al., 2010), as knocking down TBK-1 diminished cathepsin D delivery to one third of normal (Suppl. FIG. S3A). This was specific for TBK-1 as a knockdown of another Rab8b-optineurin interacting partner, Htt, did not reduce cathepsin D delivery (Suppl. FIG. S2A). TBK-1 was also needed for delivery of Cathepsin D to conventional phagolysosomes (Suppl. FIG. S2B) mirroring the Rab8a-dependent delivery of cathepsins from the TGN to the lysosomal compartments (del Toro et al., 2009).

TBK-1 is necessary for maturation of IL-1β-induced autophagic organelles and mycobacterial killing in macrophages. Although IL-1β is a key proinflammatory cytokine, its role in autophagy has not been a subject of in-depth studies. It has nevertheless been indirectly implicated in autophagy during MHC class I presentation of viral antigens (English et al., 2009) and in studies of autophagy activation via TLR4 signaling pathways (Shi and Kehrl, 2010). Since IL-1β's role in cell-autonomous autophagic defense against intracellular pathogens has not been investigated and in order to provide an immunologically relevant context in which to test the role of TBK-1 in autophagy, we examined here whether IL-1β could induce autophagy in macrophages, whether IL-1β-induced autophagy could inhibit intracellular *M. tuberculosis*, and whether TBK-1 played a role in these processes.

When RAW264.7 macrophages transiently expressing EGFP-LC3 were treated with mouse IL-1β this induced LC3 puncta formation (FIG. 3 X2A). When RAW264.7 cells transiently expressing the tandem RFP-GFP-LC3 probe were stimulated with IL-1β (FIG. 3 X2B), an increase in both early autophagosomal (R+G+) and mature, acidified puncta (R+G−) was detected indicating that IL-1β induces both autophagic initiation and maturation resulting in progression through the autophagic pathway. Induction of autophagy by IL-1β was confirmed by immunoblot analysis of lipidated LC3-II levels in the presence of autophagic maturation inhibitor bafilomycin A1, since LC3-II levels were increased in IL-1β-stimulated cells (FIG. 3 X2C). IL-1β induced autophagy in primary cells, including murine bone marrow-derived macrophages (BMM) (Suppl. FIG. S3C) and human peripheral blood monocyte-derived macrophages (Suppl. FIG. S3D). Induction of autophagy by IL-1β was dependent on MyD88, similarly to what as been reported for LPS and TLR4, as shown by expression of dominant negative MyD88 (FIG. 3 X2D) and by analyzing BMM from MyD88 knockout mice (FIG. 3E). A progression through the autophagic pathway was confirmed by detecting proteolysis of long-lived proteins (Roberts and Deretic, 2008) in macrophages stimulated with IL-1β (FIG. 3 X2F). Finally, we used mycobacterial killing as a measure of autophagic cell-autonomus defense output (Ponpuak et al., 2010). IL-1β induced killing of *M. tuberculosis*, whereas elimination of *mycobacteria* was abrogated in cells that were knocked down for Atg7 (FIG. 3 X2G), demonstrating that IL-1β-induced autophagy can, similarly to starvation (Ponpuak et al., 2010), eliminate intracellular *M. tuberculosis*.

Having established that IL-1β induces autophagy with its physiological and cell-autonomous immunity outputs, we asked whether TBK-1 was important for these processes. RAW264.7 macrophages infected with *mycobacteria* were stimulated with IL-1β or by starvation in the presence or absence of TBK-1 inhibitor BX795. Either starvation or IL-1β caused mycobacterial killing, whereas BX795 abrogated (FIG. 4 X2A) whereas TBK-1 siRNA (FIG. 4 X2B) reduced their autophagic elimination. As with starvation, TBK-1 inhibition did not affect initiation of autophagy (FIG. 4C,D) but suppressed autophagic maturation (FIG. 4 X2E, F). In conclusion, TBK-1 is important for conversion of autophagic organelles into mature and bactericidal organelles, for both physiologically (starvation) and immunologically (IL-1β) induced autophagy.

TBK-1 associates with Rab8b and colocalizes with Rab8b on autophagic organelles. We next turned to the mechanisms of how TBK-1 affects autophagy. If Rab8b and TBK-1 cooperate in the control of the autophagic pathway, we reasoned that they might associate. This was tested and shown in coimmunoprecipitation experiments with GFP-Rab8b (FIG. 5A). When we examined intracellular localization of Rab8b and TBK-1 relative to autophagic organelles, TBK-1 colocalized with endogenous LC3 and Rab8b (FIG. 5 X2B,C). The autophagic adaptor p62/sequestosome 1, recently demonstrated to be critical for autophagic killing of M. tuberculosis (Ponpuak et al., 2010) also colocalized with TBK-1 (FIG. 5 X2D,E). Supplementary FIG. S4 shows colocalization analyses of TBK-1 and LC3 with Rab8b (Suppl. FIG. S4A) and with p62 (Suppl. FIG. S4B), under different conditions: basal, induced autophagy, presence or absence of bafilomycin A1. The colocalization and a striking similarity in the overall intracellular organellar distribution were enhanced in the presence of LC3- and p62-sparing activity of bafilomycin A1 (FIG. 5 X2B-E; Suppl. FIG. S4A,B). We conclude that Rab8b and TBK-1 localize to autophagosomal organelles in keeping with their role in regulating autophagic flux.

Induction of autophagy results in assembly of membranous compartments containing Rab8b, TBK-1 and autophagy factors. When subcellular membranous compartments were separated by isopycnic centrifugation in sucrose gradients, induction of autophagy resulted in redistribution of multiple components engaged in autophagy causing them to co-fractionate with TBK-1 and Rab8b (FIG. 6A,B). These were LC3-II, the autophagic adaptors p62/sequestosome 1 (Bjorkoy et al., 2005; Johansen and Lamark, 2011) and NDP52 (Thurston et al., 2009), as well as UVRAG/VPS38, the component of the Beclin 1-hVPS34 complex II specific for autophagosomal maturation into lytic compartments (Liang et al., 2008). In keeping with its sucrose gradient cofractionation with TBK-1 (FIG. 6A,B), UVRAG colocalized with TBK-1 (FIG. 6 X2C, D). Both autophagic adaptors (Johansen and Lamark, 2011) p62 (Bjorkoy et al., 2005) and NDP52 (Thurston et al., 2009) colocalized with TBK-1 (FIG. 6 X2E-G), congruent with the biochemical analyses of intracellular organelles separated on sucrose gradients (FIG. 5 X2A-B). In the imaging experiments in FIG. 6E-G no bafilomycin A1 was added and thus as expected upon induction of autophagy by starvation, p62-TBK-1 and NDP52-TBK-1 colocalization was reduced (FIG. 6 X2F,G).

These findings expanded the spectrum of autophagic machinery components converging on Rab8b and TBK-1 containing compartments.

TBK-1 affects p62 clearance. If TBK-1 is needed for autophagic maturation, we reasoned that it might affect clearance of the autophagic adaptor p62, as it has been reported to be a good marker of autophagic maturation, matching or exceeding in performance LC3-based assays (Larsen et al., 2010). Using antibody to endogenous p62 we employed high content quantitative imaging analysis and detected significant increase in p62 puncta in BMMs treated with TBK-1 inhibitor BX795 (FIG. 7 X2A-C). Western blot analysis confirmed that p62 levels increased when TBK-1 was inhibited (FIG. 7 X2D), in keeping with the high content image analysis of p62. TBK-1 was also necessary to authorize p62/sequestosome 1 for autophagic degradation, since p62/sequestosome 1 accumulated in TBK-1–/– cells; the surplus p62/sequestosome 1 seen in TBK-1–/– MEFs showed a laddering pattern (Suppl. FIG. S5) neither previously reported nor observed here in the presence of TBK-1. Furthermore, ubiquitinated proteins accumulated in TBK-1–/– cells revealed by pull-down assays in cellular extracts using TUBE-2 (tandem ubiquitin binding entities 2), which recognizes polyubiquitinated proteins and protects them from deubiquitinating enzymes and proteasome during isolation (Hjerpe et al., 2009) (FIG. 7 X2E) This indicates that p62 is not being cleared by autophagy when TBK-1 is unavailable and accumulates in the cell, that TBK-1 is needed to enable p62's entry into autophagic degradative pathway, and that several ubiquitinated cargo do not enter degradative pathways in the absence of TBK-1.

TBK-1 phosphorylates p62 on Ser-403. To determine whether TBK-1 modified (e.g. phosphorylate) p62 in vivo and to examine the potential sites involved we co-expressed GFP-p62D69A (mutant preventing oligomerization of p62) and myc-TBK1 in HEK293 cells, immunoprecipitated GFP-p62 from cellular extracts and carried out mass spectrometry analyses on the immunoprecipitated material. As a control, we cotransfected GFP-p62D69A with myc-TBK-1K38D, a kinase defective mutant. By manual inspection of the mass spectrometry data, a peptide of 857.01 m/z (2568.03 Da) was detected in GFP-p62D69A expressing cells cotransfected with myc-TBK-1, but not when GFP-p62D69A was co-expressed with the kinase defective mutant myc-TBK-1K38D (FIG. 7 X2F). The 857.01 m/z (2568.03 Da) peptide was selected for tandem mass spectrometry and identified as the LIESLSQMLpSMGFSDEGGWLTR phosphopeptide from p62, where serine 403 in the UBA domain of p62 is phosphorylated (FIG. 7 X2G,H). The unphosphorylated peptide with the mass 2488.1 was observed in both samples. The Ser-403 site corresponds to the TBK-1 consensus sequence SxxxpS. Thus, TBK-1 affects p62 phosphorylation of the ubiquitin associated (UBA) domain, providing a specific link between TBK-1 and autophagic adaptor posttranslational modifications. A recent study (Matsumoto et al., 2011) has shown that phosphorylation of Ser-403 strongly increases affinity of the UBA domain of p62 for K48 and K63-linked ubiquitin chains, and promotes autophagic clearance of p62 and polyubiquitinated protein aggregates. Using a phosphospecific antibody developed by Matsumoto et al., (2011), we monitored phosphorylation of Ser-403 in vivo and in vitro (FIG. 7 X2I,J). TBK-1 phosphorylated Ser-403 of endogenous p62 in HEK293 cells transfected with a mycTBK-1 expression vector (FIG. 7 X2I). This was not observed when HEK293 cells were transfected with kinase defective TBK-1 or when myc-TBK-1 expressing cells where treated with the TBK-1 inhibitor BX795 (FIG. 7 X2I). When purified proteins were examined in a phosphorylation in vitro assay, TBK-1 directly phosphorylated p62 at the Ser-403 site (FIG. 7 X2J). Thus, TBK-1 phosphorylates p62 at Ser-403, a residue required for autophagic function of p62 (Matsumoto et al., 2011).

Discussion

This study has uncovered roles of TBK-1 at a specific execution stage of the autophagic pathway known as autophagic maturation, and in posttranslational modification of the prototypical SLR (Deretic, 2011), p62, at the Ser-403 residue, known to be essential for its function in autophagic clearance (Matsumoto et al., 2011). Whereas efforts have been devoted to the initiation and elongation stages of autophagy (Tooze and Yoshimori, 2010), the control of the flux and conversion of autophagic organelles into degradative compartments is just as important since in most cases autophagy exerts its physiological and immunological functions by degrading or processing the captured intracellular material. TBK-1 (McWhirter et al., 2004) is a member of the IKK family of central regulators of innate immunity (Perkins, 2007; Richmond, 2002; Shen and Hahn, 2011) and is a downstream effector of Rab8b. TBK-1 and Rab8b are found in shared protein complexes, and following induction of autophagy, TBK-1 and Rab8b colocalize and cofractionate with autophagic organelles. TBK-1 is required for the execution of the maturation program and autophagic killing of *mycobacteria* in response to physiological (starvation) and immunological (IL-1β) stimuli. Furthermore, TBK-1 phosphorylates the key Ser-403 residue of p62/sequestosome 1, an autophagic adaptor (Bjorkoy et al., 2005) that is the founding member of the new class of innate immunity receptors termed SLRs (Deretic, 2011). The phorphorylation of Ser-403 on p62 enables this PRR to recognize and autophagically clear target substrates (Matsumoto et al., 2011).

TBK-1 enables the execution of autophagosomal maturation and likely couples this stage of autophagy with cargo capture. This is evidenced by the in vivo dependence on TBK-1 of the phosphorylation of the key Ser-403 residue within the UBA domain of one of the principal autophagic adaptors, p62/seqestosome 1. While our study was in revision, phosphorylation of Ser-403 by CK2 was shown to increase affinity of p62 UBA for polyubiquitin chains on its cargo (Matsumoto et al., 2011). Our findings are congruent with these observations and suggest that TBK-1 also targets and phosphorylates directly the Ser-403 site, thus linking immunological and physiological inputs with p62 UBA activation in vivo. Of further note is that our data on the effects of TBK-1 on autophagic maturation are in keeping with the extended model recently depicted by von Muhlinen et al., (von Muhlinen et al., 2010), whereby TBK-1 plays a role not only in modifying autophagic adaptors such as NDP52 (Thurston et al., 2009), optineurin (Wild et al., 2011), and as shown here p62, but also plays additional but hitherto undefined roles in the autophagic pathway. The Rab screen performed here relied on the cell-autonomous antimicrobial defense functionality that depended on the execution of the entire autophagic pathway as previously defined (Ponpuak et al., 2010) from signaling and initiation, through maturation, to its final biological output, i.e. the bactericidal action of autophagy. We acknowledge that this approach may not account for functions of Rabs in the context of how starvation may affect viability of *mycobacteria* by a potentially unknown process other than autophagy. In this work, we focused on two Rabs, Rab34 and Rab8b, which have not been covered in prior studies. Of the two Rab8 GTPases only Rab8b showed statistically significant effect on autophagic killing of BCG. Although Rab8a and Rab8b share several interacting partners, Rab8b also features a number of unique interactors (Chen et al., 2001; Fransen et al., 2008; Heidrych et al., 2008) and the Rab8b sequence diverges from Rab8a in its variable region near the C-terminus. Since optineruin binds Rab8a as well as Rab8b, it is likely that differences in localization of Rab8b-optineurin underlie the stronger Rab8b engagement with autophagy maturation as detected here, along with potential participation of unique interacting partners specific for Rab8b, e.g. otoferlin, associated with autosomal recessive deafness (Heidrych et al., 2008), and Pex5Rp/TRP8b, a protein related to the peroxisomal targeting signal 1 receptor Pex5p (Fransen et al., 2008). The other Rab8 paralog, Rab8a, does associate with a subset of LC3 compartments, however they specialize in the alternative secretory pathway of inflammasome substrates such as IL-1β (Dupont et al., 2011).

The follow up analyses with Rab34 led to a connection with amino acid import. This is a plausible link since autophagy is controlled by amino acid starvation and can be abrogated by addition of amino acids such as leucine (Grinde and Seglen, 1981). Cells displayed reduced leucine uptake when Rab34 was knocked down and thus the negative effects of the loss of Rab34 on autophagic killing of BCG may appear paradoxical. However, a similar effect was observed in studies with myotubularins (Vergne et al., 2009) where knocking down myotubularin phosphatidylinositol 3-phosphatases led to chronic autophagy activation and exhaustion, diminishing its efficacy in antimicrobial defense. These observations underscore a requirement for precise timing of autophagy induction in order for it to exert its cell-autonomous antimicrobial defense. Since autophagy is affected by growth factors and hormones (Ezaki et al., 2011) its response to immunological signals (Delgado et al., 2008; Gutierrez et al., 2004; Harris et al., 2007; Shi and Kehrl, 2010; Tang et al., 2010; Xu et al., 2007), nutritional and hormonal imbalance may be a determinant of the efficacy of autophagic immunological outputs.

TBK-1 is spatially and biochemically associated with Rab8b in the context of autophagy, and this likely occurs via an intermediary protein optienurin. Optineurin mutants with altered binding of TBK-1 have been linked to glaucoma (Morton et al., 2008) whereas optineurin mutations linked to amyotrophic lateral sclerosis (ALS) display changes in inflammatory signaling (Maruyama et al., 2010). Optineurin is present in neuronal cytoplasmic inclusions in ASL and in a range of neurodegenerative disorders (Maruyama et al., 2010; Osawa et al., 2011). Given the neuroprotective role of autophagy (Mizushima et al., 2008), optienurin's mechanism of action in disease may now be considered in the context of autophagy. Optineurin, also known as NEMO-related protein (NRP) is a tetra-ubiquitin binding protein (Laplantine et al., 2009). NEMO (or IKK-γ) is a regulatory scaffold for IKK-α and IKK-β (canonical IKKs), controlling proinflammatory responses via NF-κB, whereas optineurin serves as a platform for assembly of multiprotein complexes including TBK-1 (Morton et al., 2008). TBK-1 is in turn linked to the autophagic adaptor NDP52 (Thurston et al., 2009) via Sinbad and Nap1, in keeping with our observations that induction of autophagy by starvation leads to co-fractionation of TBK1 and NDP52. The two (canonical IKK and TBK1) platforms show more interactions than previously appreciated (Clark et al., 2011), which opens the possibility of a sequential or coordinated action in autophagy of canonical IKKs (Comb et al., 2011; Criollo et al., 2010) and TBK-1 as revealed here.

TBK-1 turned out to be important in cell-autonomous defense against *mycobacteria* downstream of macrophage activation by inflammatory cytokine IL-1β. We show in this study that IL-1β induces autophagy in a MyD88-dependent fashion and that one of the outputs of this proinflammatory cytokine is to promote autophagic killing of *M. tuberculosis*. This is in keeping with the reports that IL-1β, IL-1R, and MyD88 are important in elimination of *M. tuberculosis* (Fremond et al., 2007; Master et al., 2008; Mayer-Barber et al., 2010). Congruent with our observations, IL-1β has been indirectly implicated in previous studies investigating immunological roles of autophagy (English et al., 2009; Shi and Kehrl, 2010). IL-1β thus joins other alarmins, such as HMGB1 (Tang et al., 2010), as an inducer of autophagy. On the flip side, autophagy-based unconventional secretion has been implicated in activation and extracellular delivery of IL-1β and HMGB1 (Dupont et al., 2011), thus indicating a possible role for autophagy in amplifying autocrine and paracrine signals of key alarmins IL-1β and HMGB-1. Whether TBK-1 primarily plays a role in promoting autophagic flux during IL-1β- or starvation-induced autophagy that has been uncovered in our present study, or also throttles autophagy-based unconventional secretion remains to be determined.

A further connection between TBK-1, autophagy, and immunological functions has been recently suggested by implicating TBK-1 via optineurinsponsored events in autophagic control of *Salmonella* when it escapes in the cytosol (Wild et al., 2011). Both the study by Wild et al., (Wild et al., 2011) and our present work are in keeping with the report by O'Riordan and colleagues (Radtke et al., 2007) uncovering the role of TBK-1 in control of intracellular bacteria, in addition to its well appreciated role in antiviral defenses. O'Riordan and colleagues (Radtke et al., 2007) pointed to the role of TBK-1 as keeping the cytosolic bacteria in check by a mechanism that at the time was characterized as prevention of bacterial escape into or multiplication in the cytosol but was deemed not to involve autophagy due to an apparent increase in LC3 puncta in Tbk-1−/− cells. Given that TBK-1, as shown here, is primarily involved in autophagosomal maturation, accumulation of LC3 in the absence of TBK1 observed by O'Riordan (Radtke et al., 2007) and colleagues remarkably fits our data showing that TBK1 controls flux and progression through the autophagic pathway (causing disappearance of the initially formed LC3 puncta via degradation in autolysosomes), rather than its initiation (characterized by appearance of LC3 puncta). Thus, all presently existing data are compatible with the role of TBK-1 in autophagic maturation and its role as an antimicrobial mechanism that can eliminate cytoplasmic bacteria.

The role of TBK-1 in autophagy maturation expands the role of IKKs in autophagy, previously limited to IKK-α and IKK-β (Comb et al., 2011; Criollo et al., 2010). IKK-α and IKK-β, play a role in the induction of autophagy (independently of NF-κB) in response to starvation (Comb et al., 2011; Criollo et al., 2010). We propose a model in which IKK-α and IKK-β serve to initiate autophagy whereas TBK-1 ensures its completion. Nevertheless, a recent report (Clark et al., 2011) has indicated a negative regulatory interaction between the canonical IKKs (IKK-α and IKK-β), and IKK-related factors (TBK-1 and IKK-ε/i). This poses the question of potential antagonism between the canonical IKKs and TBK-1 and IKK-ε/i.

We however did not observe a negative effect of TBK-1 on autophagy initiation since LC3-II levels were equal or reduced (and not increased) in Tbk−/− MEFs when the autophagic flux was blocked using bafilomycin A1. Nevertheless, at least one self-limiting feed-back loop exists at a different level in the TBK-1-autophagy system, based on the reported negative regulatory effects of several Atg factors on TBK-1 signaling (Jounai et al., 2007; Saitoh et al., 2009).

In sum, our work has expanded the role in autophagy of IKKs, the central kinases governing innate immunity, from participation of canonical IKK family members in autophagy induction (Comb et al., 2011; Criollo et al., 2010) to now include TBK-1 in the control of autophagic maturation and cell autonomous antimicrobial defense functions of autophagy. Thus, both canonical and non-canonical IKKs play key roles in inflammatory signaling and cell-autonomous defenses, and our observations and those of others may help integrate the role of different IKKs in cell-autonomous defenses specifically in the context of autophagy as an innate immunity mechanism.

Experimental Procedures

Cell culture, pharmacological and cytokine treatments, transfections, siRNA knockdowns, autophagy induction, and immunoprecipitations.

Mouse macrophage-like cell line RAW 264.7 were from ATCC. Tbk-1−/− and Tbk-1+/+ (wild type) MEFs were from M. O'Riordan, University of Michigan. Murine primary bone marrow macrophages were isolated and differentiated from mouse femur marrows. When indicated, cells were treated with 100 nM bafilomycin A1 to prevent protein degradation in lytic compartments. Cells were treated for 16 h with 10 nM TBK1 pharmacological inhibitor, BX795 (InvivoGen). Murine macrophages were treated with mouse IL-1β (Sigma and R&D Biosciences) 50 ng/ml for 16 h or 200 ng/ml for 3 h. RAW 264.7 cells were transfected by nucleoporation using Nucleofector Reagent Kit V (Amaxa/Lonza biosystems). Rabs and Rab-like factors knockdowns details are given in Suppl. Table S1). For murine TBK-1 and Huntingtin knockdowns, cells were transfected with SMART pool reagents (Dharmacon). TBK-1 SMARTpool: (GAAGCCGUCUGGUGCAAUA; UGACGGCG-CAUAAGAUUUA; CUACGAAGGACGACGCUUA; GUAUGAAG-CGUUUAAAGAU). Huntingtin SMARTpool: (GAAAUUAAGGUUCUGUUGA; CCACUCACGC-CAACUAUAA; GAUGAAGGCUUUCGAGUCG; UAACAUGGC-UCAUUGUGAA). Non-targeting siRNA pool (Scrambled) was used as a control. With Rab8's, Rab34, and Rab8 effectors individual or combinations of two siRNAs from the SMARTpool were used in separate experiments to establish SMARTpool specificity; in no case were off target effects seen within a set of targets examined in this study. For autophagy effects, cells were uninduced (in full medium) or induced for autophagy by starvation with EBSS for 90 min (parallel controls with Beclin 1 or Atg7 knockdowns were used to ascertain autophagy authenticity). Immunoprecipitation was carried out as previously described (Ponpuak et al., 2010; Singh et al., 2010). An untagged TBK-1 cDNA expression construct was from OriGene (vector: pCMV6-XL5).

Subcellular fractionation, immunoblot analysis, antibodies, and stable protein turn-over. Subcellular compartments were separated by isopycnic density equilibrium centrifugation in sucrose gradients as described (Singh et al., 2010). Cells were homogenized in 250 mM sucrose, 20 mM HEPES-NaOH and 0.5 mM EGTA, pH 7.5 (SHE). The post nuclear supernatant was layered on top of a pre-formed sucrose gradient consisting of 60%, 50%, 40%, 35%, 30%, 25%, 20%, 15% sucrose from top to bottom. The sample was centrifuged at 100,000 g in a Beckman SW 40 rotor at 4° C. for 18 hours. Equivalent density fractions (verified for refractive index match) were analyzed with antibodies to UVRAG (MBL), TBK-1 (AbCam), NDP52 (Millipore), LC3 (Sigma), p62 (Promega) and Rab8b (custom made); staining was revealed with Super Signal West Dura chemiluminescent substrate (Pierce). Long-lived protein turnover was measured as described previously (Ponpuak et al., 2009). Anti-phospho-S403 p62 antibody (Matsumoto et al., 2011) was from Nobuyuki Nukina.

Phosphorylation analysis of p62. HEK293 cells were transfected using Metafectene Pro (Biontex) with GFP-p62 D69A (a mutant in the PB1 domain, to prevent oligomerization) and myc-TBK-1 or as a control TBK-1 kinase defective mutant myc-TBK-1 K38D. Immunoprecipitation of GFP-p62 D69A from cell extracts prepared from two 10-cm plates) using a custom made GFP antibody was performed as described previously (Lamark et al., 2003). Following SDS PAGE, gel bands containing GFP-p62 (D69A) were excised and subjected to ingel reduction, alkylation, and tryptic digestion using 2-10 ng/µl trypsin (V511A; Promega) (Shevchenko et al., 1996). Peptide mixtures containing 0.1% formic acid were loaded onto a nanoACQUITY UltraPerformance LC (Waters), containing a 5-µm Symmetry C18 Trap column (180 µm×20 mm; Waters) in front of a 1.7-µm BEH130 C18 analytical column (100 µm×100 mm; Waters). Peptides were separated with a gradient of 5-95% acetonitrile, 0.1% formic acid, with a flow of 0.4 µl/min eluted to a Q-TOF Ultima mass spectrometer (Micromass/Waters). Each sample was run in ms and data dependent tandem ms mode. Peak lists were generated from MS/MS by the ProteinLynx Global server software (version 2.2; Waters). The resulting pkl files were searched against the Swiss-Prot 57.15 protein sequence databases using an in-house Mascot server (Matrix Sciences). Peptide mass tolerances used in the search were 100 ppm, and fragment mass tolerance was 0.1 Da. Mascot analysis confirmed that the sample contained p62. The Mascot analysis also confirmed that p62 was phosphorylated on Serine 403 after cotransfection with myc-TBK1. For in vitro kinase assays recombinant maltose binding protein (MBP) and MBPp62 proteins were purified from E. coli. Recombinant TBK-1 (50 ng; Millipore) was incubated with recombinant MBP, MBP-p62 or MBP-p62 S403A in the presence of 10 mM ATP and 5 mCi [γ-32P]ATP using kinase buffer (40 mM Tris-HCl pH 7.5, 10 mM MgCl2, 1 mM DTT supplemented with Calbiochem phosphatase inhibitor cocktail set II) at 30° C. The reaction was terminated by boiling in SDS sample buffer after 10 min. Samples were separated by SDS-PAGE, the gels were stained with coomassie brilliant blue, dried and analysed by autoradiography.

TUBE2 pulldown. Tandem ubiquitin binding entities (TUBE) in the form of TUBE2-agarose beads (Lifesensors) were used as described (Hjerpe et al., 2009) to pull down polyubiquitinated proteins from cell lysates precleared with agarose beads for 1 h at 4oC and incubated with 20 µl of pre-equilibrated TUBE2-agarose beads in 20 mM Tris, pH 8.0, 0.15M NaCl, 0.1% Tween-20 (TBS-T) with nutation overnight at 4oC. Agarose beads were washed three times with TBS-T, eluted with 25 µl 2× Laemmeli buffer and subjected to SDS PAGE and immunoblot analysis.

Confocal and high content quantitative microscopy. Images using a Zeiss LSM 510 Meta confocal microscope (laser wavelength, 488 nm, 543 nm and 633 nm). Antibodies against endogenous proteins TBK-1 (AbCam), Rab8b (AbCam & custom made), p62 (AbCam), NDP52 (Millipore), LC3 (Sigma) and UVRAG (MBL) were used for indirect immunofluorescence analysis. Post-imaging analyses were done with LSM 510 software and Slide Book 5.0 (Intelligent Imaging Innovations) for morphometrics. For quantitative p62 puncta analysis, Cellomics Array Scan (Thermo Scientific) was used to acquire images by computer-driven collection of 49 valid fields per well with cells in 96 well plates stained for endogenous p62, and data morphometrically and statistically analyzed using puncta-counting application within the iDev software (Thermo Scientific).

Mycobacterial survival, phagosome and phagolysosome purification purification. Microbiological analyses of bacterial viability were carried out as previously described (Gutierrez et al., 2004; Harris et al., 2007; Singh et al., 2006; Singh et al., 2010) using previously described detailed methods (Ponpuak et al., 2010; Ponpuak et al., 2009). RAW 264.7 cells were used to isolate phagosomes (Fratti et al., 2001) or magnetic bead autophagolysosomes (Ponpuak et al., 2010) as previously described.

REFERENCES FOR BACKGROUND OF THE INVENTION AND EXAMPLE 2

Bjorkoy, G., Lamark, T., Brech, A., Outzen, H., Perander, M., Overvatn, A., Stenmark, H., and Johansen, T. (2005). p62/SQSTM1 forms protein aggregates degraded by autophagy and has a protective effect on huntingtin-induced cell death. J Cell Biol 171, 603-614.

Bjorkqvist, M., Wild, E. J., Thiele, J., Silvestroni, A., Andre, R., Lahiri, N., Raibon, E., Lee, R. V., Benn, C. L. Soulet, D., et al. (2008). A novel pathogenic pathway of immune activation detectable before clinical onset in Huntington's disease. J Exp Med 205, 1869-1877.

Blanchet, F. P., Moris, A., Nikolic, D. S., Lehmann, M., Cardinaud, S., Stalder, R., Garcia, E., Dinkins, C., Leuba, F., Wu, L., et al. (2010). Human immunodeficiency virus-1 inhibition of immunoamphisomes in dendritic cells impairs early innate and adaptive immune responses. Immunity 32, 654-669.

Cadwell, K., Patel, K. K., Maloney, N. S., Liu, T. C., Ng, A. C., Storer, C. E., Head, R. D., Xavier, R., Stappenbeck, T. S., and Virgin, H. W. (2010). Virus-plus18 susceptibility gene interaction determines Crohn's disease gene Atg16L1phenotypes in intestine. Cell 141, 1135-1145.

Chaturvedi, A., Dorward, D., and Pierce, S. K. (2008). The B cell receptor governs the subcellular location of Toll-like receptor 9 leading to hyperresponses to DNA containing antigens. Immunity 28, 799-809.

Che, N., Li, S., Gao, T., Zhang, Z., Han, Y., Zhang, X., Sun, Y., Liu, Y., Sun, Z., Zhang, J., et al. (2010). Identification of a novel IRGM promoter single nucleotide polymorphism associated with tuberculosis. Clin Chim Acta 411, 1645-1649.

Chen, S., Liang, M. C., Chia, J. N., Ngsee, J. K., and Ting, A. E. (2001). Rab8b and its interacting partner TRIP8b are involved in regulated secretion in AtT20 cells. J Biol Chem 276, 13209-13216.

Clark, K., Peggie, M., Plater, L., Sorcek, R. J., Young, E. R., Madwed, J. B., Hough, J., McIver, E. G., and Cohen, P. (2011). Novel cross-talk within the IKK family controls innate immunity. The Biochemical journal 434, 93-104.

Clark, K., Plater, L., Peggie, M., and Cohen, P. (2009). Use of the pharmacological inhibitor BX795 to study the regulation and physiological roles of TBK1 and IkappaB kinase epsilon: a distinct upstream kinase mediates Ser-172 phosphorylation and activation. J Biol Chem 284, 14136-14146.

Comb, W. C., Cogswell, P., Sitcheran, R., and Baldwin, A. S. (2011). IKKdependent, NF-kappaB-independent control of autophagic gene expression. Oncogene 30, 1727-1732.

Consortium (2007). Genome-wide association study of 14,000 cases of seven common diseases and 3,000 shared controls. Nature 447, 661-678.

Cooney, R., Baker, J., Brain, O., Danis, B., Pichulik, T., Allan, P., Ferguson, D. J., Campbell, B. J., Jewell, D., and Simmons, A. (2010). NOD2 stimulation induces autophagy in dendritic cells influencing bacterial handling and antigen presentation. Nat Med 16, 90-97.

Craddock, N., Hurles, M. E., Cardin, N., Pearson, R. D., Plagnol, V., Robson, S., Vukcevic, D., Barnes, C., Conrad, D. F., Giannoulatou, E., et al. (2010). Genomewide association study of CNVs in 16,000 cases of eight common diseases and 3,000 shared controls. Nature 464, 713-720.

Criollo, A., Senovilla, L., Authier, H., Maiuri, M. C., Morselli, E., Vitale, I., Kepp, O., Tasdemir, E., Galluzzi, L., Shen, S., et al. (2010). The IKK complex contributes to the induction of autophagy. Embo J 29, 619-631.

del Toro, D., Alberch, J., Lazaro-Dieguez, F., Martin-Ibanez, R., Xifro, X., Egea, G., and Canals, J. M. (2009). Mutant huntingtin impairs post-Golgi trafficking to lysosomes by delocalizing optineurin/Rab8 complex from the Golgi apparatus. Mol Biol Cell 20, 1478-1492.

Delgado, M. A., Elmaoued, R. A., Davis, A. S., Kyei, G., and Deretic, V. (2008). Toll-like receptors control autophagy. Embo J 27, 1110-1121.

Deretic, V. (2011). Autophagy as an innate immunity paradigm: expanding the scope and repertoire of pattern recognition receptors. Curr Opin Immunol.

Deretic, V., and Levine, B. (2009). Autophagy, immunity, and microbial adaptations. Cell Host Microbe 5, 527-549.

Dupont, N., Jiang, S., Pilli, M., Ornatowski, W., Bhattacharya, D., and Deretic, V. (2011). Autophagy-based unconventional secretory pathway for extracellular delivery of IL-1β. EMBO J. In press.

Edinger, A. L., Cinalli, R. M., and Thompson, C. B. (2003). Rab7 prevents growth factor-independent survival by inhibiting cell-autonomous nutrient transporter expression. Dev Cell 5, 571-582.

English, L., Chemali, M., Duron, J., Rondeau, C., Laplante, A., Gingras, D., Alexander, D., Leib, D., Norbury, C., Lippe, R., et al. (2009). Autophagy enhances the presentation of endogenous viral antigens on MHC class 1 molecules during HSV-1 infection. Nat. Immunol.

Ezaki, J., Matsumoto, N., Takeda-Ezaki, M., Komatsu, M., Takahashi, K., Hiraoka, Y., Taka, H., Fujimura, T., Takehana, K., Yoshida, M., et al. (2011). Liver autophagy contributes to the maintenance of blood glucose and amino acid levels. Autophagy 7.

Fransen, M., Amery, L., Hartig, A., Brees, C., Rabijns, A., Mannaerts, G. P., and Van Veldhoven, P. P. (2008). Comparison of the PTS1- and Rab8b-binding properties of Pex5p and Pex5Rp/TRIP8b. Biochimica et biophysica acta 1783, 864-873.

Fratti, R. A., Backer, J. M., Gruenberg, J., Corvera, S., and Deretic, V. (2001). Role of phosphatidylinositol 3-kinase and Rab5 effectors in phagosomal biogenesis and mycobacterial phagosome maturation arrest. J Cell Biol 154, 631-644.

Fremond, C. M., Togbe, D., Doz, E., Rose, S., Vasseur, V., Maillet, I., Jacobs, M., Ryffel, B., and Quesniaux, V. F. (2007). IL-1 receptor-mediated signal is an essential component of MyD88-dependent innate response to *Mycobacterium tuberculosis* infection J Immunol 179, 1178-1189.

Gannage, M., Dormann, D., Albrecht, R., Dengjel, J., Torossi, T., Ramer, P. C., Lee, M., Strowig, T., Arrey, F., Conenello, G., et al. (2009). Matrix protein 2 of influenza A virus blocks autophagosome fusion with lysosomes. Cell Host Microbe 6, 367-380.

Grinde, B., and Seglen, P. O. (1981). Leucine inhibition of autophagic vacuole formation in isolated rat hepatocytes. Experimental cell research 134, 33-39.

Gutierrez, M. G., Master, S. S., Singh, S. B., Taylor, G. A., Colombo, M. I., and Deretic, V. (2004). Autophagy is a defense mechanism inhibiting BCG and *Mycobacterium tuberculosis* survival in infected macrophages. Cell 119, 753-766.

Harris, J., De Haro, S. A., Master, S. S., Keane, J., Roberts, E. A., Delgado, M., and Deretic, V. (2007). T helper 2 cytokines inhibit autophagic control of intracellular *Mycobacterium tuberculosis*. Immunity 27, 505-517.

Harris, J., Hartman, M., Roche, C., Zeng, S. G., O'Shea, A., Sharp, F. A., Lambe, E. M., Creagh, E. M., Golenbock, D. T., Tschopp, J., et al. (2011). Autophagy controls IL-1 {beta} secretion by targeting pro-IL-1 {beta} for degradation. J Biol. Chem.

Hattula, K., and Peranen, J. (2000). FIP-2, a coiled-coil protein, links Huntingtin to Rab8 and modulates cellular morphogenesis. Curr Biol 10, 1603-1606.

Heidrych, P., Zimmermann, U., Bress, A., Pusch, C. M., Ruth, P., Pfister, M., Knipper, M., and Blin, N. (2008). Rab8b GTPase, a protein transport regulator, is an interacting partner of otoferlin, defective in a human autosomal recessive deafness form. Human molecular genetics 17, 3814-3821.

Hirota, Y., and Tanaka, Y. (2009). A small GTPase, human Rab32, is required for the formation of autophagic vacuoles under basal conditions. Cell Mol Life Sci. Hjerpe, R., Aillet, F., Lopitz-Otsoa, F., Lang, V., England, P., and Rodriguez, M. S. (2009). Efficient protection and isolation of ubiquitylated proteins using tandem ubiquitin-binding entities. EMBO Rep 10, 1250-1258.

Huang, J., Canadien, V., Lam, G. Y., Steinberg, B. E., Dinauer, M. C., Magalhaes, M. A., Glogauer, M., Grinstein, S., and Brumell, J. H. (2009). Activation of antibacterial autophagy by NADPH oxidases. Proc Natl Acad Sci USA.

Intemann, C. D., Thye, T., Niemann, S., Browne, E. N., Amanua Chinbuah, M., Enimil, A., Gyapong, J., Osei, I., Owusu-Dabo, E., Helm, S., et al. (2009). Autophagy gene variant IRGM-261T contributes to protection from tuberculosis caused by *Mycobacterium tuberculosis* but not by *M. africanum* strains. PLoS Pathog 5, e1000577.

Itoh, T., Kanno, E., Uemura, T., Waguri, S., and Fukuda, M. (2011). OATL1, a novel autophagosome-resident Rab33B-GAP, regulates autophagosomal maturation. The Journal of cell biology 192, 839-853.

Jager, S., Bucci, C., Tanida, I., Ueno, T., Kominami, E., Saftig, P., and Eskelinen, E. L. (2004). Role for Rab7 in maturation of late autophagic vacuoles. J Cell Sci 117, 4837-4848.

Jia, W., and He, Y. W. (2011). Temporal regulation of intracellular organelle homeostasis in T lymphocytes by autophagy. J Immunol 186, 5313-5322.

Johansen, T., and Lamark, T. (2011). Selective autophagy mediated by autophagic adapter proteins. Autophagy 7.

Jounai, N., Takeshita, F., Kobiyama, K., Sawano, A., Miyawaki, A., Xin, K. Q., Ishii, K. J., Kawai, T., Akira, S., Suzuki, K., et al. (2007). The Atg5 Atg12 conjugate associates with innate antiviral immune responses. Proc Natl Acad Sci USA 104, 14050-14055.

Kimura, S., Noda, T., and Yoshimori, T. (2007). Dissection of the autophagosome maturation process by a novel reporter protein, tandem fluorescent-tagged LC3. Autophagy 3, 452-460.

Kirkin, V., Lamark, T., Sou, Y. S., Bjorkoy, G., Nunn, J. L., Bruun, J. A., Shvets, E., McEwan, D. G., Clausen, T. H., Wild, P., et al. (2009). A role for NBR1 in autophagosomal degradation of ubiquitinated substrates. Mol Cell 33, 505-516.

Korolchuk, V. I., Saiki, S., Lichtenberg, M., Siddiqi, F. H., Roberts, E. A., Imarisio, S., Jahreiss, L., Sarkar, S., Futter, M., Menzies, F. M., et al. (2011). Lysosomal positioning coordinates cellular nutrient responses. Nat Cell Biol.

Kroemer, G., and Levine, B. (2008). Autophagic cell death: the story of a misnomer. Nat Rev Mol Cell Biol 9, 1004-1010.

Kyei, G. B., Dinkins, C., Davis, A. S., Roberts, E., Singh, S. B., Dong, C., Wu, L., Kominami, E., Ueno, T., Yamamoto, A., et al. (2009). Autophagy pathway intersects with HIV-1 biosynthesis and regulates viral yields in macrophages. J Cell Biol 186, 255-268.

Lamark, T., Perander, M., Outzen, H., Kristiansen, K., Overvatn, A., Michaelsen, E., Bjorkoy, G., and Johansen, T. (2003). Interaction codes within the family of mammalian Phox and Bem1p domain-containing proteins. J Biol Chem 278, 34568-34581.

Laplantine, E., Fontan, E., Chiaravalli, J., Lopez, T., Lakisic, G., Veron, M., Agou, F., and Israel, A. (2009). NEMO specifically recognizes K63-linked poly-ubiquitin chains through a new bipartite ubiquitin-binding domain. Embo J 28, 2885-2895.

Larsen, K. B., Lamark, T., Overvatn, A., Harneshaug, I., Johansen, T., and Bjorkoy, G. (2010). A reporter cell system to monitor autophagy based on p62/SQSTM1. Autophagy 6, 784-793.

Lee, H. K., Maffei, L. M., Steinberg, B. E., Alberts, P., Lee, Y. H., Chervonsky, A., Mizushima, N., Grinstein, S., and Iwasaki, A. (2010). In vivo requirement for Atg5 in antigen presentation by dendritic cells. Immunity 32, 227-239.

Lee, J. S., Li, Q., Lee, J. Y., Lee, S. H., Jeong, J. H., Lee, H. R., Chang, H., Zhou, F. C., Gao, S. J., Liang, C., et al. (2009). FLIP-mediated autophagy regulation in cell death control. Nat Cell Biol 11, 1355-1362.

Levine, B., Mizushima, N., and Virgin, H. W. (2011). Autophagy in immunity and inflammation. Nature 469, 323-335.

Liang, C., Lee, J. S., Inn, K. S., Gack, M. U., Li, Q., Roberts, E. A., Vergne, I., Deretic, V., Feng, P., Akazawa, C., et al. (2008). Beclin1-binding UVRAG targets the class C Vps complex to coordinate autophagosome maturation and endocytic trafficking. Nat Cell Biol 10, 776-787.

Maruyama, H., Morino, H., Ito, H., Izumi, Y., Kato, H., Watanabe, Y., Kinoshita, Y., Kamada, M., Nodera, H., Suzuki, H., et al. (2010). Mutations of optineurin in amyotrophic lateral sclerosis. Nature 465, 223-226.

Master, S. S., Rampini, S. K., Davis, A. S., Keller, C., Ehlers, S., Springer, B., Timmins, G. S., Sander, P., and Deretic, V. (2008). *Mycobacterium tuberculosis* prevents inflammasome activation. Cell Host Microbe 3, 224-232.

Mathew, R., Karp, C. M., Beaudoin, B., Vuong, N., Chen, G., Chen, H. Y., Bray, K., Reddy, A., Bhanot, G., Gelinas, C., et al. (2009). Autophagy suppresses tumorigenesis through elimination of p62. Cell 137, 1062-1075.

Matsumoto, G., Wada, K., Okuno, M., Kurosawa, M., and Nukina, N. (2011). Serine 403 Phosphorylation of p62/SQSTM1 Regulates Selective Autophagic Clearance of Ubiquitinated Proteins. Molecular Cell 44, 279-289.

Matsunaga, K., Saitoh, T., Tabata, K., Omori, H., Satoh, T., Kurotori, N., Maejima, I., Shirahama-Noda, K., Ichimura, T., Isobe, T., et al. (2009). Two Beclin 1-binding proteins, Atg14L and Rubicon, reciprocally regulate autophagy at different stages. Nat Cell Biol 11, 385-396.

Mayer-Barber, K. D., Barber, D. L., Shenderov, K., White, S. D., Wilson, M. S., Cheever, A., Kugler, D., Hieny, S., Caspar, P., Nunez, G., et al. (2010). Caspase-1 independent IL-1beta production is critical for host resistance to *mycobacterium tuberculosis* and does not require TLR signaling in vivo. J Immunol 184, 3326-3330.

McWhirter, S. M., Fitzgerald, K. A., Rosains, J., Rowe, D. C., Golenbock, D. T., an Maniatis, T. (2004). IFN-regulatory factor 3-dependent gene expression is defective in Tbk1-deficient mouse embryonic fibroblasts. Proceedings of the National Academy of Sciences of the United States of America 101, 233-238.

Mizushima, N., Levine, B., Cuervo, A. M., and Klionsky, D. J. (2008). Autophagy fights disease through cellular self-digestion. Nature 451, 1069-1075.

Morton, S., Hesson, L., Peggie, M., and Cohen, P. (2008). Enhanced binding of TBK1 by an optineurin mutant that causes a familial form of primary open angle glaucoma. FEBS Lett 582, 997-1002.

Munz, C. (2009). Enhancing immunity through autophagy. Annu Rev Immunol 27, 423-449.

Nakagawa, I., Amano, A., Mizushima, N., Yamamoto, A., Yamaguchi, H., Kamimoto, T., Nara, A., Funao, J., Nakata, M., Tsuda, K., et al. (2004). Autophagy defends cells against invading group A *Streptococcus*. Science 306, 1037-1040.

Nakahira, K., Haspel, J. A., Rathinam, V. A., Lee, S. J., Dolinay, T., Lam, H. C., Englert, J. A., Rabinovitch, M., Cernadas, M., Kim, H. P., et al. (2010). Autophagy proteins regulate innate immune responses by inhibiting the release of mitochondrial DNA mediated by the NALP3 inflammasome. Nat. Immunol.

Nedjic, J., Aichinger, M., Emmerich, J., Mizushima, N., and Klein, L. (2008). Autophagy in thymic epithelium shapes the T-cell repertoire and is essential for tolerance. Nature 455, 396-400.

Olkkonen, V. M., Dupree, P., Killisch, I., Lutcke, A., Zerial, M., and Simons, K. (1993). Molecular cloning and subcellular localization of three GTP-binding proteins of the rab subfamily. J Cell Sci 106 (Pt 4), 1249-1261.

Orvedahl, A., Alexander, D., Talloczy, Z., Sun, Q., Wei, Y., Zhang, W., Burns, D., Leib, D., and Levine, B. (2007). HSV-1 ICP34.5 Confers Neurovirulence by Targeting the Beclin 1 Autophagy Protein. Cell Host and Microbe 1, 23-35.

Orvedahl, A., Macpherson, S., Sumpter, R., Jr., Talloczy, Z., Zou, Z., and Levine, B. (2010). Autophagy Protects against Sindbis Virus Infection of the Central Nervous System. Cell Host Microbe 7, 115-127.

Osawa, T., Mizuno, Y., Fujita, Y., Takatama, M., Nakazato, Y., and Okamoto, K. (2011). Optineurin in neurodegenerative diseases. Neuropathology: official journal of the Japanese Society of Neuropathology.

Ou, Y. H., Torres, M., Ram, R., Formstecher, E., Roland, C., Cheng, T., Brekken, R., Wurz, R., Tasker, A., Polyerino, T., et al. (2011). TBK1 Directly Engages Akt/PKB Survival Signaling to Support Oncogenic Transformation. Mol Cell 41, 458-470.

Paludan, C., Schmid, D., Landthaler, M., Vockerodt, M., Kube, D., Tuschl, T., and Munz, C. (2005). Endogenous MHC class II processing of a viral nuclear antigen after autophagy. Science 307, 593-596.

Pankiv, S., Clausen, T. H., Lamark, T., Brech, A., Bruun, J. A., Outzen, H., Overvatn, A., Bjorkoy, G., and Johansen, T. (2007). p62/SQSTM1 binds directly to Atg8/LC3 to facilitate degradation of ubiquitinated protein aggregates by autophagy. J Biol Chem 282, 24131-24145.

Perkins, N. D. (2007). Integrating cell-signalling pathways with NF-kappaB and IKK function. Nature reviews Molecular cell biology 8, 49-62.

Ponpuak, M., Davis, A. S., Roberts, E. A., Delgado, M. A., Dinkins, C., Zhao, Z., Virgin, H. W. t., Kyei, G. B., Johansen, T., Vergne, I., et al. (2010). Delivery of cytosolic components by autophagic adaptor protein p62 endows autophagosomes with unique antimicrobial properties. Immunity 32, 329-341.

Ponpuak, M., Delgado, M. A., Elmaoued, R. A., and Deretic, V. (2009). Monitoring autophagy during *Mycobacterium tuberculosis* infection. Methods Enzymol 452, 345-361.

Radtke, A. L., Delbridge, L. M., Balachandran, S., Barber, G. N., and O'Riordan, M. X. (2007). TBK1 protects vacuolar integrity during intracellular bacterial infection. PLoS Pathog 3, e29.

Ravikumar, B., Imarisio, S., Sarkar, S., O'Kane, C. J., and Rubinsztein, D. C. (2008). Rab5 modulates aggregation and toxicity of mutant huntingtin through macroautophagy in cell and fly models of Huntington disease. J Cell Sci 121, 1649-1660.

Richmond, A. (2002). Nf-kappa B, chemokine gene transcription and tumour growth. Nature reviews Immunology 2, 664-674.

Roberts, E. A., and Deretic, V. (2008). Autophagic proteolysis of long-lived proteins in nonliver cells. Methods Mol Biol 445, 111-117.

Saitoh, T., and Akira, S. (2010). Regulation of innate immune responses by autophagy-related proteins. J Cell Biol 189, 925-935.

Saitoh, T., Fujita, N., Hayashi, T., Takahara, K., Satoh, T., Lee, H., Matsunaga, K., Kageyama, S., Omori, H., Noda, T., et al. (2009). Atg9a controls dsDNAdriven dynamic translocation of STING and the innate immune response. Proc Natl Acad Sci USA 106, 20842-20846.

Sanjuan, M. A., Dillon, C. P., Tait, S. W., Moshiach, S., Dorsey, F., Connell, S., Komatsu, M., Tanaka, K., Cleveland, J. L., Withoff, S., et al. (2007). Toll-like receptor signalling in macrophages links the autophagy pathway to phagocytosis. Nature 450, 1253-1257.

Sarkar, S., Perlstein, E. O., Imarisio, S., Pineau, S., Cordenier, A., Maglathlin, R. L., Webster, J. A., Lewis, T. A., O'Kane, C. J., Schreiber, S. L., et al. (2007). Small molecules enhance autophagy and reduce toxicity in Huntington's disease models. Nat Chem Biol 3, 331-338.

Shen, R. R., and Hahn, W. C. (2011). Emerging roles for the non-canonical IKKs in cancer. Oncogene 30, 631-641.

Shevchenko, A., Wilm, M., Vorm, O., and Mann, M. (1996). Mass spectrometric sequencing of proteins silver-stained polyacrylamide gels. Anal Chem 68, 850-858.

Shi, C. S., and Kehrl, J. H. (2010). TRAF6 and A20 regulate lysine 63-linked ubiquitination of Beclin-1 to control TLR4-induced autophagy. Sci Signal 3, ra42.

Singh, S. B., Davis, A. S., Taylor, G. A., and Deretic, V. (2006). Human IRGM induces autophagy to eliminate intracellular *mycobacteria*. Science 313, 1438-1441.

Singh, S. B., Ornatowski, W., Vergne, I., Naylor, J., Delgado, M., Roberts, E., Ponpuak, M., Master, S., Pilli, M., White, E., et al. (2010). Human IRGM regulates autophagy and cell-autonomous immunity functions through mitochondria. Nat Cell Biol 12, 1154-1165.

Stenmark, H. (2009). Rab GTPases as coordinators of vesicle traffic. Nat Rev Mol Cell Biol 10, 513-525.

Tang, D., Kang, R., Livesey, K. M., Cheh, C. W., Farkas, A., Loughran, P., Hoppe, G., Bianchi, M. E., Tracey, K. J., Zeh, H. J., 3rd, et al. (2010). Endogenous HMGB1 regulates autophagy. J Cell Biol 190, 881-892.

Thurston, T. L., Ryzhakov, G., Bloor, S., von Muhlinen, N., and Randow, F. (2009). The TBK1 adaptor and autophagy receptor NDP52 restricts the proliferation of ubiquitin-coated bacteria. Nat Immunol 10, 1215-1221.

Tooze, S. A., and Yoshimori, T. (2010). The origin of the autophagosomal membrane. Nat Cell Biol 12, 831-835.

Travassos, L. H., Carneiro, L. A., Ramjeet, M., Hussey, S., Kim, Y. G., Magalhaes, J. G., Yuan, L., Soares, F., Chea, E., Le Bourhis, L., et al. (2009). Nod1 and Nod2 direct autophagy by recruiting ATG16L1 to the plasma membrane at the site of bacterial entry. Nat. Immunol.

Vergne, I., Roberts, E., Elmaoued, R. A., Tosch, V., Delgado, M. A., Proikas-Cezanne, T., Laporte, J., and Deretic, V. (2009). Control of autophagy initiation by phosphoinositide 3-phosphatase Jumpy. Embo J 28, 2244-2258.

von Muhlinen, N., Thurston, T., Ryzhakov, G., Bloor, S., and Randow, F. (2010). NDP52, a novel autophagy receptor for ubiquitin-decorated cytosolic bacteria. Autophagy 6, 288-289.

Wild, P., Farhan, H., McEwan, D. G., Wagner, S., Rogov, V. V., Brady, N. R., Richter, B., Korac, J., Waidmann, O., Choudhary, C., et al. (2011). Phosphorylation of the autophagy receptor optineurin restricts *Salmonella* growth. Science 333, 228-233.

Xu, Y., Jagannath, C., Liu, X. D., Sharafkhaneh, A., Kolodziejska, K. E., and Eissa, N. T. (2007). Toll-like receptor 4 is a sensor for autophagy associated with innate immunity. Immunity 27, 135-144.

Yang, Z., and Klionsky, D. J. (2010). Eaten alive: a history of macroautophagy. Nat Cell Biol 12, 814-822.

Yano, T., Mita, S., Ohmori, H., Oshima, Y., Fujimoto, Y., Ueda, R., Takada, H., Goldman, W. E., Fukase, K., Silverman, N., et al. (2008). Autophagic control of *listeria* through intracellular innate immune recognition in *drosophila*. Nat Immunol 9, 908-916.

Yoshikawa, Y., Ogawa, M., Hain, T., Yoshida, M., Fukumatsu, M., Kim, M., Mimuro, H., Nakagawa, I., Yanagawa, T., Ishii, T., et al. (2009). *Listeria monocytogenes* ActA-mediated escape from autophagic recognition. Nat Cell Biol 11, 1233-1240.

Zhong, Y., Wang, Q. J., Li, X., Yan, Y., Backer, J. M., Chait, B. T., Heintz, N., and Yue, Z. (2009). Distinct regulation of autophagic activity by Atg14L and Rubicon associated with Beclin 1-phosphatidylinositol-3-kinase complex. Nat Cell Biol.

Zhou, R., Yazdi, A. S., Menu, P., and Tschopp, J. (2011). A role for mitochondria in NLRP3 inflammasome activation. Nature 469, 221-225.

EXAMPLE 3

Autophagy-Based Unconventional Secretory Pathway for Extracellular Delivery of IL-1b Here, we have addressed the question of whether autophagy plays a direct role in inflammasome and IL-1β activation and secretion. We found that, whereas basal autophagy inhibits IL-1b secretion in concordance with the recent reports (Nakahira et al, 2010; Zhou et al, 2011), induced autophagy augments IL-1b secretion. We show that inflammasome and the autophagy apparatus synergize during IL-1β secretion in cells stimulated to undergo autophagy. We also show that autophagy induction cooperates with GRASP and Rab8a (a GTPase controlling post-Golgi polarized sorting and exocytosis) in driving IL-1β secretion. We, thus, define one of the first biogenesis functions of autophagy in mammalian cells and show that at least one type of unconventional secretion utilizes autophagic machinery in higher vertebrate cells.

Results

Induction of autophagy promotes inflammasomedependent IL1β secretion

Figure 1:
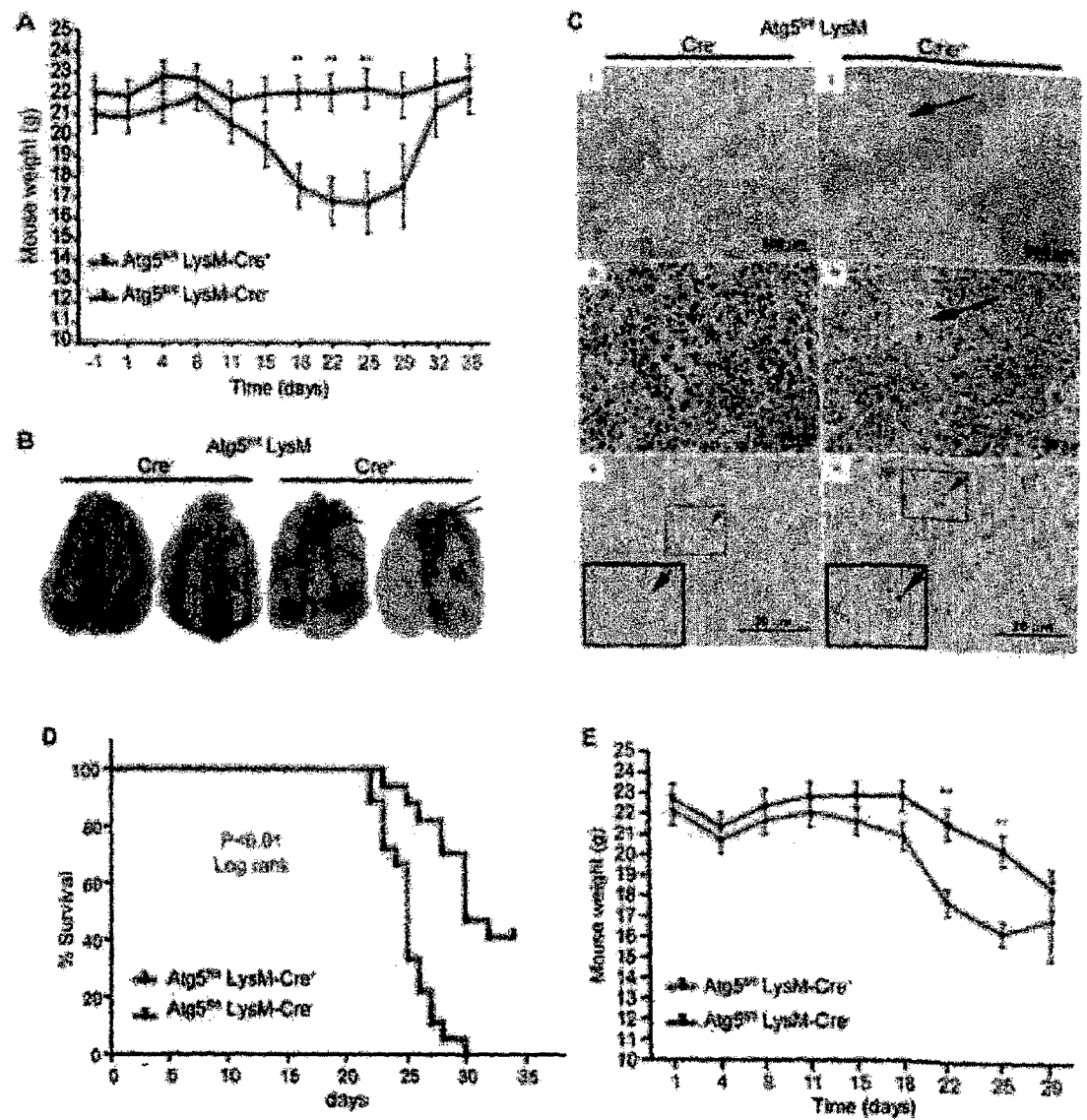
FIG. 1. Autophagy Protects from Excessive Inflammation in a Mouse Model of Tuberculosis Infection.

Whereas it has been found that basal autophagy reduces extracellular release of the major proinflammatory cytokine IL-1β (Nakahira et al, 2010; Zhou et al, 2011), we detected the opposite when autophagy was induced in primarymurine bone marrow-derived macrophages (BMMs; FIG. 1). Stimulation of autophagy by starvation strongly enhanced IL-1β secretion in response to conventional NLRP3 (NALP3) inflammasome agonist nigericin (FIG. 1X3A). This effect was also seen (FIG. 1B) in western blots of caspase 1 and mature IL-1β of culture supernatants from cells grown in the absence of serum, as conventionally done when assessing IL-1β secretion by immunoblotting (Martinon et al, 2006). A reduced secretion in BMMs from $Atg5^{fl/fl}$ LyzM-Cre þ mice, compared with BMMs from their Cre⁻ littermates, was accompanied and contrasted by the higher level of cell-associated pro-IL-1β in Cre⁻ versus Cre⁺ BMMs (FIG. 1X3B). The BMMs derived from $Atg5^{fl/fl}$ LyzM-Cre⁺ mice for these and other experiments had, as expected, no detectable Atg5 (since the Atg5 gene is excised in Cre⁺ macrophages; Zhao et al, 2008) and LC3-II, a key marker of autophagy (Supplementary FIG. S1AX3). The effects of induced autophagy on secretion of inflammasome substrates described above were not limited to IL-1b, since secretion of another inflammasome-dependent cytokine from the IL-1 family, IL-18 (IL-1F4), was enhanced when autophagy was induced (FIG. 1X3C). Pharmacological induction of autophagy by mTOR inhibition with pp242 (Torkinib) increased secretion of IL-1β by BMMs (Supplementary FIG. S1BX3). An enhancement of IL-1β secretion upon induction of autophagy was also detected when particulate inflammasome agonists, alum (Eisenbarth et al, 2008; FIG. 1D; Supplementary FIG. S1CX3), silica (FIG. 1E; Hornung et al, 2008), and amyloid-b fibrils (Halle et al, 2008; Supplementary FIG. S1DX3), were used as inflammasome inducers. The enhancement of IL-1β secretion associated with autophagy induction was inflammasome dependent, as IL-1β activation was diminished by knockdowns of the inflammasome components ASC and NLRP3, regardless of whether the inflammasome agonist used was nigericin or silica (FIG. 1F-HX3). The knockdowns of ASC and NLRP3 did not change IL-1β expression (Supplementary FIGS. S1E and F). The increased secretion of IL-1β was not due to the increased cell death or non-specific membrane permeability as LDH release showed a kinetic lag behind release of IL-1β whether the inflammasome agonist used was nigericin or silica (Supplementary FIG. S2A-DX3). The stimulation of autophagy promoted IL-1β secretion in an Atg5-dependent manner, based on comparisons between BMMs from $Atg5^{fl/}$ fi-LyzM-Creþ mice and BMMs from their Atg5-competent ($Atg5^{fl/fl}$ Cre⁻) littermates (FIG. 1AX3). However, the loss was not complete in Creþ BMMs (FIG. 1AX3). We interpret the incomplete reduction in IL-1β secretion in the absence of Atg5 as a net result of two opposing effects—one described here as a product of positive contribution of induced autophagy on extracellular delivery of IL-1β and the other being the recently reported negative regulation of IL-1β secretion by basal autophagy (Nakahira et al, 2010; Harris et al, 2011; Zhou et al, 2011). In keeping with this interpretation and in contrast to the stimulatory effects of induced autophagy (FIG. 1A-EX3; Supplementary FIG. S1B-DX3), basal autophagy negatively affected IL-1β and IL-18 secretion (Supplementary FIGS. S2E and FX3) in agreement with the recent reports in cells not induced for autophagy (Nakahira et al, 2010; Harris et al, 2011; Zhou et al, 2011).

IL-1β and autophagic protein LC3 colocalize in the cytoplasm

How might induced autophagy enhance IL-1β secretion? We considered a model in which autophagy, as a process that can translocate cytosolic proteins and other targets (en masse or specific components) from the cytosol to the inside of vesicular compartments, brought IL-1β into the lumen of autophagic vacuoles followed by exocytosis. When we examined IL-1β and the key marker of autophagosomes LC3 by immunofluorescence confocal microscopy, LC3 and IL-1β colocalized and displayed major similarities in the overall intracellular organellar distribution (FIG. 1I-LX3). The overlap between IL-1β and LC3 remained detectable when cells were treated with nigericin (Supplementary FIG. S3A-CX3). These observations indicate that autophagic organelles and IL-β intersect.

Inhibition of autophagy flux reduces IL-1β secretion

A question arose whether the LC3⁺ organelles containing IL-1β are on pathway to degradation or facilitated IL-1β secretion. We first tested the effects of bafilomycin A1, a conventional inhibitor of autophagic maturation, which acts as an antagonist of vacuolar H⁺ ATPase and prevents luminal acidification and autophagosomal cargo degradation. If induction of autophagy acted to degrade IL-1β, then bafilomycin A1 was expected to increase IL-1β levels. Instead, bafilomycin A1 decreased IL-1β secretion in cells stimulated for autophagy by starvation, whereas no change was observed with bafilomycin A1 in cells undergoing basal autophagy only (FIG. 2AX3).

Thus, autophagy flux during autophagy induction was not inhibitory to IL-1β but was instead promoting IL-1β secretion. A similar trend was detected with another inflammasome substrate IL-18 (FIG. 2BX3). Equivalent relationships have been observed for IL-1β secretion whether nigericin (FIG. 2AX3) or silica (FIG. 2CX3) was used as inflammasome agonists. The absence of IL-1β or IL-18 sparing effects of bafilomycin A1 is in keeping with the interpretation that autophagy is not degrading inflammasome components but that an unobstructed autophagy pathway is necessary for inflammasome-dependent IL-1 family members secretion.

Lysosomal hydrolase cathepsin B is a positive factor in autophagy-driven IL-1β secretion Next, we investigated the role of lysosomal hydrolases, focusing on cathepsin B. We observed that IL-1β and LC3 colocalized with cathepsin B (FIG. 2DX3 and FIG. 2EX3). However, cathepsin B did not play an inhibitory role. Similarly to bafilomycin A1, cathepsin B inhibitor CA-074 Me suppressed IL-1β production. Instead of protecting IL-1β from potential degradation, CA-074 Me strongly inhibited IL-1β secretion in cells stimulated for autophagy by starvation (FIG. 2FX3). No differences in expression of pro-IL-1β were observed in cells treated with bafilomycin A1 or CA-074 Me (Supplementary FIG. S3DX3). Of further interest was that cathepsin B (mature form) was secreted along with the inflammasome substrates in a manner dependent on an intact autophagic apparatus: loss of Atg5 in BMMs from Creþ mice ($Atg5^{fl/fl}$ LyzM-Cre) diminished the levels of the secreted mature cathepsin B relative to BMMs from Cre_littermates (FIG. 2G). The findings with cathepsin B inhibitor CA-074 Me indicate a positive role for cathepsin B in IL-1β activation and autophagy-driven pathway of extracellular delivery of IL-1b. They can also help explain in part the observations that a lysosomal hydrolase, cathepsin B, assists in inflammasome activation and IL-1β secretion in response to particulate inflammasome agonists (Halle et al, 2008; Hornung et al, 2008).

Rab8a, a regulator of polarized sorting to plasma membrane colocalizes with IL-1β and LC3 and controls IL-1β secretion We next addressed the features of the compartment where LC3 and IL-1β colocalized. We observed an overlap between the LC3⁺ IL-1b⁺ profiles and Rab8a (FIG. 3A-CX3). Rab8a is a regulator of polarized membrane trafficking, constitutive biosynthetic trafficking, and plasma membrane fusion of insulin-responsive (Sun et al, 2010) and other vesicular carriers (Moritz et al, 2001; Bravo-Cordero et al, 2007; Nachury et al, 2007; Bryant et al, 2010). Rab8a also colocalized with LC3 and IL-1β in cells exposed to nigericin (Supplementary FIG. S4A-CX3). Rab8a was required for enhanced IL-1β secretion caused by starvation-induced autophagy and inflammasome activation with nigericin, since siRNA knockdown of Rab8a diminished IL-1β secretion from BMMs under these conditions (FIG. 3DX3 and (FIG. 3EX3). Rab8a knockdown did not change pro-IL-1β mRNA levels (Supplementary FIG. S4DX3). Overexpression of dominantnegative Rab8a mutant (S22N) inhibited IL-1β secretion from RAW264.7 cells, employed in that experiment based on their high efficiency of transfection (FIG. 3FX3) (verified by flow cytometry of GFP-Rab8a for equal yields). Additionally, LC3⁺ IL-1b⁺ profiles were positive for subunits of the exocyst complex (Supplementary FIG. S4E-JX3). Exocyst has been shown to cooperate with Rab8a in polarized plasma membrane delivery of vesicular carriers (Mazelova et al, 2009; Bryant et al, 2010). The presence of exocyst components on IL-1b⁺ autophagic organelles was also in keeping with a recent report implicating exocyst in autophagy (Bodemann et al, 2011). In summary, these experiments indicate that systems involved in vectorial vesicular transport to the plasma membrane participate in autophagy-based unconventional secretion and that Rab8a is required for efficient autophagy-dependent secretion of IL-1β.

GRASP55 controls secretion of IL-1β

Two studies in yeast (Duran et al, 2010; Manjithaya et al, 2010) have reported that autophagic machinery is required for unconventional secretion of the protein Acb1, and that this pathway depends on the yeast equivalent of a Golgi-associated protein GRASP in mammals (Kinseth et al, 2007; Nickel and Rabouille, 2009). Mammalian cells encode two GRASP paralogues, GRASP55 (GORASP2) and GRASP65 (GORASP1) (Barr et al, 1997; Shorter et al, 1999). We first tested whether any of the mammalian GRASPs were required for IL-1β secretion. We could not obtain a good knockdown of GRASP65 (GORASP1) and thus could not evaluate its involvement. However, a knockdown of GRASP55 diminished IL-1β secretion (FIG. 4AX3; Supplementary FIG. S5AX3). A similar downregulation of IL-18 secretion was observed with GRASP55 knockdown (Supplementary FIG. S5BX3). We next tested whether GRASP55 showed any detectable response to inflammasome stimulation. GRASP55 in resting cells is mostly localized aligned within the perinuclear Golgi (FIG. 4BX3; Supplementary FIG. S6AX3). However, a fraction of it dispersed upon treatment of cells with the inflammasome agonist nigericin (FIG. S6BX3) and was found juxtaposed and partially overlapping with LC3 profiles (FIGS. 4B and C). Thus, GRASP55 responds to inflammasome stimulation and is important for secretion of the inflammasome substrates IL-1β and IL-18.

GRASP55 controls autophagy initiation

In addition to being required for IL-1β secretion, GRASP55 showed functional effects on LC3 and autophagy, tested by employing two core assays (Mizushima et al, 2010): LC3-II lipidation and the RFP-GFP-LC3 tandem probe. When GRASP55 was knocked down, autophagy initiation was negatively affected, as LC3-II levels were lower in both untreated and bafilomycin A1-treated cells (FIGS. 5AX3 and BX3). A partial downregulation of GRASP65 (to the extent that it could be achieved in BMMs) suggested a minor synergistic effect with GRASP55 on LC3-II levels upon induction of autophagy (Supplementary FIG. S5CX3). Knocking down GRASP55 reduced the total number of autophagic puncta, and selectively reduced the formation of autophagosomes but not their maturation (FIGS. 5CX3 and DX3). This was apparent from the data obtained with the RFP-GFP-LC3 probe following published methods (Kimura et al, 2007), which showed reduced GFP⁺ RFP⁺ LC3 profiles (early autophagosome) and equal number of GFP⁻RFP⁺ LC3 profiles (mature autophagic organdies) in cells knocked down for GRASP55 (FIG. 5DX3). Thus, mammalian GRASP55, a paralogue of GRASP from lower organisms that has thus far been the sole definitive molecular factor associated with unconventional secretion (Giuliani et al, 2011), displays important and previously unappreciated positive regulatory effects on autophagy induction. These findings strengthen the connections between autophagy and GRASPs in general, and specifically demonstrate the role of mammalian GRASP55 both in autophagy substrates such as IL-1β and IL-18.

Autophagy-based unconventional secretion is not limited to proteolytically processed inflammasome substrates We next wondered whether the unconventional process described above is limited to inflammasome substrates epitomized by IL-1β that are concomitantly with their secretion proteolytically processed from precursor pro-proteins into mature forms. We tested whether induction of autophagy affected other proteins not connected to proteolytic process sing in the inflammasome, such as HMGB1 (high mobility group box 1 protein). HMGB1 is a major proinflammatory alarmin or DAMP (damage-associated molecular pattern) normally present in the nucleus (Andersson and Tracey, 2011). This chromatin-associated nuclear protein (with additional intracellular and extracellular signalling roles), upon exposure to inputs including those that induce autophagy (Singh et al, 2010; Tang et al, 2010), undergoes a complex set of biochemical and localization changes. In the process, it first translocates from the nucleus into the cytoplasm and then is released from the cytoplasm to act in tissue remodeling signalling (when acting alone) or as an inflammatory mediator (when combined with bacterial agonists or other alarmins such as IL-1β). When tested, starvation and nigericin co-treatment caused HMGB1 extracellular release in an Atg5-dependent manner (FIG. 6AX3). HMGB1 band was detected by immunoblots in BMMs culture supernatants upon stimulation of cells with nigericin, whereas HMGB1 was largely diminished when BMMs from Atg5fl/fl Cre-LyzM mice were tested (FIG. 6BX3). Nigericin was used in these experiments as an inflammasome agonist based on the reports that HMGB1, along with additional unconventional substrates, depends on inflammasome for secretion although the protein itself is not subjected to proteolytic processing by caspase 1 (Keller et al, 2008; Willingham et al, 2009; Lamkanfi et al, 2010; Lamkanfi, 2011). These experiments show that autophagy-based unconventional secretion affects release of HMGB1 in a manner similar to IL-1β. Our findings broaden the spectrum of autophagy-based unconventional secretion substrates, and establish this type of unconventional secretion as a more general process in extracellular delivery of cytosolic proteins.

Discussion

The data presented in this work outline several elements of the autophagy-based unconventional secretory pathway in mammalian cells. This type of unconventional secretion is shown here to support the extracellular delivery of inflammasome substrates, in particular, IL-1β and IL-18 and may potentially have a broader number of clients. A relevant aspect of the process described here is that induction of autophagy is required to observe the manifestations of this type of unconventional secretion. Since basal autophagy suppresses spurious induction of inflammasome (Nakahira et al, 2010; Zhou et al, 2011), autophagy provides both avoidance of unscheduled inflammasome activation and a platform for extracellular delivery of inflammasome substrates. Since a number of hormones, cytokines, pathogen-associated molecular patterns, and danger-associated molecular patterns (Tang et al, 2010; Deretic, 2011) are known to induce or inhibit autophagy, a link between autophagy and secretion of major immunomodulatory cytokines such as IL-1β could significantly influence the extent and duration of inflammation. Connections between metabolic syndrome, high fat diet, and inflammasome activity are now beginning to be appreciated (Vandanmagsar et al, 2011; Wen et al, 2011), and we propose that autophagy-based unconventional secretion may be a key coupler between the metabolism and inflammation.

Since a number of genetic links have been found between autophagy and idiopathic inflammatory diseases or infectious diseases with significant inflammatory components (Levine et al, 2011), it is possible that at least in part the genetic associations between autophagy risk loci and disease states may stem from altered autophagy-based unconventional secretion of inflammatory cytokines. The role of autophagy was represented here by the effects of induction of autophagy and by employing conditional knockout mice with a loss of Atg5 in macrophages. We interpret the incomplete inhibition of IL-1β secretion upon Cre-dependent $Atg5^{fl/fl}$ excision as a result of the composite effects of Atg5-dependent basal autophagy (inhibitory) (Zhou et al, 2011) and induced autophagy (stimulatory) although we cannot exclude the possibility of slight leakiness of the $Atg5^{fl/fl}$ LyzM-Cre system or the existence of additional pathways. Importantly, blocking autophagic maturation has not salvaged IL-1β but rather inhibited its secretion. This appears to be in contrast to what has been reported for Acb1 in yeast (Manjithaya et al, 2010). Moreover, cathepsin B activity was needed, suggesting that autophagic organelles here did not function as mere cargo carriers but provided a platform for activation of inflammasome and IL-1b. In keeping with these observations, cathepsin B has been implicated in inflammasome activation in response to particulate inflammasome agonists (Halle et al, 2008; Hornung et al, 2008), such as those (alum, amyloid-b) used here in addition to nigericin, but how the substrate and cathepsin B meet has hitherto not been defined. Our data indicate that induction of autophagy enhances assembly of inflammasome-activating components and suggest that autophagic organelles may be a platform for concentration of components engaged in proteolytic activation of inflammasome components and inflammasome substrates. In keeping with this model of a muster station for inflammasome components, activation and subsequent extracellular delivery, is the translocation of pro-IL-1β to membranous organelles upon stimulation with the inflammasome agonist nigericin, as previously observed by Sitia and colleagues (Rubartelli et al, 1990) who have established early on that this process does not follow the conventional secretory pathway. The autophagy-based unconventional secretion pathway in mammalian cells includes GRASP, one of the peripheral Golgi proteins involved in lateral organization of Golgi ribbons. Although the role of GRASP in alternative secretory pathway has been studied, its exact mechanism of action has not been elucidated (Kinseth et al, 2007; Nickel and Rabouille, 2009). We observed here a potentially telling connection between GRASP and autophagy, by showing that GRASP affects autophagy induction, which places GRASP upstream of autophagy execution, including the conjugation systems involved in LC3 lipidation. The response of GRASP to nigericin stimulation in terms of its redistribution and juxtaposition to autophagic organelles further links autophagy, inflammasome, and GRASP, although alternative explanations are possible. The finding that Rab8a plays a functional role in autophagy-based unconventional secretionis of significance not just by assigning a trafficking regulator to this pathway but also by providing additional links with exocyst components, implicated to cooperate with Rab8a in other systems (Mazelova et al, 2009; Bryant et al, 2010) and to play a role in autophagy (Bodemann et al, 2011).

In summary, in this study we have uncovered the role of autophagy in the secretion of cytosolic proinflammatory factors that cannot enter the conventional biosynthetic pathway due to the absence of leader peptides that would bring them into the ER and the organelles of the canonical secretory pathway. Both cytosolic IL-1β and IL-18 are processed from their precursor proteins into their active forms via the inflammasome apparatus (Davis et al, 2011; Lamkanfi, 2011); however, the process that delivers the proteolytically activated IL-1β and IL-18 to the extracellular environment has hitherto remained unclear. To be eligible for export outside of the cell without invoking a pore mechanism, cytosolic proteins first need to be brought somehow into the lumen of vesicular carriers, as previously shown by others (Rubartelli et al, 1990). We have elsewhere noted (Deretic, 2005, 2011) that autophagy is a bulk topological inverter for cytosolic proteins and other molecules, ferrying them from the cytosol into the organellar lumen. We now show that induction of autophagy does that with IL-1β in the process of its secretion. In doing so, autophagic machinery cooperates with the Golgi associated factor GRASP and post-Golgi membrane trafficking and exocytosis regulator Rab8a. Autophagy captures cytosolic IL-1β and brings IL-1β into the organelles of a specialized unconventional secretory pathway. Broadening the scope of autophagy-based alternative secretion pathway is the observation that it facilitates exit from cells of the alarmin HMGB1. HMGB1 is a DAMP that is actively released from immune cells unlike its passive release from several cell types secondary to cell death (Andersson and Tracey, 2011). It has been recently shown that inflammasome, rather unexpectedly given that HMGB1 is not a known substrate for caspase-1 processing, plays a role in HMGB1 release (Lamkanfi et al, 2010). One explanation that can be offered based on our studies is that a role of inflammasome may not be related solely to proteolytic substrate processing but that it may be hardwired into the secretory pathway studied here. This is in keeping with the requirement for NLRP3 and ASC and not the caspase 1 activity for HMGB1 release as a recently recognized non-canonical inflammasome client (Willingham et al, 2009). We propose here that autophagy-based unconventional secretion may be used for extracellular delivery of a spectrum of cytosolic proteins or processed cytoplasmic substrates, not restricted to the proteins explored here, and possibly including other biological mediators such as the recently discovered cryptides (Deretic, 2005; Ponpuak et al, 2010). A recent study that appeared while this work was in revision suggests that an unconventional secretion process, also dependent on GRASP and autophagic machinery, may facilitate plasma membrane delivery of mutant CFTR, potentially expanding the range of substrates to integral membrane proteins (Gee et al, 2011). Given the capacity for either bulk transport or selectivity when coupled with autophagic adaptors, we predict that autophagy-based unconventional secretion serves a potentially broad spectrum of yet to be uncovered physiological functions.

Materials and methods

Macrophages

Murine BMM cells were prepared from femurs of C57/BL6 mice, Atg5$^{fl/fl}$ LyzM-Cre mice (Zhao et al, 2008) and their Cre-negative Atg5fl/fl littermates, and GFP-LC3 transgene knock-in mice (Mizushima et al, 2004) as previously described (Ponpuak et al, 2010). RAW 264.7 macrophages were maintained and manipulated as previously described (Ponpuak et al, 2010).

Pharmacological agonists, inhibitors, inflammasome, and autophagy

To induce pro-IL-1β expression, cells were pretreated overnight with 100 ng/ml LPS (Sigma). Inflammasome was induced with 20 mM nigericin (Sigma) for 1 h or with 250 mg/ml Alum (Thermoscientific) for 1 h or with 250 mg/ml silica crystals (MIN-U-SIL-15, US Silica) for 1 h or with 5 mM Amyloid-b peptide (Ab; American Peptide Company) fibrils prepared as described (Moore et al, 2002). Cells were treated with 100 nM bafilomycin A1 (LC Laboratories) or 10 mM cathepsin B inhibitor (CA-074 Me) (Enzo Life Science). Autophagy was induced for 1 h by starvation in EBSS or with pp242 in full medium (Torkinib; Chemidea). Starvation and other treatments (except for macrophage priming with LPS done in advance) were carried out concurrently (i.e., initiated at the same time).

Transfections and siRNA knockdowns

BMM and RAW 264.7 cells were transfected by nucleoporation using Nucleofector Reagent Kit V or Kit Mouse Macrophage (Amaxa/Lonza Biosystems). For murine NLRP3, ASC, Rab8a or GRASP knockdowns, cells were transfected with siGENOME SMARTpool reagents (Dharmacon). Rab8a SMARTpool (GAAUAAG UGUGAU-GUGAAU; GAAGACCUGUGUCCUGUUC; GACCUAC-GAUU ACCUGUUC; GAGCAGCCAUGGAGUCAAG), ASC SMARTpool (AUACAUCCCUACUUGGUGA; GCUUAGAGACAUGGGCUUA; GCAACUGCGA-GAAGGCUAU; CUGCAAACGACUAAAGAAG), NLRP3 SMARTpool (GUUCUUCGCUGCUAUGUAC; GCACCCAGGCUGUAACAUU; UGA AGGACCCACA-GUGUAA; UCACAUUCCUCUAUGGUAU), GORASP1 SMARTpool (CAUGAAGGUGCGCGAGGUA; CAGAG-GACAUUGGU UCUAG; ACUCGAG-GCUGAACAAGGA; GCUACGACCUCACAACUUA), and GORASP2 SMARTpool (GAAGACCUGUUCAGC-CUUA; UACCAAGUCUGAUGCCUUU; GUAAACCA-GUCCUUGCUU; GAUCAUCACACCAAACUCU). Non-targeting siRNA pool (Scrambled) was used as a control. Plasmid encoding tandem RFP-GFP-LC3 fusion for quantification of autophagic maturation was from T Yoshimori (Osaka, Japan). Plasmids encoding Rab8a wt (wild type) and Rab8a S22N were from Johan Peranen (University of Helsinki, Finland).

Antibodies, immunoblotting, detection assays, and microscopy

Cells extracts were analysed by standard immunoblot techniques with antibodies to pro-IL-1β (Abeam), NLRP3 (AdipoGen), ASC (Enzo Life Sciences), LC3 (Sigma), GRASP65 (Novus), GRASP55 (Abcam), Rab8a (Abeam), and Actin (Sigma); staining was revealed with Super Signal West Dura chemiluminescent substrate (Pierce). For all conditions, cell-free supernatants were assayed by immunoblotting after TCA precipitation for mouse IL-1β p17 (R&D), caspase-1 p10 (Santa Cruz Biotechnology), HMGB1 (Abcam) and Cathepsin B (R&D) or by ELISA for mouse IL-1β (R&D), IL-18 (MBL), and HMGB1 (IBL). Immunofluorescence confocal microscopy was carried out using a Zeiss LSM 510 Meta microscope (laser wavelengths 488, 543, and 633 nm). Antibodies against endogenous proteins IL-1β (Abcam), Sec6 (Shu C Hsu, Rutgers University, NJ, USA), Cathepsin B (R&D), Rab8a (Abcam), GORASP1 (Novus), GORASP2 (ProteinTech Group), GM130 (BD), LC3 (MBL) and GFP (Abcam; for BMMs from GFP-LC3 knock-in transgenic mice) were used for indirect immunofluorescence analysis. Pearson's colocalization coefficients were derived using SLIDEBOOK 5.0 (Intelligent Imaging Innovations) applying the SLIDEBOOK 5 default algorithm command 'AND'. All Pearson's coefficients were derived from three completely independent experiments with five fields or more per experiment, for a total of X15 fields contributing to the cumulative result.

Statistics

All data were analysed using two-tailed unpaired Student's t-tests. All experiments were performed at least three times, with data representing mean values±s.d. (standard deviation).

REFERENCES FOR EXAMPLE 3

Alavez S, Vantipalli M C, Zucker D J, Klang I M, Lithgow G J (2011) Amyloid-binding compounds maintain protein homeostasis during ageing and extend lifespan. Nature 472: 226-229

Andersson U, Tracey K J (2011) HMGB1 is a therapeutic target for sterile inflammation and infection. Annu Rev Immunol 29: 139-162

Barr F A, Puype M, Vandekerckhove J, Warren G (1997) GRASP65, a protein involved in the stacking of Golgi cisternae. Cell 91: 253-262

Bodemann B O, Orvedahl A, Cheng T, Ram R R, Ou Y H, Formstecher E, Maiti M, Hazelett C C, Wauson E M, Balakireva M, Camonis J H, Yeaman C, Levine B, White M A (2011) RalB and the exocyst mediate the cellular starvation response by direct activation of autophagosome assembly. Cell 144: 253-267

Bravo-Cordero J J, Marrero-Diaz R, Megias D, Genis L, Garcia-Grande A, Garcia M A, Arroyo A G, Montoya M C (2007) MT1-MMP proinvasive activity is regulated by a novel Rab8-dependent exocytic pathway. EMBO J. 26: 1499-1510

Bryant D M, Datta A, Rodriguez-Fraticelli A E, Peranen J, Martin-Belmonte F, Mostov K E (2010) A molecular network for de novo generation of the apical surface and lumen. Nat Cell Biol 12: 1035-1045

Davis B K, Wen H, Ting J P (2011) The inflammasome NLRs in immunity, inflammation, and associated diseases. Annu Rev Immunol 29: 707-735

Deretic V (2005) Autophagy in innate and adaptive immunity. Trends Immunol 26: 523-528

Deretic V (2011) Autophagy in immunity and cell-autonomous defense against intracellular microbes. Immunol Rev 240: 92-104

Deretic V, Levine B (2009) Autophagy, immunity, and microbial adaptations. Cell Host Microbe 5: 527-549

Dou Z, Chattopadhyay M, Pan J A, Guerriero J L, Jiang Y P, Ballou L M, Yue Z, Lin R Z, Zong W X (2010) The class IA phosphatidylinositol 3-kinase p110-beta subunit is a positive regulator of autophagy. J Cell Biol 191: 827-843

Duran J M, Anjard C, Stefan C, Loomis W F, Malhotra V (2010) Unconventional secretion of Acb1 is mediated by autophagosomes. J Cell Biol 188: 527-536

Egan D F, Shackelford D B, Mihaylova M M, Gelino S, Kohnz R A, Mair W, Vasquez D S, Joshi A, Gwinn D M, Taylor R, Asara J M, Fitzpatrick J, Dillin A, Viollet B, Kundu M, Hansen M, Shaw R J (2011) Phosphorylation of ULK1 (hATG1) by AMP-activated protein kinase connects energy sensing to mitophagy. Science 331: 456-461

Eisenbarth S C, Colegio O R, O0Connor W, Sutterwala F S, Flavell R A (2008) Crucial role for the Nalp3 inflammasome in the immunostimulatory properties of aluminium adjuvants. Nature 453: 1122-1126

Ezaki J, Matsumoto N, Takeda-Ezaki M, Komatsu M, Takahashi K, Hiraoka Y, Taka H, Fujimura T, Takehana K, Yoshida M, Iwata J, Tanida I, Furuya N, Zheng D M, Tada N, Tanaka K, Kominami E, Ueno T (2011) Liver autophagy contributes to the maintenance of blood glucose and amino acid levels. Autophagy 7: 727-736

Gee H Y, Noh S H, Tang B L, Kim K H, Lee M G (2011) Rescue of DeltaF508-CFTR trafficking via a GRASP-dependent unconventional secretion pathway. Cell 146: 746-760

Giuliani F, Grieve A, Rabouille C (2011) Unconventional secretion: a stress on GRASP. Curr Opin Cell Biol 23: 498-504

Gonzalez C D, Lee M S, Marchetti P, Pietropaolo M, Towns R, Vaccaro M I, Watada H, Wiley J W (2011) The emerging role of autophagy in the pathophysiology of diabetes mellitus. Autophagy 7: 2-11

Guo J Y, Chen H Y, Mathew R, Fan J, Strohecker A M, Karsli-Uzunbas G, Kamphorst J J, Chen G, Lemons J M, Karantza V, Coller H A, Dipaola R S, Gelinas C, Rabinowitz J D, White E (2011) Activated Ras requires autophagy to maintain oxidative metabolism and tumorigenesis. Genes Dev 25: 460-470

Halle A, Hornung V, Petzold G C, Stewart C R, Monks B G, Reinheckel T, Fitzgerald K A, Latz E, Moore K J, Golenbock D T (2008) The NALP3 inflammasome is involved in the innate immune response to amyloid-beta. Nat Immunol 9: 857-865

Harris J, Hartman M, Roche C, Zeng S G, O0Shea A, Sharp F A, Lambe E M, Creagh E M, Golenbock D T, Tschopp J, Kornfeld H, Fitzgerald K A, Lavelle E C (2011) Autophagy controls IL-1 {beta} secretion by targeting pro-IL-1 {beta} for degradation. J Biol Chem 286: 9587-9597

He C, Levine B (2010) The Beclin 1 interactome. Curr Opin Cell Biol 22: 140-149

Hornung V, Bauernfeind F, Halle A, Samstad E O, Kono H, Rock K L, Fitzgerald K A, Latz E (2008) Silica crystals and aluminum salts activate the NALP3 inflammasome through phagosomal destabilization. Nat Immunol 9: 847-856

Itakura E, Mizushima N (2011) p62 Targeting to the autophagosome formation site requires self-oligomerization but not LC3 binding. J Cell Biol 192: 17-27

Johansen T, Lamark T (2011) Selective autophagy mediated by autophagic adapter proteins. Autophagy 7: 279-296

Keller M, Ruegg A, Werner S, Beer H D (2008) Active caspase-1 is a regulator of unconventional protein secretion. Cell 132: 818-831

Kihara A, Kabeya Y, Ohsumi Y, Yoshimori T (2001) Beclin-phosphatidylinositol 3-kinase complex functions at the trans-Golgi network. EMBO Rep 2: 330-335

Kim J, Kundu M, Viollet B, Guan K L (2011) AMPK and mTOR regulate autophagy through direct phosphorylation of Ulk1. Nat. Cell Biol 13: 132-141

Kimura S, Noda T, Yoshimori T (2007) Dissection of the autophagosome maturation process by a novel reporter protein, tandem fluorescent-tagged LC3. Autophagy 3: 452-460

Kinseth M A, Anjard C, Fuller D, Guizzunti G, Loomis W F, Malhotra V (2007) The Golgi-associated protein GRASP is required for unconventional protein secretion during development. Cell 130: 524-534

Kroemer G, Levine B (2008) Autophagic cell death: the story of a misnomer. Nat Rev Mol Cell Biol 9: 1004-1010

Kroemer G, Marino G, Levine B (2010) Autophagy and the integrated stress response. Mol Cell 40: 280-293

Lamkanfi M (2011) Emerging inflammasome effector mechanisms. Nat Rev Immunol 11: 213-220

Lamkanfi M, Sarkar A, Vande Walle L, Vitari A C, Amer A O, Wewers M D, Tracey K J, Kanneganti T D, Dixit V M (2010) Inflammasomedependent release of the alarmin HMGB1 in endotoxemia. J Immunol 185: 4385-4392

Levine B, Mizushima N, Virgin H W (2011) Autophagy in immunity and inflammation. Nature 469: 323-335

Manjithaya R, Anjard C, Loomis W F, Subramani S (2010) Unconventional secretion of *Pichia pastoris* Acb1 is dependent on GRASP protein, peroxisomal functions, and autophagosome formation. J Cell Biol 188: 537-546

Martinon F, Petrilli V, Mayor A, Tardivel A, Tschopp J (2006) Goutassociated uric acid crystals activate the NALP3 inflammasome. Nature 440: 237-241

Mazelova J, Ransom N, Astuto-Gribble L, Wilson M C, Deretic D (2009) Syntaxin 3 and SNAP-25 pairing, regulated by omega-3 docosahexaenoic acid, controls the delivery of rhodopsin for the biogenesis of cilia-derived sensory organelles, the rod outer segments. J Cell Sci 122: 2003-2013

Mizushima N, Levine B (2010) Autophagy in mammalian development and differentiation. Nat Cell Biol 12: 823-830

Mizushima N, Levine B, Cuervo A M, Klionsky D J (2008) Autophagy fights disease through cellular self-digestion. Nature 451: 1069-1075

Mizushima N, Yamamoto A, Matsui M, Yoshimori T, Ohsumi Y (2004) In vivo analysis of autophagy in response to nutrient starvation using transgenic mice expressing a fluorescent autophagosome marker. Mol Biol Cell 15: 1101-1111

Mizushima N, Yoshimori T, Levine B (2010) Methods in mammalian autophagy research. Cell 140: 313-326

Moore K J, El Khoury J, Medeiros L A, Terada K, Geula C, Luster A D, Freeman M W (2002) A CD36-initiated signaling cascade mediates inflammatory effects of beta-amyloid. J Biol Chem 277: 47373-47379

Moritz O L, Tam B M, Hurd L L, Peranen J, Deretic D, Papermaster D S (2001) Mutant rab8 Impairs docking and fusion of rhodopsinbearing post-Golgi membranes and causes cell death of transgenic *Xenopus* rods. Mol Biol Cell 12: 2341-2351

Nachury M V, Loktev A V, Zhang Q, Westlake C J, Peranen J, Merdes A, Slusarski D C, Scheller R H, Bazan J F, Sheffield V C, Jackson P K (2007) A core complex of BBS proteins cooperates with the GTPase Rab8 to promote ciliary membrane biogenesis. Cell 129: 1201-1213

Nakahira K, Haspel J A, Rathinam V A, Lee S J, Dolinay T, Lam H C, Englert J A, Rabinovitch M, Cemadas M, Kim H P, Fitzgerald K A, Ryter S W, Choi A M (2010) Autophagy proteins regulate innate immune responses by inhibiting the release of mitochondrial DNA mediated by the NALP3 inflammasome. Nat Immunol 12: 222-230

Nickel W, Rabouille C (2009) Mechanisms of regulated unconventional protein secretion. Nat Rev Mol Cell Biol 10: 148-155

Ponpuak M, Davis A S, Roberts E A, Delgado M A, Dinkins C, Zhao Z, Virgin 3rd HW, Kyei G B, Johansen T, Vergne I, Deretic V (2010) Delivery of cytosolic components by autophagic adaptor protein p62 endows autophagosomes with unique antimicrobial properties. Immunity 32: 329-341

Renna M, Jimenez-Sanchez M, Sarkar S, Rubinsztein D C (2010) Chemical inducers of autophagy that enhance the clearance of mutant proteins in neurodegenerative diseases. J Biol Chem 285: 11061-11067

Romanello V, Guadagnin E, Gomes L, Roder I, Sandri C, Petersen Y, Milan G, Masiero E, Del Piccolo P, Foretz M, Scorrano L, Rudolf R, Sandri M (2010) Mitochondrial fission and remodelling contributes to muscle atrophy. EMBO J. 29: 1774-1785

Rubartelli A, Cozzolino F, Talio M, Sitia R (1990) A novel secretory pathway for interleukin-1 beta, a protein lacking a signal sequence. EMBO J. 9: 1503-1510

Shorter J, Watson R, Giannakou M E, Clarke M, Warren G, Barr F A (1999) GRASP55, a second mammalian GRASP protein involved in the stacking of Golgi cisternae in a cell-free system. EMBO J. 18: 4949-4960

Singh S B, Ornatowski W, Vergne I, Naylor J, Delgado M, Roberts E, Ponpuak M, Master S, Pilli M, White E, Komatsu M, Deretic V (2010) Human IRGM regulates autophagy and cell-autonomous immunity functions through mitochondria. Nat Cell Biol 12: 1154-1165

Strappazzon F, Vietri-Rudan M, Campello S, Nazio F, Florenzano F, Fimia G M, Piacentini M, Levine B, Cecconi F (2011) Mitochondrial BCL-2 inhibits AMBRA1-induced autophagy.

Sun Y, Bilan P J, Liu Z, Klip A (2010) Rab8A and Rab13 are activated by insulin and regulate GLUT4 translocation in muscle cells. Proc Natl Acad Sci USA 107: 19909-19914

Tang D, Kang R, Livesey K M, Cheh C W, Farkas A, Loughran P, Hoppe G, Bianchi M E, Tracey K J, Zeh 3rd H J, Lotze M T (2010) Endogenous HMGB1 regulates autophagy. J Cell Biol 190: 881-892

Vandanmagsar B, Youm Y H, Ravussin A, Galgani J E, Stadler K, Mynatt R L, Ravussin E, Stephens J M, Dixit V D (2011) The NLRP3 inflammasome instigates obesity-induced inflammation and insulin resistance. Nat Med 17: 179-188

Wen H, Gris D, Lei Y, Jha S, Zhang L, Huang M T, Brickey W J, Ting J P (2011) Fatty acid-induced NLRP3-ASC inflammasome activation interferes with insulin signaling. Nat Immunol 12: 408-415

Willingham S B, Allen I C, Bergstralh D T, Brickey W J, Huang M T, Taxman D J, Duncan J A, Ting J P (2009) NLRP3 (NALP3, Cryopyrin) facilitates in vivo caspase-1 activation, necrosis, and HMGB1 release via inflammasome-dependent and -independent pathways. J Immunol 183: 2008-2015

Wong E, Cuervo A M (2010) Autophagy gone awry in neurodegenerative diseases. Nat Neurosci 13: 805-811

Yang Z, Geng J, Yen W L, Wang K, Klionsky D J (2010) Positive or negative roles of different cyclin-dependent kinase Pho85-cyclin complexes orchestrate induction of autophagy in *Saccharomyces cerevisiae*. Mol Cell 38: 250-264

Youle R J, Narendra D P (2011) Mechanisms of mitophagy. Nat Rev Mol Cell Biol 12: 9-14

Zhao Z, Fux B, Goodwin M, Dunay I R, Strong D, Miller B C, Cadwell K, Delgado M A, Ponpuak M, Green K G, Schmidt R E, Mizushima N, Deretic V, Sibley L D, Virgin H W (2008) Autophagosomeindependent essential function for the autophagy protein Atg5 in cellular immunity to intracellular pathogens. Cell Host Microbe 4: 458-469

Zhou R, Yazdi A S, Menu P, Tschopp J (2011) A role for mitochondria in NLRP3 inflammasome activation. Nature 469: 221-225

EXAMPLE 4

LC3B-II autophagy marker can be detected on the surface of cells

Counterintuitively, given the engagement of autophagy and intracellular membranes, we tested whether an autophagy marker can be detected on the surface of cells. We find surprisingly that LC3B-II (which has been found only on intracellular membranes detectable by complicated methods of microscopy) is detected by simple antibody staining on the cell surface of primary lymphocytes using antibodies and flow cytometry or other simple assays of detection (FIG. 1X4). Based on prior art about autophagy one could not predict that LC3B would be exposed on the surface of the plasma membrane (Scheme 1, PM) of the cell, such as a blood lymphocyte. This is due to the accepted topology of the LC3 distribution on the intracellular membranes. Even if the intracellular membranes were to fuse with the plasma membrane (PM), LC3 would not be exposed to the outside (see Scheme 1, conventional process A; according to the current knowledge LC3 would always be shielded from the exposure to the outside and not accessible to antibodies, unless the cells were permeabilized). Scheme 1 process B, depicts what we experimentally detect, i.e. LC3 is exposed on the cell surface on the side of the plasma membrane facing the outside of the cell and thus being accessible to the exogenously added antibody to recognize LC3.

The first application of this finding is that, as shown in FIG. 1X4, blood from patients or subjects can be drawn, and white blood cells (or more specifically different cell populations including CD4 and CD8 cells and their subsets) untreated or exposed to starvation in a buffer (simple PBS or EBSS) for a period of time (FIG. 1X4 is 90 min in EBSS) and LC3 detected on the surface by antibody staining without specifically permeabilizing the cells. This new principle is the basis for the following: (i) clinical tests for patients (blood drawing and staining for LC3 on lymphocytes or whole white blood cells), (b) biomarker in clinical studies (same as above), (iii) drug screening and development for induction or blocking of autophagy, and (iv) target for treatment with blocking antibodies should LC3 on the cell surface show biological functions.

EXAMPLE 5

Use of high-content imaging to determine autophagy-associated effects on cytoplasmic puncta The experiment of this example showed that high-content imaging can be used in a high-throughput format to determine autophagy-associated effects on cytoplasmic puncta of *M. tuberculosis*-infected lung cells and cells implicated in a lipid-related metabolic disorder.

Our high-content imaging system is represented schematically in FIG. 3X5 and can be used to screen for a composition's autophagy-associated effect on cytoplasmic puncta of either *M. tuberculosis*-infected lung cells or cells implicated in a lipid-related metabolic disorder. The following steps were performed:

(a) culturing a sample of the cells; (b) plating the cell sample on multi-well plates; (c) contacting the cell sample with the composition; and (d) using high-content imaging to examine the cell sample for an autophagy-associated effect on cytoplasmic puncta. The screen was conducted using a high-throughput format.

More specifically, the multi-well plates were 384-well plates, the cells were transfected with RFP-LC3 or GFP-LC3 prior to plating, and the observed cytoplasmic puncta were RFP-LC3 puncta or GFP-LC3 puncta. See FIGS. 2X5, 3X5, 4X5. Positive controls and read times are summarized in FIG. 5AX5.

Red puncta and green puncta number, intensity, and area were considered as selection parameters. FIG. 6X5. Screens using compounds from the Prestwick library were conducted and total GFP+ puncta area/cell and toal GFP area/cell were determined. FIG. 7X5. An approximately 34% overlap of hits from two separate Prestwick screens from induction of autophagy was observed. Compound hits, both real and imagined, were determined, FIG. 9X5, and dose response curve to pp242 were generated. FIG. 10X5. Comparable TPIMS screen results are summarized in FIG. 11X5.

EXAMPLE 6

A number of compounds have been identified by screening small molecule libraries for their autophagic regulatory capacities by using a Cellomics ArrayScan to quantitate LC3-GFP/RFP puncta in HeLa cells. LC3 is a widely-used marker for autophagic vacuoles. HeLa cells stably transduced with LC3-GFP/RFP tandem construct generate fluorescent autophagic puncta, which are either green/yellow (early autophagosomes) or red (late autophagosomes fused with lysosomes, which degrades the GFP). By quantitating the number or total area of fluorescent puncta per cell, we can detect alterations in autophagic flux and regulation.

Prior to any actual screening, however, preliminary experiments to modify our protocols for use in 384-well plate high-content screening had to be conducted. To that end, we ran a series of experiments to show that ~5,000 LC3-GFP/RFP HeLa cells per well of a 384-well plate was optimal for imaging on the Cellomics ArrayScan. The next question was which parameter was most sensitive for detecting changes in autophagy. We tested total puncta area, number, or intensity per cell for both GFP+ and RFP+ puncta after treatment with pp242, an mTOR inhibitor and known inducer of autophagy. As shown in FIG. 1X6, GFP+ puncta area was the most distinct readout for induction of autophagy, although other parameters in both the RFP and GFP channels also showed changes. Other methods of induction of autophagy were tested for use as positive controls, including starvation and the mTOR inhibitor rapamycin (data not shown). However, pp242 was consistently the stronger inducer of autophagy in our hands in this assay, and was used in most studies.

Using the above system, we performed two separate screens on a chemical library. This library contains 1,200 FDA-approved compounds, and represents wide functional and chemical diversity. This library spans four 384-well plates, with 64 wells on each plate with DMSO only as negative controls. We used 32 of these wells for addition of our positive control (pp242 or rapamycin), and left the other 32 for DMSO negative controls. FIG. 2X6 shows the raw data from one of these screens. The first screen revealed 266 "hits"—compounds that induced or decreased autophagy in the LC3-GFP/RFP HeLa cells. A hit was defined as 3 standard deviations above or below the mean of the negative control wells on a given plate. The second screen gave 182 hits. Overall, 96 compounds were found to affect autophagy in both screens, for an overlap rate of ~34% (FIG. 3X6). Analysis of the images from the experiments revealed that 6 of these compounds were false positives (due to autofluorescence, etc). Therefore, a total of 90 compounds were identified from the two chemical library screens and appear in the present specification.

In order to further dissect the ability of the 90 hits to affect autophagy, we wished to test whether the screening system we used was sufficient to determine dose responses for each compound. To that end, we performed dose response experiments using pp242. As shown in FIG. 4, dose responses could be performed successfully.

Therefore, we performed two separate dose response experiments on 85 of the 90 hits obtained from the two Prestwick Chemical Library screens. As shown in Appendix 2, a range of dose response curves were identified in the different compounds. This assay resulted in 25 compounds that showed acceptable dose response curves in both experiments; 20 of these compounds were not previously known to induce autophagy. Current studies are underway to measure LC3-I and LC3-II levels by western blot, and p62 levels by Cellomics and western blot, to further confirm the autophagic activity of these compounds.

In parallel to the second Prestwick Chemical Library screen, we also wished to test which compounds might be useful for combinatorial drug products. Using the data from FIG. 4, we treated LC3-GFP/RFP HeLa cells with a suboptimal dose of pp242 that did not induce autophagy (~0.06 uM), then added the Prestwick Chemical Library to these cells and analyzed as before. After two separate screens, we found 8 compounds (Appendix 4) that altered autophagy in the presence, but not the absence, of suboptimal pp242 concentration. Four of these 8 compounds were found in either of our prior Prestwick Chemical Library screen or are known mTOR pathway modulators (and therefore merely exerting additive effects). Therefore, 4 compounds in this screen could modulate autophagy in concert with, but not without, suboptimal amounts of pp242. We are currently testing these compounds in dose response experiments to confirm the pp242 effects and to test whether any activity is additive or synergistic.

Wild-type HIV-1 viruses will be used in further tests to determine whether the compounds in our screens will alter HIV-1 replication. We have already grown and titered a wild-type macrophage-tropic HIV-1. Two separate wild-type CD4+ T cell-tropic HIV strains have also been generated. Compounds that inhibit or induce autophagy, as identified in our ongoing screens, will be incubated with human peripheral blood monocyte-derived macrophages that have been infected with wild-type HIV-1 in 96-well plates. At different time points, supernatants will be harvested and added to TMZ-b1/JC53BL cells, which express luciferase after HIV replication. Replication will be assessed by luciferase levels relative to DMSO-treated controls. Alternately, p24 levels will be assessed.

We have also performed two separate screens using the LC3-GFP/RFP HeLa cells against the Spectrum 2000 library. As shown in FIG. 5, 207 compounds were identified as regulators of autophagy. After visual inspection of the images, 21 compounds were excluded due to autofluorescence or other false positive characteristics. Of the remaining 186 compounds, 94 were also present in the Prestwick Chemical Library, so these were excluded. This left 92 compounds, 83 of which were not known to be regulators of autophagy. There is a range of compound types in this group (FIG. 5). These compounds have been described in the specification as set forth above.

SUMMARY

We have optimized our high-content imaging screening system for measurement of regulation of autophagy. We have used this system to screen two different drug libraries and have identified up to 182 compounds (125 of which have been used in humans) that regulate autophagy, and have conducted dose response studies to begin to narrow down these hits to identify the most promising compounds. In addition, we have found 4 compounds that only induce autophagy in a combination setting (with low doses of pp242). We are in the process of setting up our HIV in vitro replication assay to further test these hits. Additional library screens are planned.

What is claimed is:

1. A method of treating tuberculosis in a patient in need thereof comprising administering to said patient an effective amount of a composition comprising an effective amount of flubendazole or its pharmaceutically acceptable salt as an autophagy modulator in combination with curcumin and a pharmaceutically-acceptable carrier, additive and/or excipient.

2. The method according to claim 1, wherein said composition further includes bromhexine or its pharmaceutically acceptable salt and/or rapamycin.

3. The method according to claim 1, wherein said composition further includes bromhexine or its pharmaceutically salt.

4. The method according to claim 1, wherein said composition further includes rapamycin.

5. The method according to claim 1 wherein said composition further includes bromhexine or its pharmaceutically acceptable salt and rapamycin.

* * * * *

```
                        SEQUENCE LISTING

<160> NUMBER OF SEQ ID NOS: 44

<210> SEQ ID NO 1
<211> LENGTH: 22
<212> TYPE: PRT
<213> ORGANISM: Artificial Sequence
<220> FEATURE:
<223> OTHER INFORMATION: synthetic sequence

<400> SEQUENCE: 1

Leu Ile Glu Ser Leu Ser Gln Met Leu Ser Met Gly Phe Ser Asp Glu
1               5                   10                  15

Gly Gly Trp Leu Thr Arg
            20

<210> SEQ ID NO 2
<211> LENGTH: 19
<212> TYPE: DNA
<213> ORGANISM: Artificial Sequence
<220> FEATURE:
<223> OTHER INFORMATION: synthetic sequence

<400> SEQUENCE: 2
gcattgaagt ggatattga                                              19

<210> SEQ ID NO 3
<211> LENGTH: 19
<212> TYPE: DNA
<213> ORGANISM: Artificial Sequence
<220> FEATURE:
<223> OTHER INFORMATION: synthetic sequence

<400> SEQUENCE: 3
gacgatgact ggacccatt                                              19

<210> SEQ ID NO 4
<211> LENGTH: 19
<212> TYPE: DNA
<213> ORGANISM: Artificial Sequence
<220> FEATURE:
<223> OTHER INFORMATION: synthetic sequence

<400> SEQUENCE: 4
tcggaggatc ccagtgtga                                              19

<210> SEQ ID NO 5
<211> LENGTH: 19
<212> TYPE: DNA
<213> ORGANISM: Artificial Sequence
<220> FEATURE:
<223> OTHER INFORMATION: synthetic sequence

<400> SEQUENCE: 5
```

-continued

```
cagcaagccg ggtgggaat                                                  19

<210> SEQ ID NO 6
<211> LENGTH: 19
<212> TYPE: RNA
<213> ORGANISM: Artificial Sequence
<220> FEATURE:
<223> OTHER INFORMATION: synthetic sequence

<400> SEQUENCE: 6
ccaauugguu uacuauuug                                                  19

<210> SEQ ID NO 7
<211> LENGTH: 19
<212> TYPE: RNA
<213> ORGANISM: Artificial Sequence
<220> FEATURE:
<223> OTHER INFORMATION: synthetic sequence

<400> SEQUENCE: 7
cgaauuccaa cuugcuuua                                                  19

<210> SEQ ID NO 8
<211> LENGTH: 19
<212> TYPE: RNA
<213> ORGANISM: Artificial Sequence
<220> FEATURE:
<223> OTHER INFORMATION: synthetic sequence

<400> SEQUENCE: 8
uuagugagau augguuuga                                                  19

<210> SEQ ID NO 9
<211> LENGTH: 19
<212> TYPE: RNA
<213> ORGANISM: Artificial Sequence
<220> FEATURE:
<223> OTHER INFORMATION: synthetic sequence

<400> SEQUENCE: 9
gcauaaaagu caagugauc                                                  19

<210> SEQ ID NO 10
<211> LENGTH: 19
<212> TYPE: RNA
<213> ORGANISM: Artificial Sequence
<220> FEATURE:
<223> OTHER INFORMATION: synthetic sequence

<400> SEQUENCE: 10
uagcgacuaa acacaucaa                                                  19

<210> SEQ ID NO 11
<211> LENGTH: 19
<212> TYPE: RNA
<213> ORGANISM: Artificial Sequence
<220> FEATURE:
<223> OTHER INFORMATION: synthetic sequence

<400> SEQUENCE: 11
uaaggcuaug aagagauac                                                  19

<210> SEQ ID NO 12
<211> LENGTH: 19
<212> TYPE: RNA
```

<213> ORGANISM: Artificial Sequence
<220> FEATURE:
<223> OTHER INFORMATION: synthetic sequence

<400> SEQUENCE: 12
auguauuggc cuguauuag                                                    19

<210> SEQ ID NO 13
<211> LENGTH: 19
<212> TYPE: RNA
<213> ORGANISM: Artificial Sequence
<220> FEATURE:
<223> OTHER INFORMATION: synthetic sequence

<400> SEQUENCE: 13
augaacguga auugcucaa                                                    19

<210> SEQ ID NO 14
<211> LENGTH: 20
<212> TYPE: DNA
<213> ORGANISM: Artificial Sequence
<220> FEATURE:
<223> OTHER INFORMATION: synthetic sequence

<400> SEQUENCE: 14
gcaacgggaa gattctgaag                                                   20

<210> SEQ ID NO 15
<211> LENGTH: 20
<212> TYPE: DNA
<213> ORGANISM: Artificial Sequence
<220> FEATURE:
<223> OTHER INFORMATION: synthetic sequence

<400> SEQUENCE: 15
tgacaaactt ctgcctgacg                                                   20

<210> SEQ ID NO 16
<211> LENGTH: 19
<212> TYPE: RNA
<213> ORGANISM: Artificial Sequence
<220> FEATURE:
<223> OTHER INFORMATION: synthetic sequence

<400> SEQUENCE: 16
gaagccgucu ggugcaaua                                                    19

<210> SEQ ID NO 17
<211> LENGTH: 19
<212> TYPE: RNA
<213> ORGANISM: Artificial Sequence
<220> FEATURE:
<223> OTHER INFORMATION: synthetic sequence

<400> SEQUENCE: 17
ugacggcgca uaagauuua                                                    19

<210> SEQ ID NO 18
<211> LENGTH: 19
<212> TYPE: RNA
<213> ORGANISM: Artificial Sequence
<220> FEATURE:
<223> OTHER INFORMATION: synthetic sequence

<400> SEQUENCE: 18
cuacgaagga cgacgcuua                                                    19

```
<210> SEQ ID NO 19
<211> LENGTH: 19
<212> TYPE: RNA
<213> ORGANISM: Artificial Sequence
<220> FEATURE:
<223> OTHER INFORMATION: synthetic sequence

<400> SEQUENCE: 19
guaugaagcg uuuaaagau                                                    19

<210> SEQ ID NO 20
<211> LENGTH: 19
<212> TYPE: RNA
<213> ORGANISM: Artificial Sequence
<220> FEATURE:
<223> OTHER INFORMATION: synthetic sequence

<400> SEQUENCE: 20
gaaauuaagg uucuguuga                                                    19

<210> SEQ ID NO 21
<211> LENGTH: 19
<212> TYPE: RNA
<213> ORGANISM: Artificial Sequence
<220> FEATURE:
<223> OTHER INFORMATION: synthetic sequence

<400> SEQUENCE: 21
ccacucacgc caacuauaa                                                    19

<210> SEQ ID NO 22
<211> LENGTH: 19
<212> TYPE: RNA
<213> ORGANISM: Artificial Sequence
<220> FEATURE:
<223> OTHER INFORMATION: synthetic sequence

<400> SEQUENCE: 22
gaugaaggcu uucgagucg                                                    19

<210> SEQ ID NO 23
<211> LENGTH: 19
<212> TYPE: RNA
<213> ORGANISM: Artificial Sequence
<220> FEATURE:
<223> OTHER INFORMATION: synthetic sequence

<400> SEQUENCE: 23
uaacauggcu cauugugaa                                                    19

<210> SEQ ID NO 24
<211> LENGTH: 19
<212> TYPE: RNA
<213> ORGANISM: Artificial Sequence
<220> FEATURE:
<223> OTHER INFORMATION: synthetic sequence

<400> SEQUENCE: 24
gaauaagugu gaugugaau                                                    19

<210> SEQ ID NO 25
<211> LENGTH: 19
<212> TYPE: RNA
<213> ORGANISM: Artificial Sequence
<220> FEATURE:
```

<223> OTHER INFORMATION: synthetic sequence

<400> SEQUENCE: 25
gaagaccugu guccuguuc                                                                19

<210> SEQ ID NO 26
<211> LENGTH: 19
<212> TYPE: RNA
<213> ORGANISM: Artificial Sequence
<220> FEATURE:
<223> OTHER INFORMATION: synthetic sequence

<400> SEQUENCE: 26
gaccuacgau uaccuguuc                                                                19

<210> SEQ ID NO 27
<211> LENGTH: 19
<212> TYPE: RNA
<213> ORGANISM: Artificial Sequence
<220> FEATURE:
<223> OTHER INFORMATION: synthetic sequence

<400> SEQUENCE: 27
gagcagccau ggagucaag                                                                19

<210> SEQ ID NO 28
<211> LENGTH: 19
<212> TYPE: RNA
<213> ORGANISM: Artificial Sequence
<220> FEATURE:
<223> OTHER INFORMATION: synthetic sequence

<400> SEQUENCE: 28
auacaucccu acuugguga                                                                19

<210> SEQ ID NO 29
<211> LENGTH: 19
<212> TYPE: RNA
<213> ORGANISM: Artificial Sequence
<220> FEATURE:
<223> OTHER INFORMATION: synthetic sequence

<400> SEQUENCE: 29
gcuuagagac augggcuua                                                                19

<210> SEQ ID NO 30
<211> LENGTH: 19
<212> TYPE: RNA
<213> ORGANISM: Artificial Sequence
<220> FEATURE:
<223> OTHER INFORMATION: synthetic sequence

<400> SEQUENCE: 30
gcaacugcga gaaggcuau                                                                19

<210> SEQ ID NO 31
<211> LENGTH: 19
<212> TYPE: RNA
<213> ORGANISM: Artificial Sequence
<220> FEATURE:
<223> OTHER INFORMATION: synthetic sequence

<400> SEQUENCE: 31
cugcaaacga cuaaagaag                                                                19

```
<210> SEQ ID NO 32
<211> LENGTH: 19
<212> TYPE: RNA
<213> ORGANISM: Artificial Sequence
<220> FEATURE:
<223> OTHER INFORMATION: synthetic sequence

<400> SEQUENCE: 32
guucuucgcu gcuauguac                                               19

<210> SEQ ID NO 33
<211> LENGTH: 19
<212> TYPE: RNA
<213> ORGANISM: Artificial Sequence
<220> FEATURE:
<223> OTHER INFORMATION: synthetic sequence

<400> SEQUENCE: 33
gcacccaggc uguaacauu                                               19

<210> SEQ ID NO 34
<211> LENGTH: 19
<212> TYPE: RNA
<213> ORGANISM: Artificial Sequence
<220> FEATURE:
<223> OTHER INFORMATION: synthetic sequence

<400> SEQUENCE: 34
ugaaggaccc acaguguaa                                               19

<210> SEQ ID NO 35
<211> LENGTH: 19
<212> TYPE: RNA
<213> ORGANISM: Artificial Sequence
<220> FEATURE:
<223> OTHER INFORMATION: synthetic sequence

<400> SEQUENCE: 35
ucacauuccu cuaugguau                                               19

<210> SEQ ID NO 36
<211> LENGTH: 19
<212> TYPE: RNA
<213> ORGANISM: Artificial Sequence
<220> FEATURE:
<223> OTHER INFORMATION: synthetic sequence

<400> SEQUENCE: 36
caugaaggug cgcgaggua                                               19

<210> SEQ ID NO 37
<211> LENGTH: 19
<212> TYPE: RNA
<213> ORGANISM: Artificial Sequence
<220> FEATURE:
<223> OTHER INFORMATION: synthetic sequence

<400> SEQUENCE: 37
cagaggacau ugguucuag                                               19

<210> SEQ ID NO 38
<211> LENGTH: 19
<212> TYPE: RNA
<213> ORGANISM: Artificial Sequence
<220> FEATURE:
<223> OTHER INFORMATION: synthetic sequence
```

```
<400> SEQUENCE: 38
acucgaggcu gaacaagga                                              19

<210> SEQ ID NO 39
<211> LENGTH: 19
<212> TYPE: RNA
<213> ORGANISM: Artificial Sequence
<220> FEATURE:
<223> OTHER INFORMATION: synthetic sequence

<400> SEQUENCE: 39
gcuacgaccu cacaacuua                                              19

<210> SEQ ID NO 40
<211> LENGTH: 19
<212> TYPE: RNA
<213> ORGANISM: Artificial Sequence
<220> FEATURE:
<223> OTHER INFORMATION: synthetic sequence

<400> SEQUENCE: 40
gaagaccugu ucagccuua                                              19

<210> SEQ ID NO 41
<211> LENGTH: 19
<212> TYPE: RNA
<213> ORGANISM: Artificial Sequence
<220> FEATURE:
<223> OTHER INFORMATION: synthetic sequence

<400> SEQUENCE: 41
uaccaagucu gaugccuuu                                              19

<210> SEQ ID NO 42
<211> LENGTH: 19
<212> TYPE: RNA
<213> ORGANISM: Artificial Sequence
<220> FEATURE:
<223> OTHER INFORMATION: synthetic sequence

<400> SEQUENCE: 42
guaaaccagu cccuugcuu                                              19

<210> SEQ ID NO 43
<211> LENGTH: 19
<212> TYPE: RNA
<213> ORGANISM: Artificial Sequence
<220> FEATURE:
<223> OTHER INFORMATION: synthetic sequence

<400> SEQUENCE: 43
gaucaucaca ccaaacucu                                              19

<210> SEQ ID NO 44
<211> LENGTH: 4
<212> TYPE: PRT
<213> ORGANISM: Artificial Sequence
<220> FEATURE:
<223> OTHER INFORMATION: synthetic sequence

<400> SEQUENCE: 44

Tyr Val Ala Asp
1
```